United States Patent
Oerum et al.

(10) Patent No.: US 12,291,708 B2
(45) Date of Patent: *May 6, 2025

(54) ORAL DELIVERY OF ANTISENSE CONJUGATES TARGETING PCSK9

(71) Applicant: CiVi Biopharma, Inc., Chevy Chase, MD (US)

(72) Inventors: Henrik Oerum, Copenhagen (DK); Stewart Alwyn Noble, San Diego, CA (US); Charles Lester Shear, Collegeville, PA (US)

(73) Assignee: CiVi Biopharma, Inc., Chevy Chase, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/547,879

(22) Filed: Dec. 10, 2021

(65) Prior Publication Data

US 2022/0213476 A1    Jul. 7, 2022

Related U.S. Application Data

(60) Provisional application No. 63/261,505, filed on Sep. 22, 2021, provisional application No. 63/178,340, filed on Apr. 22, 2021, provisional application No. 63/134,884, filed on Jan. 7, 2021, provisional application No. 63/124,581, filed on Dec. 11, 2020.

(51) Int. Cl.
| | |
|---|---|
| *C12N 15/113* | (2010.01) |
| *A61K 31/7088* | (2006.01) |
| *A61P 3/06* | (2006.01) |
| *A61P 43/00* | (2006.01) |
| *C12N 15/11* | (2006.01) |

(52) U.S. Cl.
CPC ........ *C12N 15/113* (2013.01); *A61K 31/7088* (2013.01); *A61P 3/06* (2018.01); *A61P 43/00* (2018.01); *C12N 15/111* (2013.01); *C12N 2310/11* (2013.01); *C12N 2310/313* (2013.01); *C12N 2310/315* (2013.01); *C12N 2310/321* (2013.01); *C12N 2310/3231* (2013.01); *C12N 2310/341* (2013.01); *C12N 2310/351* (2013.01); *C12N 2320/33* (2013.01)

(58) Field of Classification Search
CPC . C12N 15/113; C12N 15/111; C12N 2310/11; C12N 2310/315; C12N 2310/321; C12N 2310/3231; C12N 2310/341; C12N 2310/351; C12N 2320/33; C12N 15/1137; C12N 2310/3515; C12N 2320/32; C12N 2310/3125; C12N 2310/313; C12N 2310/314; A61K 31/7088; A61K 47/549; A61K 47/554; A61K 48/00; A61K 45/06; A61K 47/542; A61K 9/2013; A61K 9/2833; A61K 9/4858; A61K 9/4891; A61P 43/00; A61P 3/06; A61P 9/10; C12Y 304/21061

See application file for complete search history.

(56) References Cited

U.S. PATENT DOCUMENTS

| | | |
|---|---|---|
| 4,043,996 A | 8/1977 | Donnelly et al. |
| 4,064,008 A | 12/1977 | Petersen et al. |
| 4,176,117 A | 11/1979 | Oudem |
| 4,232,425 A | 11/1980 | Wojcik |
| 4,374,063 A | 2/1983 | Consolazio et al. |
| 4,402,873 A | 9/1983 | Vollmer et al. |
| 4,427,583 A | 1/1984 | England et al. |
| 4,587,044 A | 5/1986 | Miller et al. |
| 4,667,025 A | 5/1987 | Miyoshi et al. |
| 4,889,920 A | 12/1989 | Mueller |
| 4,948,882 A | 8/1990 | Ruth |
| 5,093,474 A | 3/1992 | Grossman et al. |
| 5,112,963 A | 5/1992 | Pieles et al. |
| 5,210,182 A | 5/1993 | Nasrallah et al. |
| 5,245,022 A | 9/1993 | Weis et al. |
| 5,254,469 A | 10/1993 | Warren, III et al. |
| 5,288,408 A | 2/1994 | Schmidt et al. |
| 5,391,723 A | 2/1995 | Priest |
| 5,459,241 A | 10/1995 | Moy et al. |
| 5,486,603 A | 1/1996 | Buhr |
| 5,510,475 A | 4/1996 | Agrawal et al. |
| 5,512,667 A | 4/1996 | Reed et al. |
| 5,525,465 A | 6/1996 | Haralambidis et al. |
| 5,541,313 A | 7/1996 | Ruth |
| 5,545,730 A | 8/1996 | Urdea et al. |
| 5,552,538 A | 9/1996 | Urdea et al. |

(Continued)

FOREIGN PATENT DOCUMENTS

| | | | | |
|---|---|---|---|---|
| EP | 1535625 A1 | 6/2005 | | |
| JP | 2016506389 A | * | 3/2016 | ............... A61P 7/02 |

(Continued)

OTHER PUBLICATIONS

Walpole et al. 2012. The weight of nations: an estimation of adult human biomass. BMC Pub. Heal. 12:439 (Year: 2012).*
Mahmoud et al. 2014. Modulatory role of chelating agents in diet-induced hypercholesterolemia in rats. Bull. Fac. Pharm. Cairo U. 52:27-35 (Year: 2014).*
Superior Capsule Size Chart—Complete Guide (Feb. 11, 2020. Superior Supplement Manufacturing; available online at: https://www.superiorsupplementmfg.com/capsule-size-chart/ (Year: 2020).*
English translation of Japan Patent Application Publication No. JP 2016506389, published Mar. 3, 2016 (Year: 2016).*
U.S. Appl. No. 18/230,058, filed Aug. 2023.*
U.S. Appl. No. 18/555,229, filed Oct. 2023.*
Tillman et al. 2008. Oral Delivery of Antisense Oligonucleotides in Man. J. Pharmaceut. Sci 97[1]:225-236 (Year: 2008).*

(Continued)

*Primary Examiner* — Nancy J Leith
*Assistant Examiner* — Ruth Sophia Arieti
(74) *Attorney, Agent, or Firm* — Sterne, Kessler, Goldstein & Fox P.L.L.C.

(57) ABSTRACT

The present disclosure provides pharmaceutic compositions for oral delivery comprising an antisense oligonucleotide (e.g., CIVI 008) and an oral delivery agent such as 5-CNAC. In some aspects, the disclosure provides a capsule comprising a dry blend of CIVI 008 and 5-CNAC, and optionally a statin.

14 Claims, 41 Drawing Sheets

Specification includes a Sequence Listing.

(56) References Cited

U.S. PATENT DOCUMENTS

| | | |
|---|---|---|
| 5,574,142 A | 11/1996 | Meyer, Jr. et al. |
| 5,580,731 A | 12/1996 | Chang et al. |
| 5,608,046 A | 3/1997 | Cook et al. |
| 5,650,386 A | 7/1997 | Leone-Bay et al. |
| 5,684,142 A | 11/1997 | Mishra et al. |
| 5,770,716 A | 6/1998 | Khan et al. |
| 5,773,647 A | 6/1998 | Leone-Bay et al. |
| 5,851,579 A | 12/1998 | Wu et al. |
| 5,866,536 A | 2/1999 | Leone-Bay et al. |
| 6,090,915 A | 7/2000 | Herreid |
| 6,096,875 A | 8/2000 | Khan et al. |
| 6,268,490 B1 | 7/2001 | Imanishi et al. |
| 6,335,432 B1 | 1/2002 | Segev |
| 6,335,437 B1 | 1/2002 | Manoharan |
| 6,375,981 B1 | 4/2002 | Gilleland et al. |
| 6,399,798 B2 | 6/2002 | Gschneidner et al. |
| 6,440,480 B2 | 8/2002 | Dorp et al. |
| 6,458,383 B2 | 10/2002 | Chen et al. |
| 6,525,191 B1 | 2/2003 | Ramasamy |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,384,982 B2 | 6/2008 | Bay et al. |
| 7,399,845 B2 | 7/2008 | Punit et al. |
| 7,427,672 B2 | 9/2008 | Imanishi et al. |
| 7,544,833 B2 | 6/2009 | Bay et al. |
| 7,569,539 B2 | 8/2009 | Azria et al. |
| 7,659,311 B2 | 2/2010 | Bay et al. |
| 7,741,457 B2 | 6/2010 | Punit et al. |
| 8,003,697 B2 | 8/2011 | Bay et al. |
| 8,110,674 B2 | 2/2012 | Manoharan et al. |
| 8,207,227 B2 | 6/2012 | Bay et al. |
| 8,420,799 B2 | 4/2013 | Manoharan |
| 8,435,946 B2 | 5/2013 | Li et al. |
| 8,501,805 B2 | 8/2013 | Punit et al. |
| 8,530,640 B2 | 9/2013 | Punit et al. |
| 8,546,556 B2 | 10/2013 | Punit et al. |
| 8,658,695 B2 | 2/2014 | Bay et al. |
| 8,748,383 B2 | 6/2014 | Li et al. |
| 8,809,516 B2 | 8/2014 | Manoharan et al. |
| 9,222,091 B2 | 12/2015 | Manoharan et al. |
| 9,278,123 B2 | 3/2016 | Sauerberg et al. |
| 9,290,760 B2 | 3/2016 | Rajeev et al. |
| 9,708,615 B2 | 7/2017 | Manoharan et al. |
| 9,796,974 B2 | 10/2017 | Rajeev et al. |
| 9,879,265 B2 | 1/2018 | Albaek et al. |
| 10,086,047 B2 | 10/2018 | Sauerberg et al. |
| 10,091,764 B2 | 10/2018 | Hsu et al. |
| 10,233,448 B2 | 3/2019 | Maier et al. |
| 10,273,477 B2 | 4/2019 | Manoharan et al. |
| 10,370,668 B2 | 8/2019 | Albaek et al. |
| 10,385,342 B2 | 8/2019 | Albaek et al. |
| 10,443,058 B2 | 10/2019 | Albaek et al. |
| 10,517,953 B2 | 12/2019 | Swayze et al. |
| 2004/0171570 A1 | 9/2004 | Allerson et al. |
| 2007/0287831 A1 | 12/2007 | Punit et al. |
| 2008/0039618 A1 | 2/2008 | Manoharan et al. |
| 2011/0092426 A1 | 4/2011 | Arnold et al. |
| 2012/0264834 A1 | 10/2012 | Bay et al. |
| 2013/0303444 A1 | 11/2013 | Dhoot et al. |
| 2014/0309287 A1 | 10/2014 | Rusconi et al. |
| 2014/0323543 A1 | 10/2014 | Graff |
| 2015/0283212 A1 | 10/2015 | Arnold et al. |
| 2018/0216116 A1 | 8/2018 | Albaek et al. |
| 2018/0258427 A1 | 9/2018 | Manoharan et al. |
| 2018/0360918 A1 | 12/2018 | Sauerberg et al. |
| 2019/0375786 A1 | 12/2019 | Girard et al. |
| 2020/0157548 A1 | 5/2020 | Prakash et al. |
| 2022/0025376 A1 | 1/2022 | Albaek et al. |
| 2022/0213476 A1 | 7/2022 | Oerum et al. |
| 2022/0380761 A1 | 12/2022 | Oerum et al. |
| 2024/0067965 A1 | 2/2024 | Oerum et al. |

FOREIGN PATENT DOCUMENTS

| | | | |
|---|---|---|---|
| WO | WO-9414226 A1 | 6/1994 | |
| WO | WO-9611205 A1 | 4/1996 | |
| WO | WO-9852614 A2 | 11/1998 | |
| WO | WO-9914226 A2 | 3/1999 | |
| WO | WO-0059863 A | 10/2000 | |
| WO | WO-0123613 A1 | 7/2002 | |
| WO | WO-2004046160 A2 | 6/2004 | |
| WO | WO-2004106356 A1 | 12/2004 | |
| WO | WO-2005021570 A1 | 3/2005 | |
| WO | WO-2007031091 A2 * | 3/2007 | ......... C12N 15/1135 |
| WO | WO-2007134181 A2 | 11/2007 | |
| WO | WO-2007146511 A2 | 12/2007 | |
| WO | WO-2008113832 A2 | 9/2008 | |
| WO | WO-2008150729 A2 | 12/2008 | |
| WO | WO-2008154401 A2 | 12/2008 | |
| WO | WO-2009006478 A2 | 1/2009 | |
| WO | WO-2009043354 A2 | 4/2009 | |
| WO | WO-2009124238 A1 | 10/2009 | |
| WO | WO-2010142805 A1 | 12/2010 | |
| WO | WO-2011009697 A1 | 1/2011 | |
| WO | WO-2012083046 A2 | 6/2012 | |
| WO | WO-2014046983 A1 * | 3/2014 | ........... A61K 31/192 |
| WO | WO-2014207232 A1 * | 12/2014 | ........... A61K 31/713 |
| WO | WO-2018098328 A1 | 5/2018 | |
| WO | WO-2020069055 A1 | 4/2020 | |
| WO | WO-2020236600 A1 | 11/2020 | |
| WO | WO-2022125913 A1 | 6/2022 | |
| WO | WO-2022226217 A1 | 10/2022 | |

OTHER PUBLICATIONS

Shirahama (et al. 2018. Coronary Artery Plaque Regression by a PCSK9 Antibody and Rosuvastatin in Double-heterozygous Familial Hypercholesterolemia with an LDL Receptor Mutation and a PCSK9 V4I Mutation. Intern. Med. 57:3551-3557) (Year: 2018).*
Yurtseven (et al. Jan. 2020. An Update on the Role of PCSK9 in Atherosclerosis. J. Artheroscler. Thromb. 27:909-918) (Year: 2020).*
Wikipedia. 2020. "Enteric coating". Available online at Wikipedia.org. Accessed on Nov. 20, 2024 (Year: 2020).*
International Search Report and Written Opinion for International Application No. PCT/US2021/062831, mailed on Apr. 15, 2022, 15 pages.
Altschul et al., "Gapped BLAST and PSI-BLAST: a new generation of protein database search programs", Nucleic Acids Res. 25(17): 3389-3402, Oxford University Press, United States (1991).
Braasch et al., "Locked nucleic acid (LNA): fine-tuning the recognition of DNA and RNA", Chem. Biol. 8(1): 1-7, Elsevier Science Ltd., Untied States (2001).
Christensen et al., "Intercalating nucleic acids containing insertions of 1-O-(1-pyrenylmethyl)glycerol: stabilisation of dsDNA and discrimination of DNA over RNA", Nucl. Acids. Res. 30(22):4918-4925, Oxford University Press, United States (2002).
Freier et al., "The ups and downs of nucleic acid duplex stability: Structure-stability studies on chemically-modified DNA:RNA duplexes", Nucl. Acid Res., 25(22): 4429-4443, Oxford University Press, United States (1997).
Karlin et al., "Applications and statistics for multiple high-scoring segments in molecular sequences", Proc. Natl. Acad. Sci., 90(12): 5873-5877, PMCID, United States (1993).
Karlin et al., "Methods for assessing the statistical significance of molecular sequence features by using general scoring schemes", Proc. Natl. Acad. Sci., 87(6):2264-2268, PMCID, United States (1990).
Kumar et al., "The first analogues of LNA (Locked Nucleic Acids): Phosphorothioate-LNA and 2'-thio-LNA", Bioorg. Med. Chem. Lett. 8(16):2219-2222, Elsevier Ltd., Amsterdam, Netherlands (1998).
Lindholm et al., "PCSK9 LNA Antisense Oligonucleotides Induce Sustained Reduction of LDL Cholesterol in Nonhuman Primates", Molecular Therapy, 20 (2):376-381, Cell Press, United States (2012).
Singh et al., "Synthesis of 2¢-Amino-LNA: A Novel Conformationally Restricted High-Affinity Oligonucleotide Analogue with a Handle", J. Org. Chem., 63: 10035-10039, University of Copenhagen, Denmark (1998).

(56) References Cited

OTHER PUBLICATIONS

Wahlestedt et al., "Potent and nontoxic antisense oligonucleotides containing locked nucleic acids", Proc. Natl. Acad. Sci. USA, 97(10): 5633-5638, University of Copenhagen, Denmark (2000).
Chadeganipour, M., et al., "Antifungal activities of pelargonic and capric acid on Microsporum gypseum," Mycoses 44:109-112, Wiley, United States (May 2001).
Cox, A.B., et al., "In vitro Interactions Between the Oral Absorption Promoter, Sodium Caprate (C10) and S. typhimurium in Rat Intestinal Ileal Mucosae," Pharm. Res. 25:114-122, Springer Science+Business Media, Germany (Jan. 2008).
Crooke, S.T., et al., "Antisense technology: A review," J. Biol. Chem. 296:1-39, American Society for Biochemistry and Molecular Biology, United States (Jan. 2021).
Haynes, D.A., et al., "Occurrence of Pharmaceutically Acceptable Anions and Cations in the Cambridge Structural Database," J. Pharmaceutical Sci. 94(10):2111-2120, Elsevier, Netherlands (Oct. 2005).
Moumne, L., et al., "Oligonucleotide Therapeutics: From Discovery and Development to Patentability," Pharmaceutics 14(2):1-24, MDPI, Switzerland (Jan. 2022).
Petschow, B.W., et al., "Susceptibility of Helicobacter pylori to bactericidal properties of medium-chain monoglycerides and free fatty acids," Antimicrob. Agents Chemother 40:302-306, American Society for Microbiology, United States (Feb. 1996).
Setten, R.L., et al., "Development of MTLCEBPA: Small Activating RNA Drug for Hepatocellular Carcinoma," Curr. Pharm. Biotechnol. 19(8):611-621, Bentham Science Publishers B.V., Netherlands (2018).
Van Immerseel, F., et al., "Medium-Chain Fatty Acids Decrease Colonization and Invasion through hilA Suppression Shortly after Infection of Chickens with Salmonella enterica Serovar Enteritidis," Appl. Environ. Microbiol., 70:3582-3587, American Society for Microbiology, United States (Jun. 2004).
Altschul et al., "[27] Local alignment statistics", Methods in Enzymology, 266: 460-480, Elsevier Ltd., Amsterdam, Netherlands (Jan. 1996).
Elayadi et al., "Application of PNA and LNA oligomers to chemotherapy", Curr. Opinion Invens. Drugs, 2(4): 558-561, National Library of Medicine, United States (Apr. 2001).
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition", Tetrahedron, 54(14): 3607-3630, Elsevier Ltd., Amsterdam, Netherlands (Apr. 1998).
Kumar et al., "The first analogues of LNA (Locked Nucleic Acids): Phosphorothioate-LNA and 2'-thio-LNA", Bioorg. Med. Chem. Lett. 8(16):2219-2222, Elsevier Ltd., Amsterdam, Netherlands (Aug. 1998).
Myers et al., "Optimal alignments in linear space", CABIOS, 4(1): 11-17, IRL Press Ltd, Oxford, England (Mar. 1988).
Needleman et al., "A general method applicable to the search for similarities in the amino acid sequence of two proteins", J. Mol. Biol., 48(3): 444-453, Elsevier Ltd., Amsterdam, Netherlands (Mar. 1970).
Oerum et al., "Locked nucleic acids: a promising molecular family for gene-function analysis and antisense drug development", Curr. Opinion Mol. Ther. 3(3): 239-243, National Library of Medicine, United States (Jun. 2001).
Singh et al., "Synthesis of 2¢-Amino-LNA: A Novel Conformationally Restricted High-Affinity Oligonucleotide Analogue with a Handle", J. Org. Chem., 63: 10035-10039, University of Copenhagen, Denmark (Dec. 1998).
Srivastava et al., "Five- and Six-Membered Conformationally Locked 2',4'-Carbocyclic ribo-Thymidines: Synthesis, Structure, and Biochemical Studies", J. Am. Chem. Soc., 129(26): 8362-8379, ACS Publications, United States (Jul. 2007).
Uhlmann, Eugen, "Recent advances in the medicinal chemistry of antisense oligonucleotides", Curr. Opinion in Drug Development, 3(2): 203-213, PMID, United States (Mar. 2000).
Van Poelgeest et al., "Acute Kidney Injury During Therapy With an Antisense Oligonucleotide Directed Against PCSK9", American Journal of Kidney Disease, 62(4): 796-800, Elsevier Ltd., Amsterdam, Netherlands (Oct. 2013).
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties", J. Org. Chem., 74(1): 118-134, ACS Publications, United States (Jan. 2009).
International Search Report and Written Opinion for International Application No. PCT/US2022/025807, mailed on Jul. 22, 2022, 10 pages.
Juo, P.S., "The Concise Dictionary of Biomedicine and Molecular Biology," 2nd Edition, CRC Press, United States (2002), 4 pages.
The Oxford Dictionary of Biochemistry and Molecular Biology, Revised Edition, Smith, A.D., ed., Oxford University Press, United Kingdom, 2 pages (2000).
The Dictionary of Cell and Molecular Biology, Lackie, J.M., and Dow, J.A.T., eds., 3rd Ed., Academic Press, London, United Kingdom (1999).
Bollinger, H., "Wheat Fiber Gel in the Food Industry," Food Marketing & Technology, 4-6, Dr. Harnisch Verlag, Germany (Oct. 1995).
King, R.E., "Chapter 89: Tablets, Capsules, and Pills," in *Remington's Pharmaceutical Sciences*, Osol, A., ed., 16th Ed., pp. 1553-1593, Mack Publishing, Easton PA, United States (1980).
Singh, S.K., et al., "LNA (locked nucleic acids): Synthesis and High-affinity Nucleic acid Recognition," Chemical Communication 4:455-456, Royal Society of Chemistry, United States (Jan. 1998).

\* cited by examiner

Conj 4 = 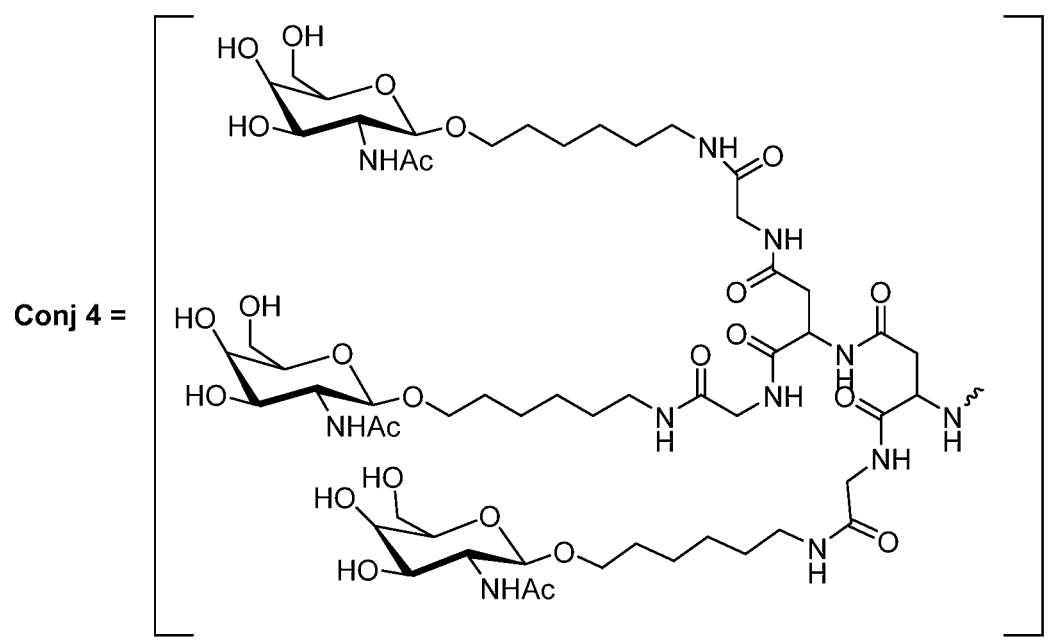
Conj 4a = 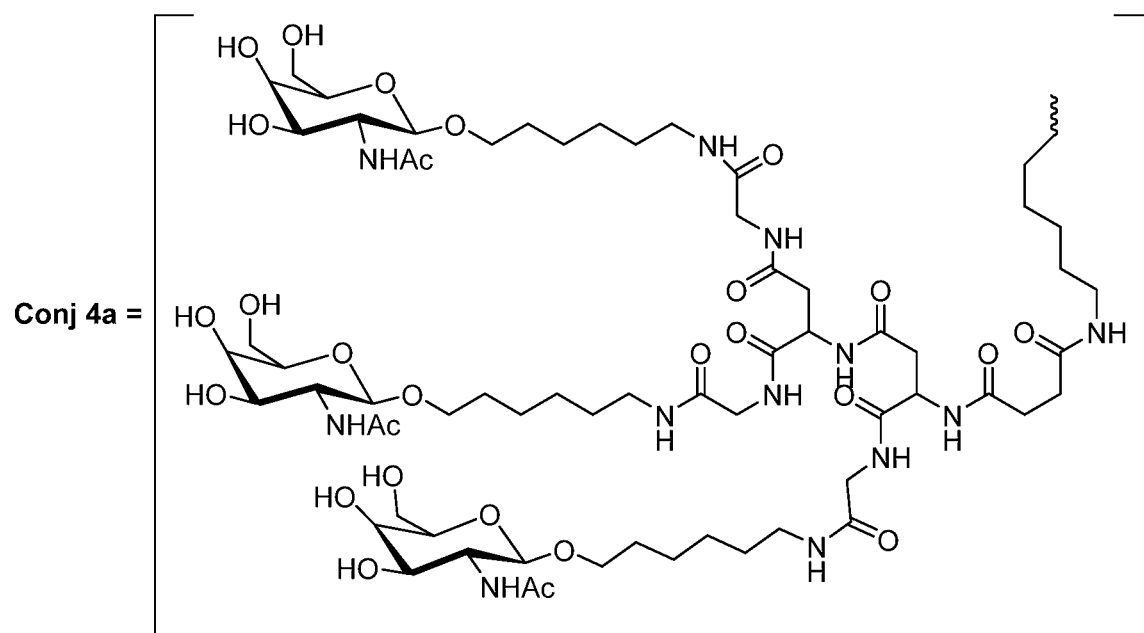
FIG. 1B

5'-T$^L_S$G$^L_S$$^{Me}$C$^L_S$T$_S$A$_S$C$_S$A$_S$A$_S$A$_S$A$_S$A$_S$C$_S$$^{Me}$C$^L_S$$^{Me}$C$^L_S$$^{Me}$C$^L_S$A$^L$-3'
SEQ ID 1

5'-A$^L_S$A$^L_S$T$^L_S$G$_S$C$_S$T$_S$A$_S$C$_S$A$_S$A$_S$A$_S$A$_S$A$_S$C$_S$$^{Me}$C$^L_S$$^{Me}$C$^L_S$$^{Me}$C$^L_S$A$^L$-3'
SEQ ID 2

5'-A$^L_S$A$^L_S$T$^L_S$G$_S$C$_S$T$_S$A$_S$C$_S$A$_S$A$_S$A$_S$A$_S$A$_S$C$_S$$^{Me}$C$^L_S$$^{Me}$C$^L_S$A$^L$-3'
SEQ ID 3

5'-G$^L_S$$^{Me}$C$^L_S$T$_S$G$_S$T$_S$G$_S$T$_S$G$_S$A$_S$G$_S$C$_S$T$_S$T$_S$G$^L_S$G$^L$-3'
SEQ ID 4

5'-T$^L_S$G$^L_S$C$_S$T$_S$G$_S$T$_S$G$_S$T$_S$G$_S$A$_S$G$_S$C$_S$T$_S$T$^L_S$G$^L_S$G$^L$-3'
SEQ ID 5

5'-T$^L_S$G$^L_S$$^{Me}$C$^L_S$T$_S$G$_S$T$_S$G$_S$T$_S$G$_S$A$_S$G$_S$C$_S$T$_S$T$^L_S$G$^L_S$G$^L$-3'
SEQ ID 6

5'-T$^L_S$$^{Me}$C$^L_S$T$_S$G$_S$G$_S$T$_S$C$_S$T$_S$G$_S$T$_S$G$_S$T$_S$T$^L_S$$^{Me}$C$^L_S$$^{Me}$C$^L_S$-3'
SEQ ID 7

5'-T$^L_S$$^{Me}$C$^L_S$$^{Me}$C$^L_S$T$_S$G$_S$G$_S$T$_S$C$_S$T$_S$G$_S$T$_S$G$_S$T$_S$T$^L_S$$^{Me}$C$_S$$^{Me}$C$^L_S$-3'
SEQ ID 8

FIG. 3

SEQ ID NO: 19

*Legend*
Superscript $^L$ = beta-D-oxy LNA unit
$^{Me}$C = 5-methylcytosine unit
Subscript s = phosphorothioate internucleoside linkage
 = Conj 2a asialoglycoprotein receptor targeting moiety
5'-$A^L_sA^L_sT^L_sG_sC_sT_sA_sC_sA_sA_sA_sA_sC_s{}^{Me}C^L_s{}^{Me}C^L_s{}^{Me}C^L_sA^L$-3'
SEQ ID NO: 18
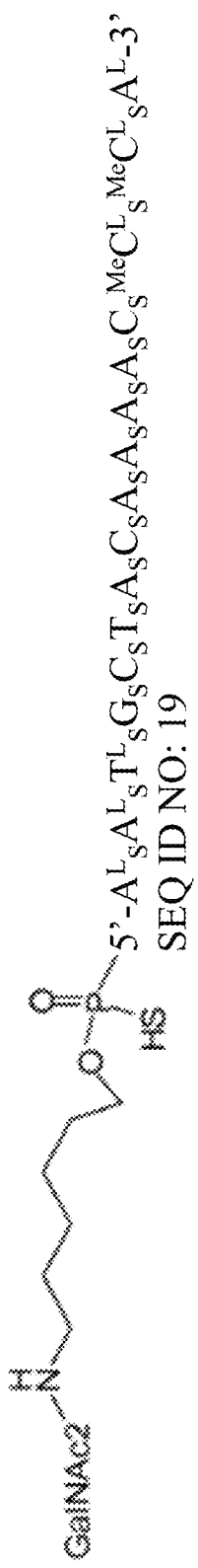
5'-$A^L_sA^L_sT^L_sG_sC_sT_sA_sC_sA_sA_sA_sA_sC_s{}^{Me}C^L_s{}^{Me}C^L_s{}^{Me}C^L_sA^L$-3'
SEQ ID NO: 19
FIG. 18A

| Dose group | End of dosing (μg/gram tissue) | End of recovery (μg/gram tissue) |
|---|---|---|
| SQ Q2W x 3 | 33.8 (19.1) | N.A. |
| 1 capsule QD x 42 | 2.3 (1.2) | 0.6 (0.2) |
| 2 capsules QD x 42 | 4.0 (1.6) | 0.9 (0.7) |

FIG. 23

| | No. animals | Mean AUC$_{0-5}$ (ng·h/ml) | SD | Mean C$_{max}$ (ng/ml) | SD |
|---|---|---|---|---|---|
| CIVI008/SNAC | 6 | 67.1 | 50.7 | 50.7 | 52.3 |
| CIVI008/5-CNAC | 10 | 122.5 | 98.6 | 106.9 | 91.2 |

FIG. 29

SEQUENCE LISTING

```
<160> NUMBER OF SEQ ID NOS: 46

<210> SEQ ID NO 1
<211> LENGTH: 14
<212> TYPE: DNA
<213> ORGANISM: ARTIFICIAL
```

```
<220> FEATURE:
<223> OTHER INFORMATION: LNA antisense gapmer oligonucleotide
<220> FEATURE:
<221> NAME/KEY: misc_feature
<222> LOCATION: (1)..(14)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (12)..(14)
<223> OTHER INFORMATION: LNA nucleosides, LNA C are 5-methyl C

<400> SEQUENCE: 1
tgctacaaaa ccca                                                      14

<210> SEQ ID NO 2
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides
<220> FEATURE:
<221> NAME/KEY: misc_feature
<222> LOCATION: (13)..(16)
<223> OTHER INFORMATION: LNA nucleosides, LNA C are 5-methyl C

<400> SEQUENCE: 2
aatgctacaa aaccca                                                    16

<210> SEQ ID NO 3
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 3
aatgctacaa aaccca                                                    16

<210> SEQ ID NO 4
<211> LENGTH: 15
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(15)
<223> OTHER INFORMATION: phosphorothioate lnternucleoside linkages
<220> FEATURE:
```

<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (14)..(15)
<223> OTHER INFORMATION: LNA nucleosides

<400> SEQUENCE: 4
gctgtgtgag cttgg                                                         15

<210> SEQ ID NO 5
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (14)..(16)
<223> OTHER INFORMATION: LNA nucleosides

<400> SEQUENCE: 5
tgctgtgtga gcttgg                                                        16

<210> SEQ ID NO 6
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides

<400> SEQUENCE: 6
tgctgtgtga gcttgg                                                        16

<210> SEQ ID NO 7
<211> LENGTH: 16
<212> TYPE: DNA
<213> ORGANISM: ARTIFICIAL
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 7
tcctggtctg tgttcc                                                              16

<210> SEQ ID NO 8
<211> LENGTH: 16
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (15)..(16)
<223> OTHER INFORMATION: LNA nucleosides, LNA C are 5-methyl C

<400> SEQUENCE: 8
tcctggtctg tgttcc                                                              16

<210> SEQ ID NO 9
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(16)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 9
catgctacaa aaccca                                                              16

<210> SEQ ID NO 10
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(18)

```
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides
<220> FEATURE:
<221> NAME/KEY: misc_feature
<222> LOCATION: (15)..(18)
<223> OTHER INFORMATION: LNA nucleosides, LNA C are 5-methyl C

<400> SEQUENCE: 10
caaatgctac aaaaccca                                                       18

<210> SEQ ID NO 11
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides
<220> FEATURE:
<221> NAME/KEY: misc_feature
<222> LOCATION: (16)..(18)
<223> OTHER INFORMATION: LNA nucleosides, LNA C are 5-methyl C

<400> SEQUENCE: 11
caaatgctac aaaaccca                                                       18

<210> SEQ ID NO 12
<211> LENGTH: 17
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(17)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (16)..(17)
<223> OTHER INFORMATION: LNA nucleosides

<400> SEQUENCE: 12
cagctgtgtg agcttgg                                                        17
```

```
<210> SEQ ID NO 13
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (16)..(18)
<223> OTHER INFORMATION: LNA nucleosides

<400> SEQUENCE: 13
catgctgtgt gagcttgg                                                 18

<210> SEQ ID NO 14
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (16)..(18)
<223> OTHER INFORMATION: LNA nucleosides

<400> SEQUENCE: 14
catgctgtgt gagcttgg                                                 18

<210> SEQ ID NO 15
<211> LENGTH: 18
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
```

<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (16)..(18)
<223> OTHER INFORMATION: LNA nucleosides, LNA C are 5-methyl C

<400> SEQUENCE: 15
catcctggtc tgtgttcc                                                       18

<210> SEQ ID NO 16
<211> LENGTH: 18
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(18)
<223> OTHER INFORMATION: phosphorothioate lnternucleoside linkages
<220> FEATURE:
<221> NAME/KEY: misc_feature
<222> LOCATION: (3)..(5)
<223> OTHER INFORMATION: LNA nucleosides, LNA C are 5-methyl C
<220> FEATURE:
<221> NAME/KEY: misc_feature
<222> LOCATION: (17)..(18)
<223> OTHER INFORMATION: LNA nucleosides, LNA C are 5-methyl C

<400> SEQUENCE: 16
catcctggtc tgtgttcc                                                       18

<210> SEQ ID NO 17
<211> LENGTH: 14
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(14)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (12)..(14)
<223> OTHER INFORMATION: LNA nucleosides, LNA C are 5-methyl C

<400> SEQUENCE: 17
tgctacaaaa ccca                                                           14

<210> SEQ ID NO 18
<211> LENGTH: 16

```
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides
<220> FEATURE:
<221> NAME/KEY: misc_feature
<222> LOCATION: (13)..(16)
<223> OTHER INFORMATION: LNA nucleosides, LNA C are 5-methyl C

<400> SEQUENCE: 18
aatgctacaa aaccca                                                  16

<210> SEQ ID NO 19
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 19
aatgctacaa aaccca                                                  16

<210> SEQ ID NO 20
<211> LENGTH: 15
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(15)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (14)..(15)
<223> OTHER INFORMATION: LNA nucleosides

<400> SEQUENCE: 20
```

```
gctgtgtgag cttgg                                                     15

<210> SEQ ID NO 21
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (14)..(16)
<223> OTHER INFORMATION: LNA nucleosides

<400> SEQUENCE: 21
tgctgtgtga gcttgg                                                    16

<210> SEQ ID NO 22
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides

<400> SEQUENCE: 22
tgctgtgtga gcttgg                                                    16

<210> SEQ ID NO 23
<211> LENGTH: 16
<212> TYPE: DNA
<213> ORGANISM: ARTIFICIAL
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
```

```
<222> LOCATION: (14)..(16)
<223> OTHER INFORMATION: LNA nucleosides, LNA C are 5-methyl C

<400> SEQUENCE: 23
tcctggtctg tgttcc                                                   16

<210> SEQ ID NO 24
<211> LENGTH: 16
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: GalNAc Conj2a
<220> FEATURE:
<221> NAME/KEY: misc_feature
<222> LOCATION: (1)..(16)
<223> OTHER INFORMATION: phosphorothioate lnternucleoside linkages
<220> FEATURE:
<221> NAME/KEY: misc_feature
<222> LOCATION: (1)..(3)
<223> OTHER INFORMATION: LNA nucleosides, LNA C are 5-methyl C
<220> FEATURE:
<221> NAME/KEY: misc_feature
<222> LOCATION: (15)..(16)
<223> OTHER INFORMATION: LNA nucleosides, LNA C are 5-methyl C

<400> SEQUENCE: 24
tcctggtctg tgttcc                                                   16

<210> SEQ ID NO 25
<211> LENGTH: 14
<212> TYPE: DNA
<213> ORGANISM: Artificial Sequence
<220> FEATURE:
<223> OTHER INFORMATION: nucleobase sequence motif

<400> SEQUENCE: 25
tgctacaaaa ccca                                                     14

<210> SEQ ID NO 26
<211> LENGTH: 16
<212> TYPE: DNA
<213> ORGANISM: ARTIFICIAL
<220> FEATURE:
<223> OTHER INFORMATION: nucleobase sequence motif

<400> SEQUENCE: 26
aatgctacaa aaccca                                                   16

<210> SEQ ID NO 27
<211> LENGTH: 15
<212> TYPE: DNA
<213> ORGANISM: ARTIFICIAL
<220> FEATURE:
<223> OTHER INFORMATION: nucleobase sequence motif

<400> SEQUENCE: 27
gctgtgtgag cttgg                                                    15

<210> SEQ ID NO 28
<211> LENGTH: 16
<212> TYPE: DNA
<213> ORGANISM: ARTIFICIAL
<220> FEATURE:
<223> OTHER INFORMATION: nucleobase sequence motif
```

```
<400> SEQUENCE: 28
tgctgtgtga gcttgg                                                    16

<210> SEQ ID NO 29
<211> LENGTH: 16
<212> TYPE: DNA
<213> ORGANISM: ARTIFICIAL
<220> FEATURE:
<223> OTHER INFORMATION: nucleobase sequence motif

<400> SEQUENCE: 29
tcctggtctg tgttcc                                                    16

<210> SEQ ID NO 30
<211> LENGTH: 14
<212> TYPE: RNA
<213> ORGANISM: Homo sapiens

<400> SEQUENCE: 30
uggguuuugu agca                                                      14

<210> SEQ ID NO 31
<211> LENGTH: 16
<212> TYPE: RNA
<213> ORGANISM: Homo sapiens

<400> SEQUENCE: 31
uggguuuugu agcauu                                                    16

<210> SEQ ID NO 32
<211> LENGTH: 15
<212> TYPE: RNA
<213> ORGANISM: Homo sapiens

<400> SEQUENCE: 32
ccaagcucac acagc                                                     15

<210> SEQ ID NO 33
<211> LENGTH: 16
<212> TYPE: RNA
<213> ORGANISM: Homo sapiens

<400> SEQUENCE: 33
ccaagcucac acagca                                                    16

<210> SEQ ID NO 34
<211> LENGTH: 16
<212> TYPE: RNA
<213> ORGANISM: Homo sapiens

<400> SEQUENCE: 34
ggaacacaga ccagga                                                    16

<210> SEQ ID NO 35
<211> LENGTH: 16
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester internucleoside linkages
<220> FEATURE:
<221> NAME/KEY: misc_feature
```

```
<222> LOCATION: (1)..(1)
<223> OTHER INFORMATION: FAM conjugate
<220> FEATURE:
<221> NAME/KEY: misc_feature
<222> LOCATION: (4)..(16)
<223> OTHER INFORMATION: phosphorothioate lnternucleoside linkages
<220> FEATURE:
<221> NAME/KEY: misc_feature
<222> LOCATION: (4)..(5)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 35
tcagcattgg tattca                                                    16

<210> SEQ ID NO 36
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: FAM conjugate
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (3)..(4)
<223> OTHER INFORMATION: LNA nucleosides, LNA C are 5-methyl C
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 36
cagcattggt attca                                                     15

<210> SEQ ID NO 37
<211> LENGTH: 14
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: FAM conjugate
<220> FEATURE:
<221> NAME/KEY: misc_feature
<222> LOCATION: (2)..(14)
<223> OTHER INFORMATION: phosphorothioate lnternucleoside linkages
<220> FEATURE:
<221> NAME/KEY: misc_feature
<222> LOCATION: (2)..(3)
<223> OTHER INFORMATION: LNA nucleosides, LNA C are 5-methyl C
<220> FEATURE:
<221> NAME/KEY: misc_feature
<222> LOCATION: (12)..(14)
<223> OTHER INFORMATION: LNA nucleosides, LNA C are 5-methyl C
```

```
<400> SEQUENCE: 37
agcattggta ttca                                                       14

<210> SEQ ID NO 38
<211> LENGTH: 16
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(3)
<223> OTHER INFORMATION: phosphodiester lnternucleoside linkages
<220> FEATURE:
<221> NAME/KEY: misc_feature
<222> LOCATION: (1)..(1)
<223> OTHER INFORMATION: FAM conjugate
<220> FEATURE:
<221> NAME/KEY: misc_feature
<222> LOCATION: (4)..(16)
<223> OTHER INFORMATION: phosphorothioate lnternucleoside linkages
<220> FEATURE:
<221> NAME/KEY: misc_feature
<222> LOCATION: (4)..(5)
<223> OTHER INFORMATION: LNA nucleosides, LNA C are 5-methyl C
<220> FEATURE:
<221> NAME/KEY: misc_feature
<222> LOCATION: (14)..(16)
<223> OTHER INFORMATION: LNA nucleosides, LNA C are 5-methyl C

<400> SEQUENCE: 38
gacgcattgg tattca                                                     16

<210> SEQ ID NO 39
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides, LNA C are 5-methyl C
<220> FEATURE:
<221> NAME/KEY: misc_feature
<222> LOCATION: (1)..(1)
<223> OTHER INFORMATION: FAM conjugate
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 39
gcattggtat tca                                                        13

<210> SEQ ID NO 40
<211> LENGTH: 13
<212> TYPE: DNA
<213> ORGANISM: artificial
<220> FEATURE:
<223> OTHER INFORMATION: LNA antisense gapmer oligonucleotide
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides
```

```
-continued

<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 40
gtctgtggaa gcg                                                           13

<210> SEQ ID NO 41
<211> LENGTH: 13
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(13)
<223> OTHER INFORMATION: phosphorothioate lnternucleoside linkages
<220> FEATURE:
<221> NAME/KEY: misc_feature
<222> LOCATION: (1)..(2)
<223> OTHER INFORMATION: LNA nucleosides
<220> FEATURE:
<221> NAME/KEY: misc_feature
<222> LOCATION: (11)..(13)
<223> OTHER INFORMATION: LNA nucleosides, LNA C are 5-methyl C

<400> SEQUENCE: 41
gtctgtggaa gcg                                                           13

<210> SEQ ID NO 42
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 42
cagtctgtgg aagcg                                                         15

<210> SEQ ID NO 43
<211> LENGTH: 15
<212> TYPE: DNA
<213> ORGANISM: artificial
<220> FEATURE:
<223> OTHER INFORMATION: LNA antisense gapmer oligonucleotide conjugate
<220> FEATURE:
<221> NAME/KEY: misc_feature
<222> LOCATION: (1)..(1)
```

```
<223> OTHER INFORMATION: Cholesterol-C6
<220> FEATURE:
<221> NAME/KEY: misc_feature
<222> LOCATION: (1)..(2)
<223> OTHER INFORMATION: phosphodiester lnternucleoside linkages
<220> FEATURE:
<221> NAME/KEY: misc_feature
<222> LOCATION: (3)..(4)
<223> OTHER INFORMATION: LNA nucleosides
<220> FEATURE:
<221> NAME/KEY: misc_feature
<222> LOCATION: (3)..(15)
<223> OTHER INFORMATION: phosphorothioate lnternucleoside linkages
<220> FEATURE:
<221> NAME/KEY: misc_feature
<222> LOCATION: (13)..(15)
<223> OTHER INFORMATION: LNA nucleosides, LNA C are 5-methyl C

<400> SEQUENCE: 43
ctgtctgtgg aagcg                                                    15

<210> SEQ ID NO 44
<211> LENGTH: 13
<212> TYPE: DNA
<213> ORGANISM: artificial
<220> FEATURE:
<223> OTHER INFORMATION: nucleobase sequence motif

<400> SEQUENCE: 44
gtctgtggaa gcg                                                      13

<210> SEQ ID NO 45
<211> LENGTH: 13
<212> TYPE: RNA
<213> ORGANISM: Homo sapiens

<400> SEQUENCE: 45
cgcuuccaca gac                                                      13

<210> SEQ ID NO 46
<211> LENGTH: 3731
<212> TYPE: DNA
<213> ORGANISM: homo sapiens

<400> SEQUENCE: 46
gtccgatggg gctctggtgg cgtgatctgc gcgcccagg cgtcaagcac ccacaccta      60 gaaggtttcc gcagcgacgt cgaggcgctc atggttgcag gcgggcgccg ccgttcagtt   120
cagggtctga gcctggagga gtgagccagg cagtgagact ggctcgggcg ggccgggacg   180
cgtcgttgca gcagcggctc ccagctccca gccaggattc cgcgcgcccc ttcacgcgcc   240
ctgctcctga acttcagctc ctgcacagtc ctccccaccg caaggctcaa ggcgccgccg   300
gcgtggaccg cgcacggcct ctaggtctcc tcgccaggac agcaacctct cccctggccc   360
tcatgggcac cgtcagctcc aggcggtcct ggtggccgct gccactgctg ctgctgctgc   420
tgctgctcct gggtcccgcg ggcgcccgtg cgcaggagga cgaggacggc gactacgagg   480
agctggtgct agccttgcgt tccgaggagg acggcctggc cgaagcaccc gagcacggaa   540
ccacagccac cttccaccgc tgcgccaagg atccgtggag gttgcctggc acctacgtgg   600
tggtgctgaa ggaggagacc cacctctcgc agtcagagcg cactgcccgc cgcctgcagg   660
cccaggctgc ccgccgggga tacctcacca gatcctgca tgtcttccat ggccttcttc   720
ctggcttcct ggtgaagatg agtggcgacc tgctggagct ggccttgaag ttgccccatg   780
tcgactacat cgaggaggac tcctctgtct ttgcccagag catcccgtgg aacctggagc   840
```

```
ggattacccc tccacggtac cgggcggatg aataccagcc ccccgacgga ggcagcctgg    900
tggaggtgta tctcctagac accagcatac agagtgacca ccgggaaatc gagggcaggg    960
tcatggtcac cgacttcgag aatgtgcccg aggaggacgg gacccgcttc cacagacagg   1020
ccagcaagtg tgacagtcat ggcacccacc tggcaggggt ggtcagcggc cgggatgccg   1080
gcgtggccaa gggtgccagc atgcgcagcc tgcgcgtgct caactgccaa gggaagggca   1140
cggttagcgg caccctcata ggcctggagt ttattcggaa aagccagctg gtccagcctg   1200
tggggccact ggtggtgctg ctgccccctgg cgggtgggta cagccgcgtc ctcaacgccg   1260
cctgccagcg cctggcgagg gctggggtcg tgctggtcac cgctgccggc aacttccggg   1320
acgatgcctg cctctactcc ccagcctcag ctcccgaggt catcacagtt ggggccacca   1380
atgcccaaga ccagccggtg accctgggga ctttggggac caactttggc cgctgtgtgg   1440
acctctttgc cccaggggag gacatcattg gtgcctccag cgactgcagc acctgctttg   1500
tgtcacagag tgggacatca caggctgctg cccacgtggc tggcattgca gccatgatgc   1560
tgtctgccga gccggagctc accctggccg agttgaggca gagactgatc cacttctctg   1620
ccaaagatgt catcaatgag gcctggttcc ctgaggacca gcgggtactg accccccaacc   1680 tggtggccgc cctgccccccc agcacccatg gggcaggttg gcagctgttt tgcaggactg   1740
tatggtcagc acactcgggg cctacacgga tggccacagc cgtcgcccgc tgcgcccccag   1800 atgaggagct gctgagctgc tccagttctct ccaggagtgg gaagcggcgg ggcgagcgca   1860
tggaggccca aggggggcaag ctggtctgcc gggcccacaa cgcttttggg ggtgagggtg   1920
tctacgccat tgccaggtgc tgcctgctac cccaggccaa ctgcagcgtc cacacagctc   1980
caccagctga ggccagcatg gggacccgtg tccactgcca ccaacagggc cacgtcctca   2040
caggctgcag ctcccactgg gaggtggagg accttggcac ccacaagccg cctgtgctga   2100
ggccacgagg tcagcccaac cagtgcgtgg ccacaggga ggccagcatc cacgcttcct   2160
gctgccatgc cccaggtctg gaatgcaaag tcaaggagca tggaatcccg gcccctcagg   2220
agcaggtgac cgtggcctgc gaggagggct ggaccctgac tggctgcagt gccctccctg   2280
ggacctccca cgtcctgggg gcctacgccg tagacaacac gtgtgtagtc aggagccggg   2340
acgtcagcac tacaggcagc accagcgaag gggccgtgac agccgttgcc atctgctgcc   2400
ggagccggca cctggcgcag gcctcccagg agctccagtg acagccccat cccaggatgg   2460
gtgtctgggg agggtcaagg gctggggctg agctttaaaa tggttccgac ttgtccctct   2520
ctcagccctc catggcctgg cacgagggga tggggatgct tccgcctttc cggggctgct   2580
ggcctggccc ttgagtgggg cagcctcctt gcctggaact cactcactct gggtgcctcc   2640
tccccaggtg gaggtgccag gaagctccct ccctcactgt ggggcatttc accattcaaa   2700
caggtcgagc tgtgctcggg tgctgccagc tgctcccaat gtgccgatgt ccgtgggcag   2760
aatgactttt attgagctct tgttccgtgc caggcattca atcctcaggt ctccaccaag   2820
gaggcaggat tcttcccatg gatagggag ggggcggtag gggctgcagg gacaaacatc   2880 gttgggggt gagtgtgaaa ggtgctgatg gccctcatct ccagctaact gtggagaagc   2940
ccctgggggc tccctgatta atggaggctt agctttctgg atggcatcta gccagaggct   3000
ggagacaggt gcgcccctgg tggtcacagg ctgtgccttg gtttcctgag ccacctttac   3060
```

```
tctgctctat gccaggctgt gctagcaaca cccaaaggtg gcctgcgggg agccatcacc    3120
taggactgac tcggcagtgt gcagtggtgc atgcactgtc tcagccaacc cgctccacta    3180
cccggcaggg tacacattcg cacccctact tcacagagga agaaacctgg aaccagaggg    3240
ggcgtgcctg ccaagctcac acagcaggaa ctgagccaga aacgcagatt gggctggctc    3300
tgaagccaag cctcttctta cttcacccgg ctgggctcct cattttacg ggtaacagtg     3360 aggctgggaa ggggaacaca gaccaggaag ctcggtgagt gatggcagaa cgatgcctgc    3420
aggcatggaa cttttccgt tatcacccag gcctgattca ctggcctggc ggagatgctt     3480
ctaaggcatg gtcgggggag agggccaaca actgtccctc cttgagcacc agccccaccc    3540
aagcaagcag acatttatct tttgggtctg tcctctctgt tgcctttta cagccaactt     3600 ttctagacct gttttgcttt tgtaacttga agatatttat tctgggtttt gtagcatttt    3660
tattaatatg gtgactttt aaaataaaaa caaacaaacg ttgtcctaac aaaaaaaaaa     3720 aaaaaaaaa a                                                         3731
```

ORAL DELIVERY OF ANTISENSE CONJUGATES TARGETING PCSK9

CROSS-REFERENCE TO RELATED APPLICATIONS AND INCORPORATION BY REFERENCE

This application claims the priority benefit of U.S. Provisional Application No. 63/124,581, filed on Dec. 11, 2020, 63/134,884, filed on Jan. 7, 2021, 63/178,340, filed on Apr. 22, 2021, and 63/261,505, filed on Sep. 22, 2021, which are herein incorporated by reference in their entireties.

REFERENCE TO SEQUENCE LISTING SUBMITTED ELECTRONICALLY

The content of the electronically submitted sequence listing in ASCII text file (Name 4009-0210005_Sequence_listing_ST25.txt; Size: 26,230 bytes; and Date of Creation: Dec. 10, 2021) filed with the application is incorporated herein by reference in its entirety.

FIELD

The present disclosure relates to oral formulations of antisense oligonucleotide conjugates that target Proprotein Convertase Subtilisin/Kexin type 9 (PCSK9) mRNA in a cell, leading to reduced expression of PCSK9. Reduction of PCSK9 expression is beneficial for a range of medical disorders, such as hypercholesterolemia and related disorders.

BACKGROUND

Proprotein convertase subtilisin/kexin type 9 (PCSK9) has emerged as a therapeutic target for the reduction of low-density lipoprotein cholesterol (LDL-C). PCSK9 increases the degradation of the LDL receptor, resulting in high LDL-C in individuals with high PCSK9 activity. Lindholm et al., Molecular Therapy (2012); 20 2, 376-381 reported an LNA antisense oligonucleotide targeting PCSK9 that produced sustained reduction of LDL-C in nonhuman primates. The compound used was a 14-mer named SPC5001, which was likewise disclosed in Int'l. Appl. Publ. WO2011/009697. This compound was discontinued during clinical trial due to severe kidney toxicity and acute kidney injury. See, e.g., van Poelgeest et al. (2013) American Journal of Kidney Disease 62(4):796-800.

Oral delivery of pharmacologically active agents is generally the delivery route of choice since it is convenient, relatively easy and generally painless, resulting in greater patient compliance relative to other modes of delivery. However, biological, chemical and physical barriers such as varying pH in the gastrointestinal tract, powerful digestive enzymes, and active agent impermeable gastrointestinal membranes, makes oral delivery of some pharmacologically active agents to mammals problematic, e.g., the oral delivery of therapeutic nucleic acids, such as antisense oligonucleotides. Accordingly, there is a need to develop systems that allow the oral delivery of therapeutic nucleic acids, such as antisense oligonucleotides.

BRIEF SUMMARY

The present disclosure provides a pharmaceutical composition comprising an antisense oligomer (e.g., an antisense oligonucleotide, ASO), an and an oral delivery agent (e.g., SNAC, C10, 5-CNAC, or a salt, hydrate, or solvate thereof, or a combination thereof), wherein the antisense oligomer is 16 to 22 contiguous nucleotides in length, wherein the sequence of the antisense oligomer comprises a contiguous sequence 16 nucleotides in length which is 100% complementary to the sequence of SEQ ID NO: 31, wherein the antisense oligomer is a gapmer comprising at least one LNA unit, and wherein the antisense oligomer targets an RNA encoding PCSK9. In some aspects, the RNA is a pre-mRNA, splice variant of a pre-mRNA, mature mRNA, or an allelic variant or mutant thereof. In some aspects, the antisense oligomer targets a sequence within an exon. In some aspects, the antisense oligomer targets a sequence within an intron. In some aspects, the antisense oligomer targets a sequence comprising a junction between an exon and an intron. In some aspects, the antisense oligomer targets a sequence upstream from the 5' end of an open reading frame encoding PCSK9 (e.g., the 5' UTR). In some aspects, the antisense oligomer targets a sequence downstream from the 3' end of an open reading frame encoding PCSK9 (e.g., the 3' UTR).

In some aspects, the LNA is oxy-LNA, thio-LNA, amino-5 LNA, 5'-methyl-LNA, ENA, cET, cMOE or a combination thereof. In some aspects, the LNA is a stereoisomer in the β-D-configuration or the α-L configuration. In some aspects, the antisense oligomer comprises at least one cET unit. In some aspects, the antisense oligomer comprises 2, 3, 4, 5, 6 or 7 LNA units. In some aspects, every LNA unit in the antisense oligomer is a stereoisomer in the same configuration. In some aspects, every LNA unit in the antisense oligomer is a β-D-oxy LNA unit. In some aspects, every LNA unit in the antisense oligomer is an α-L-oxy-LNA unit.

In some aspects, the sequence of the antisense oligomer comprises at least one phosphorothioate, phosphorodithioate, methylphosphonate, phosphoramidate, or boranophosphate internucleoside linkage. In some aspects, all the internucleoside linkages are phosphorothioate. In some aspects, one or more of the internucleoside linkages comprises a chiral center in the R conformation and/or in the S conformation. In some aspects, all chiral centers are in the R conformation. In some aspects, all chiral centers are in the S conformation. In some aspects, the antisense oligomer and an oligomer of SEQ ID NO: 31 can form a duplex with increased thermal stability with respect to a corresponding duplex comprising the corresponding antisense oligomer without LNA.

The present disclosure also provides a pharmaceutical composition comprising an antisense oligonucleotide conjugate and an oral delivery agent (e.g., SNAC, C10, 5-CNAC, or a salt, hydrate, or solvate thereof, or a combination thereof), wherein the antisense oligonucleotide conjugate comprises (i) an antisense oligomer that is 16 to 22 contiguous nucleotides, wherein the sequence of the antisense oligomer comprises a contiguous sequence 16 nucleotides in length which is 100% complementary to the sequence of SEQ ID NO: 31, and wherein the antisense oligomer is a gapmer comprising at least one LNA unit, and (ii) at least one non-nucleotide or non-polynucleotide moiety covalently attached to said antisense oligomer directly or via a linker positioned between the contiguous oligomer sequence and the non-nucleotide or non-polynucleotide moiety, wherein the antisense oligonucleotide conjugate targets an RNA encoding PCSK9, e.g., an mRNA.

In some aspects, the RNA is a pre-mRNA, splice variant of a pre-mRNA, mature mRNA, or an allelic variant or mutant thereof, as disclosed above.

In some aspects, the non-nucleotide or non-polynucleotide moiety is a liver targeting moiety that is attached to the 5'-end or to the 3'-end of the antisense oligomer. In some aspects, the liver targeting moiety is linked to the antisense oligomer via a linker. In some aspects, the liver targeting moiety comprises a carbohydrate conjugate moiety comprising a carbohydrate selected from the group consisting of galactose, lactose, N-acetylgalactosamine (GalNAc), mannose, mannose-6-phosphate, and combinations thereof.

In some aspects, the carbohydrate conjugate moiety is not a linear carbohydrate polymer. In some aspects, the carbohydrate conjugate moiety is a carbohydrate group comprising 1, 2, 3, or 4 carbohydrate moieties. In some aspects, all the carbohydrate moieties are identical. In some aspects, at least one carbohydrate moiety is different (non-identical) with respect to the other carbohydrate moieties. In some aspects, the carbohydrate conjugate moiety comprises at least one asialoglycoprotein receptor targeting conjugate moiety. In some aspects, the asialoglycoprotein receptor targeting conjugate moiety comprises a monovalent, divalent, trivalent, or tetravalent GalNAc cluster. In some aspects, each GalNAc in the GalNAc cluster is attached to a branch point group via a spacer. In some aspects, the branch point group comprises a peptide, e.g., di-lysine. In some aspects, the spacer comprises a PEG spacer. In some aspects, the linker comprises a C6 to C12 amino alkyl group or a biocleavable phosphate nucleotide linker comprising between 1 to 6 nucleotides. In some aspects, the trivalent GalNAc cluster comprises a Conj 1, Conj 2, Conj 1a, or Conj 2a GalNAc conjugate moiety. In some aspects, the non-nucleotide or non-polynucleotide moiety is covalently attached to the antisense oligomer via a covalent bond.

The present disclosure also provides a pharmaceutical composition comprising an antisense oligonucleotide conjugate of SEQ ID NO: 18 or SEQ ID NO: 19 as shown in FIG. 18A and an oral delivery agent (e.g., SNAC, C10, 5-CNAC, or a salt, hydrate, or solvate thereof, or a combination thereof), wherein the antisense oligonucleotide conjugate targets an RNA encoding PCSK9. In some aspects, the RNA is a pre-mRNA, splice variant of a pre-mRNA, mature mRNA, or an allelic variant or mutant thereof. In some aspects, the antisense oligomer targets a sequence within an exon. In some aspects, the antisense oligomer targets a sequence within an intron. In some aspects, the antisense oligomer targets a sequence comprising a junction between an exon and an intron. In some aspects, the antisense oligomer targets a sequence upstream from the 5' end of an open reading frame encoding PCSK9. In some aspects, the antisense oligomer targets a sequence downstream from the 3' end of an open reading frame encoding PCSK9.

In some aspects, a pharmaceutical composition disclosed herein further comprises at least one pharmaceutically acceptable excipient or combination thereof. In some aspects, the at least one pharmaceutically acceptable excipient or combination thereof is selected from the group consisting of a pH adjuster, a preservative, a flavorant; a taste-masking agent; a fragrance; a humectant; a tonicifier a colorant; a surfactant; a plasticiser; a lubricant; a flow aid; a compression aid; a solubilizer; an excipient; a diluent; a phosphate buffer salt; citric acid, glycol, a dispersing agent, crospovidone, povidone, or any combination thereof. In some aspects, a pharmaceutical compositions disclosed herein further comprises a therapeutic agent selected from the group consisting of a statin, a bile sequestering resin, nicotinic acid, a fibric acid derivative, probucol, neomycin, dextrothyroxine, a plant stanol ester, a cholesterol absorption inhibitor, implitapide, an inhibitor of bile acid transporters, a regulator of hepatic CYP7a, an estrogen replacement therapeutic, an anti-inflammatory, or a combination thereof. In some aspects, the statin is selected from the group consisting of lovastatin, cerivastatin, pravastatin, atorvastatin, simvastatin, rosuvastatin, fluvastatin, and a combination thereof.

The present disclosure also provides a method of treating a disease or condition caused by abnormal expression levels and/or activity of PCSK9 in a subject in need thereof comprising administering an effective amount of a pharmaceutical composition disclosed herein, e.g., a composition comprising an antisense oligonucleotide conjugate of the present disclosure (e.g., CIVI 008) and an oral delivery agent (e.g., SNAC, C10, 5-CNAC, or a salt, hydrate, or solvate thereof, or a combination thereof), wherein the administration of the pharmaceutical composition reduces the level of serum PCSK9 and/or reduces the level of serum LDL cholesterol in the subject. In some aspects, the PCSK9 is (i) a PCSK9 allelic variant; (ii) a PCSK9 mutant; or, (iii) a PCSK9 splice variant. In some aspects, the PCSK9 mutant is a PCSK9 gain of function mutant.

In some aspects, the disease or condition is selected from the group consisting of atherosclerosis, hypercholesterolemia, HDL/LDL cholesterol imbalance, dyslipidemia, coronary artery disease (CAD), and coronary heart disease (CHD). In some aspects, the dyslipidemia is familial hyperlipidemia (FCHL) or acquired hyperlipidemia. In some aspects, the hypercholesterolemia is familiar hypercholesterolemia or statin resistant hypercholesterolemia.

In some aspects, the methods of treatment disclosed herein further comprise the administration of a therapeutic agent selected from the group consisting of a statin, a bile sequestering resin, nicotinic acid, a fibric acid derivative, probucol, neomycin, dextrothyroxine, a plant stanol ester, a cholesterol absorption inhibitor, implitapide, an inhibitor of bile acid transporters, a regulator of hepatic CYP7a, an estrogen replacement therapeutic, an anti-inflammatory, or a combination thereof. In some aspects, the statin is selected from the group consisting of lovastatin, cerivastatin, pravastatin, atorvastatin, simvastatin, rosuvastatin, fluvastatin, and a combination thereof.

In some aspects, the pharmaceutical compositions disclosed herein are administered orally. In some aspects, the pharmaceutical composition is administered as a single dose. In some aspects, the pharmaceutical composition is administered as multiple doses.

The present disclosure also provides a method of treating a disorder selected from the group consisting of atherosclerosis, hyperlipidemia, hypercholesterolemia, HDL/LDL cholesterol imbalance, coronary artery disease (CAD), or coronary heart disease (CHD) in a subject in need thereof, the method comprising administering an effective amount of a pharmaceutical composition disclosed herein, e.g., a composition comprising an antisense oligonucleotide conjugate of the present disclosure (e.g., CIVI 008) and an oral delivery enhancer (e.g., SNAC, C10, 5-CNAC, or a salt, hydrate, or solvate thereof, or a combination thereof), to the subject.

The present disclosure also provides an in vitro or in vivo method of reducing expression levels and/or activity of PCSK9 in a cell comprising administering an effective amount of a pharmaceutical composition disclosed herein, e.g., a composition comprising an antisense oligonucleotide conjugate of the present disclosure (e.g., CIVI 008) and an oral delivery enhancer (e.g., SNAC, C10, 5-CNAC, or a salt, hydrate, or solvate thereof, or a combination thereof), to the cell.

Also provided is a method of reducing PCSK9 expression levels and/or PCSK9 activity in a subject in need thereof comprising administering an effective amount of a pharmaceutical composition disclosed herein, e.g., a composition comprising an antisense oligonucleotide conjugate of the present disclosure (e.g., CIVI 008) and an oral delivery enhancer (e.g., SNAC, C10, 5-CNAC, or a salt, hydrate, or solvate thereof, or a combination thereof) to the subject.

The present disclosure also provides a method of reducing cholesterol levels in a subject in need thereof comprising administering to said subject an effective amount of a pharmaceutical composition disclosed herein, e.g., a composition comprising an antisense oligonucleotide conjugate of the present disclosure (e.g., CIVI 008) and an oral delivery enhancer (e.g., SNAC, C10, 5-CNAC, or a salt, hydrate, or solvate thereof, or a combination thereof).

Also provided is a method of manufacturing a pharmaceutical composition comprising admixing (i) an antisense oligomer 16 to 22 contiguous nucleotides in length, wherein the sequence of the antisense oligomer comprises a contiguous sequence 16 nucleotides in length which is 100% complementary to the sequence of SEQ ID NO: 31, wherein the antisense oligomer is a gapmer comprising at least one LNA unit, and wherein the antisense oligomer targets an RNA encoding PCSK9; and, (ii) an oral delivery agent (e.g., SNAC, C10, 5-CNAC, or a salt, hydrate, or solvate thereof, or a combination thereof).

The present disclosure also provides a method of manufacturing a pharmaceutical composition comprising admixing (i) a conjugate comprising (a) an antisense oligomer that is 16 to 22 contiguous nucleotides, wherein the sequence of the antisense oligomer comprises a contiguous sequence 16 nucleotides in length which is 100% complementary to the sequence of SEQ ID NO: 31, and wherein the antisense oligomer is a gapmer comprising at least one LNA unit, and (b) at least one non-nucleotide or non-polynucleotide moiety covalently attached to said antisense oligomer directly or via a linker positioned between the contiguous oligomer sequence and the non-nucleotide or non-polynucleotide moiety, wherein the antisense oligonucleotide conjugate targets an RNA encoding PCSK9; and, (ii) an oral delivery agent (e.g., SNAC, C10, 5-CNAC, or a salt, hydrate, or solvate thereof, or a combination thereof).

In some aspects, the sequence of the antisense oligomer comprises or consists of SEQ ID NO: 26, i.e., a sequence 100% complementary to SEQ ID NO: 31 having the same length as SEQ ID NO: 31. In some aspects, the sequence of the antisense oligomer comprises or consists of SEQ ID NO: 2 or SEQ ID NO: 3, i.e., a sequence having a base sequence of SEQ ID NO: 26, but with a specific patter of base and backbone modifications. In some aspects, antisense oligomer conjugate comprises or consists of SEQ ID NO: 18 or SEQ ID NO: 19, i.e., SEQ ID NO: 2 or SEQ ID NO: 3 conjugated to a GalNAc2 moiety.

In some aspects of the pharmaceutical compositions and methods of the present disclosure, the oral delivery agent comprises, e.g., caprylic acid (C8), capric acid (C10), a derivative thereof, a pharmaceutically acceptable hydrate, solvate, or salt thereof, or any combination thereof. In some aspects, the pharmaceutically acceptable salt is a sodium salt, a potassium salt, or a combination thereof. In some aspects, the pharmaceutical composition is solid.

In some aspects, the pharmaceutical composition is in the form of a tablet or a capsule. In some aspects, the capsule is a liquid capsule. In some aspects, the pharmaceutical composition is enterically coated. In some aspects, the tablet or capsule is enterically coated. In some aspects, the tablet or capsule has a weight between 5 mg and 1000 mg, 10 mg and 500 mg, 10 mg and 250 mg, 100 mg and 200 mg, or 250 mg and 500 mg. In some aspects, the amount of antisense oligomer or antisense oligonucleotide conjugate the tablet or capsule is in the range of 1 mg to 100 mg, 5 mg to 100 mg, 10 mg to 100 mg, 20 mg to 100 mg, 20 mg and 50 mg.

In some aspects, the oral delivery agent is a salt, hydrate, or solvate of N-(8-(2-hydroxybenzoyl)amino)caprylic acid, or a combination thereof. In some aspects, the salt of N-(8-(2-hydroxybenzoyl)amino)caprylic acid is selected from the group consisting of a sodium salt, a potassium salt, a calcium salt of N-(8-(2-hydroxybenzoyl)amino)caprylic acid, and any combination thereof. In some aspects, the salt of N-(8-(2-hydroxybenzoyl)amino)caprylic acid is sodium salt. In some aspects, the salt of N-(8-(2-hydroxybenzoyl)amino)caprylic acid is a monosodium salt (Salcaprozate sodium 203787-91-1, SNAC, sodium 8-(2-hydroxybenzamido)octanoate). In some aspects, the salt of N-(8-(2-hydroxybenzoyl)amino)caprylic acid is a disodium salt In some aspects, the oral delivery agent is a salt, hydrate, or solvate of N-(5-chlorosalicyloyl)-8-aminocaprylic acid, or a combination thereof. In some aspects, the salt of N-(5-chlorosalicyloyl)-8-aminocaprylic acid is selected from the group consisting of a sodium salt, a potassium salt, a calcium salt of N-(5-chlorosalicyloyl)-8-aminocaprylic, and any combination thereof. In some aspects, the salt of N-(5-chlorosalicyloyl)-8-aminocaprylic acid is sodium salt. In some aspects, the salt of N-(5-chlorosalicyloyl)-8-aminocaprylic is a monosodium salt (5-SNAC). In some aspects, the salt of N-(5-chlorosalicyloyl)-8-aminocaprylic is a disodium salt In some aspects, the oral delivery agent is a salt, hydrate or solvate of capric acid (C10), or a combination. In some aspects, the salt of capric acid (C10) is selected from the group consisting of the sodium salt, potassium salt and calcium salt of capric acid (C10), and any combination thereof. In some aspects, the salt of capric acid (C10) is sodium caprate.

In some aspects, the pharmaceutical composition is administered about 5 to about 60 minutes prior to a meal. In some aspects, the pharmaceutical composition is administered at least about 5, at least about 10, at least about 15, at least about 20, at least about 25, at least about 30, at least about 35, at least about 40, at least about 45, at least about 50, at least about 55 or at least about 60 minutes prior to a meal.

In some aspects, the pharmaceutical composition further comprises a pH sensitive coating. In some aspects, the pH sensitive coating is a pH-sensitive polymer. In some aspects, the pH-sensitive polymer comprises cellulose, acrylic acid, a derivative thereof, or a combination thereof. In some aspects, the pH sensitive coating comprises a pH-sensitive hydrogel, pH-activated drug delivery system, pH-sensitive liposome, micelle or lipid nanoparticle, pH-sensitive microsphere, pH-sensitive nanoparticle, or any combination thereof.

The present disclosure also provides a pill or capsule comprising (GalNAc)3-amino-hexamethylene-5' phosphorothioyl)-2'-O,4'-C-methylene Adenosylyl-(3'>5' O,O-phosphorothioyl)-2'-O,4'-C-methylene Adenosylyl-(3'>5' O,O-phosphorothioyl)-2'-O,4'-C-methylene Thymidinyl-(3'>5' O,O-phosphorothioyl)-2'-deoxyGuanosylyl-(3'>5' O,O-phosphorothioyl)-2'-deoxyCytidinylyl-(3'>5' O,O-phosphorothioyl)-2'-deoxyThymidylyl-(3'>5' O,O-phosphorothioyl)-2'-deoxyAdenosylyl-(3'>5' O,O-phosphorothioyl)-2'-deoxyCytidinylyl-(3'>5' O,O-phosphorothioyl)-2'-deoxyAdenosylyl-(3'>5' O,O-phosphorothioyl)-2'-deoxyAdenosylyl-(3'>5' O,O-phosphorothioyl)-2'-deoxyAdenosylyl-(3'>5' O,O-phosphorothioyl)-2'-deoxyCytidinylyl-(3'>5'O,O-phosphorothioyl)-2'-deoxyCytidinylyl-( 3'>5' O,O-phosphorothioyl)-2'-O,4'-C-methylene (5-methyl-Cytidinylyl)-(3'>5' O,O-phosphorothioyl)-2'-O,4'-C-methylene (5-methyl-Cytidinylyl)-(3'>5' O,O-phosphorothioyl)-2'-O,4'-C-methylene Adenosylyl hexadeca sodium salt, and an oral delivery agent selected from the group consisting of SNAC, C10, 5-CNAC, hydrates, solvates, or salts thereof, and combinations thereof.

The present disclosure also provides pill or capsule comprising CIVI 008 as shown in FIG. 18B and an oral delivery agent selected from the group consisting of SNAC, C10, 5-CNAC, hydrates, solvates, or salts thereof, and combinations thereof. In some aspects, the pill or capsule comprises CIVI 008 and SNAC. In some aspects, the pill or capsule comprises CIVI 008 and C10. In some aspects, the pill or capsule comprises CIVI 008 and 5-CNAC.

In some aspects of the compositions and methods disclosed herein the oral delivery agent is

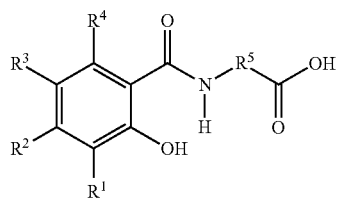

wherein
$R^1$, $R^2$, $R^3$, and $R^4$ are independently hydrogen, —OH, —$NR^6R^7$, halogen, $C_1$-$C_4$ alkyl, or $C_1$-$C_4$ alkoxy;
$R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_4$ alkylene); and
$R^6$ and $R^7$ are independently hydrogen, oxygen, or $C_1$-$C_4$ alkyl.

In some aspects of the compositions and methods disclosed herein the oral delivery agent is selected from the group consisting of N-(8-[2-hydroxybenzoyl]amino) caprylic acid (SNAC), N-(5-chlorosalicyloyl)-8-aminocaprylic acid (5-CNAC), N-(10-[2-hydroxybenzoly] amino)decanoic acid (SNAD), 4-[(4-chloro-2-hydroxybenzoyl)amino]butanoic acid (4-CNAB), N-(8-[4-methoxychloro-2-hydroxybenzoyl-amino) octanoic acid (4-MOAC), 8-(4-hydroxyphenoxy) octanoic acid (4-HPO), 4-m-tolyloxybutyric acid (3-TBA), 4-(3-hydroxyphenylsulfanyl)butyric acid (3-HPSB), 5-phenylpentanoic acid (5-PPA), 8-(2-hydroxyphenoxy)octylethanolamine (2-HPOD), (4-isopropylbenzyloxy)acetic acid (4-IBOA), 2-(5-pentanoic acid)-5-(2-hydroxyphenyl)-1,3,4-oxadiazole (2-PHOD), 7-oxo-7-phenylheptanoic acid (7-OPHA), 4-(3-fluorophenylsulfonyl)butyric acid (3-FPSB), or any combination thereof.

In some aspects, the oral delivery agent is a disodium salt of N-(8-(2-hydroxybenzoyl)amino)caprylic acid.

In some aspects, the oral delivery agent is a salt, hydrate, or solvate of N-(5-chlorosalicyloyl)-8-aminocaprylic acid, or a combination thereof. In some aspects, the salt of N-(5-chlorosalicyloyl)-8-aminocaprylic acid is selected from the group consisting of a sodium salt, a potassium salt, a calcium salt of N-(5-chlorosalicyloyl)-8-aminocaprylic acid, and any combination thereof. In some aspects, the salt of N-(5-chlorosalicyloyl)-8-aminocaprylic acid is sodium salt. In some aspects, the salt of N-(5-chlorosalicyloyl)-8-aminocaprylic acid is a monosodium salt. In some aspects, the salt of N-(8-(2-hydroxybenzoyl)amino)caprylic acid is a disodium salt.

The present disclosure also provides a capsule comprising (i) a composition comprising CIVI 008 and (ii) a composition comprising 5-CNAC. In some aspects, the composition comprising CIVI 008 and the composition comprising 5-CNAC are in a dry blend. In some aspects, the capsule is a gelatin capsule. In some aspects, the gel capsule is a hard-shell gelatin capsule. In some aspects, the capsule is enterically coated. In some aspects, the capsule comprises between 5 mg and 30 mg of CIVI 008 and between 100 mg and 200 mg of 5-CNAC. In some aspects, the capsule comprises about 5 mg, about 10 mg, about 20 mg, about 25 mg, or about 30 mg of CIVI 008. In some aspects, wherein the capsule comprises: 10 mg of CIVI 008 and 100 mg of 5-CNAC; 20 mg of CIVI 008 and 200 mg of 5-CNAC; 5 mg of CIVI 008 and 200 mg of 5-CNAC; 10 mg of CIVI 008 and 200 mg of 5-CNAC; 25 mg of CIVI 008 and 200 mg of 5-CNAC; or, 30 mg of CIVI 008 and 200 mg of 5-CNAC. In some aspects, the capsule contains a statin.

In some aspects, the present disclosure provides a method of treating a disorder selected from the group consisting of atherosclerosis, hyperlipidemia, hypercholesterolemia, HDL/LDL cholesterol imbalance, coronary artery disease (CAD), or coronary heart disease (CHD) in a subject in need thereof, the method comprising administering a capsule comprising (i) a composition comprising CIVI 008 and (ii) a composition comprising 5-CNAC to the subject. The present disclosure also provides a method of reducing expression levels and/or activity of PCSK9 in a subject in need thereof comprising administering a capsule comprising (i) a composition comprising CIVI 008 and (ii) a composition comprising 5-CNAC to the subject. Also provides is a method of reducing cholesterol levels in a subject in need thereof comprising administering to said subject a capsule comprising (i) a composition comprising CIVI 008 and (ii) a composition comprising 5-CNAC. Also provided is a capsule comprising: (i) a composition comprising CIVI 008 and (ii) a composition comprising 5-CNAC for use in the treatment of a disorder selected from the group consisting of atherosclerosis, hyperlipidemia, hypercholesterolemia, HDL/LDL cholesterol imbalance, coronary artery disease (CAD), or coronary heart disease (CHD). Also provides is a capsule comprising: (i) a composition comprising CIVI 008 and (ii) a composition comprising 5-CNAC for use as a medicament to reduce expression levels and/or activity of PCSK9 in a subject. The present disclosure also provides a capsule comprising (i) a composition comprising CIVI 008 and (ii) a composition comprising 5-CNAC for use as a medicament to reduce cholesterol levels in a subject. Also provided is a method to manufacture a capsule comprising a composition comprising CIVI 008 and a composition comprising 5-CNAC comprising: (i) dry blending a first composition comprising CIVI 008 and a second composition comprising 5-CNAC; and, (ii) encapsulating the resulting dry blend of step (i) in a capsule.

BRIEF DESCRIPTION OF THE DRAWINGS/FIGURES

FIGS. 1A, 1B, and 1C show examples of tri-GalNAc conjugates which can be used in the oral compositions disclosed herein. Conjugates 1-4 illustrate four suitable GalNAc conjugate moieties, and conjugates 1a-4a refer to the same conjugates with an additional linker moiety (Y) which is used to link the conjugate to the oligomer (region A or to a bio-cleavable linker, such as region B). The wavy line represents the covalent link to the oligomer.

FIG. 2 shows examples of cholesterol and tocopherol conjugate moieties which can be used in the oral compositions disclosed herein. Conjugates 5a and 6a refer to the same conjugates with an additional linker moiety (Y) which is used to link the conjugate to the oligomer (region A or to a bio-cleavable linker, such as region B). The wavy line represents the covalent link to the oligomer.

FIG. 3 shows specific LNA compounds. Beta-D-oxy LNA are identified by a superscript L after the letter, subscript s represents a phosphorothioate linkage, superscript Me preceding a capital C represents 5-methyl cytosine LNA, non LNA nucleotides are DNA nucleotides (no superscript L).

FIG. 4 shows examples of cholesterol conjugates of LNA compounds which can be used in the oral compositions disclosed herein. Beta-D-oxy LNA are identified by a superscript L after the letter, subscript s represents a phosphorothioate linkage, o subscript represents a phosphodiester linkage, superscript Me preceding a capital C represents 5-methyl cytosine LNA, non LNA nucleotides are DNA nucleotides (no superscript L).

FIG. 5A shows examples of GalNAc conjugates of LNA compounds which can be used in the oral compositions disclosed herein. The conjugates essentially correspond to Conj2a in FIG. 1 where the wavy line is substituted with the LNA oligomer. Beta-D-oxy LNA are identified by a superscript L after the letter, subscript s represents a phosphorothioate linkage, superscript Me preceding a capital C represents 5-methyl cytosine LNA, non LNA nucleotides are DNA nucleotides (no superscript L).

FIG. 5B shows the detailed structure of SEQ ID NO 18.
FIG. 5C shows the detailed structure of SEQ ID NO 19.
FIG. 6 presents an example of FAM conjugate group.
FIG. 7 shows LNA-FAM conjugates with and without cleavable phosphodiester linkages. Beta-D-oxy LNA are identified by a superscript L after the letter, subscript s represents a phosphorothioate linkage, o subscript represents a phosphodiester linkage, superscript Me preceding a capital C represents 5-methyl cytosine LNA, non LNA nucleotides are DNA nucleotides (no superscript L).

Figure 12:
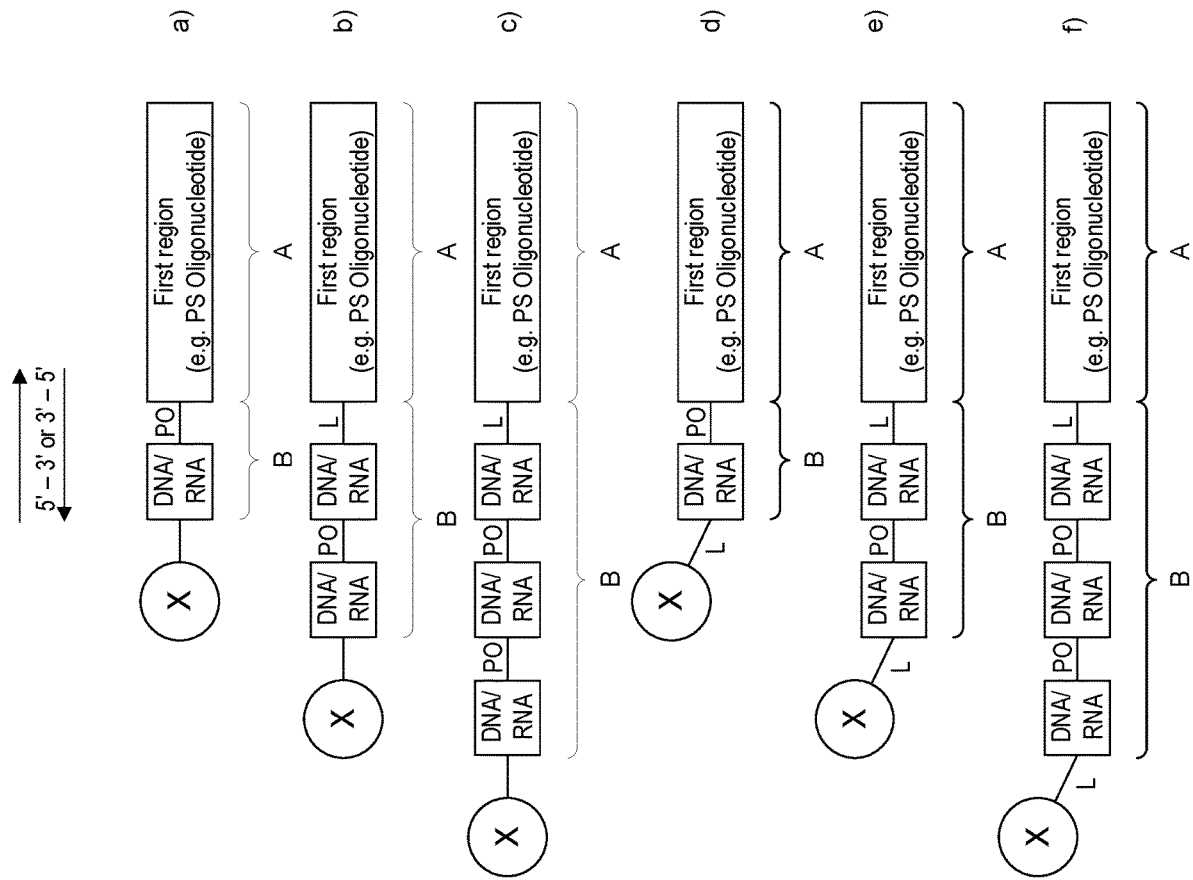

FIG. 12 shows that the inter-nucleoside linkage L can be, for example phosphodiester, phosphorothioate, phosphorodithioate, boranophosphate or methylphosphonate, such as phosphodiester. PO is a phosphodiester linkage. Compound (a) has a region B with a single DNA (or RNA), the linkage between the second and the first region is PO. Compound (b) has two DNA/RNA (such as DNA) nucleosides linked by a phosphodiester linkage. Compound (c) has three DNA/RNA (such as DNA) nucleosides linked by phosphodiester linkages. In some aspects, Region B can be further extended by further phosphodiester DNA/RNA (such as DNA nucleosides). The conjugate group (Marked X, otherwise region C herein) is illustrated on the left side of each compound (e.g. Cholesterol, GalNAc, Conj1-4, 1a-4a, and 5 or 6), and can, optionally be covalently attached to the terminal nucleoside of region B via a phosphorus nucleoside linkage group, such as phosphodiester, phosphorothioate, phosphorodithioate, boranophosphate, phosphoroamidate, or methylphosphonate, or can be linked via an alternative linkage, e.g. a triazol linkage (see L in compounds d, e, and f).

Figure 13:
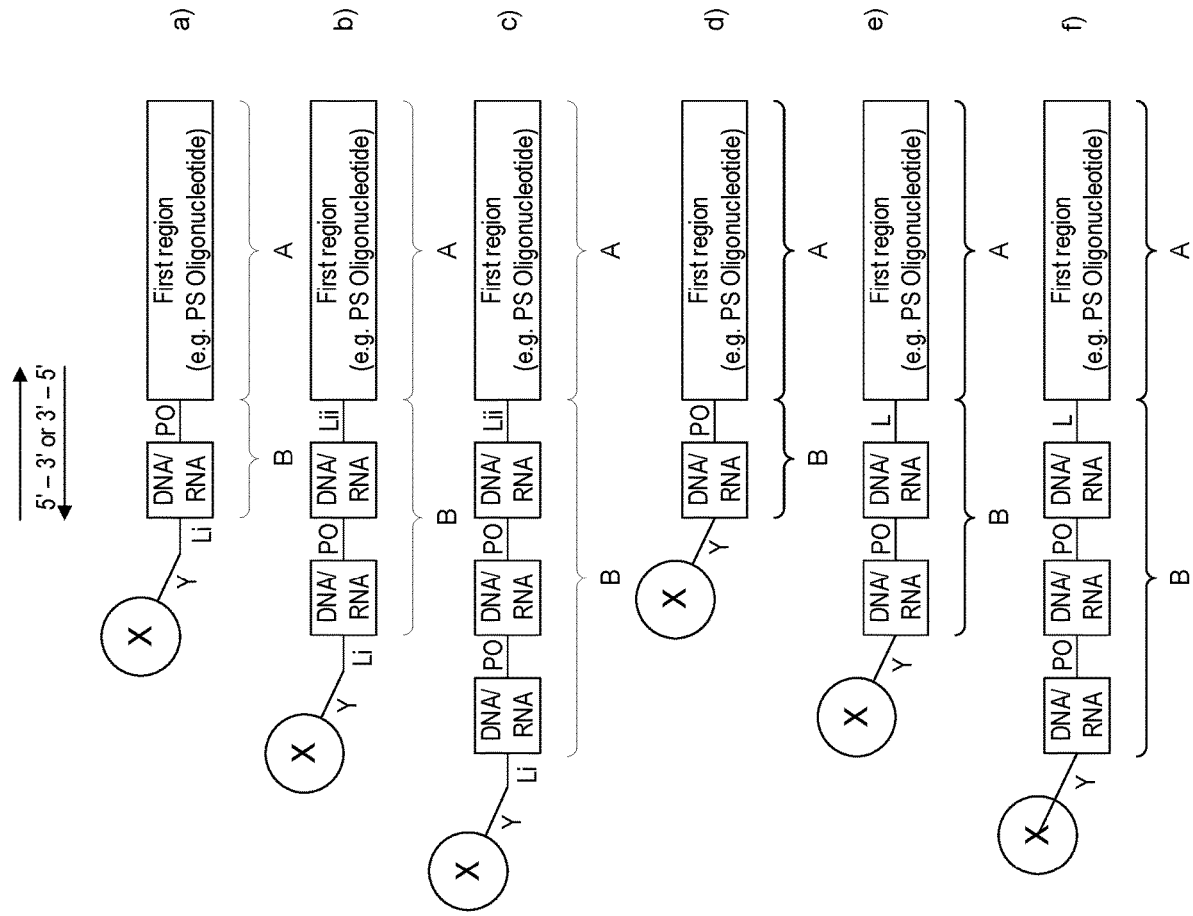

FIG. 13 shows where the compounds comprise the optional linker (Y) between the third (conjugate) region (X) and the second region (region B), using the nomenclature presented in FIG. 12. Suitable linkers are disclosed herein, and include, e.g., alkyl linkers such as C6 linkers. In compounds a), b) and c), the linker between X and region B is attached to region B via a phosphorus nucleoside linkage group, such as phosphodiester, phosphorothioate, phosphorodithioate, boranophosphate, phosphoroamidate, or methylphosphonate, or can be linked via an alternative linkage, e.g., a triazol linkage (Li). In these compounds Lii represents the internucleoside linkage between the first (A) and second regions (B). Compounds d), e), and f) further comprise a linker (Y) between region B and the conjugate group, and region Y can be linked to region B via, e.g., a phosphorus nucleoside linkage group, such as phosphodiester, phosphorothioate, phosphorodithioate, phosphoroamidate, boranophosphate or methylphosphonate, or in some aspects a triazole linkage. In addition or alternatively, X can be an activation group or a reactive group. X can be covalently attached to region B via a phosphorus nucleoside linkage group, such as phosphodiester, phosphorothioate, phosphoroamidate, phosphorodithioate, boranophosphate or methylphosphonate, or can be linked via an alternative linkage, e.g., a triazol linkage.

Figure 14:
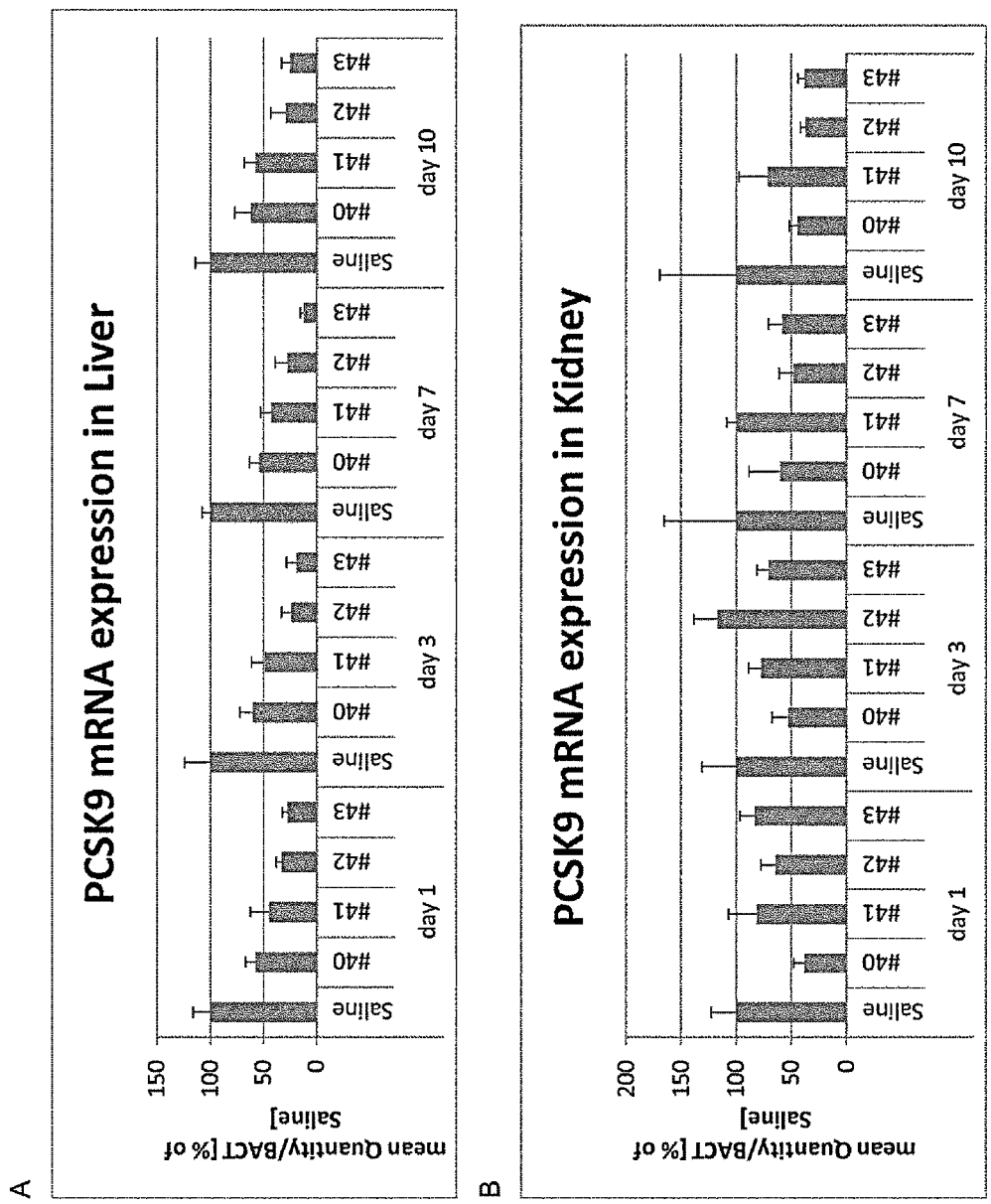

FIG. 14 shows in vivo silencing of PCSK9 mRNA following administration of cholesterol-conjugates. Mice were injected with a single dose of 10 mg/kg unconjugated LNA-antisense oligonucleotide (#40) or equimolar amounts of LNA antisense oligonucleotides conjugated to Cholesterol with different linkers and sacrificed at days 1, 3, 7 and 10 after dosing. RNA was isolated from liver and kidney and subjected to PCSK9 specific RT-qPCR. Panel A shows quantification of PCSK9 mRNA from liver samples was normalized to BACT and shown as percentage of the average of equivalent saline controls. Panel B shows quantification of PCSK9 mRNA from kidney samples was normalized to BACT and shown as percentage of the average of equivalent saline controls.

Figure 15:
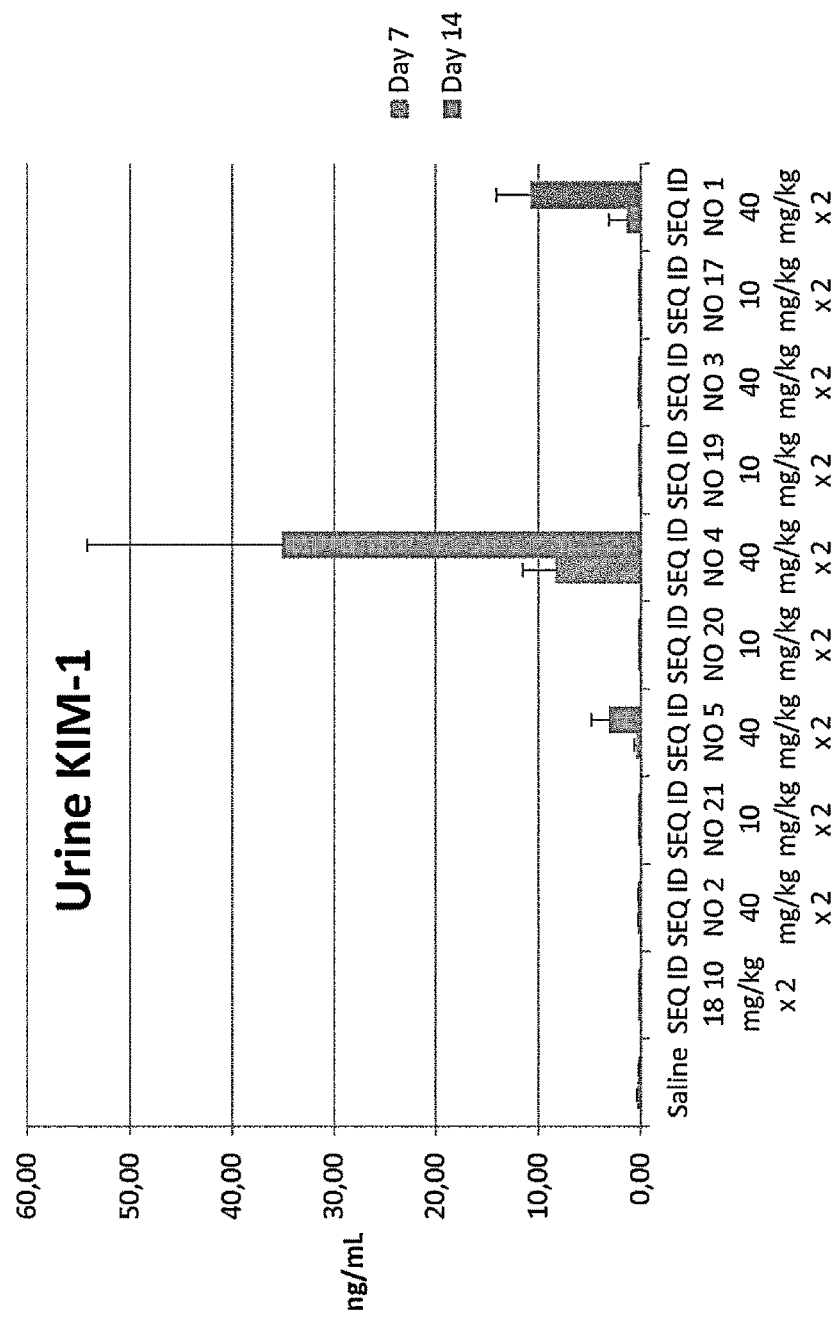

FIG. 15 shows Kim-1 expression from a rat safety study (see Example 5).

Figure 16:
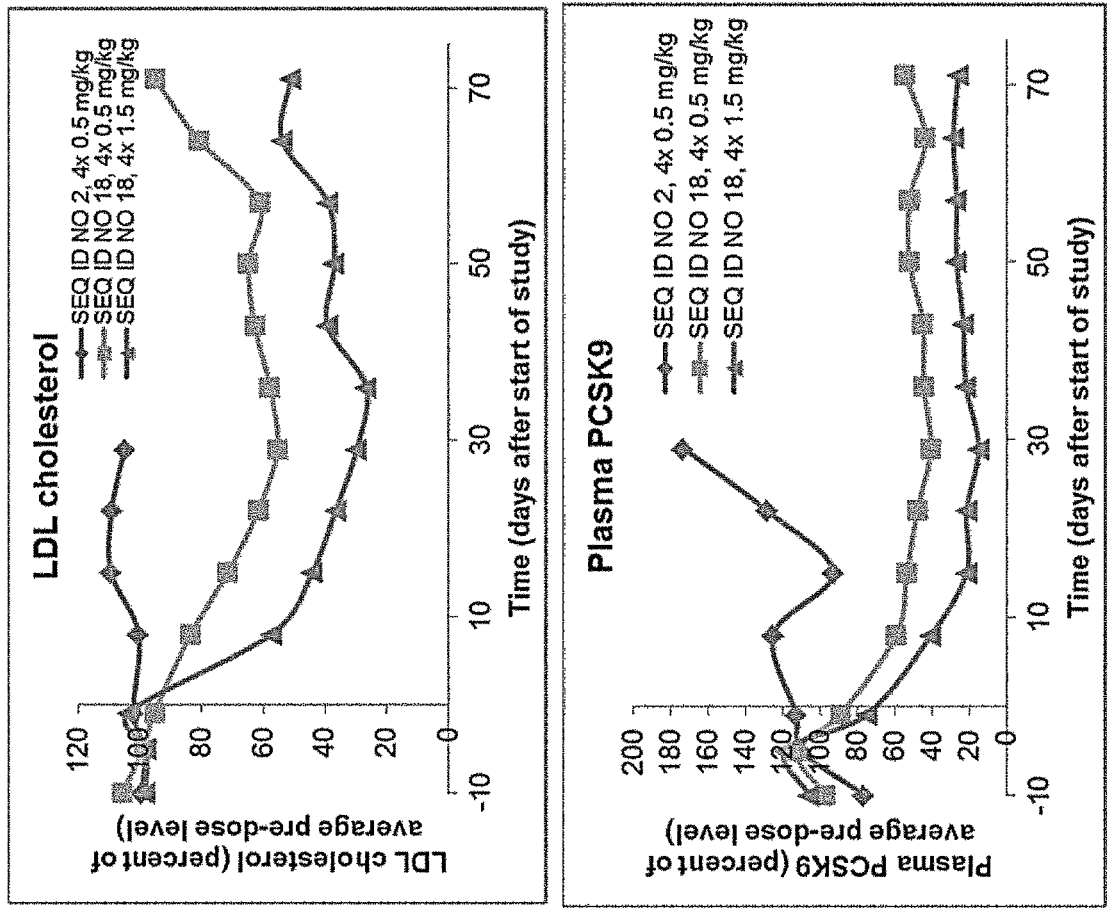

FIG. 16 shows serum PCSK9 and LDL cholesterol in samples from cynomolgus monkeys injected four times (one injection/week) with 0.5 mg/kg/week or 1.5 mg/kg/week of SEQ ID NO:2 or SEQ ID NO:18.

Figure 17:
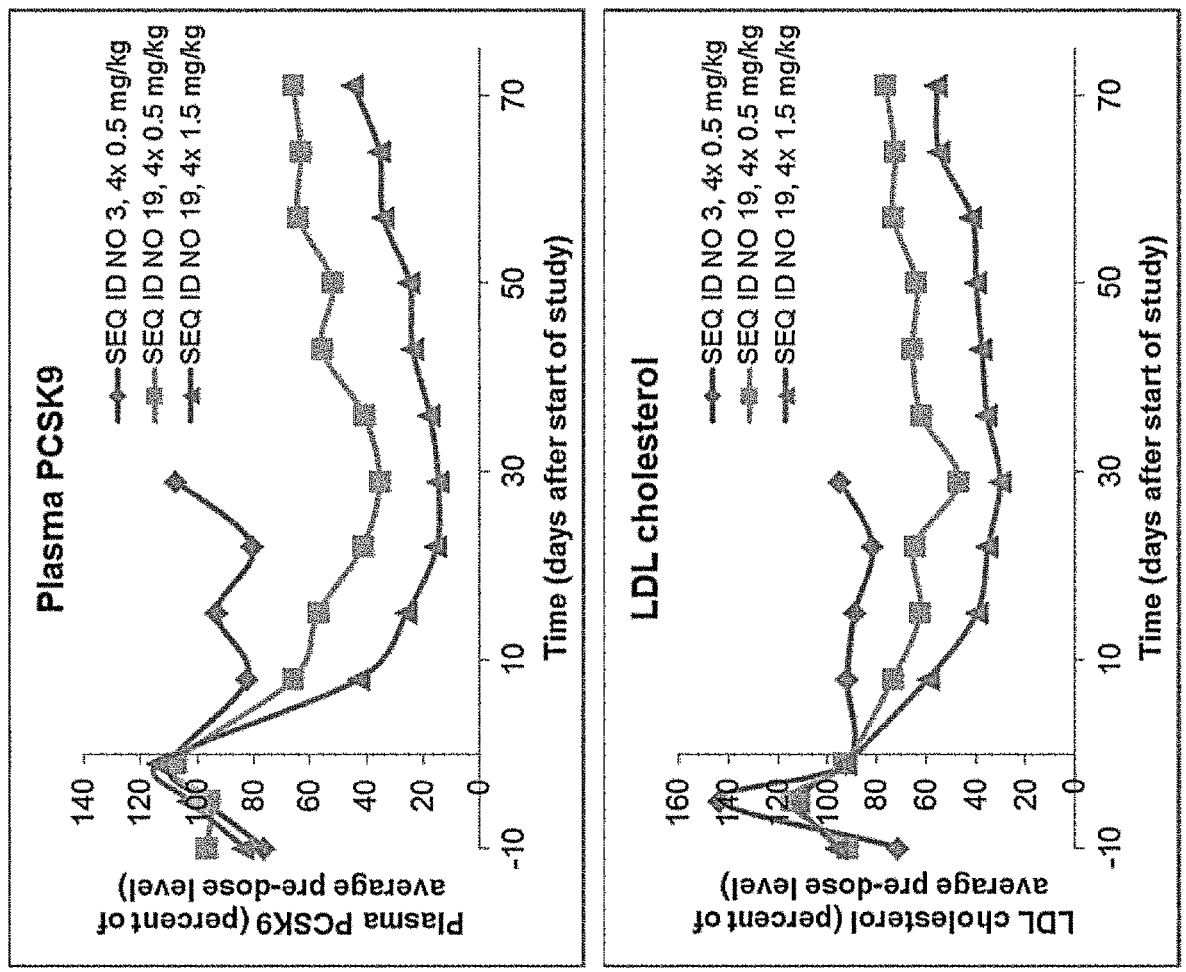

FIG. 17 shows serum PCSK9 and LDL cholesterol in samples from cynomolgus monkeys injected four times (one injection/week) with 0.5 or 1.5 mg/kg/week of SEQ ID NO: 3 and SEQ ID NO: 19.

FIG. 18A shows schematics structures of the antisense oligonucleotide conjugates of SEQ ID NO: 18 and SEQ ID NO: 19.

Figure 18B:
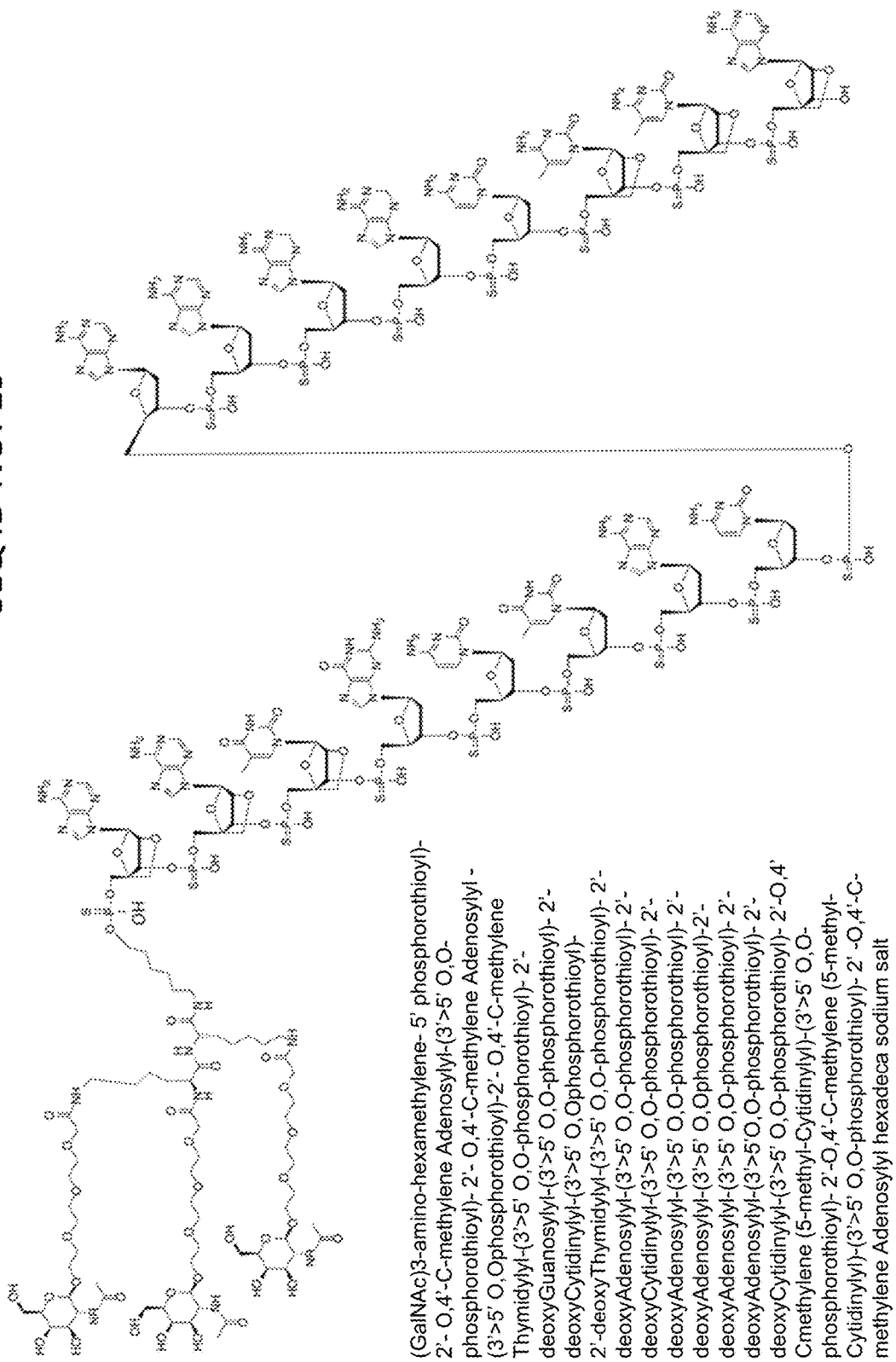

FIG. 18B shows the detailed chemical structure and full name of the antisense oligonucleotide conjugate CIVI 008 (cepadacursen).

Figure 19:
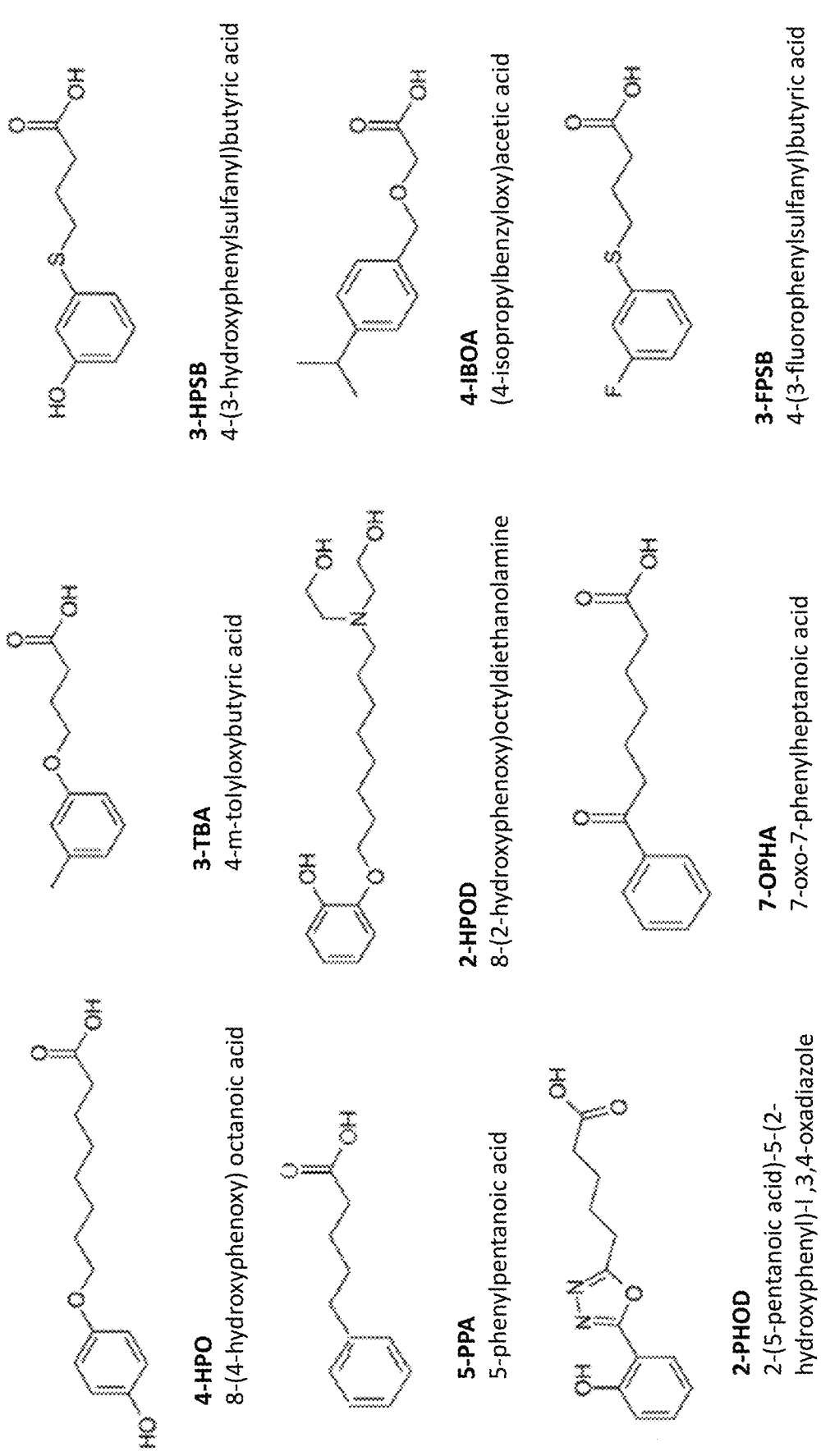

FIG. 19 shows the chemical structures of exemplary oral delivery agents.

Figure 20:
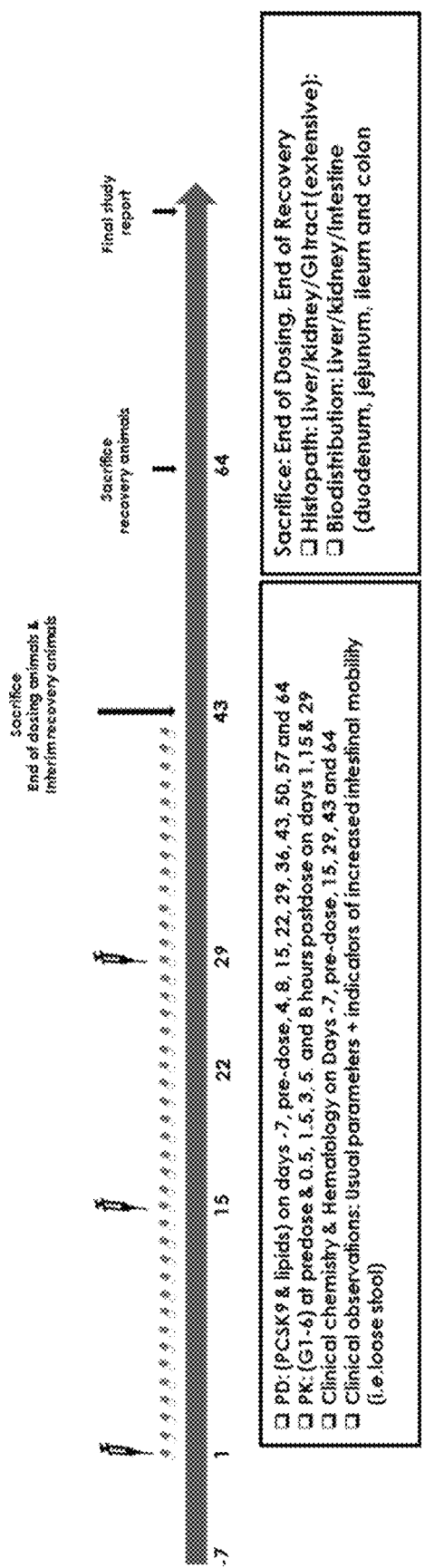

FIG. 20 shows the design of the clinical trial presented in Example 9.

Figure 21:
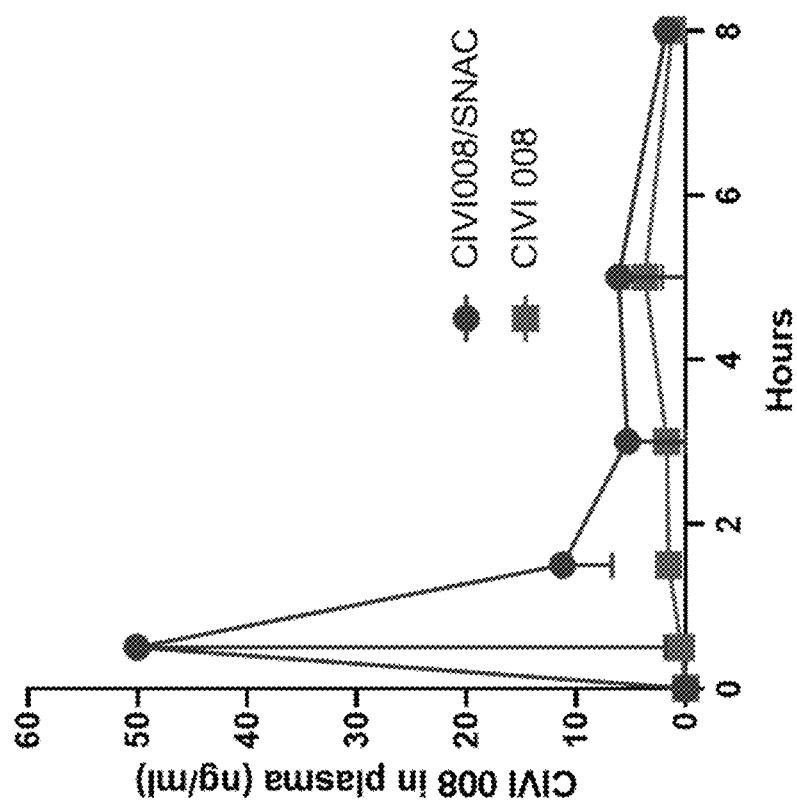

FIG. 21 shows plasma concentration levels of CIVI 008 after administration with or without SNAC.

Figure 22:
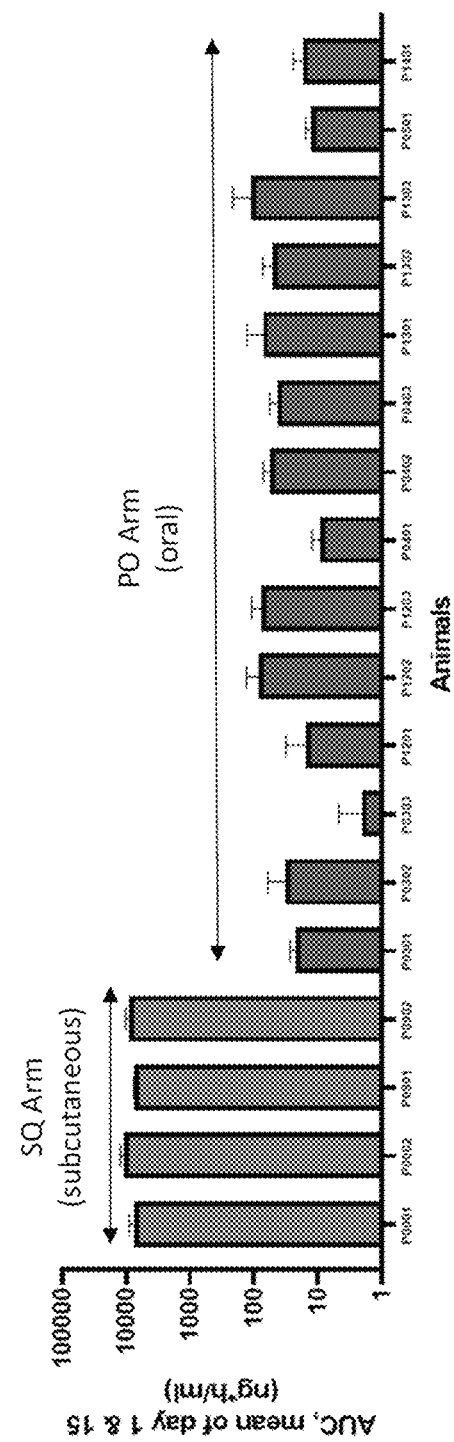

FIG. 22 shows plasma AUC levels in the SQ (subcutaneous) arm (P0001, P0002, P0901, and P0902) and PO (oral) arm of the study of Example 9 (P0301, P0302, P0303, P1201, P1202, P1203, P0401, P0402, P0403, P1301, P1302, P1303, P0501, and P1401).

FIG. 23 shows liver concentration levels of CIVI 008 in the SQ and PO arms of the study presented in Example 9.

Figure 24:
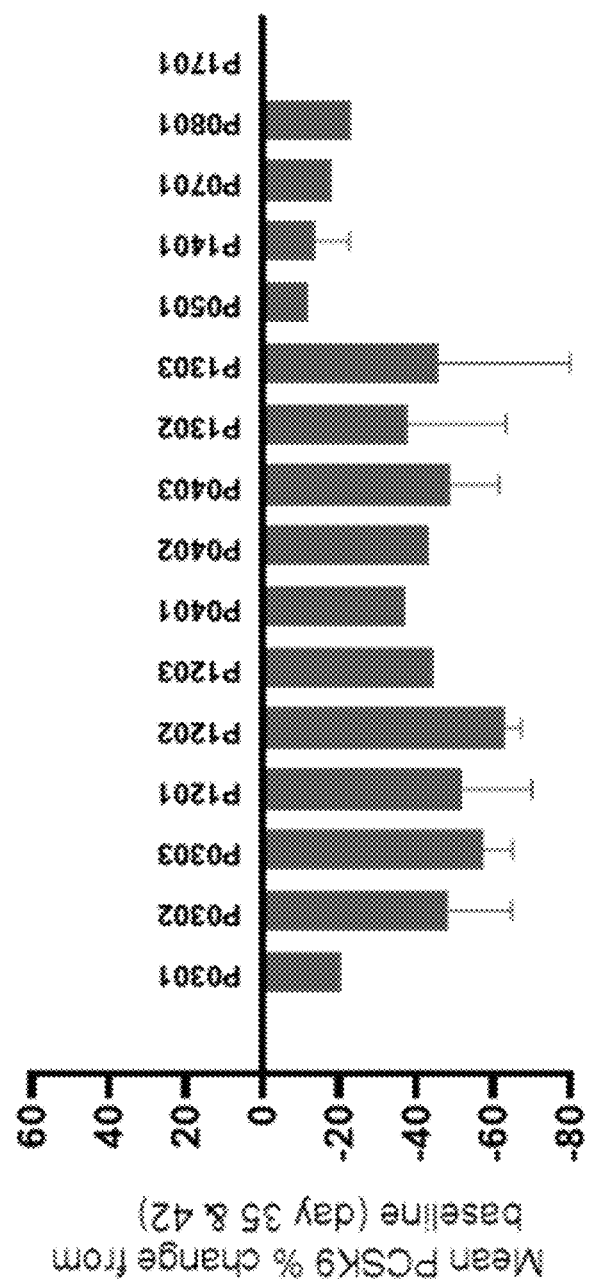

FIG. 24 shows mean changes in PCSK9 expression levels with respect to baseline level at days 35 and 42 after oral CIVI 008 administration.

Figure 25A:
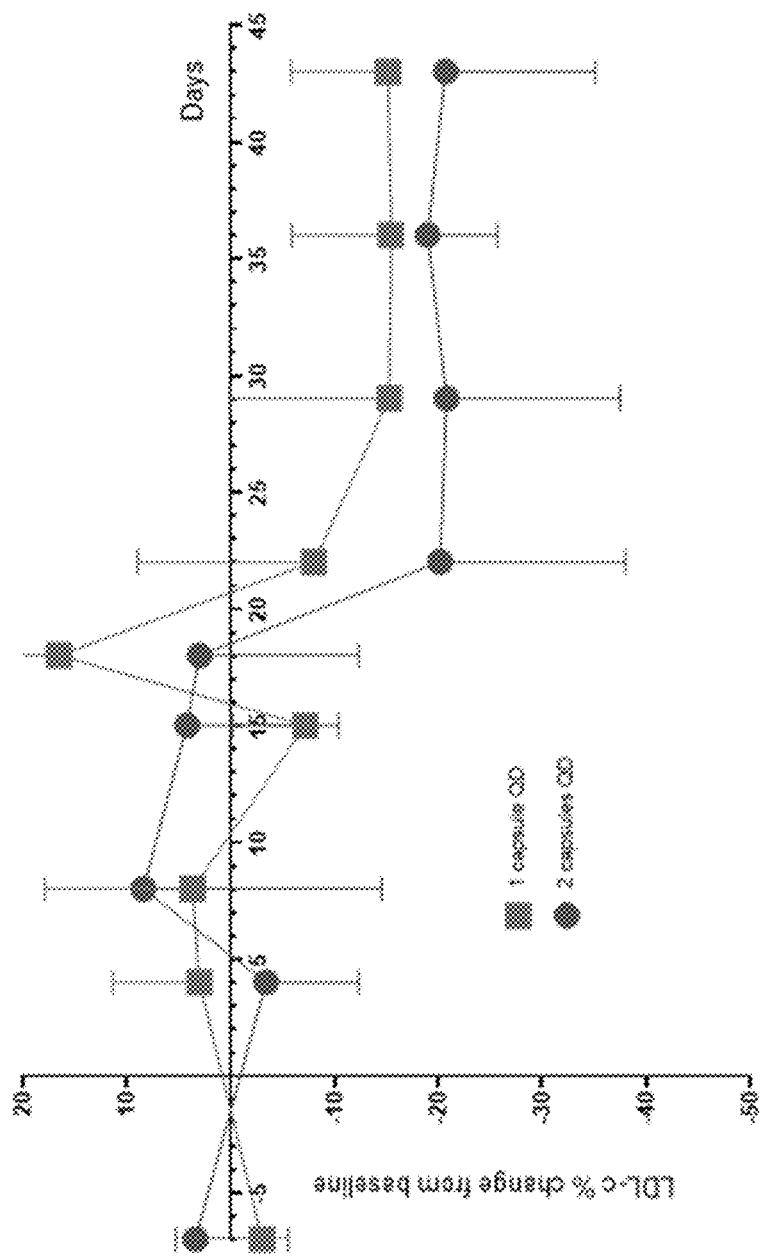
Figure 25B:
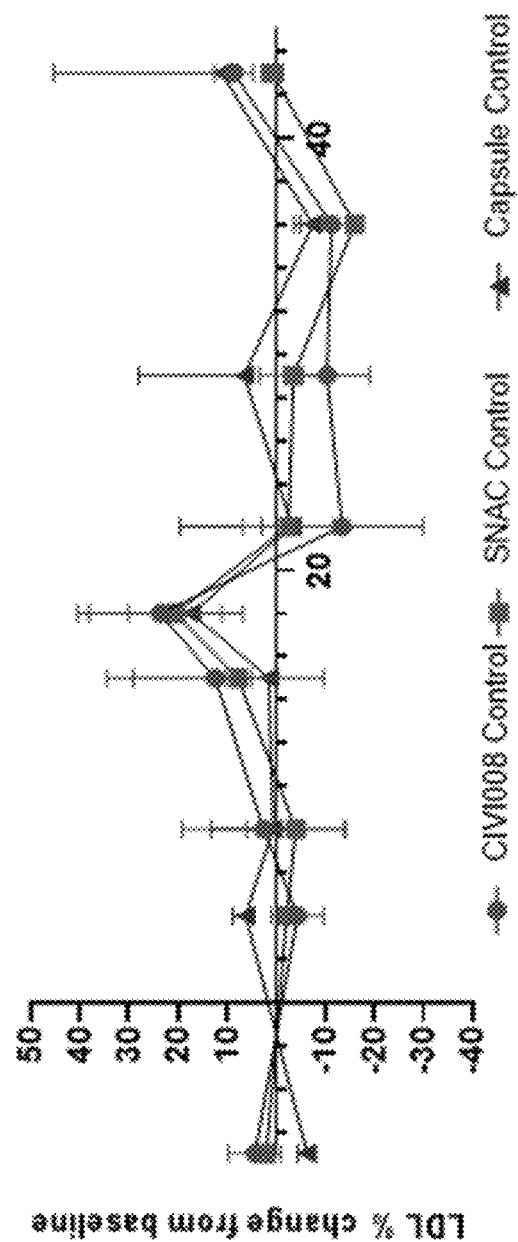

FIGS. 25A and 25B show changes in plasma LDL cholesterol levels with respect to baseline after administration of one or two capsules of CIVI 008 (FIG. 25A) or under control conditions (FIG. 25B).

Figure 26:
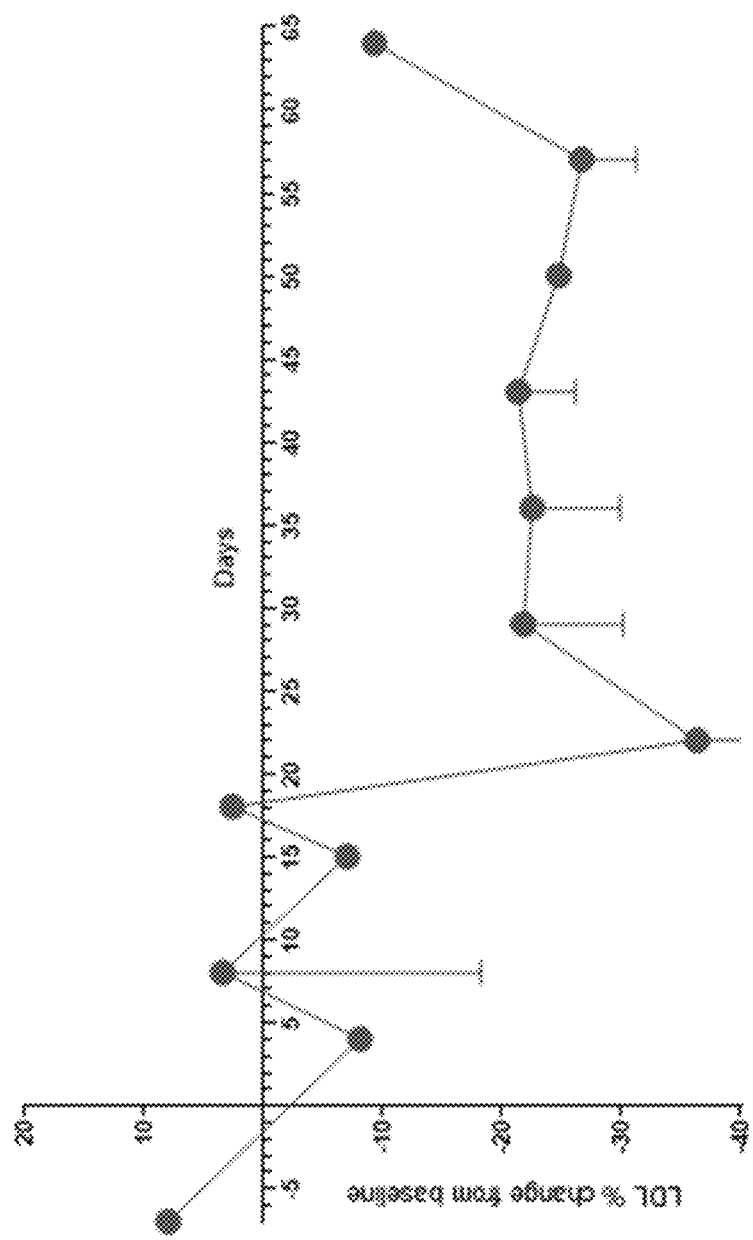

FIG. 26 shows changes in plasma LDL cholesterol levels with respect to baseline during the study presented in Example 9.

Figure 27:
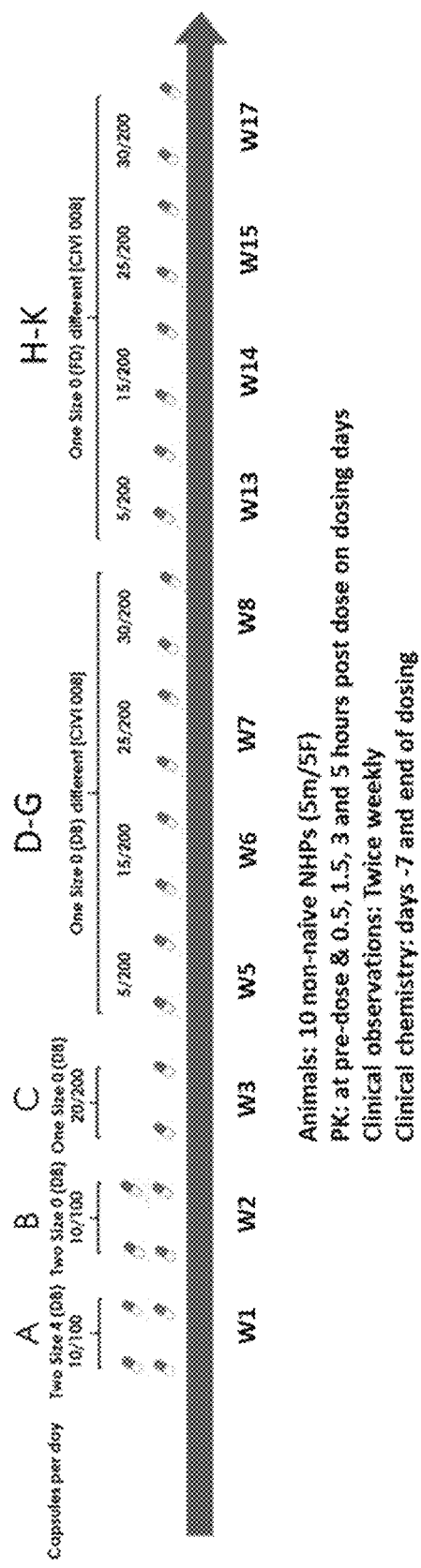

FIG. 27 shows a schematic description of the study presented in Example 11.

Figure 28:
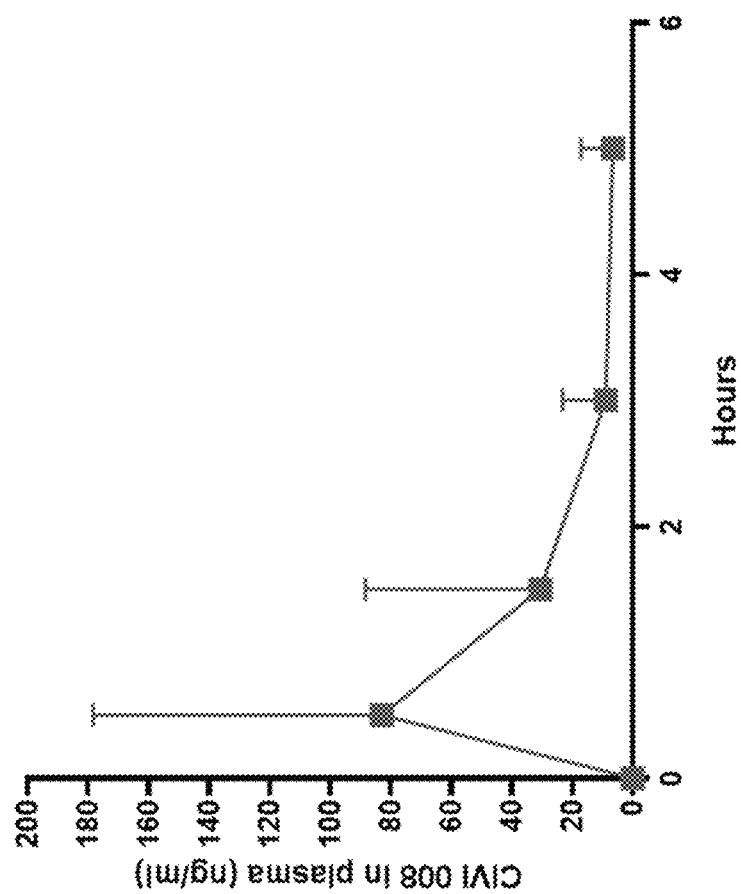

FIG. 28 shows plasma concentration levels of CIVI 008 after administration with 5-CNAC.

FIG. 29 shows a comparison between pharmacokinetic parameters (mean $AUC_{0-5}$ and mean $C_{max}$) corresponding to the administration of CIVI 008 capsules comprising either SNAC or 5-CNAC.

Figure 30:
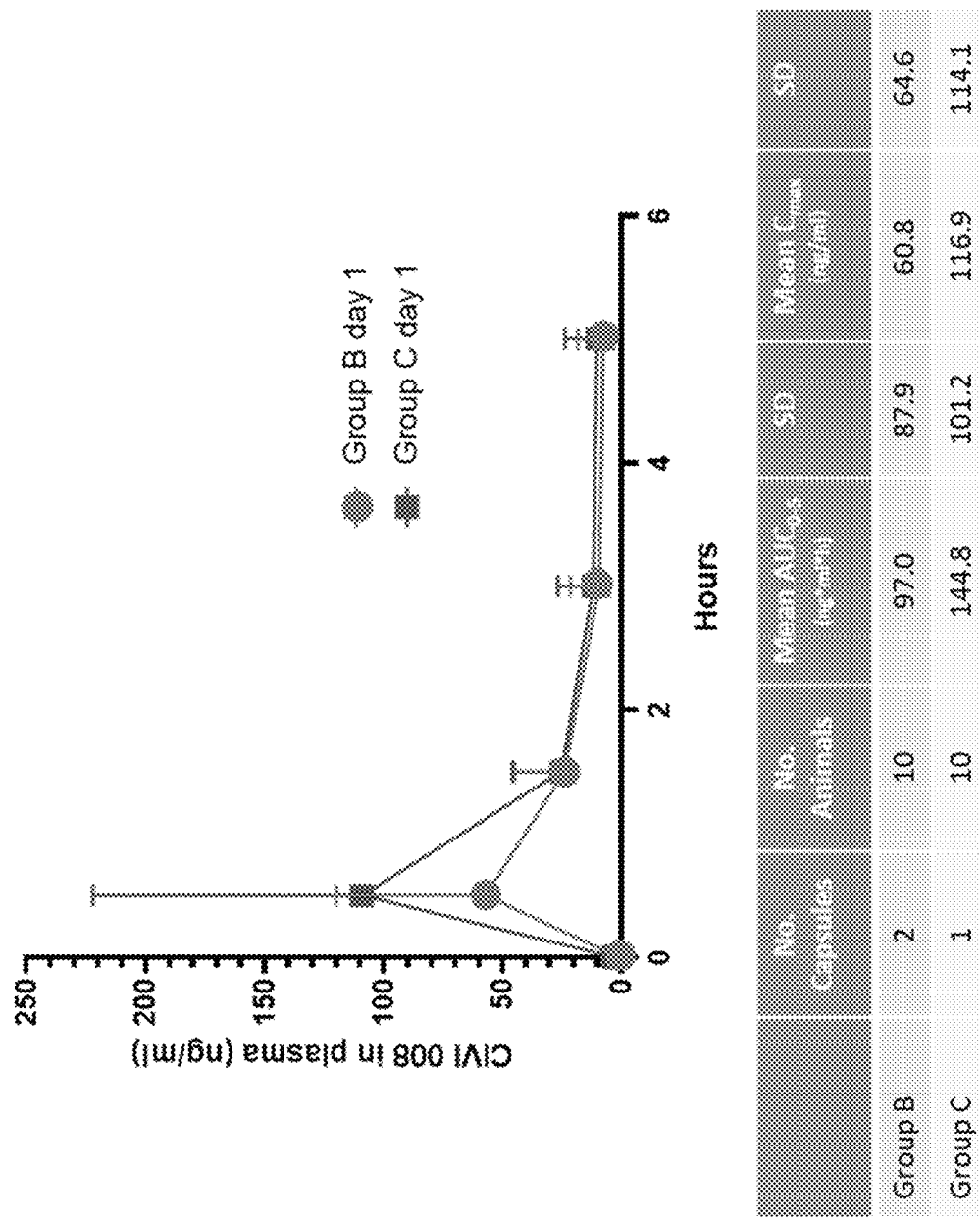

FIG. 30 shows plasma concentration levels and pharmacokinetic parameters (mean $AUC_{0-5}$ and mean $C_{max}$) corresponding to administration of CIVI 008 with 5-CNAC in size 4 capsules (Group A) or size 0 capsules (Group B).

Figure 31:
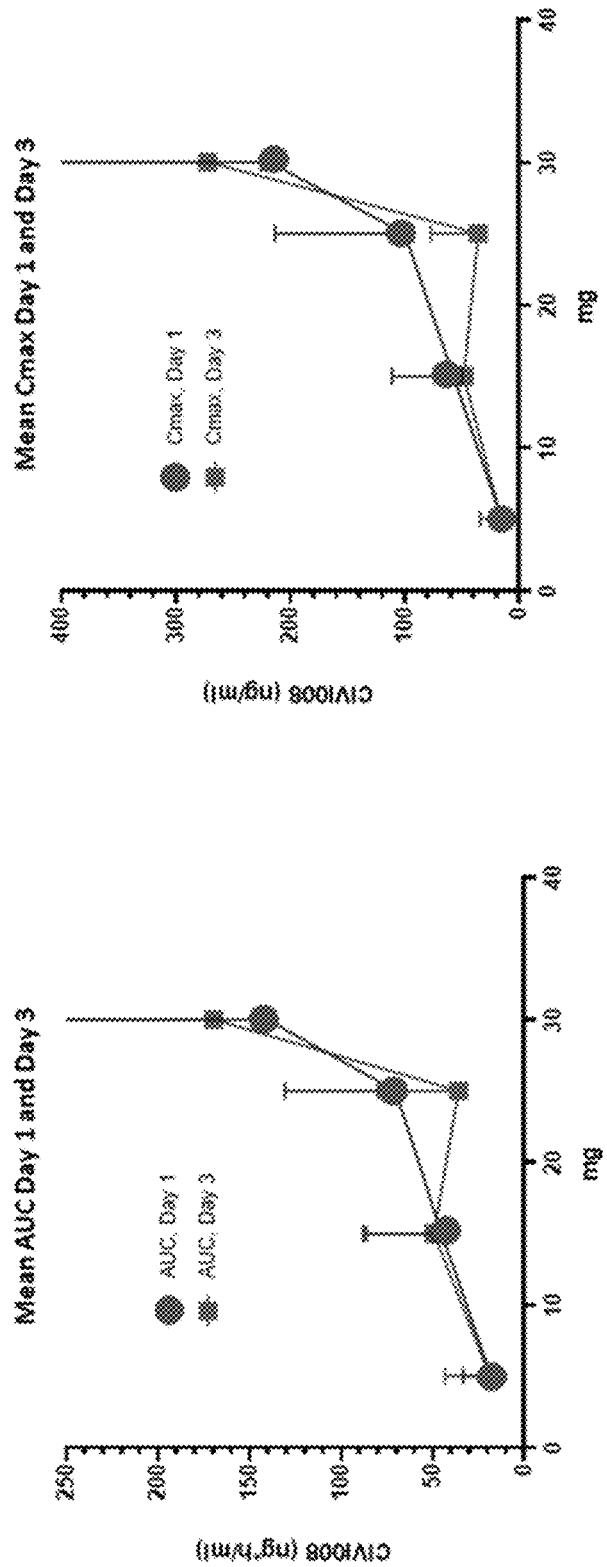

FIG. 31 shows the Mean AUC and mean $C_{max}$ at Days 1 and 3, in monkeys administered from 5 mg to 30 mg of CIVI 008 formulated with 5-CNAC.

Figure 32A:
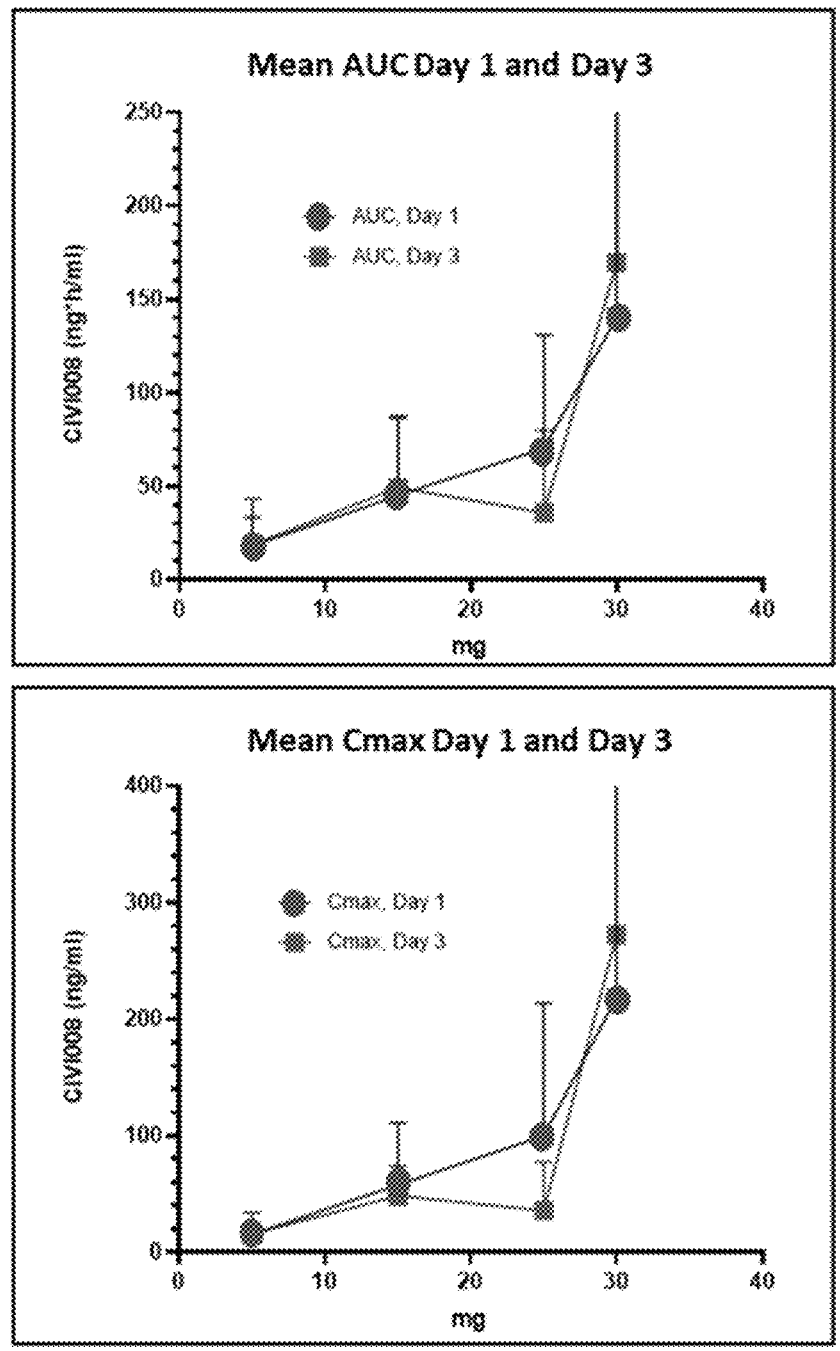
Figure 32B:
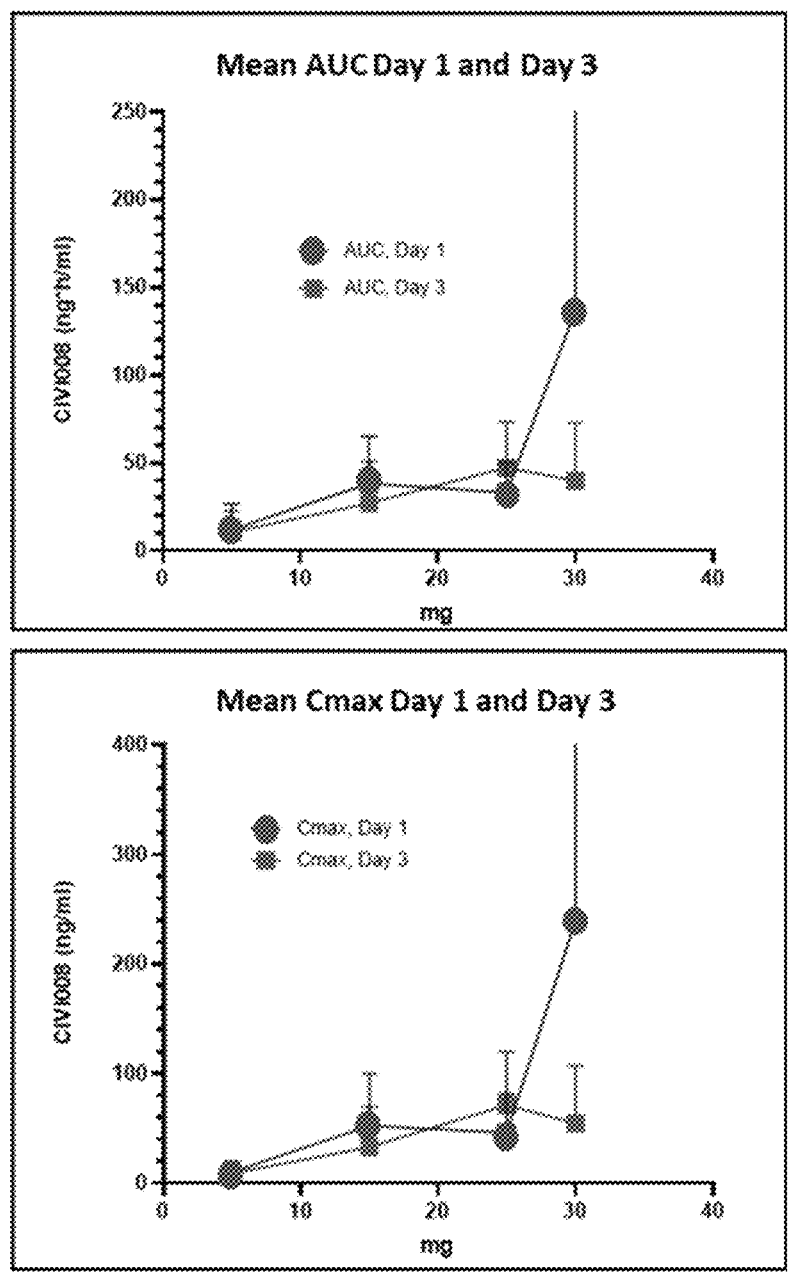

FIG. 32A and FIG. 32B show a comparison of mean pharmacokinetic parameters on Day 1 and 3, in monkeys administered similar doses of CIVI 008 in capsules prepared by either dry blending (FIG. 32A) or freeze-drying (FIG. 32B).

Figure 33:
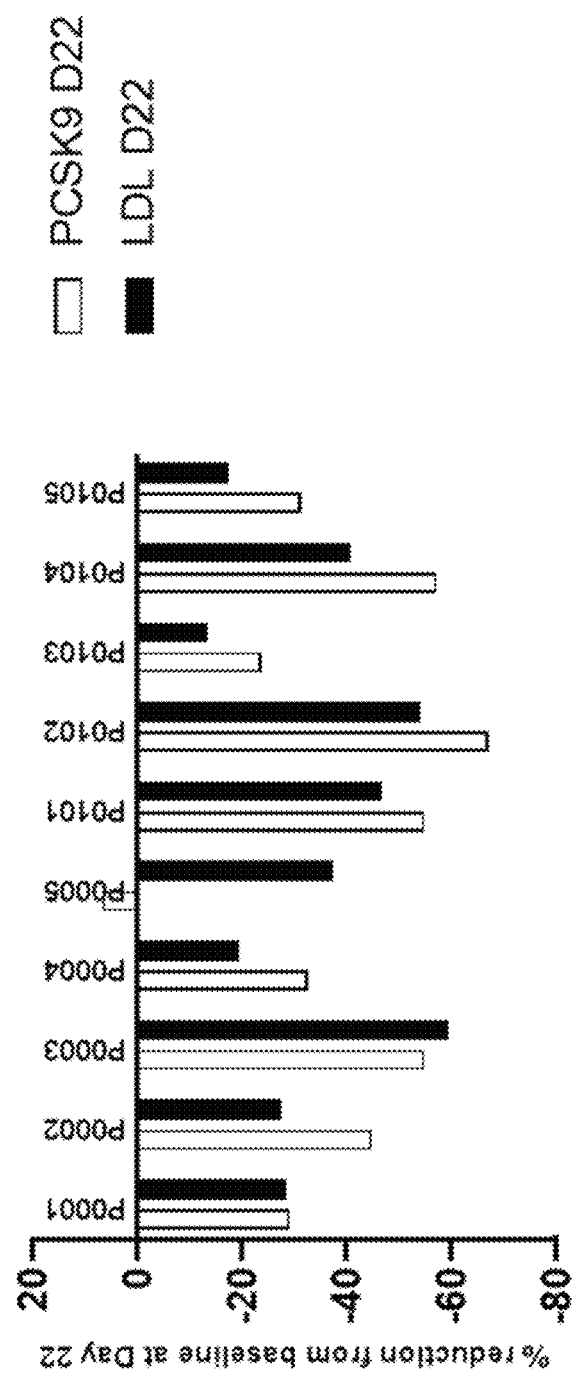

FIG. 33 shows the reduction from baseline in PCSK9 and plasma LDL after 22 days of dosing.

Figure 34:
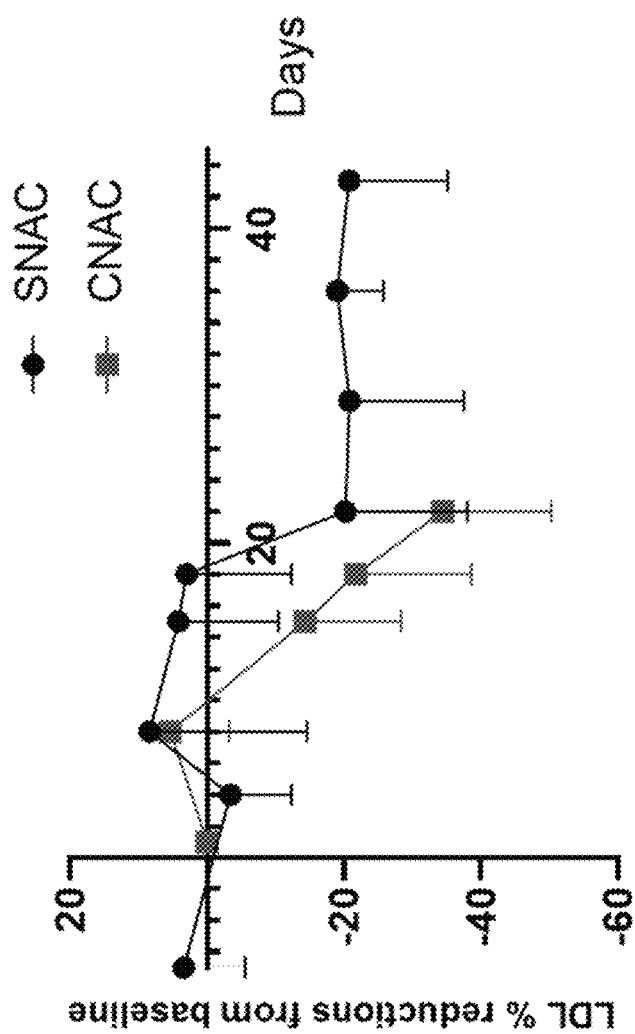

FIG. 34 shows the % LDL reduction from baseline in monkeys administered CIVI 008 formulated with either SNAC or 5-CNAC.

DETAILED DESCRIPTION

The present disclosure provides pharmaceutical compositions for oral delivery comprising an antisense oligomer (e.g., an antisense oligonucleotide) or an antisense oligonucleotide conjugate (e.g., CIVI 008) and an oral delivery agent, e.g., C10, SNAC, or 5-CNAC. In some aspects, the antisense oligomer is 16 to 22 contiguous nucleotides in length and its sequence comprises a contiguous sequence 16 nucleotides in length which is 100% complementary to a PCSK9 target sequence of SEQ ID NO: 31, wherein the antisense oligomer is a gapmer comprising at least one LNA unit, and wherein the antisense oligomer targets an RNA encoding PCSK9.

In some aspects, the oligomer comprises the sequence set forth in SEQ ID NO: 18 or SEQ ID NO: 19. In some aspects, the antisense oligonucleotide conjugate comprises (i) an antisense oligomer moiety which is 16 to 22 contiguous nucleotides in length, wherein its sequence comprises a contiguous sequence 16 nucleotides in length which is 100% complementary to a PCSK9 target sequence of SEQ ID NO: 31, wherein the antisense oligomer is a gapmer comprising at least one LNA unit, and wherein the antisense oligomer targets an RNA encoding PCSK9, and (ii) a GalNAc moiety conjugated to the 5' end of the oligomer. In some aspects, the antisense oligonucleotide conjugate is CIVI 008, as depicted in FIG. 18B.

The oral pharmaceutical compositions disclosed herein, e.g., compositions comprising CIVI 008, e.g., in pill or capsule form, comprise at least one oral delivery agent that protects the payload (e.g., CIVI 008) during passage through the gastrointestinal tract (e.g., through the stomach and upper portion of the small intestine). In some aspects, the oral delivery agent is a salt (e.g., a sodium salt) of a fatty acid, such as caprylic acid (octanoic acid, C8), capric acid (decanoic acid or decylic acid, C10), a derivative thereof (e.g., 8-[2-hydroxybenzoyl]amino) caprylic acid, SNAC, or 5-CNAC), or a combination thereof. In a particular aspect, the oral delivery agent is a salt, e.g., a sodium salt of SNAC or a sodium salt of 5-CNAC.

Also provided are methods of manufacturing the pharmaceutical compositions disclose herein. The disclosure also provides methods to treat a subject a subject if need thereof comprising administering an oral pharmaceutical compositions disclosed herein.

Definitions

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower). For example, if it is stated that an antisense oligomer or antisense oligonucleotide conjugate (e.g., CIVI 008) reduces expression of PCSK9 protein in a cell following administration of the oligomer or conjugate by at least about 60%, it is implied that the PCSK9 expression levels are reduced by a range of 50% to 70%.

The term "oligomer" or "oligonucleotide" in the context of the present disclosure are used interchangeably, and refer to a molecule formed by covalent linkage of two or more nucleotides. Herein, a single nucleotide (unit) can also be referred to as a monomer or unit.

The term "derivative" as used herein refers to a chemical compound related structurally to a compound disclosed herein (e.g., C10, SNAC, or 5-CNAC), e.g., a compound having the same carbon skeleton, but chemically modified to introduce, e.g., a side chain or group disclosed herein, in one or more positions, and wherein the derivative possesses a biological activity (either the ability to function as an oral delivery agent) that is substantially similar to a biological activity of the entity or molecule it is a derivative.

The term "nucleotide" as used herein, refers to a glycoside comprising a sugar moiety, a base moiety and a covalently linked group (linkage group), such as a phosphate or phosphorothioate internucleoside linkage group, and covers both naturally occurring nucleotides, such as DNA or RNA, and non-naturally occurring nucleotides comprising modified sugar and/or base moieties, which are also referred to as "nucleotide analogs" herein. Herein, a single nucleotide can be referred to as a monomer or unit. In certain aspects, the term "nucleotide analogs" refers to nucleotides having modified sugar moieties. Non-limiting examples of the nucleotides having modified sugar moieties (e.g., LNA) are disclosed elsewhere herein. In other aspects, the term "nucleotide analogs" refers to nucleotides having modified nucleobase moieties. The nucleotides having modified nucleobase moieties include, but are not limited to, 5-methyl-cytosine, isocytosine, pseudoisocytosine, 5-bromouracil, 5-propynyluracil, 6-aminopurine, 2-aminopurine, inosine, diaminopurine, and 2-chloro-6-aminopurine. In some aspects, the terms "nucleotide", "unit" and "monomer" are used interchangeably. It will be recognized that when referring to a sequence of nucleotides or monomers, what is referred to is the sequence of bases, such as A, T, G, C or U, and analogs thereof.

The term "nucleoside" as used herein is used to refer to a glycoside comprising a sugar moiety and a base moiety, and can therefore be used when referring to the nucleotide units, which are covalently linked by the internucleoside linkages between the nucleotides of the oligomer (e.g., an antisense oligomer, ASO) or antisense oligonucleotide conjugate (e.g., CIVI 008) disclosed herein. In the field of biotechnology, the term "nucleotide" is often used to refer to a nucleic acid monomer or unit. In the context of an oligomer (e.g., an antisense oligomer, ASO) or antisense oligonucleotide conjugate (e.g., CIVI 008) disclosed herein, the term "nucleotide" can refer to the base alone, i.e., a nucleobase sequence comprising cytosine (DNA and RNA), guanine (DNA and RNA), adenine (DNA and RNA), thymine (DNA) and uracil (RNA), in which the presence of the sugar backbone and internucleoside linkages are implicit. Likewise, particularly in the case of oligonucleotides where one or more of the internucleoside linkage groups are modified, the term "nucleotide" can refer to a "nucleoside." For example, the term "nucleotide" can be used, even when specifying the presence or nature of the linkages between the nucleosides.

In some aspects, the terms "nucleoside", "nucleotide", "unit" and "monomer" are used interchangeably. It will be recognized that when referring to a sequence of nucleotides or monomers, what is referred to is the sequence of bases, such as A, T, G, C or U.

The plural terms "nucleic acids" or "nucleotides" is intended to encompass plural nucleic acids. In some aspects, the term "nucleic acids" or "nucleotides" refers to a target sequence, e.g., pre-mRNAs, mRNAs, or DNAs in vivo or in vitro. When the term refers to the nucleic acids or nucleotides in a target sequence, the nucleic acids or nucleotides can be naturally occurring sequences within a cell. In other aspects, "nucleic acids" or "nucleotides" refer to a sequence in an oligomer or conjugate of the disclosure. When the term refers to a sequence in an oligomer (e.g., an antisense oligomer, ASO) or antisense oligonucleotide conjugate (e.g., CIVI 008) disclosed herein, the nucleic acids or nucleotides can be non-naturally occurring, i.e., chemically synthesized, enzymatically produced, recombinantly produced, or any combination thereof. In some aspects, the nucleic acids or nucleotides in the oligomer (e.g., an antisense oligomer, ASO) or antisense oligonucleotide conjugate (e.g., CIVI 008) disclosed herein are produced synthetically or recombinantly, but are not a naturally occurring sequence or a fragment thereof. In some aspects, the nucleic acids or nucleotides in the oligomer (e.g., an antisense oligomer, ASO) or antisense oligonucleotide conjugate (e.g., CIVI 008) disclosed herein are not naturally occurring because they contain at least one nucleoside analog that is not naturally occurring in nature.

The terms "reverse complement", "reverse complementary" and "reverse complementarity" as used herein are interchangeable with the terms "complement", "complementary" and "complementarity".

The term, "complementary" means that two sequences are complementary when the sequence of one can bind to the sequence of the other in an anti-parallel sense wherein the 3-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least 90%, preferably 95%, most preferably 100%, complementarity to a defined sequence.

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine. Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine. In some aspects the nucleobases can be independently selected from the group consisting of adenine, guanine, cytosine, thymidine, uracil, 5-methylcytosine. In some aspects the nucleobases can be independently selected from the group consisting of adenine, guanine, cytosine, thymidine, and 5-methylcytosine. In some aspects, at least one of the nucleobases present in an oligomer of the present disclosure is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e., have no functional effect on the way the oligonucleotide works to inhibit target gene expression. Such "equivalent" analogues can nevertheless be useful if, for example, they are easier or cheaper to manufacture, or are more stable to storage or manufacturing conditions, or represent a tag or label.

As used herein the term "PCSK9" refers to Proprotein convertase subtilisin/kexin type 9, is an enzyme encoded by the PCSK9 gene in humans on chromosome 1. The PCSK9 gene resides on chromosome 1 at the band 1p32.3. It is the 9th member of the proprotein convertase family of proteins that activate other proteins. Similar genes (orthologs) are found across many species. The solved structure of PCSK9 reveals four major components in the pre-processed protein: the signal peptide (residues 1-30); the N-terminal prodomain (residues 31-152); the catalytic domain (residues 153-425); and the C-terminal domain (residues 426-692), which is further divided into three modules. The N-terminal prodomain has a flexible crystal structure and is responsible for regulating PCSK9 function by interacting with and blocking the catalytic domain, which otherwise binds the epidermal growth factor-like repeat A (EGF-A) domain of the LDLR. While previous studies indicated that the C-terminal domain was uninvolved in binding LDLR, recent studies have demonstrated that the C-terminal domain does bind LDLR. The secretion of PCSK9 is largely dependent on the autocleavage of the signal peptide and N-terminal prodomain, though the N-terminal prodomain retains its association with the catalytic domain. In particular, residues 61-70 in the N-terminal prodomain are crucial for its autoprocessing.

The term "naturally occurring variant thereof" refers to variants of the PCSK9 polypeptide of nucleic acid sequence which exist naturally within the defined taxonomic group, such as mammalian, such as mouse, monkey, and preferably human. Typically, when referring to "naturally occurring variants" of a polynucleotide the term also can encompass any allelic variant of the PCSK9 encoding genomic DNA which are found at the chromosome 4, at 4 $C_7$ by chromosomal translocation or duplication, and the RNA, such as mRNA derived therefrom. "Naturally occurring variants" can also include variants derived from alternative splicing of the PCSK9 mRNA. When referenced to a specific polypeptide sequence, e.g., the term also includes naturally occurring forms of the protein which can therefore be processed, e.g. by co- or post-translational modifications, e.g., signal peptide cleavage, proteolytic cleavage, or glycosylation.

As used herein, "2'-F" refers to a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

The term "nucleotide length" as used herein means the total number of the nucleotides (monomers) in a given sequence. As one of ordinary skill in the art would recognize, the 5' terminal nucleotide of an oligonucleotide does not comprise a 5' internucleoside linkage group, although it can comprise a 5' terminal group.

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates. In some aspects, the asymmetric center can be an asymmetric carbon atom. The term "asymmetric carbon atom" means a carbon atom with four different substituents. According to the Cahn-Ingold-Prelog Convention an asymmetric carbon atom can be of the "R" or "S" configuration.

As used herein, the term "bicyclic sugar" refers to a modified sugar moiety comprising a 4 to 7 membered ring comprising a bridge connecting two atoms of the 4 to 7 membered ring to form a second ring, resulting in a bicyclic structure. In some aspects, the bridge connects the C2' and C4' of the ribose sugar ring of a nucleoside (i.e., 2'-4' bridge), as observed in LNA nucleosides.

As used herein, a "coding region," "coding sequence," or "open reading frame" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, untranslated regions ("UTRs"), and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. In some aspects, an oligomer (e.g., an antisense oligomer, ASO) or antisense oligonucleotide conjugate (e.g., CIVI 008) disclosed herein can target a PCSK9 coding region of a nucleic acid encoding the PCSK9 protein, e.g., an RNA.

The term "non-coding region" as used herein means a nucleotide sequence that is not a coding region. Examples of non-coding regions include, but are not limited to, promoters, ribosome binding sites, transcriptional terminators, introns, untranslated regions ("UTRs"), non-coding exons and the like. Some of the exons can be wholly or part of the 5' untranslated region (5' UTR) or the 3' untranslated region (3' UTR) of each transcript. The untranslated regions are important for efficient translation of the transcript and for controlling the rate of translation and half-life of the transcript. In some aspects, an oligomer (e.g., an antisense oligomer, ASO) or antisense oligonucleotide conjugate (e.g., CIVI 008) disclosed herein can target a PCSK9 non-coding region of a nucleic acid encoding the PCSK9 protein, e.g., an RNA.

The term "region" when used in the context of a nucleotide sequence refers to a section of that sequence. For example, the phrase "region within a nucleotide sequence" or "region within the complement of a nucleotide sequence" refers to a sequence shorter than the nucleotide sequence, but longer than at least 10 nucleotides located within the particular nucleotide sequence or the complement of the nucleotides sequence, respectively. The term "sub-sequence" or "subsequence" can also refer to a region of a nucleotide sequence.

The term "downstream," when referring to a nucleotide sequence, means that a nucleic acid or a nucleotide sequence is located 3' to a reference nucleotide sequence. In certain aspects, downstream nucleotide sequences relate to sequences that follow the starting point of transcription. For example, the translation initiation codon of a gene is located downstream of the start site of transcription. In some aspects, an oligomer (e.g., an antisense oligomer, ASO) or antisense oligonucleotide conjugate (e.g., CIVI 008) disclosed herein can target a region of a nucleic acid encoding the PCSK9 protein, e.g., an RNA, downstream of the PCSK9 open reading frame (ORF).

The term "upstream" refers to a nucleotide sequence that is located 5' to a reference nucleotide sequence. In some aspects, an oligomer (e.g., an antisense oligomer, ASO) or antisense oligonucleotide conjugate (e.g., CIVI 008) disclosed herein can target a region of a nucleic acid encoding the PCSK9 protein, e.g., an RNA, upstream of the PCSK9 open reading frame (ORF).

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites, UTRs, and stem-loop structures. If a coding region is intended for expression in a eukaryotic cell, a polyadenylation signal and transcription termination sequence will usually be located 3' to the coding sequence. In some aspects, an oligomer (e.g., an antisense oligomer, ASO) or antisense oligonucleotide conjugate (e.g., CIVI 008) disclosed herein can target a regulatory region.

The term "transcript" as used herein can refer to a primary transcript that is synthesized by transcription of DNA and becomes a messenger RNA (mRNA) after processing, i.e., a precursor messenger RNA (pre-mRNA), and the processed mRNA itself. The term "transcript" can be interchangeably used with "pre-mRNA" and "mRNA." After DNA strands are transcribed to primary transcripts, the newly synthesized primary transcripts are modified in several ways to be converted to their mature, functional forms to produce different proteins and RNAs, such as mRNA, tRNA, rRNA, lncRNA, miRNA and others. Thus, the term "transcript" can include exons, introns, 5' UTRs, and 3' UTRs.

The term "expression" as used herein refers to a process by which a polynucleotide produces a gene product, for example, an RNA or a polypeptide. It includes, without limitation, transcription of the polynucleotide into messenger RNA (mRNA) and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

The terms "identical" or percent "identity" in the context of two or more nucleic acids refer to two or more sequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

One such non-limiting example of a sequence alignment algorithm is the algorithm described in Karlin et al., 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain aspects, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, California) or Megalign (DNASTAR) are additional publicly available software programs that can be used to align sequences. In certain aspects, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative aspects, the GAP program in the GCG software package, which incorporates the algorithm of Needleman and Wunsch (*J. Mol. Biol.* (48):444-453 (1970)) can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain aspects, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain aspects, the default parameters of the alignment software are used.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI (European Bioinformatics Institute).

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

In certain aspects, the percentage identity "X" of a first nucleotide sequence to a second nucleotide sequence is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

Different regions within a single polynucleotide target sequence that align with a polynucleotide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In determining the degree of "complementarity" between oligomers of the disclosure (or regions thereof) and the target region, such as those disclosed herein, the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the two sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the disclosure and the target region.

As used herein, the terms "inhibiting" and "reducing," e.g., the expression of PCSK9 gene transcript and/or PCSK9 protein level or PCSK9 activity refers to the oligomer (e.g., an antisense oligomer, ASO) or antisense oligonucleotide conjugate (e.g., CIVI 008) disclosed herein reducing the expression of the PCSK9 gene transcript and/or PCSK9 protein level and/or activity in a cell, a tissue, or a subject.

In some aspects, the terms "inhibiting" and "reducing" refer to complete inhibition (100% inhibition or non-detectable level) of PCSK9 gene transcript or PCSK9 protein level and/or activity. In other aspects, the terms "inhibiting" and "reducing" refer, e.g., to at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least 90%, at least 95% or at least 99% inhibition of PCSK9 gene transcript and/or PCSK9 protein expression and/or activity in a cell, a tissue, or a subject.

The polynucleotide variants can contain alterations in the coding regions, non-coding regions, or both. In one aspect, the polynucleotide variants contain alterations which produce silent substitutions, additions, or deletions, but do not alter the properties or activities of the encoded polypeptide. In another aspect, nucleotide variants are produced by silent substitutions due to the degeneracy of the genetic code. In other aspects, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as E. coli).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

As used herein the term "linked to" or "conjugated to" are used interchangeably and refer to a covalent or non-covalent bond formed between a first moiety and a second moiety, e.g., an oligomer of the present disclosure (e.g., an antisense oligonucleotide) and a conjugate moiety (e.g., GalNAc).

The terms "individual," "subject," "host," and "patient," are used interchangeably herein and refer to any mammalian subject for whom diagnosis, treatment, or therapy is desired, particularly humans. The compositions and methods described herein are applicable to both human therapy and veterinary applications. In some aspects, the subject is a mammal, and in other aspects the subject is a human. As used herein, a "mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

The term "pharmaceutical composition" refers to a preparation which is in such form as to permit the biological activity of the active ingredient to be effective, and which contains no additional components which are unacceptably toxic to a subject to which the composition would be administered. Such composition can be sterile. The term "oral pharmaceutical composition" refers to a pharmaceutical composition that can be administered orally. Oral administration is a route of administration where a substance is taken through the mouth. "Per os" abbreviated to P.O. is sometimes used as a direction for medication to be taken orally. Many medications are taken orally because they are intended to have a systemic effect, reaching different parts of the body via the bloodstream, for example.

The term "delivery agent" as used herein refers to carrier compounds or carrier molecules that are useful in the delivery of a therapeutic agent of the present disclosure. The term "oral delivery agent" as used herein refers to carrier compounds or carrier molecules that are useful in the oral delivery of therapeutic agents of the present disclosure.

In some aspects, the pharmaceutical composition of the present disclosure is administered orally. The term "oral," as used herein, and grammatical variants thereof (e.g., orally) comprises any kind of oral delivery routes (comprising buccal, sublabial, and sublingual routes). Medications for oral administration can come in various forms, including oral solid dosage (OSD) forms (e.g., tablets to swallow, chew or dissolve in water or under the tongue; capsules and chewable capsules, e.g., with a coating that dissolves in the stomach or bowel to release the medication there; time-release or sustained-release tablets and capsules which release the medication gradually; powders; or granules), and oral liquid dosage forms (e.g., teas, drops, liquid medications, suspensions, or syrups).

"Administering," as used herein, means to give a composition, e.g., an oral pharmaceutical composition comprising an oligomer (e.g., an antisense oligomer, ASO) or antisense oligonucleotide conjugate (e.g., CIVI 008) disclosed herein to a subject via a pharmaceutically acceptable route, e.g., orally. An "effective amount" of, e.g., e.g., an oral pharmaceutical composition comprising an oligomer (e.g., an antisense oligomer, ASO) or antisense oligonucleotide conjugate (e.g., CIVI 008) disclosed herein, is an amount sufficient to carry out a specifically stated purpose. An "effective amount" can be determined empirically and in a routine manner, in relation to the stated purpose.

"Treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also includes prophylaxis or prevention of a disease or condition or its symptoms thereof.

"Prevent" or "preventing," as used herein, refers to decreasing or reducing the occurrence or severity of a particular outcome. In some aspects, preventing an outcome is achieved through prophylactic treatment. In some aspects, an oral pharmaceutical composition comprising an oligomer (e.g., an antisense oligomer, ASO) or antisense oligonucleotide conjugate (e.g., CIVI 008) disclosed herein is administered to a subject prophylactically. In some aspects, the subject is at risk of developing, e.g., hypercholesterolemia or heart disease.

I. Oral Pharmaceutical Compositions

The present disclosure provides pharmaceutical compositions for oral administration, i.e., oral pharmaceutical compositions or formulations, comprising an antisense oligomer and an oral delivery agent. In some aspects, wherein the antisense oligomer is 16 to 22 contiguous nucleotides in length, wherein the sequence of the antisense oligomer comprises a contiguous sequence 16 nucleotides in length which is 100% complementary to the sequence of SEQ ID NO: 31, wherein the antisense oligomer is a gapmer comprising at least one LNA unit, and wherein the antisense oligomer targets an RNA encoding PCSK9. In some aspects, the antisense oligomer can be conjugated to a moiety capable of targeting a particular tissue, e.g., liver. Thus, in some aspects, the present disclosure provides a pharmaceutical composition for oral administration, i.e., an oral pharmaceutical composition or formulation, comprising an antisense oligonucleotide conjugate and an oral delivery agent, wherein the antisense oligonucleotide conjugate comprises, e.g., (i) an antisense oligomer that is 16 to 22 contiguous nucleotides, wherein the sequence of the antisense oligomer comprises a contiguous sequence 16 nucleotides in length which is 100% complementary to the sequence of SEQ ID NO: 31, and wherein the antisense oligomer is a gapmer comprising at least one LNA unit, and (ii) at least one non-nucleotide or non-polynucleotide moiety covalently attached to said antisense oligomer directly or via a linker positioned between the contiguous oligomer sequence and the non-nucleotide or non-polynucleotide moiety, wherein the antisense oligonucleotide conjugate targets an RNA encoding PCSK9. In some aspects, the oligomer can be any oligomer disclosed in Section II of the present disclosure. In some aspects, the antisense oligonucleotide conjugate can be any oligonucleotide conjugate disclosed in Section III of the present disclosure.

In some aspects, the antisense oligonucleotide conjugate is the molecule set forth in SEQ ID NO: 18 or SEQ ID NO: 19, presented in FIG. 18A. In some aspects, the antisense oligonucleotide conjugate is (GalNAc)$_3$-amino-hexamethylene-5' phosphorothioyl)-2'-O,4'-C-methylene Adenosylyl-(3'>5' O,O-phosphorothioyl)-2'-O,4'-C-methylene Adenosylyl-(3'>5' O,O-phosphorothioyl)-2'-O,4'-C-methylene Thymidinyl-(3'>5' O,O-phosphorothioyl)-2'-deoxyGuanosylyl-(3'>5' O,O-phosphorothioyl)-2'-deoxyCytidinylyl-(3'>5' O,O-phosphorothioyl)-2'-deoxyThymidylyl-(3'>5' O,O-phosphorothioyl)-2'-deoxyAdenosylyl-(3'>5' O,O-phosphorothioyl)-2'-deoxyCytidinylyl-(3'>5' O,O-phosphorothioyl)-2'-deoxyAdenosylyl-(3'>5' O,O-phosphorothioyl)-2'-deoxyAdenosylyl-(3'>5'O,O-phosphorothioyl)-2'-deoxyAdenosylyl-(3'>5' O,O-phosphorothioyl)-2'-deoxyAdenosylyl-(3'>5'O,O-phosphorothioyl)-2'-deoxyCytidinylyl-(3'>5' O,O-phosphorothioyl)-2'-O,4' Cmethylene (5-methyl-Cytidinylyl)-(3'>5' O,O-phosphorothioyl)-2'-O,4'-C-methylene (5-methyl-Cytidinylyl)-(3'>5' O,O-phosphorothioyl)-2'-O,4'-C-methylene Adenosylyl hexadeca sodium salt, i.e., CIVI 008. See also the detailed chemical formula of CIVI 008 on FIG. 18B.

In some aspects, the oral pharmaceutical compositions of the present disclosure comprise an oligomer or oligonucleotide conjugate disclosed herein (e.g., CIVI 008) and an oral delivery agent selected from the group consisting of SNAC, C10, 5-CNAC, hydrates, solvates, or salts thereof, and combinations thereof. In some aspect, the oral delivery agents useful in the present disclosure can include, e.g., agents are any one of the 123 modified amino acids disclosed, e.g., in U.S. Pat. No. 5,866,536, or any one of the 193 modified amino acids described, e.g., in U.S. Pat. No. 5,773,647, or any combination thereof. The contents of the aforementioned U.S. Pat. Nos. 5,773,647 and 5,866,536 are hereby incorporated by reference in their entirety.

In some aspects, the oral delivery agent comprises a single compound (e.g., C8, C10, SNAC, or 5-CNAC). In other aspects, the oral delivery agent comprises a combination of compounds (e.g., any combination of C8, C10, SNAC, or 5-CNAC). In some aspects, the oral delivery agent comprises C8, C10, SNAC, 5-CNAC, 4-CNAB, 4-MOAC, SNAD, 4-HPO (8-(4-hydroxyphenoxy) octanoic acid), 5-PPA (5-phenylpentanoic acid), 2-PHOD (8-(2-hydroxyphenoxy)octyldiethanolamine), 3-TBA (4-m-tolyloxybutyric acid), 2-HPOD (2-(5-pentanoic acid)-5-(2-hydroxyphenyl)-1,3,4-oxadiazole), 7-OPHA (7-oxo-7-phenylheptanoic acid), 3-HPSB (4-(3-hydroxyphenylsulfanyl)butyric acid), 4-IBOA ((4-isopropylbenzyloxy)acetic acid), 3-FPSB (4-(3-fluorophenylsulfonyl)butyric acid), or any combination thereof. See, e.g., FIG. 22.

In some aspects, the SNAC may optionally be replaced with a similar compound, such as SNAD (sodium 10-N-(2-hydroxybenzoyl)aminodecanoic acid). The structure of SNAD differs from that of SNAC only in the length of the fatty acid moiety. In some aspects of the present disclosure, the SNAC may optionally be replaced with a similar compound, wherein the caprylic acid moiety of SNAC is replaced by another fatty acid moiety at least 6 carbon atoms in length, for example, from 6 to 20 carbon atoms in length, optionally from 6 to 18 carbon atoms in length, optionally from 6 to 16 carbon atoms in length, optionally from 6 to 14 carbon atoms in length, optionally from 6 to 12 carbon atoms in length and optionally from 6 to 10 carbon atoms in length. The fatty acid moiety may be saturated (e.g., as are caprylic acid in SNAC and decanoic acid in SNAD) or unsaturated (i.e., comprising at least one unsaturated carbon-carbon bond).

In some aspects, the oral delivery agent comprises N-(8-(2-hydroxybenzoyl)amino)caprylic acid, as shown below.

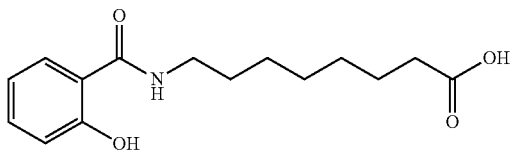

MW = 279.34
MF = C15H21NO4

In some aspects, the oral delivery agent comprises a salt of N-(8-(2-hydroxybenzoyl)amino)caprylic acid. In some aspects, the oral delivery agent comprises a solvate of N-(8-(2-hydroxybenzoyl)amino)caprylic acid. In some aspects, the oral delivery agent comprises a hydrate of N-(8-(2-hydroxybenzoyl)amino)caprylic acid. In some aspects, the oral delivery agent comprises a salt, hydrate, or solvate of N-(8-(2-hydroxybenzoyl)amino)caprylic acid, or any combination thereof.

In some aspects, the salt of N-(8-(2-hydroxybenzoyl)amino)caprylic acid is selected from the group consisting of a sodium salt, a potassium salt, a calcium salt of N-(8-(2-hydroxybenzoyl)amino)caprylic acid, and any combination thereof. In some aspects, the salt of N-(8-(2-hydroxybenzoyl)amino)caprylic acid is a sodium salt. In some aspects, the salt of N-(8-(2-hydroxybenzoyl)amino)caprylic acid is a disodium salt. In some aspects, the salt of N-(8-(2-hydroxybenzoyl)amino)caprylic acid is a monosodium salt (Salcaprozate sodium 203787-91-1, SNAC, sodium 8-(2-hydroxybenzamido)octanoate), as shown below.

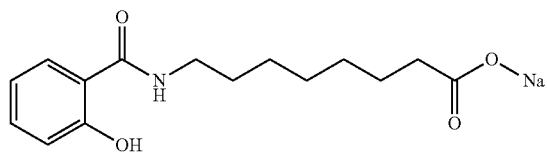

MW = 301.32
MF = C15H2ONNaO4

In some aspects, the oral delivery agent comprises 5-CNAC (N-(5-chlorosalicyloyl)-8-aminocaprylic acid), as shown below

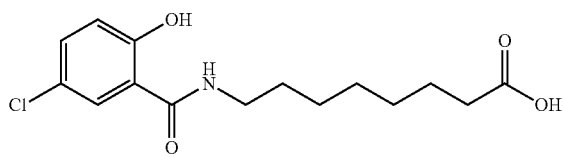 [SMILES: O=C(O)CCCCCCCNC(=O)c1cc(Cl)ccc1O]

In some aspects, the oral delivery agent comprises a salt of N-(5-chlorosalicyloyl)-8-aminocaprylic acid. In some aspects, the oral delivery agent comprises a solvate of N-(5-chlorosalicyloyl)-8-aminocaprylic acid. In some aspects, the oral delivery agent comprises a hydrate of N-(5-chlorosalicyloyl)-8-aminocaprylic acid. In some aspects, the oral delivery agent comprises a salt, hydrate, or solvate of N-(5-chlorosalicyloyl)-8-aminocaprylic acid, or any combination thereof.

In some aspects, the salt of N-(5-chlorosalicyloyl)-8-aminocaprylic acid is selected from the group consisting of a sodium salt, a potassium salt, a calcium salt of N-(5-chlorosalicyloyl)-8-aminocaprylic acid, and any combination thereof. In some aspects, the salt of N-(5-chlorosalicyloyl)-8-aminocaprylic acid is a sodium salt. In some aspects, the salt of N-(5-chlorosalicyloyl)-8-aminocaprylic acid is a disodium salt. In some aspects, the salt of N-(5-chlorosalicyloyl)-8-aminocaprylic acid is a monosodium salt.

In some aspects, the oral delivery agent comprises 4-CNAB (4-[(4-chloro-2-hydroxy-benzoyl)amino]butanoic acid: Salclobuzate), as shown below

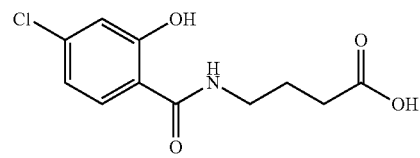 [SMILES: O=C(O)CCCNC(=O)c1ccc(Cl)cc1O]

In some aspects, the oral delivery agent comprises a salt of 4-[(4-chloro-2-hydroxy-benzoyl)amino]butanoic acid. In some aspects, the oral delivery agent comprises a solvate of 4-[(4-chloro-2-hydroxy-benzoyl)amino]butanoic acid. In some aspects, the oral delivery agent comprises a hydrate of 4-[(4-chloro-2-hydroxy-benzoyl)amino]butanoic acid. In some aspects, the oral delivery agent comprises a salt, hydrate, or solvate of 4-[(4-chloro-2-hydroxy-benzoyl)amino]butanoic acid, or any combination thereof.

In some aspects, the salt of 4-[(4-chloro-2-hydroxy-benzoyl)amino]butanoic acid is selected from the group consisting of a sodium salt, a potassium salt, a calcium salt of 4-[(4-chloro-2-hydroxy-benzoyl)amino]butanoic acid, and any combination thereof. In some aspects, the salt of 4-[(4-chloro-2-hydroxy-benzoyl)amino]butanoic acid is a sodium salt. In some aspects, the salt of 4-[(4-chloro-2-hydroxy-benzoyl)amino]butanoic acid is a disodium salt. In some aspects, the salt of 4-[(4-chloro-2-hydroxy-benzoyl)amino]butanoic acid is a monosodium salt.

In some aspects, the oral delivery agent comprises 4-MOAC (N-(8-[4-methoxy-chloro-2-hydroxybenzoyl-amino) octanoic acid), as shown below

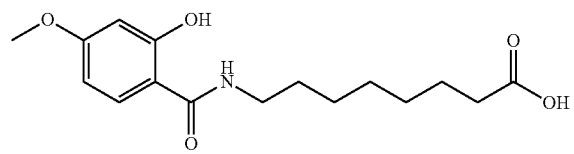 [SMILES: COc1ccc(C(=O)NCCCCCCCC(=O)O)c(O)c1]

In some aspects, the oral delivery agent comprises a salt of N-(8-[4-methoxy-chloro-2-hydroxybenzoyl-amino) octanoic acid. In some aspects, the oral delivery agent comprises a solvate of N-(8-[4-methoxy-chloro-2-hydroxybenzoyl-amino) octanoic acid. In some aspects, the oral delivery agent comprises a hydrate of N-(8-[4-methoxy-chloro-2-hydroxybenzoyl-amino) octanoic acid. In some aspects, the oral delivery agent comprises a salt, hydrate, or solvate of N-(8-[4-methoxy-chloro-2-hydroxybenzoyl-amino) octanoic acid, or any combination thereof.

In some aspects, the salt of N-(8-[4-methoxy-chloro-2-hydroxybenzoyl-amino) octanoic acid is selected from the group consisting of a sodium salt, a potassium salt, a calcium salt of N-(8-[4-methoxy-chloro-2-hydroxybenzoyl-amino) octanoic acid, and any combination thereof. In some aspects, the salt of N-(8-[4-methoxy-chloro-2-hydroxybenzoyl-amino) octanoic acid is a sodium salt. In some aspects, the salt of N-(8-[4-methoxy-chloro-2-hydroxybenzoyl-amino) octanoic acid is a disodium salt. In some aspects, the salt of N-(8-[4-methoxy-chloro-2-hydroxybenzoyl-amino) octanoic acid is a monosodium salt.

In some aspects, the oral delivery agent comprises SNAD (N-(10-[2-hydroxybenzoyl]-amino) decanoic acid), as shown below

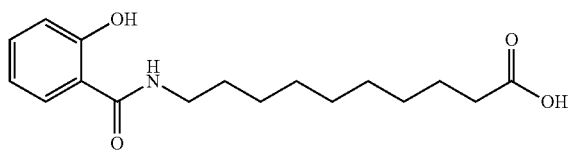 [SMILES: O=C(O)CCCCCCCCCNC(=O)c1ccccc1O]

In some aspects, the oral delivery agent comprises a salt of N-(10-[2-hydroxybenzoyl]-amino) decanoic acid. In some aspects, the oral delivery agent comprises a solvate of N-(10-[2-hydroxybenzoyl]-amino) decanoic acid. In some aspects, the oral delivery agent comprises a hydrate of N-(10-[2-hydroxybenzoyl]-amino) decanoic acid. In some aspects, the oral delivery agent comprises a salt, hydrate, or solvate of N-(10-[2-hydroxybenzoyl]-amino) decanoic acid, or any combination thereof.

In some aspects, the salt of N-(10-[2-hydroxybenzoyl]-amino) decanoic acid is selected from the group consisting of a sodium salt, a potassium salt, a calcium salt of N-(10-[2-hydroxybenzoyl]-amino) decanoic acid, and any combination thereof. In some aspects, the salt of N-(10-[2-hydroxybenzoyl]-amino) decanoic acid is a sodium salt. In some aspects, the salt of N-(10-[2-hydroxybenzoyl]-amino) decanoic acid is a disodium salt. In some aspects, the salt of N-(10-[2-hydroxybenzoyl]-amino) decanoic acid is a monosodium salt.

In some aspects, the oral delivery agent comprises a compound presented in FIG. 22. In some aspects, the oral delivery agent comprises a salt of a compound presented in FIG. 22. In some aspects, the oral delivery agent comprises a solvate of a compound presented in FIG. 22. In some aspects, the oral delivery agent comprises a hydrate of a compound presented in FIG. 22. In some aspects, the oral delivery agent comprises a salt, hydrate, or solvate of a compound presented in FIG. 22, or any combination thereof.

In some aspects, the salt of a compound presented in FIG. 22 is selected from the group consisting of a sodium salt, a potassium salt, a calcium salt of a compound presented in FIG. 22, and any combination thereof. In some aspects, the salt of a compound presented in FIG. 22 is a sodium salt. In some aspects, the salt of a compound presented in FIG. 22 is a disodium salt. In some aspects, the salt of a compound presented in FIG. 22 is a monosodium salt.

See US5650386A, US6399798B2, US7384982B2, US7659311B2, US8003697B2, US8207227B2, US8658695B2, US7544833B2, US7659311, US8003697, US8207227, US8658695, US7384982, US9278123B2, US10086047B2, US20180360918A1, US20110092426A1, US20150283212A1, US8435946B2, US8748383B2, US7569539B2, all of which are herein incorporated by reference in their entireties.

In some aspects, the oral delivery agent comprises a compound of the formula presented below

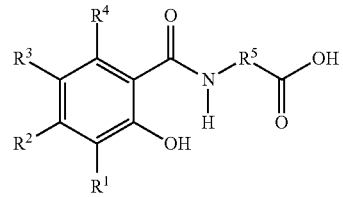

wherein $R^1$, $R^2$, $R^3$, and $R^4$ are independently hydrogen, —OH, —$NR^6R^7$, halogen, $C_1$-$C_4$ alkyl, or $C_1$-$C_4$ alkoxy;

$R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_4$ alkylene); and $R^6$ and $R^7$ are independently hydrogen, oxygen, or $C_1$-$C_4$ alkyl.

In some aspects, the oral delivery agent comprises a compound of formula

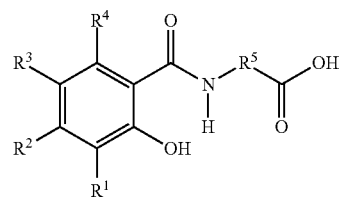

as describes above, wherein the compound is a free acid or a sodium salt, e.g., a monosodium or a disodium salt. In some aspects, the compound is a hydrate or a solvate. In some aspects, the compound is an alcohol solvate. In some aspects, the alcohol solvate is an ethanol solvate. In some aspects, the ethanol solvate is a solvate of a salt. In some aspects, the ethanol solvate is an ethanol solvate of a monosodium salt. In some aspects, the ethanol solvate is an ethanol solvate of a disodium salt. In some aspects, the compound is a hydrate. In some aspects, the hydrate is a hydrate of a salt. In some aspects, the hydrate is a hydrate of a monosodium salt. In some aspects, the hydrate is a hydrate of a disodium salt In some aspects, the oral delivery agents useful in the present disclosure can include medium chain fatty acids (MCFA) such as C8 (caprylic acid), C10 (capric acid), or C12 (lauric acid), a derivative thereof, a pharmaceutically acceptable salt, hydrate, or solvate thereof, or any combination thereof.

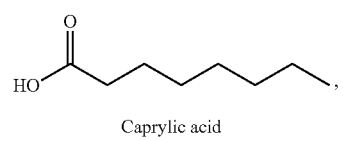

Caprylic acid

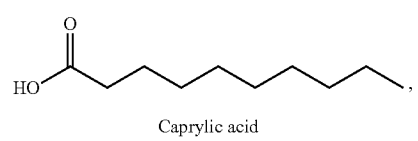

Caprylic acid

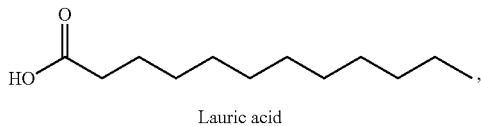
Lauric acid

In some aspects, the oral delivery agent comprises a solvate of the salts of C8, C10, SNAC, or 5-CNAC. The term "solvate" as used herein includes, but is not limited to, a molecular or ionic complex of molecules or ions of a solvent with molecules or ions of the delivery agent compound or salt thereof, or hydrate or solvate thereof.

In some aspects, the oral delivery agent comprises a hydrate of the salts of C8, C10, SNAC, or 5-CNAC. The term "hydrate" as used herein includes, but is not limited to, (i) a substance containing water combined in the molecular form and (ii) a crystalline substance containing one or more molecules of water of crystallization or a crystalline material containing free water.

In some aspects, the oral delivery agent comprises a solvate of a salt of C8, C10, SNAC, or 5-CNAC, wherein the salt is a sodium salt, potassium salt, calcium salt, or a combination thereof. In some aspects, the oral delivery agent comprises a solvate of a salt of C8, C10, SNAC, or 5-CNAC wherein the salt is a sodium salt.

In some aspects, the oral delivery agent comprises a solvate of a salt of C8, C10, SNAC, or 5-CAN, wherein the salt is a monosodium salt. In some aspects, the oral delivery agent comprises a sodium salt of C8, e.g., monosodium caprate. In some aspects, the oral delivery agent comprises a sodium salt of C10, e.g., monosodium caprylate. In some aspects, the oral delivery agent comprises a sodium salt of SNAC, e.g., monosodium SNAC. In some aspects, the oral delivery agent comprises a sodium salt of 5-CNAC, e.g., monosodium 5-CNAC.

In some aspects, the oral delivery agent comprises an alcohol solvate of a salt of C8, C10, SNAC, or 5-CNAC, wherein the salt is a sodium salt. In some aspects, the oral delivery agent comprises an alcohol solvate of the salts of C8, C10, SNAC, or 5-0CNAC, wherein the salt is a monosodium salt. In some aspects, the oral delivery agent comprises a hydrate of a salt of C8, C10, SNAC, or 5-CNAC, wherein the salt is a sodium salt. In some aspects, the oral delivery agent comprises a hydrate of a salt of C8, C10, SNAC, or 5-CNAC, wherein the salt is a monosodium salt. In some aspects, the oral delivery agent comprises a hydrate of a salt of C8, C10, SNAC, or 5-CNAC, wherein the salt is a sodium salt, and the hydrate is a monohydrate.

Methods to prepare sodium salts, alcohol solvates, and hydrates are described, e.g., in Int'l Publ. WO 00/059863, which is herein incorporated by reference in its entirety. For example, a sodium salt may be prepared from the ethanol solvate by evaporating or drying the ethanol solvate by methods known in the art to form the anhydrous sodium salt. Drying is generally carried out at a temperature of from about 80° C. to about 120° C., e.g., from about 85° C. to about 90° C. In some aspects, drying is conducted at about 85° C. The drying step is generally performed at a pressure of about 660 mm Hg (8.8 kPa) or greater. The anhydrous sodium salt generally contains less than about 5% by weight of ethanol and preferably less than about 2% by weight of ethanol, based on 100% total weight of anhydrous sodium salt.

The sodium salt of an oral delivery agent disclosed herein can also be prepared by making a slurry of the delivery agent in water and adding aqueous sodium hydroxide, sodium alkoxide or the like. Suitable sodium alkoxides include, but are not limited to, sodium methoxide, sodium ethoxide, and combinations thereof. A still further method of preparing the sodium salt is by reacting the delivery agent with sodium hydroxide to yield the sodium salt.

The sodium salt can be isolated as a solid by concentrating the solution containing the sodium salt to a thick paste by vacuum distillation. This paste may be dried in a vacuum oven to obtain the sodium salt of the delivery agent as a solid. The solid can also be isolated by spray drying an aqueous solution of the disodium salt. The oral delivery agents disclosed herein may be prepared by methods known in the art, e.g., as mentioned above, by methods described in U.S. Pat. Nos. 5,773,647 and 5,866,536, which are herein incorporated by reference in their entireties.

Ethanol solvates of the oral delivery agent molecules disclosed herein (e.g., C8, C10, SNAC, 5-CNAC, or any combination thereof) include, but are not limited to, a molecular or ionic complex of molecules or ions of ethanol solvent with molecules or ions of the sodium salt of the delivery agent. Typically, the ethanol solvate contains about one ethanol molecule or ion for every molecule of sodium salt of the delivery agent.

Ethanol solvates of sodium salts of the delivery agents can be prepared by dissolving the delivery agent in ethanol. The delivery agent/ethanol solution is then reacted with a molar excess of a sodium containing salt, such as a monosodium containing salt, relative to delivery agent, i.e., for every mole of delivery agent there is more than one mole of sodium cations, yielding the ethanol solvate. Suitable monosodium salts include, but are not limited to, sodium hydroxide; sodium alkoxides, such as sodium methoxide and sodium ethoxide; and any combination of the foregoing. Generally, the reaction is performed at or below the reflux temperature of the mixture, such as at ambient temperature. The ethanol solvate is then recovered by methods known is the art, such as, concentration of the resulting slurry at atmospheric distillation, cooling the concentrated slurry and filtering the solid. The recovered solid can then be vacuum dried to obtain the ethanol solvate.

Hydrates of the sodium salts of the delivery agents may be prepared by drying the ethanol solvate to from an anhydrous disodium salt, as described above, and hydrating the anhydrous sodium salt. In some aspects, the monohydrate of the sodium salt is formed. Since the anhydrous sodium salts are very hygroscopic, the hydrates form upon exposure to atmospheric moisture. Generally, the hydrating step is performed at from about ambient temperature to about 50° C., preferably ambient temperature to about 30° C. and in an environment having at least 50% relative humidity. Alternatively, the anhydrous sodium salt may be hydrated with steam.

The oral pharmaceutical compositions of the present disclosure typically contain an effective amount of one or more of the delivery agents (e.g., C8, C10, SNAC, 5-CNAC, or any combination thereof) disclosed herein, i.e., an amount sufficient to deliver the active agent (e.g., CIVI 008) for the desired effect. Generally, the oral delivery agent (e.g., C8, C10, SNAC, 5-CNAC, or any combination thereof) is present in an amount of about 2.5% to about 99.4% by weight. In some aspects, the oral delivery agent (e.g., C8, C10, SNAC, 5-CNAC, or any combination thereof) is present in an amount of about 15% to about 75% by weight. In some aspects, the oral delivery agent (e.g., C8, C10, SNAC, 5-CNAC, or any combination thereof) is present in an amount of least about 25%, at least about 30%, or at least about 35% but equal to or less than about 60 or about 70% by weight. Accordingly, in some aspects the oral delivery agent (e.g., C8, C10, SNAC, 5-CNAC, or any combination thereof) is present in an amount of least about 25%, at least about 30%, at least about 35%, at least about 40%, at least about 45%, at least about 50%, at least about 55%, at least about 60%, at least about 65%, or at least about 70% by weight. In some aspects, the oral delivery agent (e.g., C8, C10, SNAC, 5-CNAC, or any combination thereof) is present in an amount of about 25%, about 30%, about 35%, about 40%, about 45%, about 50%, about 55%, about 60%, about 65%, or about 70% by weight.

In some aspects, the oral pharmaceutical composition of the present disclosure is administered as a single dose. The term "single dose" means that the oral pharmaceutical composition according to the invention comprising an oligomer or oligonucleotide conjugate disclosed herein (e.g., CIVI 008) and an oral delivery agent selected from the group consisting of SNAC, C10, or 5-CNAC, hydrates, solvates, or salts thereof, and combinations thereof, e.g., in form of an oral unit dose, is administered to a human or animal patient in a single dose.

In some aspects, the oral pharmaceutical composition of the present disclosure is administered as multiple doses. The term "multiple dose" means that the oral pharmaceutical composition according to the invention comprising an oligomer or oligonucleotide conjugate disclosed herein (e.g., CIVI 008) and an oral delivery agent selected from the group consisting of SNAC, C10, or 5-CNAC, hydrates, solvates, or salts thereof, and combinations thereof, e.g., in form of an oral unit dose, is administered to a human or animal patient in at least two doses in accordance with the dosing interval appropriate for that composition.

As used herein, the term "oral unit-dose form" refers to physically discrete units suitable for human and animal consumption and packaged individually as is known in the art. It is contemplated for purposes of the present disclosure that dosage forms comprising therapeutically effective amounts of oligomer or oligonucleotide conjugate disclosed herein (e.g., CIVI 008) and an oral delivery agent may include one or more unit doses (e.g., tablets, capsules) to achieve the therapeutic effect.

Oral dosage forms (e.g., tablets or capsules) of the oral pharmaceutical compositions of the present disclosure (e.g., an antisense oligonucleotide conjugate such as CIVI 008 combined with an oral delivery agent such as SNAC, C10, or 5-CNAC) can be administered from about 5 minutes to about 60 minutes prior to a meal. Oral dosage forms of the oral pharmaceutical compositions of the present disclosure (e.g., an antisense oligonucleotide conjugate such as CIVI 008 combined with an oral delivery agent such as SNAC, C10, or 5-CNAC) can be administered from about 30 minutes to about 60 minutes prior to a meal. Oral dosage forms (e.g., tablets or capsules) of the oral pharmaceutical compositions of the present disclosure (e.g., an antisense oligonucleotide conjugate such as CIVI 008 combined with an oral delivery agent such as SNAC, C10, or 5-CNAC) can be administered from about 45 minutes to about 90 minutes prior to a meal. Oral dosage forms (e.g., tablets or capsules) of the oral pharmaceutical compositions of the present disclosure (e.g., an antisense oligonucleotide conjugate such as CIVI 008 combined with an oral delivery agent such as SNAC, C10, pr 5-CNAC) can be administered from about 60 minutes (1 hour) to about 120 minutes (2 hours) prior to a meal.

In some aspects, the oral pharmaceutical composition of the present disclosure (e.g., an antisense oligonucleotide conjugate such as CIVI 008 combined with an oral delivery agent such as SNAC, C10, or 5-CNAC) can be administered at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 115, or at least about 120 minutes prior to a meal.

In some aspects, the oral pharmaceutical composition of the present disclosure (e.g., an antisense oligonucleotide conjugate such as CIVI 008 combined with an oral delivery agent such as SNAC, C10, or 5-CNAC) is administered about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, or about 120 minutes prior to a meal.

In some aspects, the oral pharmaceutical composition of the present disclosure (e.g., an antisense oligonucleotide conjugate such as CIVI 008 combined with an oral delivery agent such as SNAC, C10, or 5-CNAC) is administered at least about 30 minutes before the intake of food. In some aspects, the oral pharmaceutical composition of the present disclosure (e.g., an antisense oligonucleotide conjugate such as CIVI 008 combined with an oral delivery agent such as SNAC, C10, or 5-CNAC) is administered at least about 45 minutes before the intake of food. In some aspects, the oral pharmaceutical composition of the present disclosure (e.g., an antisense oligonucleotide conjugate such as CIVI 008 combined with an oral delivery agent such as SNAC, C10, or 5-CNAC) is administered at least about 60 minutes before the intake of food. In some aspects, the oral pharmaceutical composition of the present disclosure (e.g., an antisense oligonucleotide conjugate such as CIVI 008 combined with an oral delivery agent such as SNAC, C10, or 5-CNAC) is administered at least about 2 hours before the intake of food.

The oral pharmaceutical compositions of the present disclosure (e.g., an antisense oligonucleotide conjugate such as CIVI 008 combined with an oral delivery agent such as SNAC, C10, or 5-CNAC) can be provided in a solid form. In some aspects, the solid form is a capsule, e.g., a soft-gel capsule or liquid filled capsule (liquid capsule). The oral pharmaceutical compositions of the present disclosure can also be provided as a tablet, caplet or other solid oral dosage form, all of which can be prepared by methods well known in the art.

In some aspects, the oral dosage form (e.g., a tablet or a capsule) can have a weight between about 5 mg and about 1000 mg, about 10 mg and about 500 mg, about 10 mg and about 250 mg, about 100 mg and about 200 mg, or about 250 mg and about 500 mg. In some aspects, the weight of the oral dosage form (e.g., a tablet or a capsule) is about 5 mg, about 10 mg, about 20 mg, about 25 mg, about 50 mg, about 100 mg, about 200 mg, about 250 mg, about 375 mg, about 500 mg, about 750 mg, or about 1000 mg.

In some aspects, the amount of antisense oligomer or antisense oligonucleotide conjugate (e.g. CIVI 008) in the oral dosage form (e.g., a tablet or a capsule) is in the range of about 1 mg to about 100 mg, about 5 mg to about 100 mg, about 10 mg to about 100 mg, about 20 mg to about 100 mg, or about 20 mg and about 50 mg.

In some aspects of the present disclosure, CIVI 008 is formulated in a capsule form, wherein the capsule is a hard shell gelatin capsule. In some aspects, the capsule is a size 0 capsule (Closed Length 21.7 mm×External Diameter 7.6 mm). In some aspects, the capsule is a size 4 capsule (Closed Length 14.3 mm×External Diameter 5.05 mm). In some aspects, the capsule contains between about 5 mg and about 30 mg of CIVI 008 (cepadacursen sodium), e.g., about 5 mg, about 10 mg, about 15 mg, about 20 mg, about 25 mg, or about 30 mg of CIVI 008. In some aspects, the capsule contains about 100 mg or about 200 mg of 5-CNAC, e.g., about 100 mg, about 125 mg, about 150 mg, about 175 mg, or about 200 mg of 5-CNAC. In some aspects, the filling of the capsule is manufactured by dry blending the ingredients (i.e., dry CIVI 008 and dry 5-CNAC). In some aspects, the filling of the capsule is manufactured by freeze-drying a co-dissolved mixture of the ingredients (i.e., CIVI 008 and 5-CNAC). In some aspects, the capsule comprises about 10 mg CIVI 008 and about 100 mg 5-CNAC. In some aspects, the capsule comprises about 20 mg CIVI 008 and about 200 mg 5-CNAC. In some aspects, the capsule comprises about 5 mg CIVI 008 and about 200 mg 5-CNAC. In some aspects, the capsule comprises about 25 mg CIVI 008 and about 200 mg 5-CNAC. In some aspects, the capsule comprises about 30 mg CIVI 008 and about 200 mg 5-CNAC.

In some, the present disclosure provides a pharmaceutical composition, e.g., in a capsule form, comprising, e.g., about 10 mg CIVI 008 and about 100 mg 5-CNAC, about 20 mg CIVI 008 and about 200 mg 5-CNAC, about 5 mg CIVI 008 and about 200 mg 5-CNAC, about 25 mg CIVI 008 and about 200 mg 5-CNAC, or about 30 mg CIVI 008 and about 200 mg 5-CNAC, wherein the administration of the pharmaceutical composition to a subject results in an increase of the mean $AUC_{0-50}$ of at least about 10%, at least about 20%, at least about 30%, at least about 40%, at least about 50%, at least about 60%, at least about 70%, at least about 80%, at least about 90%, or at least about 100% with respect to the mean $AUC_{0-50}$ measured when a corresponding pharmaceutical composition comprising SNAC instead of 5-CNAC is administered to the subject. In a specific aspect, the increase of the mean $AUC_{0-50}$ with respect to the mean $AUC_{0-50}$ measured when a corresponding pharmaceutical composition comprising SNAC instead of 5-CNAC is administered to the subject is about 80%.

The term "a corresponding pharmaceutical composition comprising SNAC instead of 5-CNAC" as used herein refers to a reference pharmaceutical composition that comprises the same components as a test pharmaceutical compositions, wherein the only different between the reference pharmaceutical composition and the test composition is the substitution of SNAC present in the reference pharmaceutical composition with 5-CNAC. For example, if the test pharmaceutical composition was in a size 4 capsule containing 10 mg CIVI 008 and 100 mg 5-CNAC, the corresponding reference pharmaceutical composition would be also in a size 4 capsule and would contain 10 mg CIVI 008 and 100 mg SNAC.

In some aspects, the present disclosure provides a pharmaceutical composition, e.g., in a capsule form, comprising, e.g., about 10 mg CIVI 008 and about 100 mg 5-CNAC, about 20 mg CIVI 008 and about 200 mg 5-CNAC, about 5 mg CIVI 008 and about 200 mg 5-CNAC, about 25 mg CIVI 008 and about 200 mg 5-CNAC, or about 30 mg CIVI 008 and about 200 mg 5-CNAC, wherein the administration of the pharmaceutical composition to a subject results in an increase of the mean $C_{max}$ of at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, or at least about 150% with respect to the mean $C_{max}$ a measured when a corresponding pharmaceutical composition comprising SNAC instead of 5-CNAC is administered to the subject. In a specific aspect, the increase of the mean $C_{max}$ with respect to the mean $C_{max}$ measured when a corresponding pharmaceutical composition comprising SNAC instead of 5-CNAC is administered to the subject is about 110%.

In some aspects, the amount of antisense oligomer or antisense oligonucleotide conjugate (e.g. CIVI 008) in the oral dosage form (e.g., a tablet or a capsule) is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 73, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, or about 100 mg.

In some aspects, the oral pharmaceutical composition of the present disclosure can comprise, in addition to an antisense oligonucleotide conjugate (e.g., CIVI 008) disclosed herein and an oral delivery agent (e.g., SNAC, C10, or 5-CNAC), at least one pharmaceutically acceptable excipient or combination thereof. In some aspects, the at least one pharmaceutically acceptable excipient or combination thereof, e.g., in amounts customarily employed, is selected from the group consisting of, but not limited to, a pH adjuster, a preservative, a flavorant, a taste-masking agent, a fragrance, a humectant, a tonicifier, a colorant, a surfactant, a plasticizer, a lubricant such as magnesium stearate, a flow aid, a compression aid, a solubilizer, an excipient, a diluent such as microcrystalline cellulose (e.g., Avicel PH 102), or any combination thereof. In some aspects, the oral pharmaceutical composition of the present disclosure (e.g., an antisense oligonucleotide conjugate such as CIVI 008 combined with an oral delivery agent such as SNAC, C10, or 5-CNAC) comprises microcrystalline cellulose. In some aspects, the oral pharmaceutical composition of the present disclosure (e.g., an antisense oligonucleotide conjugate such as CIVI 008 combined with an oral delivery agent such as SNAC, C10, or 5-CNAC) comprises phosphate buffer salts, citric acid, glycols, other dispersing agents, or any combination thereof.

In some aspects, the oral pharmaceutical composition of the present disclosure (e.g., an antisense oligonucleotide conjugate such as CIVI 008 combined with an oral delivery agent such as SNAC, C10, or 5-CNAC) can include a diluent, e.g., as microcrystalline cellulose (e.g., Avicel), and a lubricant, e.g., magnesium stearate. In some aspects, the oral pharmaceutical composition of the present disclosure (e.g., an antisense oligonucleotide conjugate such as CIVI 008 combined with an oral delivery agent such as SNAC, C10, or 5-CNAC) can comprise povidone and/or crospovidone. The crospovidone can be any crospovidone. Crospovidone is a synthetic crosslinked homopolymer of N-vinyl-2-pyrrolidinone, also called 1-ethenyl-2-pyrrolidinone, having a molecular weight of 1,000,000 or more. Commercially available crospovidones include Polyplasdone XL, Polyplasdone XL-10, Polyplasdone INF-10 available from ISP, Kollidon CL, available from BASF Corporation. In some aspect, the crospovidone is Polyplasdone XL. Povidone is a synthetic polymer consisting of linear 1-vinyl-2-pyrrolidinone groups having a molecular weight generally between 2,500 and 3,000,000. Commercially available povidones include Kollidon K-30, Kollidon K-90F available from BASF Corporation and Plasdone K-30 and Plasdone K-29/32, available from ISP. As mentioned above, the crospovidones and povidones are commercially available. Alternatively, they may be synthesized by known processes. The crospovidone, povidone or combination thereof can be present in the oral pharmaceutical composition of the present disclosure in an amount of from 0.5 to 50 percent by weight relative to the total weight of the overall oral pharmaceutical composition, e.g., from about 2 to about 25 percent, or from about 5 to about 20 percent by weight relative to the total weight of the oral pharmaceutical composition.

In some aspects, an oral dosage form (e.g., a tablet or a capsule) comprising an oral pharmaceutical composition of the present disclosure (e.g., an antisense oligonucleotide conjugate such as CIVI 008 and an oral delivery agent such as SNAP or C10, and optional a statin) can comprise a coating, e.g., an enteric coatings and/or a pH sensitive coating, and optionally comprise enzyme-inhibiting agents. Accordingly, in some aspects, the solid oral dosage form does not substantially disintegrate or dissolve in the stomach, but does substantially disintegrate or dissolve in the intestine. In some aspect, the oral pharmaceutical composition of the present disclosure (e.g., an antisense oligonucleotide conjugate such as CIVI 008 and an oral delivery agent such as SNAP, C10, or 5-CNAC, and optional a statin) can further comprise one or more enzyme-inhibiting agents that prevent enzymatic degradation of active agents in the pharmaceutical formulation, for example, an antisense oligonucleotide conjugate (e.g., CIVI 008) and/or an optional therapeutic agent such as a statin, in the stomach or the upper intestine.

In some aspects, an oral pharmaceutical composition of the present disclosure or an oral dosage form disclosed herein (e.g., a tablet or a capsule) is enterically coated to retard disintegration in the stomach. Enteric coatings include, but are not limited to, hydroxypropyl methylcellulose phthalate, hydroxypropyl methylcellulose acetate succinate, polyvinyl acetate phthalate, cellulose acetate trimellitate, cellulose acetate phthalate, poly(methacrylic acid-ethylacrylate), poly(methacrylic acid-methyl methacrylate), and combinations thereof. In yet another aspect, the oral pharmaceutical formulations may be formulated to erode from the surface of oral the dosage form, rather than disintegrate.

In some aspects, an oral pharmaceutical composition of the present disclosure or an oral dosage form disclosed herein (e.g., a tablet or a capsule) further comprises a pH sensitive coating, e.g., a pH-sensitive polymer, which protects the oral pharmaceutical composition or oral dosage form thereof from the acidic environment in the stomach. In some aspects, the pH-sensitive polymer comprises cellulose, acrylic acid, or a derivative thereof. In some aspects, the pH sensitive coating comprises a pH-sensitive hydrogel, pH-activated drug delivery system, pH-sensitive liposome, micelle or lipid nanoparticle, pH-sensitive microsphere, pH-sensitive nanoparticle, or any combination thereof.

Enteric (gastro-resistant) coatings, pH sensitive coatings, enzyme inhibiting agent, and gelatin based formulations used, for example, in liquid or gel capsules are described more in detail below.

In some aspects, oral pharmaceutical compositions of the present disclosure can comprise, in addition to an antisense oligonucleotide conjugate (e.g., CIVI 008) disclosed herein and an oral delivery agent (e.g., SNAC, C10, or 5-CNAC), a second therapeutically active compound (therapeutic agent) selected from the group consisting of a statin (e.g., lovastatin, cerivastatin, pravastatin, atorvastatin, simvastatin, rosuvastatin, fluvastatin, or a combination thereof), ezetimibe, a bile sequestering resin, nicotinic acid, a fibric acid derivative, probucol, neomycin, dextrothyroxine, a plant stanol ester, a cholesterol absorption inhibitor, implitapide, an inhibitor of bile acid transporters, a regulator of hepatic CYP7a, an estrogen replacement therapeutic, and an anti-inflammatory. In general, the oral pharmaceutical compositions of the present disclosure can comprise, in addition to an antisense oligonucleotide conjugate (e.g., CIVI 008) disclosed herein and an oral delivery agent (e.g., SNAC, C10, or 5-CNAC), a second therapeutically active compound used in the art to treat a disease or condition associate with an increase in PCSK9 expression and/or PCSK9 activity.

In some aspects, the present disclosure provides an in vitro method of reducing expression levels and/or activity of PCSK9 in a cell comprising administering an effective amount of an oral pharmaceutical composition of the present disclosure comprising, e.g., an antisense oligonucleotide conjugate (e.g., CIVI 008) disclosed herein, an oral delivery agent (e.g., SNAC, C10, or 5-CNAC), and optionally a second therapeutic agent such as a statin.

The present disclosure also provides a method of reducing PCSK9 expression levels and/or PCSK9 activity levels in a subject in need thereof comprising administering an effective amount of a pharmaceutical composition of an oral pharmaceutical composition of the present disclosure comprising, e.g., an antisense oligonucleotide conjugate (e.g., CIVI 008) disclosed herein, an oral delivery agent (e.g., SNAC, C10, or 5-CNAC), and optionally a second therapeutic agent such as a statin. Also provided is a method of reducing cholesterol levels in a subject in need thereof comprising administering to said subject an effective amount of an oral pharmaceutical composition of the present disclosure comprising, e.g., an antisense oligonucleotide conjugate (e.g., CIVI 008) disclosed herein, an oral delivery agent (e.g., SNAC, C10, or 5-CNAC), and optionally a second therapeutic agent such as a statin.

The oral pharmaceutical compositions of the present disclosure can be prepared by conventional methods e.g. by blending a mixture of the active agent or active agents, the oral delivery agent, and other ingredients, kneading, and filling into capsules or, instead of filling into capsules, molding followed by further tableting or compression-molding to give tablets. In addition, a solid dispersion may be formed by known methods followed by further processing to form a tablet or capsule. In some aspects, the ingredients of the oral pharmaceutical compositions of the present disclosure are homogeneously or uniformly mixed throughout the solid dosage form.

The term "capsule" as used herein is intended to mean a pharmaceutical preparation comprising a hard or soft shell (e.g., a gelatin shell) typically containing a single dose of active substance (e.g., CIVI 008). In one aspect, the capsule is intended for oral administration. In some aspects, the capsule shell (also known as capsule body) will disintegrate in the stomach after ingestion (e.g., swallowing) to release the capsule contents (e.g., a dry blend of disclosed herein comprising, e.g., CIVI 008 and 5-CNAC).

As used herein, the term dry blending the term "dry blending" means thoroughly mixing several components together (e.g., CIVI 800 and 5-CNAC) in the absence of a liquid medium. In some aspects, a component of the dry blend (e.g., CIVI 800, 5-CNAC, or both) can be in powder form. In some aspects, a component of the dry blend (e.g., CIVI 800 and 5-CNAC) can be in a particulate form, e.g., granulated.

In some aspects, the present disclosure provides a pharmaceutical composition comprising 10 mg of CIVI 008 (cepadacursen) and 100 mg of 5-CNAC, wherein both components are in a dry blend. In some aspects, the present disclosure provides a pharmaceutical composition comprising 20 mg of CIVI 008 (cepadacursen) and 200 mg of 5-CNAC, wherein both components are in a dry blend. In some aspects, the present disclosure provides a pharmaceutical composition comprising 5 mg of CIVI 008 (cepadacursen) and 200 mg of 5-CNAC, wherein both components are in a dry blend. In some aspects, the present disclosure provides a pharmaceutical composition comprising 10 mg of CIVI 008 (cepadacursen) and 200 mg of 5-CNAC, wherein both components are in a dry blend. In some aspects, the present disclosure provides a pharmaceutical composition comprising 25 mg of CIVI 008 (cepadacursen) and 200 mg of 5-CNAC, wherein both components are in a dry blend. In some aspects, the present disclosure provides a pharmaceutical composition comprising 30 mg of CIVI 008 (cepadacursen) and 200 mg of 5-CNAC, wherein both components are in a dry blend.

In some aspects, the present disclosure provides a capsule (e.g., a hard shell gelatin capsule enterically coated) comprising 10 mg of CIVI 008 (cepadacursen) and 100 mg of 5-CNAC, wherein both components are in a dry blend. In some aspects, the present disclosure provides a capsule comprising 20 mg of CIVI 008 (cepadacursen) and 200 mg of 5-CNAC, wherein both components are in a dry blend. In some aspects, the present disclosure provides a capsule comprising 5 mg of CIVI 008 (cepadacursen) and 200 mg of 5-CNAC, wherein both components are in a dry blend. In some aspects, the present disclosure provides a capsule comprising 10 mg of CIVI 008 (cepadacursen) and 200 mg of 5-CNAC, wherein both components are in a dry blend. In some aspects, the present disclosure provides a capsule comprising 25 mg of CIVI 008 (cepadacursen) and 200 mg of 5-CNAC, wherein both components are in a dry blend. In some aspects, the present disclosure provides a capsule comprising 30 mg of CIVI 008 (cepadacursen) and 200 mg of 5-CNAC, wherein both components are in a dry blend.

In some aspects, the present disclosure provides a method of treating a disease or condition caused by high expression levels and/or activity of PCSK9 in a subject in need thereof comprising administering an effective amount of a pharmaceutical composition comprising 10 mg of CIVI 008 (cepadacursen) and 100 mg of 5-CNAC, wherein both components are in a dry blend, and optionally wherein the components are in a capsule (e.g., a hard shell gelatin capsule enterically coated). In some aspects, the present disclosure provides a method of treating a disease or condition caused by high expression levels and/or activity of PCSK9 in a subject in need thereof comprising administering an effective amount of a pharmaceutical composition comprising 20 mg of CIVI 008 (cepadacursen) and 200 mg of 5-CNAC, wherein both components are in a dry blend, and optionally wherein the components are in a capsule. In some aspects, the present disclosure provides a method of treating a disease or condition caused by high expression levels and/or activity of PCSK9 in a subject in need thereof comprising administering an effective amount of a pharmaceutical composition comprising 5 mg of CIVI 008 (cepadacursen) and 200 mg of 5-CNAC, wherein both components are in a dry blend, and optionally wherein the components are in a capsule. In some aspects, the present disclosure provides a method of treating a disease or condition caused by high expression levels and/or activity of PCSK9 in a subject in need thereof comprising administering an effective amount of a pharmaceutical composition comprising 10 mg of CIVI 008 (cepadacursen) and 200 mg of 5-CNAC, wherein both components are in a dry blend, and optionally wherein the components are in a capsule. In some aspects, the present disclosure provides a method of treating a disease or condition caused by high expression levels and/or activity of PCSK9 in a subject in need thereof comprising administering an effective amount of a pharmaceutical composition comprising 25 mg of CIVI 008 (cepadacursen) and 200 mg of 5-CNAC, wherein both components are in a dry blend, and optionally wherein the components are in a capsule. In some aspects, the present disclosure provides a method of treating a disease or condition caused by high expression levels and/or activity of PCSK9 in a subject in need thereof comprising administering an effective amount of a pharmaceutical composition comprising 30 mg of CIVI 008 (cepadacursen) and 200 mg of 5-CNAC, wherein both components are in a dry blend, and optionally wherein the components are in a capsule.

In some aspects, the present disclosure provides a pharmaceutical composition comprising CIVI 008 (cepadacursen) and 5-CNAC at a ratio of 1:5, 1:6, 1:7, 1:8, 1:9, 1:10, 1:15, 1:20, 1:30, 1:40, or 1:50 wherein both components are in a dry blend. In some aspects, the present disclosure provides a pharmaceutical composition comprising CIVI 008 (cepadacursen) and 5-CNAC at a ratio of 1:5 wherein both components are in a dry blend. In some aspects, the present disclosure provides a pharmaceutical composition comprising CIVI 008 (cepadacursen) and 5-CNAC at a ratio of 1:10 wherein both components are in a dry blend. In some aspects, the present disclosure provides a pharmaceutical composition comprising CIVI 008 (cepadacursen) and 5-CNAC at a ratio of 1:20 wherein both components are in a dry blend. In some aspects, the present disclosure provides a pharmaceutical composition comprising CIVI 008 (cepadacursen) and 5-CNAC at a ratio of 1:40 wherein both components are in a dry blend.

In some aspects, the present disclosure provides a capsule comprising CIVI 008 (cepadacursen) and 5-CNAC at a ratio of 1:5, 1:6, 1:7, 1:8, 1:9, 1:10, 1:15, 1:20, 1:30, 1:40, or 1:50 wherein both components are in a dry blend. In some aspects, the present disclosure provides a capsule comprising CIVI 008 (cepadacursen) and 5-CNAC at a ratio of 1:5 wherein both components are in a dry blend. In some aspects, the present disclosure provides a capsule comprising CIVI 008 (cepadacursen) and 5-CNAC at a ratio of 1:10 wherein both components are in a dry blend. In some aspects, the present disclosure provides a capsule comprising CIVI 008 (cepadacursen) and 5-CNAC at a ratio of 1:20 wherein both components are in a dry blend. In some aspects, the present disclosure provides a capsule comprising CIVI 008 (cepadacursen) and 5-CNAC at a ratio of 1:40 wherein both components are in a dry blend.

In some aspects, the present disclosure provides a method of treating a disease or condition caused by high expression levels and/or activity of PCSK9 in a subject in need thereof comprising administering an effective amount of a pharmaceutical composition comprising CIVI 008 (cepadacursen) and 5-CNAC at a ratio of 1:5, 1:6, 1:7, 1:8, 1:9, 1:10, 1:15, 1:20, 1:30, 1:40, or 1:50 wherein both components are in a dry blend, and optionally wherein the components are in a capsule. In some aspects, the present disclosure provides a method of treating a disease or condition caused by high expression levels and/or activity of PCSK9 in a subject in need thereof comprising administering an effective amount of a pharmaceutical composition comprising CIVI 008 (cepadacursen) and 5-CNAC at a ratio of 1:5 wherein both components are in a dry blend, and optionally wherein the components are in a capsule. In some aspects, the present disclosure provides a method of treating a disease or condition caused by high expression levels and/or activity of PCSK9 in a subject in need thereof comprising administering an effective amount of a pharmaceutical composition comprising CIVI 008 (cepadacursen) and 5-CNAC at a ratio of 1:10 wherein both components are in a dry blend, and optionally wherein the components are in a capsule. In some aspects, the present disclosure provides a method of treating a disease or condition caused by high expression levels and/or activity of PCSK9 in a subject in need thereof comprising administering an effective amount of a pharmaceutical composition comprising CIVI 008 (cepadacursen) and 5-CNAC at a ratio of 1:20 wherein both components are in a dry blend, and optionally wherein the components are in a capsule. In some aspects, the present disclosure provides a method of treating a disease or condition caused by high expression levels and/or activity of PCSK9 in a subject in need thereof comprising administering an effective amount of a pharmaceutical composition comprising CIVI 008 (cepadacursen) and 5-CNAC at a ratio of 1:40 wherein both components are in a dry blend, and optionally wherein the components are in a capsule.

The present disclosure also provides a kit comprising an oral pharmaceutical composition of the present disclosures (e.g., comprising CIVI 008 and an oral delivery agent such as SNAC or 5-CNAC) and written instructions indicating, e.g., that the oral pharmaceutical composition may be taken prior to the consumption of food.

In some aspects, oral pharmaceutical compositions of the present disclosure comprise an antisense oligonucleotide conjugate comprising an antisense oligomer that is 16 to 22 contiguous nucleotides in length, wherein the sequence of the antisense oligomer comprises a contiguous sequence 16 nucleotides in length which is 100% complementary to the sequence of SEQ ID NO: 31 (or another suitable PCSK9 target region disclosed herein), and wherein the antisense oligomer is a gapmer (e.g., a 3-10-3 gapmer) comprising at least one LNA unit and at least one non-nucleotide or non-polynucleotide moiety (e.g., a liver targeting moiety such as GalNAc) covalently attached to said antisense oligomer directly or via a linker positioned between the contiguous oligomer sequence and the non-nucleotide or non-polynucleotide moiety, wherein the antisense oligonucleotide conjugate targets an RNA encoding PCSK9.

In some aspects, the antisense oligonucleotide conjugate comprises or consists of SEQ ID NO: 18 or SEQ ID NO: 19. In some aspects, the antisense oligonucleotide conjugate is a pharmaceutically acceptable salt of an antisense oligonucleotide conjugate disclosed herein, e.g., an antisense oligonucleotide conjugate of SEQ ID NO: 18 or SEQ ID NO: 19. In some aspects, the salt is a sodium salt. In some aspects, the antisense oligonucleotide conjugate comprises a sodium ion per nucleotide unit. Thus, in a particular aspect, the antisense oligonucleotide of the present disclosure is a sodium salt of SEQ ID NO: 19 designated CIVI 008, which is the hexadecasodium salt of the antisense oligonucleotide conjugate of SEQ ID NO: 19 as depicted in FIG. 18B.

The type of oligonucleotide conjugates in the oral pharmaceutical compositions of the present disclosure that can be used to target a nucleic acid encoding a PCSK9 protein, e.g., an RNA, is not limited to antisense oligonucleotides (ASO). In some aspects, as described more in detail below, the oligomer in an oligonucleotide conjugate of the present disclosure can be a siRNA, shRNA, aptamer, or any nucleic acid capable of modulating the expression and/or activity of PCSK9. In some aspects, the oligomer in an oligonucleotide conjugate of the present disclosure can be a monomer or a multimer, e.g., multiple concatenated units of an oligomer of the present disclosure, e.g., an oligomer derived from SEQ ID NO:26, e.g., SEQ ID NO:2 or SEQ ID NO:3. Accordingly, in some aspects, the oligomer comprises multiple concatenated copies of SEQ ID NO: 2 or SEQ ID NO: 3, which cleavable linkers interposed between each ASO unit in the multimeric oligomer. In some aspects, the oligomers of the present disclosure can be single stranded or double stranded.

In some aspects, the oligomers or oligonucleotide conjugates disclosed herein can target an RNA, e.g., a pre-mRNA, a splice variant of a pre-mRNA, or a mature mRNA. In some aspects, the RNA, e.g., a pre-mRNA, a splice variant of a pre-mRNA, or a mature mRNA, corresponds to an allelic variant of a normal PCSK9 gene. In some aspects, the RNA, e.g., a pre-mRNA, a splice variant of a pre-mRNA, or a mature mRNA, corresponds to a mutant of a normal PCSK9 gene. In some aspects, the mutant is a gain of function mutant. In some aspects, it may be desirable to inhibit the expression and/or activity of a gain of function mutant in order to lower PCSK9 activity. However, in some aspects, inhibit the expression of a loss of function mutants may be desirable if expression of the mutant form can be deleterious or results in the accumulation of deposits of mutant or inactive PCSK9 protein.

In some aspects, an oligomer or oligonucleotide conjugate disclosed herein can target a sequence within a PCSK9 exon. In some aspects, an oligomer or oligonucleotide conjugate disclosed herein can target a sequence within a PCSK9 intron. In some aspects, an oligomer or oligonucleotide conjugate disclosed herein can target a sequence comprising a junction between an exon and an intron. In some aspects, an oligomer or oligonucleotide conjugate disclosed herein can target a sequence upstream from the 5' end of an open reading frame encoding PCSK9. In some aspects, an oligomer or oligonucleotide conjugate disclosed herein can target a sequence downstream from the 3' end of an open reading frame encoding PCSK9.

Sections II (Antisense Oligomers) and III (Oligonucleotide Conjugates) provide oligomers (e.g., antisense oligonucleotides, ASO) and oligonucleotide conjugates (e.g., antisense oligonucleotide conjugates) that can be used in the oral pharmaceutical compositions of the present disclosure. As such, it is understood that any of the antisense oligomers (e.g., oligomer of SEQ ID NO: 2 or 3) and/or antisense oligonucleotides conjugates (e.g., oligonucleotide conjugates of SEQ ID NO: 18 or 19) can be combined with at least one oral delivery agent disclosed herein, e.g., SNAC, C10, or 5-CNAC to produce an oral pharmaceutical composition of the present disclosure (e.g., a pill or capsule comprising, for example, CIVI 008 and SNAC or 5-CNAC). Such oral pharmaceutical compositions can also comprise pharmaceutically acceptable diluents, carriers, salt, or adjuvant disclosed herein or known in the art. For example, WO2007/

031091 provides suitable pharmaceutically acceptable diluent, carrier and adjuvants, suitable dosages, formulations, administration routes, compositions, dosage forms, combinations with other therapeutic agents, and pro-drug formulations that can used in the oral pharmaceutical compositions of the present disclosure.

The oral antisense pharmaceutical compositions disclosed herein can be used to treat diseases or conditions caused by abnormal expression levels and/or activity of PCSK9. Accordingly, the present disclosure provides methods of treating a disease or condition caused by abnormal expression levels and/or activity of PCSK9 in a subject in need thereof comprising administering an effective amount of an oral pharmaceutical composition disclosed herein (e.g., an oral pharmaceutic composition comprising an antisense oligonucleotide conjugate such as CIVI 008 and an oral delivery agent such as SNAC, C10, or 5-CNAC) to the subject, wherein the administration of the pharmaceutical composition reduces the level of serum PCSK9 and/or reduces the level of serum LDL cholesterol in the subject.

In some aspects, the disease or condition is selected from the group consisting of atherosclerosis, hypercholesterolemia (e.g., familiar hypercholesterolemia or statin resistant hypercholesterolemia), HDL/LDL cholesterol imbalance, dyslipidemia (e.g., familial hyperlipidemia (FCHL) or acquired hyperlipidemia), coronary artery disease (CAD), and coronary heart disease (CHD). Accordingly, the present disclosure provides a method of treating a disease or condition selected from the group consisting of atherosclerosis, hypercholesterolemia (e.g., familiar hypercholesterolemia or statin resistant hypercholesterolemia), HDL/LDL cholesterol imbalance, dyslipidemia (e.g., familial hyperlipidemia (FCHL) or acquired hyperlipidemia), coronary artery disease (CAD), and coronary heart disease (CHD) in a subject in need thereof, the method comprising administering an effective amount of an oral pharmaceutical composition disclosed herein (e.g., an oral pharmaceutic composition comprising an antisense oligonucleotide conjugate such as CIVI 008 and an oral delivery agent such as SNAC, C10, or 5-CNAC).

The present disclosure also provides a method of manufacturing an oral pharmaceutical composition comprising admixing (i) an antisense oligomer or antisense oligonucleotide conjugate disclosed herein (e.g., CIVI 008); and, (ii) an oral delivery agent (e.g., SNAC, C10, or 5-CNAC).

In some aspects, the oral delivery agent (e.g., SNAC, C10, or 5-CNAC) is covalently attached to an antisense oligomer or antisense oligonucleotide conjugate disclosed herein (e.g., CIVI 008), either directly or via a linker or combination of linkers, wherein the linker or combination of linkers can comprise a cleavable linker. In some aspects, the oral delivery agent (e.g., SNAC, C10, or 5-CNAC) is covalently attached to an oligomer moiety directly or via a spacer. In some aspects, the oral delivery agent (e.g., SNAC, C10, or 5-CNAC) is covalently attached to a non-nucleotide or non-polynucleotide moiety of an antisense oligonucleotide conjugate disclosed herein (e.g., the GalNAc moiety CIVI 008), directly or via a linker, spacer, or combination thereof. Accordingly, in some aspects, the oral delivery agent (e.g., SNAC, C10, or 5-CNAC) or a combination thereof is attached, e.g., to a GalNAc conjugate moiety comprising a cleavable linker. Cleavage of the cleavable linker or combination thereof can release both the GalNAc and the oral delivery agent (e.g., SNAC, C10, or 5-CNAC) from the conjugate. In other aspects, the GalNAc moiety and the oral delivery agent are attached via two separate cleavable linkers, which can be the same or different. In some aspects, both cleavable linkers may be cleaved according to the same mechanism (e.g., two pH sensitive linkers). In other aspects, each cleavable linker may be cleaved according to a different mechanism (e.g., a linker could be a pH sensitive linker, and the second linker could be enzymatically cleaved, e.g., by esterases).

In some aspects, the oral delivery agent (e.g., SNAC, C10, or 5-CNAC) can be covalently attached to the 5' of an oligomer moiety disclosed herein. In some aspects, the oral delivery agent (e.g., SNAC, C10, or 5-CNAC) can be covalently attached to the 3' of an oligomer moiety disclosed herein. In some aspects, the oral delivery agent (e.g., SNAC, C10, or 5-CNAC) can be covalently attached to the 5' or 3' of an oligomer moiety disclosed herein directly (e.g., to the 5' or 3' nucleotides). In some aspects, the oral delivery agent (e.g., SNAC, C10, or 5-CNAC) can be covalently attached to the 5' or 3' of an oligomer moiety disclosed herein indirectly to the 5' or 3' nucleotide via a linker, a spacer, or a combination thereof.

In some aspects, the oral delivery agent (e.g., SNAC, C10, or 5-CNAC) can be covalently attached to an antisense oligonucleotide conjugate disclosed herein. In some aspects, the oral delivery agent (e.g., SNAC, C10, or 5-CNAC) can be covalently attached to the oligomer moiety of an antisense oligonucleotide conjugate disclosed herein. In some aspects, the oral delivery agent (e.g., SNAC, C10, or 5-CNAC) can be covalently attached to the non-nucleotide or non-polynucleotide moiety (e.g., GalNAc moiety) of an antisense oligonucleotide conjugate disclosed herein.

In some aspects, the oral delivery agent (e.g., SNAC, C10, or 5-CNAC) can be covalently attached to an antisense oligonucleotide conjugate disclosed herein via a linker, spacer, or a combination thereof. In some aspects, the oral delivery agent (e.g., SNAC, C10, or 5-CNAC) can be covalently attached to the oligomer moiety of an antisense oligonucleotide conjugate disclosed herein via a linker, spacer, or a combination thereof. In some aspects, the oral delivery agent (e.g., SNAC, C10, or 5-CNAC) can be covalently attached to the non-nucleotide or non-polynucleotide moiety (e.g., GalNAc moiety) of an antisense oligonucleotide conjugate disclosed herein via a linker, spacer, or a combination thereof.

In some aspects, an oligomer moiety disclosed herein or an antisense oligonucleotide conjugate disclosed herein can be covalently attached to more than one oral delivery agent (e.g., SNAC, C10, or 5-CNAC) disclosed herein. In some aspects, an oligomer moiety disclosed herein or an antisense oligonucleotide conjugate disclosed herein can have more than one oral delivery agent (e.g., SNAC, C10, or 5-CNAC) disclosed herein covalently attached at different positions (e.g., an oral delivery agent attached to the oligomer and an oral delivery agent attached to a GalNAc moiety).

II. Oligomers

In some aspects, the oligomer of the present disclosure is LNA gapmer of between 16-20 nucleotides in length and comprises a contiguous sequence of 16 nucleotides that are complementary to a corresponding length of SEQ ID NO 31. Also disclosed are oligomers comprising a contiguous sequence selected from the group consisting of SEQ ID NO 26, 27, 28, 29 and 44. The antisense oligomers or conjugates of the present disclosure target PCSK9, and as such they are capable of down regulating the expression of and/or inhibiting PCSK9, such as PCSK9 in a human or in a cell expressing PCSK9. In some aspects, the oligomer of the present disclosure can be 10, 11, 12, 13, 14, 15, 16, 17, 18, 19, 20, 21, or 22 nucleotides in length. In some aspects, the oligomer of the present disclosure is more than 14 nucleotides in length. In some aspects, the internucleoside linkages of a contiguous sequence of 10-16 nucleotides which are complementary to a corresponding length of SEQ ID NO: 33 or 34 or 45 can be phosphorothioate linkages.

In some aspects, the oligomer of the present disclosure (e.g., an oligomer complementary to SEQ ID NO: 31) comprises, consists, or consists essentially of a contiguous sequence selected from the group consisting of SEQ ID NO: 2 and SEQ ID NO: 3.

In some aspects, the oligomer of the present disclosure (e.g., an oligomer complementary to SEQ ID NO: 31) comprises 10-16 phosphorothioate linked nucleosides. In some aspects, the oligomer of the present disclosure (e.g., an oligomer complementary to SEQ ID NO: 31) comprises more than 14 phosphorothioate linked nucleosides. In some aspects, the oligomer (e.g., an oligomer complementary to SEQ ID NO: 31) is 15, 16, 17, 18, 18, 19, 20, 21, or 22 nucleotides in length.

In some aspects, the oligomer of the present disclosure (e.g., an oligomer complementary to SEQ ID NO: 31) is an LNA gapmer comprising a contiguous sequence of more than 14 nucleotides, e.g., 15, 16, 17, 18, 19, 20, 21 or 22 nucleotides, which are complementary to a corresponding length of SEQ ID NO 31, wherein the contiguous sequence comprises nucleotide analogues. In a specific aspect, the oligomer is 16 nucleotides in length. In one aspect, the oligomer of the present disclosure comprises affinity enhancing nucleotide analogues. In some aspects, the nucleotide analogues are sugar modified nucleotides, such as sugar modified nucleotides independently or dependently selected from the group consisting of 2'-O-alkyl-RNA units, 2'-OMe-RNA units, 2'-amino-DNA units, and 2'-fluoro-DNA units.

In some aspects, the oligomer of the present disclosure (e.g., an oligomer complementary to SEQ ID NO: 31) is a LNA gapmer oligonucleotide. In some aspects, the LNA gapmer comprises a wing on each side (5' and 3') of 2 to 4 nucleotide analogues, preferably LNA analogues. In some aspects, the oligomer of the present disclosure (e.g., an oligomer complementary to SEQ ID NO: 31) can optionally comprise a further 1 to 6 nucleotides (e.g., one, two, three, four, five or six nucleotides), which can form or comprise a biocleavable nucleotide region, such as a phosphate nucleotide linker. In some aspects, the biocleavable nucleotide region is formed of a short stretch of nucleotides (e.g. 1, 2, 3, 4, 5 or 6 nucleotides) which are physiologically labile. This can be achieved by using phosphodiester linkages with DNA/RNA nucleosides, or if physiological liability can be maintained, other nucleoside can be used. Physiological lability can be measured using a liver extract, e.g., as illustrated in Example 6.

In some aspects, the oligomer of the present disclosure comprises a contiguous sequence of 16 nucleotides which are complementary to a corresponding length of SEQ ID NO 31 (A first region, or region A). The oligomer of the present disclosure can comprise a further nucleotide region. In some aspects, the further nucleotide region comprises a biocleavable nucleotide region, such as a phosphate nucleotide sequence (a second region, region B), which can covalently link region A to a non-nucleotide moiety, such as a conjugate group, (a third region, or region C). In some aspects the contiguous nucleotide sequence of the oligomer of the present disclosure (region A) is directly covalently linked to region C. In some aspects region C is biocleavable.

In some aspects, the oligomer consists or comprises of a contiguous nucleotide sequence of from 16-22, such as 16, 17, 18, 19, 20, 21, or 22 nucleotides in length, such as 16 nucleotides in length. Accordingly, in some aspects, the oligomer can refer to the combined length of region A and region B, e.g., 16-22 nucleotides (such as 16 nucleotides) from region A and, e.g., 1 to 6 nucleotides from Region B.

In some aspects, the oligomer of the present disclosure does not comprise RNA (units), e.g., in some aspects, it can comprise only DNA units. In some aspects, the oligomer of the present disclosure comprises DNA and RNA units. In some aspects, the oligomer according to the present disclosure, the first region of the oligomer, or the first and second regions of the oligomer together (e.g., as a single contiguous sequence), is a linear molecule. In some aspects, the oligomer according to the present disclosure, the first region of the oligomer, or the first and second regions of the oligomer together (e.g., as a single contiguous sequence), is synthesized as a linear molecule. Thus, in some aspects, the oligomer can be a single stranded molecule. In some aspects, the oligomer does not comprise short regions of, for example, at least 3, 4 or 5 contiguous nucleotides, which are complementary to equivalent regions within the same oligomer (i.e., duplexes).

In some aspects, the oligomer is not a double stranded nucleic acid. In some aspects, the oligomer of the present disclosure is not a siRNA. In some aspects, the oligomer of the present disclosure is not a shRNA. In some aspects, the oligomer is a double stranded nucleic acid. In some aspects, the oligomer of the present disclosure is a siRNA. In some aspects, the oligomer of the present disclosure is a shRNA.

In some aspects, the oligomer of the present disclosure in an antisense oligonucleotide (ASO). In some aspects, the oligomer of the present disclosure is multimeric. In some aspects, the oligomer of the present disclosure is a multimeric ASO, e.g., it can comprise several concatenated oligomers of the present disclosure. In some aspects, the oligomer of the present disclosure comprises 1, 2, 3, 4, 5, 6, 7, 8, 9, 10, or more than 10 concatenated oligomers. In some aspects, the concatenated oligomers are connected via cleavable linkers interposed between each ASO unit in the ASO multimer.

The terms "corresponding to" and "corresponds to" as applied to the comparison of two oligonucleotides disclosed herein, refer to the comparison between the nucleotide sequence of an oligomer (i.e., the nucleobase or base sequence) of the present disclosure and the reverse complement of the nucleic acid target or sub-region thereof (e.g. SEQ ID NO 31, 32 33, 34 or 45). Nucleotide analogues are compared directly to their equivalent or corresponding nucleotides. Some aspects, the oligomers (or first region thereof) are complementary to the target region or sub-region thereof (e.g. SEQ ID NO 31, 32, 33, 34 or 45), such as fully complementary.

II.a Oligomer Sequences

In some aspects, an oligomer of the present disclosure can target a target region disclosed in TABLE 1A. TABLE 1A presents the sequences of target regions as well as their positions in the PCSK9 mRNA. In some aspects, an oligomer of the present disclosure comprises a complementarity region that is complementary to at least 5, 6, 7, 8, 9, 10, 11, 12, 13, 14, 15, or 16 nucleotides of one of the target sequences of TABLE 1A. In some aspects, an oligomer of the present disclosure comprises a complementarity region that is complementary to at least 5, 6, 7, 8, 9, 10, 11, 12, 13, 14, 15, or 16 nucleotides of one of the target sequences of TABLE 1A, wherein the complementary region is at the 5' end of the oligomer. In some aspects, an oligomer of the present disclosure comprises a complementarity region that is complementary to at least 5, 6, 7, 8, 9, 10, 11, 12, 13, 14, 15, or 16 nucleotides of one of the target sequences of TABLE 1A, wherein the complementary region is at the 3' end of the oligomer. In some aspects, an oligomer of the present disclosure comprises a complementarity region that is complementary to at least 5, 6, 7, 8, 9, 10, 11, 12, 13, 14, 15, or 16 nucleotides of one of the target sequences of TABLE 1A, wherein the complementary region is at the 5' end of the oligomer, and wherein the oligomer is 12, 13, 14, 15, 16, 17, 18, 19, 20, 21, 22, 23, 24, 25, 26, 27, 28, 29 or 30 nucleotides in length. In some aspects, an oligomer of the present disclosure comprises a complementarity region that is complementary to at least 5, 6, 7, 8, 9, 10, 11, 12, 13, 14, 15, or 16 nucleotides of one of the target sequences of TABLE 1A, wherein the complementary region is at the 3' end of the oligomer, and wherein the oligomer is 12, 13, 14, 15, 16, 17, 18, 19, 20, 21, 22, 23, 24, 25, 26, 27, 28, 29 or 30 nucleotides in length.

TABLE 1A

PCSK9 target sequences

| SEQ ID NO | Target Sequence | Length | Position on PCSK9 mRNA |
|---|---|---|---|
| 30 | UGGGUUUUGUAGCA | 14 | 3643-3656 |
| 31 | UGGGUUUUGUAGCAUU | 16 | 3643-3658 |

TABLE 1A-continued

PCSK9 target sequences

| SEQ ID NO | Target Sequence | Length | Position on PCSK9 mRNA |
|---|---|---|---|
| 32 | CCAAGCUCACACAGC | 15 | 3251-3265 |
| 33 | CCAAGCUCACACAGCA | 16 | 3251-3266 |
| 34 | GGAACACAGACCAGGA | 16 | 3373-3388 |
| 45 | CGCUUCCACAGAC | 13 | 1005-1017 |

TABLE 1B shows SEQ ID NO:25 to 29 and 44, which are base sequences or nucleobase motif sequence. For example, SEQ ID NO: 26 is a 16-mer targeting SEQ ID NO: 31. In some aspects, the nucleobase motif sequence can comprise 1, 2, 3, 4, 5, 6, 7, 8, 9, 10, 11, 12, 13, 14, 15, 16, 17, 18, 19, 20, or more than 20 nucleotides complementary to extended from the 5' end, 3' end, or both of a motif sequence presented in TABLE 1B. The oligomer sequences of the present disclosure are derived from motif sequences disclosed herein which comprise a particular pattern of nucleobase analogs and/or internucleoside linkages.

TABLE 1B

Motif sequences.

| SEQ ID NO | Motif sequence | Position on PCSK9 mRNA | SEQ ID NO of target sequence |
|---|---|---|---|
| 25 | tgctacaaaaccca | 3643-3656 | 30 |
| 26 | aatgctacaaaaccca | 3643-3658 | 31 |
| 27 | gctgtgtgagcttgg | 3251-3265 | 32 |
| 28 | tgctgtgtgagcttgg | 3251-3266 | 33 |
| 29 | tcctggtctgtgttcc | 3373-3388 | 34 |
| 44 | gtctgtggaagcg | 1005-1017 | 45 |

TABLE 1C presents different oligomers sequences, conjugate forms thereof, and target corresponding target regions on the PCKS9 gene.

TABLE 1C

Oligomers and conjugates

| SEQ ID NO | Oligomer sequence | Conjugate | | | Target Position on the PCSK9 mRNA |
|---|---|---|---|---|---|
| | | PO | Chol-C6 | GalNAc | |
| 1 | TGCtacaaaacCCA | | | | 3643-3656 |
| 2 | AATgctacaaaaCCCA | | | | 3643-3658 |
| 3 | AATgctacaaaaCCCA | | | | 3643-3658 |
| 4 | GCtgtgtgagcttGG | | | | 3251-3265 |
| 5 | TGctgtgtgagctTGG | | | | 3251-3266 |
| 6 | TGCtgtgtgagctTGG | | | | 3251-3266 |

TABLE 1C-continued

Oligomers and conjugates

| SEQ ID NO | Oligomer sequence | Conjugate PO | Conjugate Chol-C6 | Conjugate GalNAc | Target Position on the PCSK9 mRNA |
|---|---|---|---|---|---|
| 7 | TCCtggtctgtgtTCC | | | | 3373-3388 |
| 8 | TCCtggtctgtgttCC | | | | 3373-3388 |
| 9 | TGCtacaaaacCCA | Yes | Yes | | 3643-3656 |
| 10 | AATgctacaaaaCCCA | Yes | Yes | | 3643-3658 |
| 11 | AATgctacaaaacCCA | Yes | Yes | | 3643-3658 |
| 12 | GCtgtgtgagcttGG | Yes | Yes | | 3251-3265 |
| 13 | TGctgtgtgagctTGG | Yes | Yes | | 3251-3266 |
| 14 | TGCtgtgtgagctTGG | Yes | Yes | | 3251-3266 |
| 15 | TCCtggtctgtgtTCC | Yes | Yes | | 3373-3388 |
| 16 | TCCtggtctgtgttCC | Yes | Yes | | 3373-3388 |
| 17 | TGCtacaaaacCCA | | | Yes | 3643-3656 |
| 18 | AATgctacaaaaCCCA | | | Yes | 3643-3658 |
| 19 | AATgctacaaaacCCA | | | Yes | 3643-3658 |
| 20 | GCtgtgtgagcttGG | | | Yes | 3251-3265 |
| 21 | TGctgtgtgagctTGG | | | Yes | 3251-3266 |
| 22 | TGCtgtgtgagctTGG | | | Yes | 3251-3266 |
| 23 | TCCtggtctgtgtTCC | | | Yes | 3373-3388 |
| 24 | TCCtggtctgtgttCC | | | Yes | 3373-3388 |
| 40 | GTctgtggaaGCG | | | | 1005-1017 |
| 41 | GTctgtggaaGCG | | Yes | | 1005-1017 |
| 42 | GTctgtggaaGCG | Yes | Yes | | 1005-1017 |
| 43 | GTctgtggaaGCG | Yes | Yes | | 1005-1017 |

SEQ ID NO: 1 is SPC5001, an antisense oligomer disclosed in WO2011/009697, which is known to cause severe kidney toxicity when administered to human subject. SEQ ID NOs 1-24 and 40 to 43 are oligomers comprising nucleotide analogues such as LNA gapmer oligomers, where lower case letters are DNA units (nucleoside/nucleotide) where capital letters are LNA units. In some aspects, all LNA C are 5-methyl cytosine. In some aspects, all LNA units are beta-D-oxy LNA. In some aspects, the internucleoside linkages between the nucleosides of SEQ ID NOs 1-24 and 40 to 43 are all phosphorothioate linkages. In some aspects, phosphorothioate linkages are present only in the first and/or second 5' phosphorothioate linkages. In some aspects, phosphorothioate linkages are present only in the first and/or second 3' phosphorothioate linkages. In some aspects, phosphorothioate linkages are present in the first and/or second 5' phosphorothioate linkages, and in the first and/or second 3' phosphorothioate linkages.

SEQ ID NOS: 1-24 and 40-43 are gapmers, wherein each wing comprises 2, 3, or 4 LNA units. In some aspects, the oligomer of the present disclosure corresponds to a variant of SEQ ID NOS: 1-24 and 40-43, wherein the variant comprises 1, 2, 3, or 4 additional LNA units in the 5' wing of the gapmer. In some aspects, the oligomer of the present disclosure corresponds to a variant of SEQ ID NOS: 1-24 and 40-43, wherein the variant comprises 1, 2, 3, or 4 additional LNA units in the 3' wing of the gapmer. In some aspects, the oligomer of the present disclosure corresponds to a variant of SEQ ID NOS: 1-24 and 40-43, wherein the variant comprises 1, 2, 3, or 4 additional LNA units in the 5' wing of the gapmer and 1, 2, 3, or 4 additional LNA units in the 3' wing of the gapmer. In some aspects, the LNA units of a gapmer disclosed herein, e.g., a gapmer of TABLE 1C or a variant thereof can be oxy-LNA, thio-LNA, amino-5 LNA, 5'-methyl-LNA, ENA, cET, or cMOE.

Figure 1A:
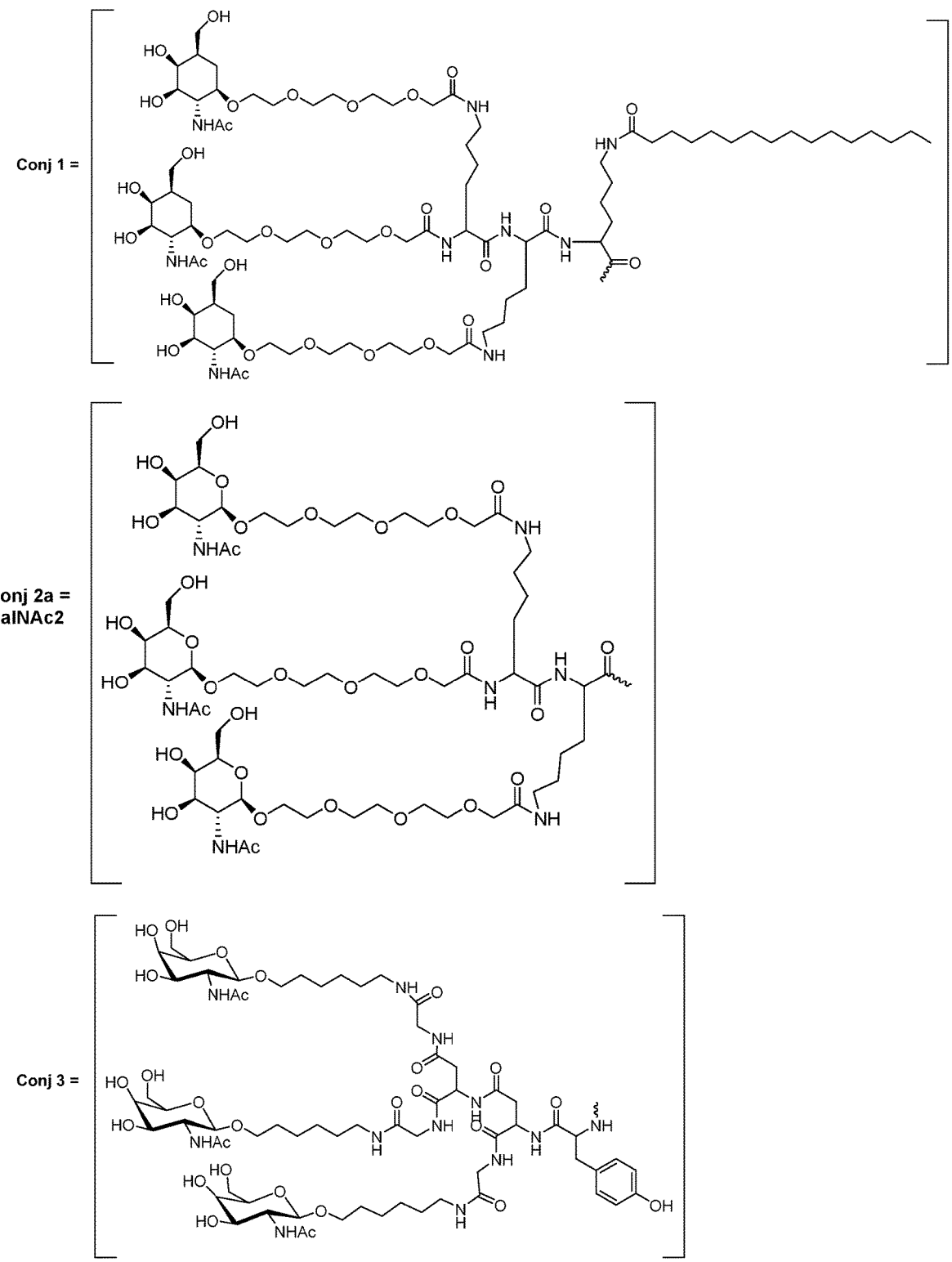
Figure 1C:
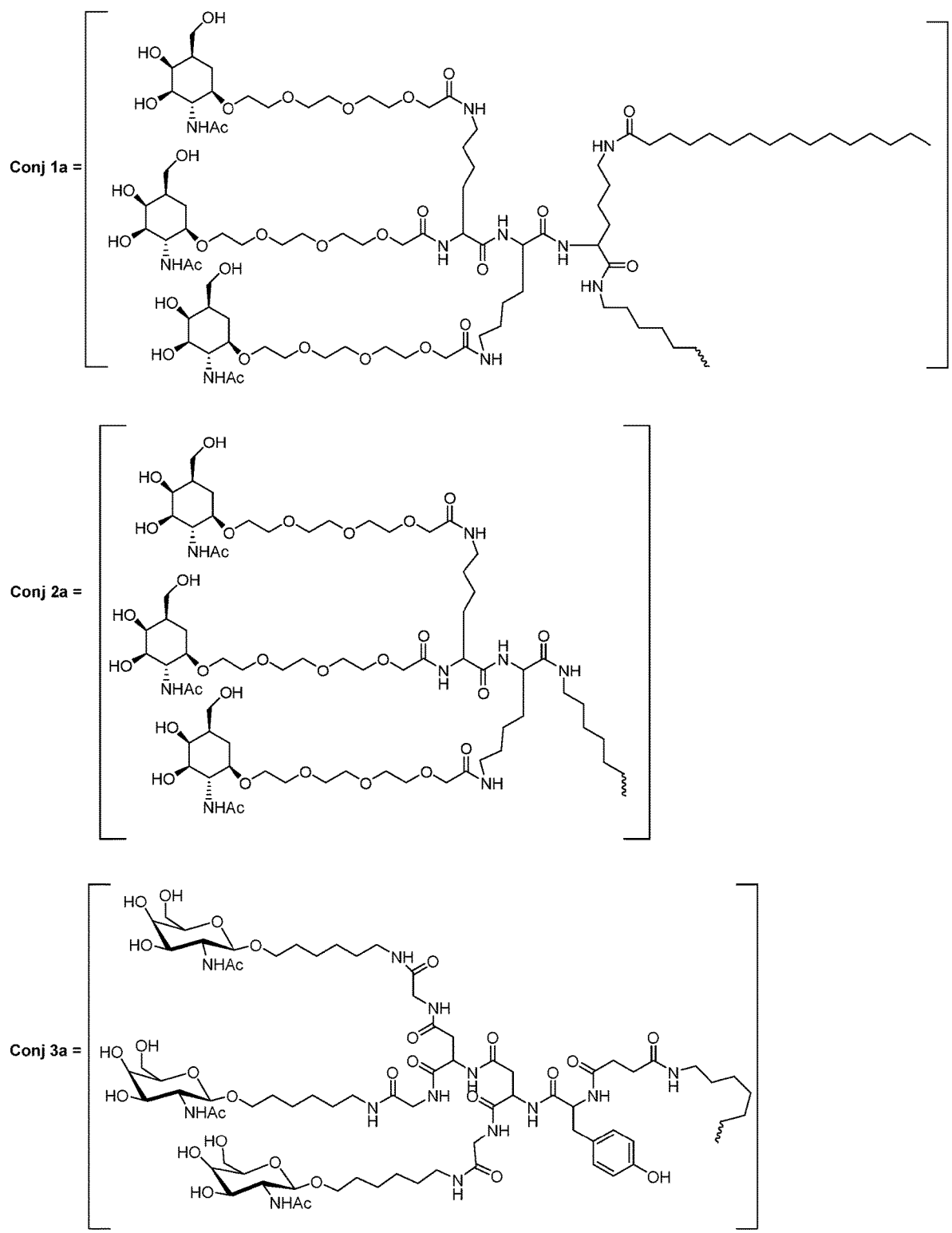
Figure 2:
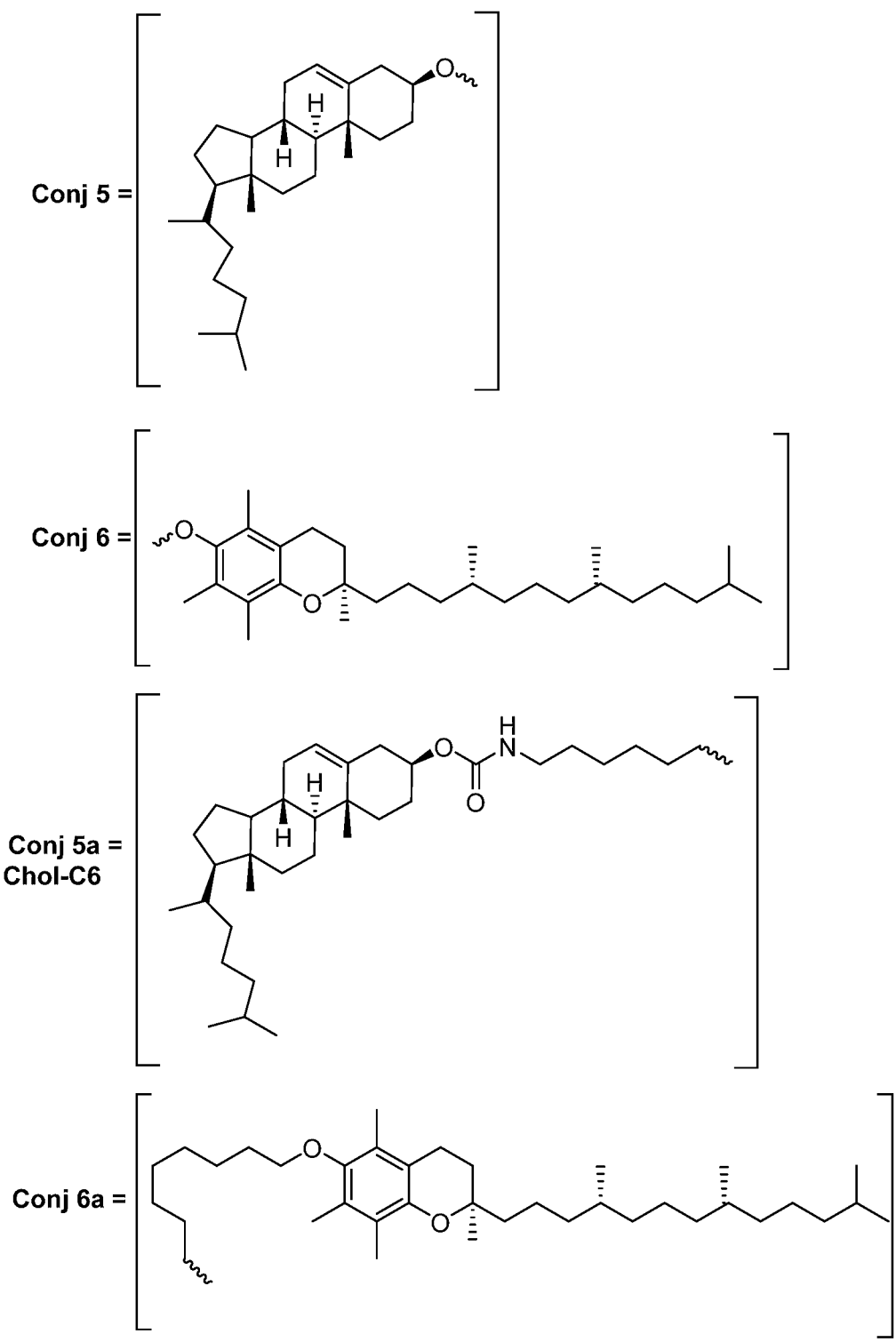

SEQ ID NOs 9-16 and 41 to 43 comprise the oligomer (as indicated by the SEQ ID) as well as a cholesterol conjugate which can be covalently linked to the oligomer 5' or 3' end of the oligomer, optionally via a biocleavable linker, such as a phosphate nucleoside linker. In some aspects, the cholesterol conjugate is linked at the 5' end of the oligomer. SEQ ID NOs 17-24 comprise the oligomer (as indicated by the SEQ ID) as well as a GalNAc conjugate which can be covalently linked to the oligomer 5' or 3' end of the oligomer, optionally via a biocleavable linker, such as a phosphate nucleoside linker or cleavable peptide linker. In some aspects, the GalNAc conjugate is linked at the 5' end of the oligomer. Specific oligomers and conjugates used herein are illustrated in FIG. 3 (nonconjugated oligomers), FIG. 4 (cholesterol conjugates), and FIGS. 5A, 5B and 5C (GalNAc conjugates). Other examples of conjugate moieties which can be used with the oligomers of the present disclosure are illustrated in FIGS. 1A, 1C, and 1C and FIG. 2, and described in the section GalNAc Conjugate Moieties, below.

TABLE 2 provides specific combinations of oligomer and conjugates.

The terms "target nucleic acid" or "target region," as used herein refer to a subsequence of nucleic acid, e.g., an RNA such an mRNA encoding a mammalian PCSK9 or a naturally occurring variants or mutant form thereof, for example, human PCSK9. In some aspects, the nucleic acid encoding a mammalian PCSK9 or naturally occurring variant or mutant form thereof is an RNA. In some aspects, the RNA is an mRNA, such as pre-mRNA. In some aspects, the RNA is a mature mRNA. The oligomer according to the present disclosure is preferably capable of hybridizing to the target nucleic acid. It will be recognized that SEQ ID NO: 46 is a cDNA sequence, and as such, corresponds to the mature

TABLE 2

Oligomer/conjugate moiety combinations

| SEQ ID NO | Conjugate Moiety Number (see FIGS. 1A-1C) | | | | | | | | | | | |
|---|---|---|---|---|---|---|---|---|---|---|---|---|
| | Conj1 | Conj2 | Conj3 | Conj4 | Conj1a | Conj2a | Conj3a | Conj4a | Conj5 | Conj6 | Conj5a | Conj6a |
| 2 | C1 | C2 | C3 | C4 | C5 | C6 | C7 | C8 | C9 | C10 | C70 | C71 |
| 3 | C11 | C12 | C13 | C14 | C15 | C16 | C17 | C18 | C19 | C20 | C72 | C73 |
| 4 | C12 | C13 | C14 | C15 | C16 | C17 | C18 | C19 | C20 | C21 | C74 | C75 |
| 5 | C30 | C31 | C32 | C33 | C34 | C35 | C36 | C37 | C38 | C39 | C76 | C77 |
| 6 | C40 | C41 | C42 | C43 | C44 | C45 | C46 | C47 | C48 | C49 | C78 | C79 |
| 7 | C50 | C51 | C52 | C53 | C54 | C55 | C56 | C57 | C58 | C59 | C80 | C81 |
| 8 | C60 | C61 | C62 | C63 | C64 | C65 | C66 | C67 | C68 | C69 | C82 | C83 |

The oligomer conjugates represented TABLE 2 correspond to the oligomers of SEQ ID NOS: 1-8 conjugated via either their 5' end to a conjugate moiety presented in FIG. 1A, FIG. 1B, FIG. 1C or FIG. 2. The oligomer is covalently attached to the position indicated by the wavy line in wavy FIG. 1A, FIG. 1B, FIG. 1C or FIG. 2. In some aspects, the conjugate moiety is attached to the 3' end of the oligomer.

Figure 5A:
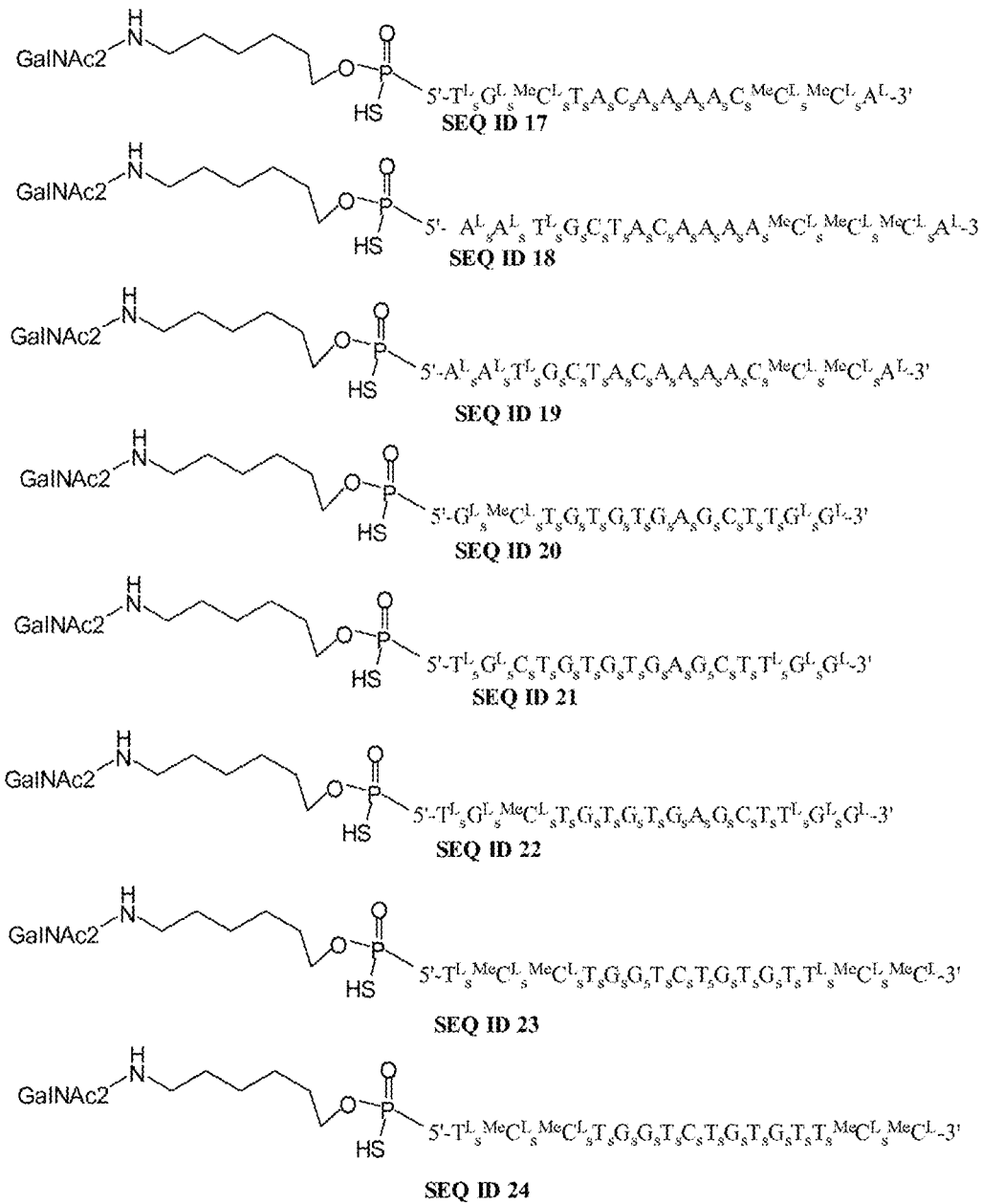
Figure 5B:
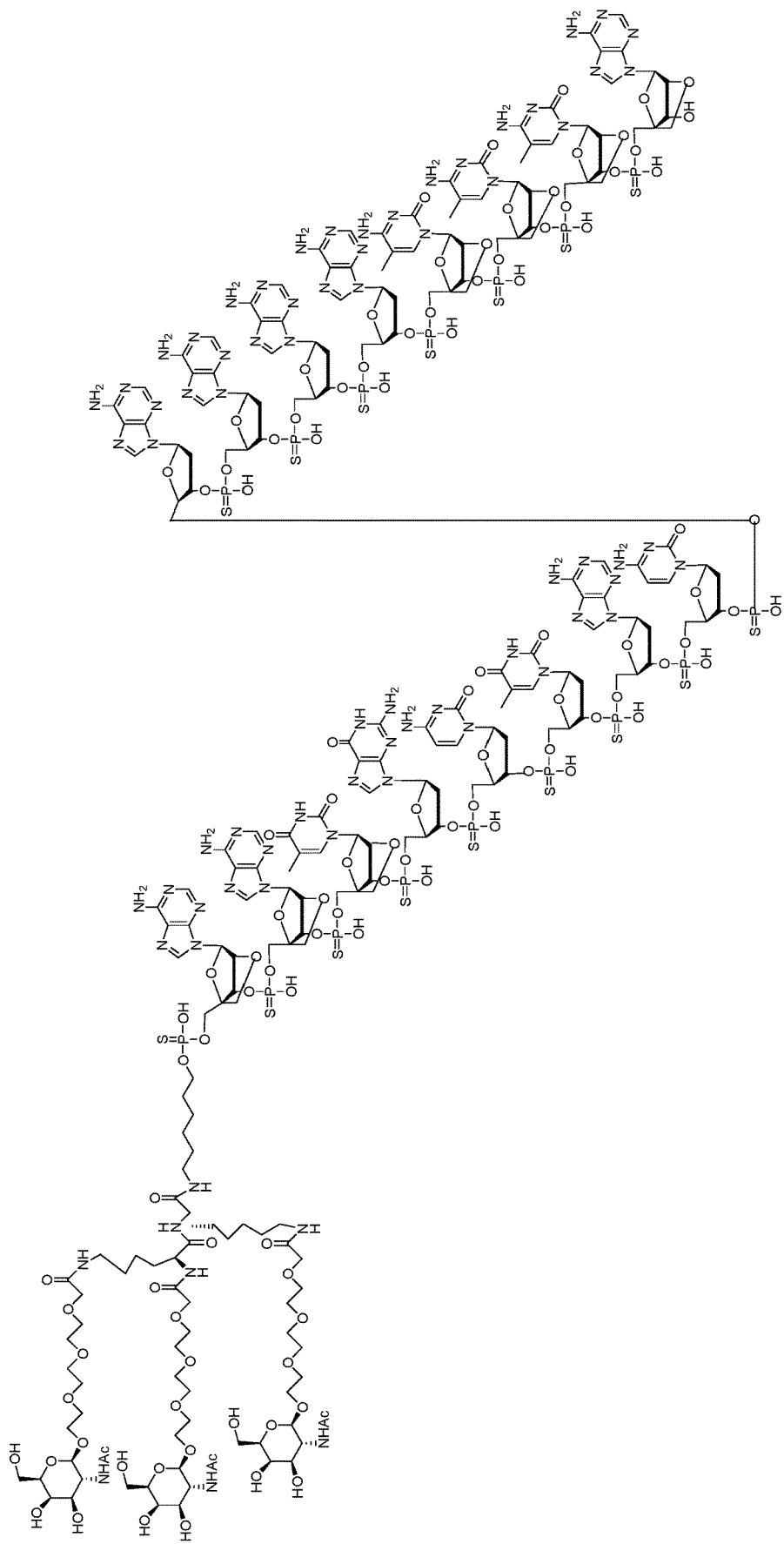
Figure 5C:
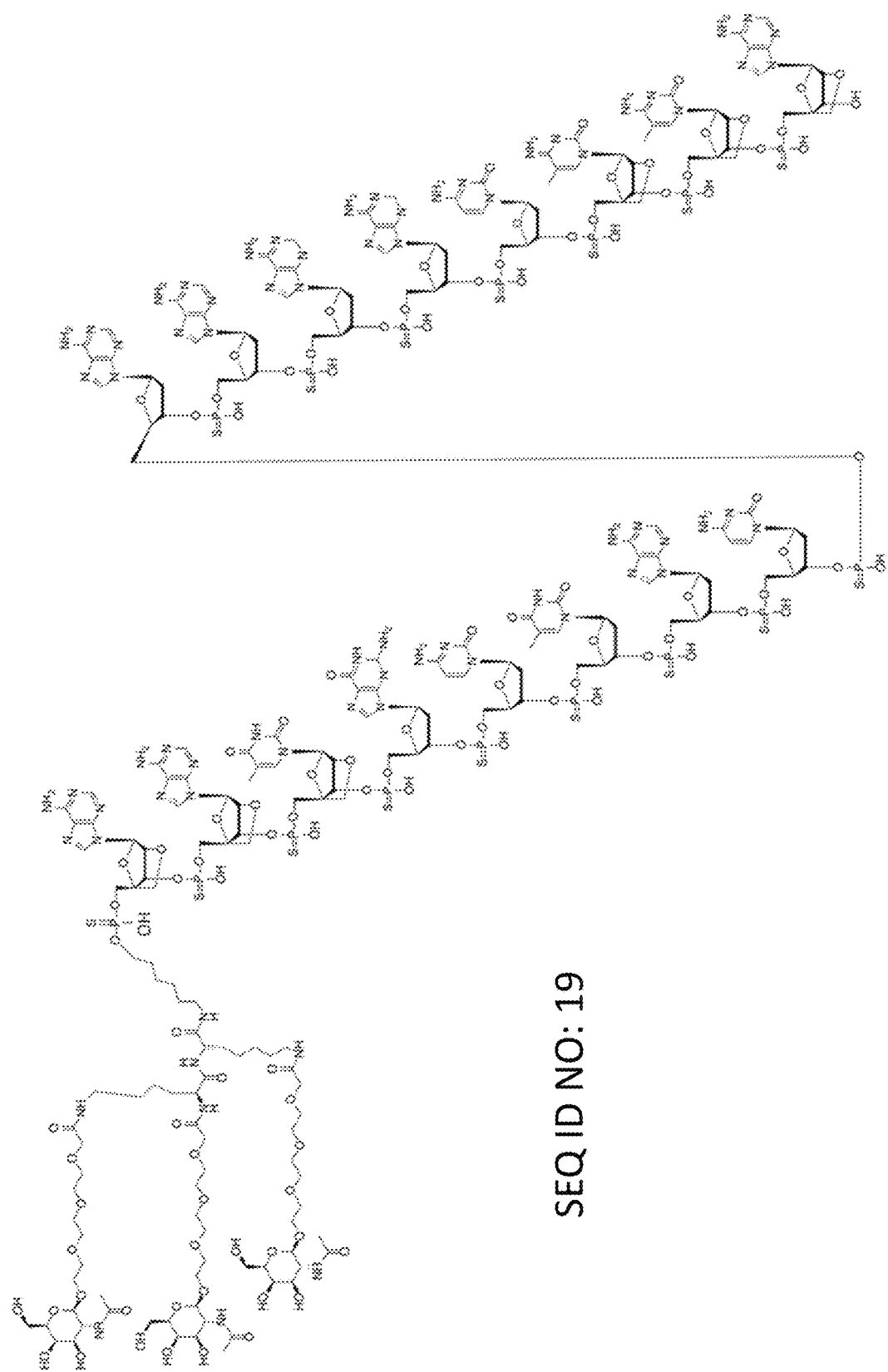

FIGS. 5A, 5B, and 5C show the combination of Conj2a with the indicated SEQ ID NO's above. FIGS. 5B and 5C are two detailed examples of the compounds in FIG. 5A and correspond to the conjugates of SEQ ID NO: 18 and SEQ ID NO: 19, respectively.

Figure 4:
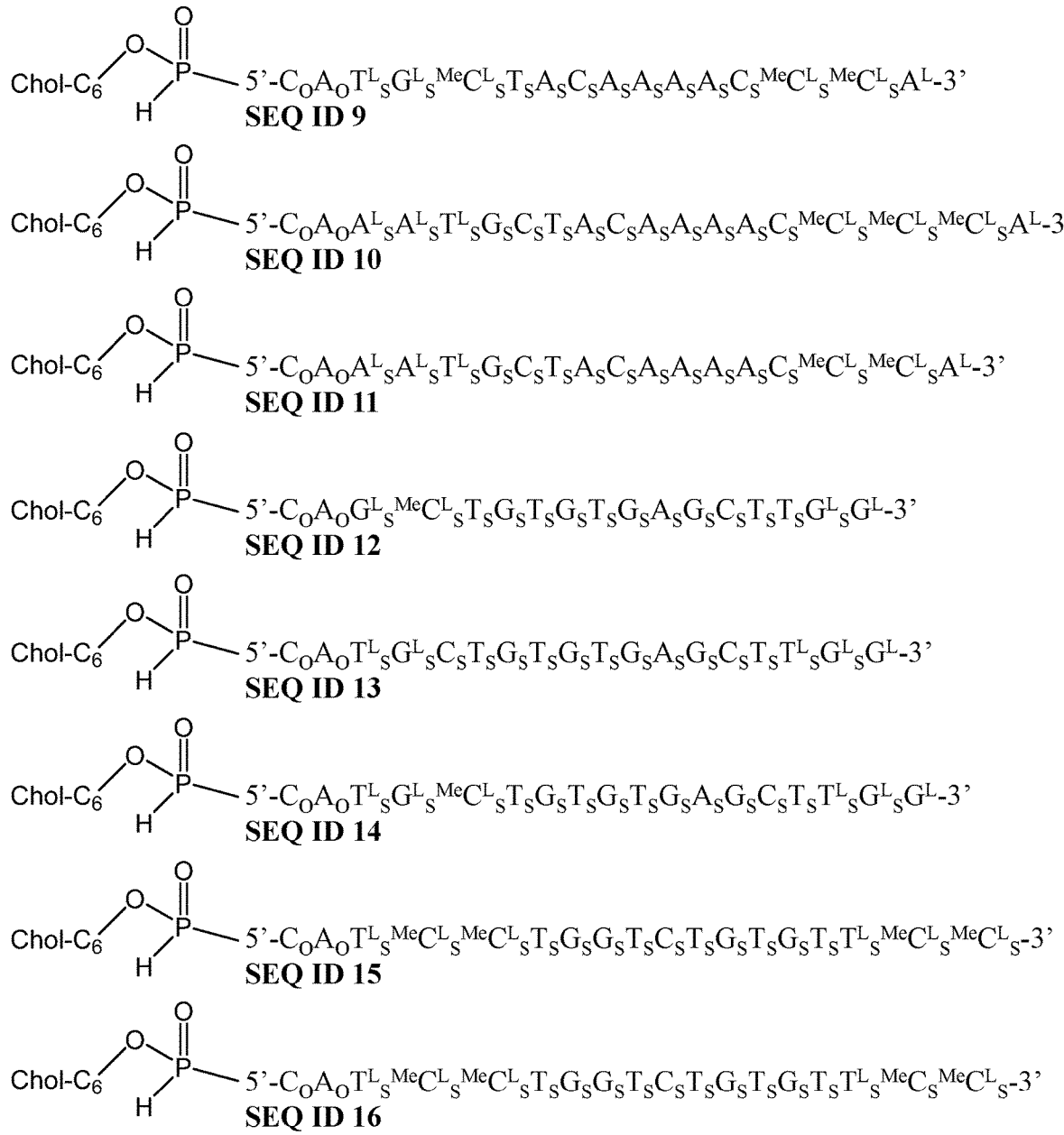

In some aspects, an optional biocleavable linker (B) can be present between the conjugate moiety (C) and the oligomer (A). For Conj1-4 and 1a-4a the GalNAc conjugate itself is biocleavable, utilizing a peptide linker in the GalNAc cluster, and as such a further biocleavable linker (B) may or may not be used. In some aspects, inclusion of a biocleavable linker (B), such as the phosphate nucleotide linkers disclosed herein, can enhance activity of GalNAc cluster oligomer conjugates. FIG. 4 shows the combination of Conj5a (Cholesterols-C6) with the indicated SEQ ID NO's above.

II.b PCSK9 Target Region

The present disclosure is directed to pharmaceutical compositions for oral administrations comprising an oligomer of the present disclosure (e.g., an ASO) which is capable of modulating the expression of the PCSK9 gene by specifically targeting a targeting region in a PCSK9 RNA, e.g., an mRNA. In some aspects, the oligomer is capable of down-regulating expression of the PCSK9 gene by binding to such target region. Thus, in some aspects, the oligomer of the present disclosure can affect the expression of PCSK9, e.g., in a mammalian subject such a human, by binding to a specific target region in a PCSK9 RNA, e.g., an mRNA. In some aspects, the oligomer of the present disclosure can affect the expression of PCSK9 in a human cell, e.g., a liver cell, by binding to a specific target region in a PCSK9 RNA, e.g., an mRNA.

mRNA target sequence, although uracil is replaced with thymidine in the cDNA sequences.

In some aspects, the target sequence corresponds to a subsequence of a sequence encoding PCSK9 set forth in SEQ ID NO: 46. Specific target sequences are presented in TABLE 1A, above, e.g., SEQ ID NO: 30, corresponding to positions 3643-3656 of SEQ ID NO:46; SEQ ID NO: 31, corresponding to positions 3643-3658 of SEQ ID NO:46; SEQ ID NO: 32, corresponding to positions 3251-3265 of SEQ ID NO:46; SEQ ID NO: 33, corresponding to positions 3251-3266 of SEQ ID NO:46; SEQ ID NO: 34, corresponding to positions 3373-3388 of SEQ ID NO:46; and SEQ ID NO: 45, corresponding to positions 1005-1017 of SEQ ID NO:46.

In some aspects, the target sequence can extend 1, 2, 3, 4, 5, 6, 7, 8, 9, or 10 nucleotides beyond the 5' end of a target region of SEQ ID NO: 30, 31, 32, 33, 34, or 45. In some aspects, the target sequence can extend 1, 2, 3, 4, 5, 6, 7, 8, 9, or 10 nucleotides beyond the 3' end of a target region of SEQ ID NO: 30, 31, 32, 33, 34, or 45. In some aspects, the target sequence can extend 1, 2, 3, 4, 5, 6, 7, 8, 9, or 10 nucleotides beyond the 5' end and/or 1, 2, 3, 4, 5, 6, 7, 8, 9, or 10 nucleotides beyond the 3' end of a target region of SEQ ID NO: 30, 31, 32, 33, 34, or 45. In some aspects, the extended target region overlaps with 5, 6, 7, 8, 9, 10, 11, 12, 13, 14, 15, or 16 nucleotides of a target region of SEQ ID NO: 30, 31, 32, 33, 34, or 45.

In some aspects, the target region comprises or consists of a corresponding target sequence region derived from the sequence of mutant or allelic variant of PCSK9 gene encoding the mRNA of SEQ ID NO: 46. In other aspects, the target region can be a subsequence present in another mRNA transcript variant encoding PCSK9. In some aspects, the target region comprises or consists of a corresponding target sequence region derived from the sequence of a paralog or ortholog of the PCSK9 gene encoding the mRNA of SEQ ID NO: 46.

In some aspect, the target region corresponds to a subsequence of the sequence set forth in NCBI Ref Seq accession number NM_174936, i.e., the mRNA encoding *Homo sapiens* proprotein convertase subtilisin/kexin type 9 (PCSK9), transcript variant 1. This NCBI Ref Seq database entry can be accessed at www.ncbi.nlm.nih.gov/nuccore/NM_174936, and is herein incorporated by reference in its entirety.

The PCSK9 coding sequence in the NM_174936 mRNA transcript is located at positions 291 . . . 2369. Accordingly, in some aspects, the target region in located between position 291 and 2369 of the NM_174936 mRNA transcript. In some aspects, the target region in located within the 5' non-coding region. In some aspects, the target region in located within the 3' non-coding region. The NM_174936 mRNA transcript comprises exons located at positions 1 . . . 497 (exon 1), 498 . . . 689 (exon 2), 690 . . . 813 (exon 3), 814 . . . 947 (exon 4), 948 . . . 1089 (exon 5), 1090 . . . 1286 (exon 6), 1287 . . . 1470 (exon 7), 1471 . . . 1644 (exon 8), 1645 . . . 1793 (exon 9), 1794 . . . 1971 (exon 10), 1972 . . . 2153 (exon 11), and 2154 . . . 3637 (exon 12). Exons 1 to 12 are separated by introns 1 to 11, e.g., intron 1 is located between exon 1 and exon 2, intron 2 is located between exon 2 and exon 3, and so forth.

In some aspects, the target region is within exon 1. In some aspects, the target region is within exon 2. In some aspects, the target region is within exon 3. In some aspects, the target region is within exon 4. In some aspects, the target region is within exon 5. In some aspects, the target region is within exon 6. In some aspects, the target region is within exon 7. In some aspects, the target region is within exon 8. In some aspects, the target region is within exon 9. In some aspects, the target region is within exon 10. In some aspects, the target region is within exon 11. In some aspects, the target region is within exon 12.

In some aspects, the target region is within an intron in the PCSK9 pre mRNA. In some aspects, the target region is within intron 1. In some aspects, the target region is within intron 2. In some aspects, the target region is within intron 3. In some aspects, the target region is within intron 4. In some aspects, the target region is within intron 5. In some aspects, the target region is within intron 6. In some aspects, the target region is within intron 7. In some aspects, the target region is within intron 8. In some aspects, the target region is within intron 9. In some aspects, the target region is within intron 10. In some aspects, the target region is within intron 11. In some aspects, the target region comprises the junction between exon 1 and intron 1. In some aspects, the target region comprises the junction between intro 1 and exon 2. In some aspects, the target region comprises the junction between exon 2 and intron 2. In some aspects, the target region comprises the junction between intron 2 and exon 3. In some aspects, the target region comprises the junction between exon 3 and intron 3. In some aspects, the target region comprises the junction between exon 4 and intron 4. In some aspects, the target region comprises the junction between intron 4 and exon 5. In some aspects, the target region comprises the junction between exon 5 and intron 5. In some aspects, the target region comprises the junction between intron 5 and exon 6. In some aspects, the target region comprises the junction between exon 6 and intron 6. In some aspects, the target region comprises the junction between intron 6 and exon 7. In some aspects, the target region comprises the junction between exon 7 and intron 7. In some aspects, the target region comprises the junction between intron 7 and exon 8. In some aspects, the target region comprises the junction between exon 8 and intron 8. In some aspects, the target region comprises the junction between intron 8 and exon 9. In some aspects, the target region comprises the junction between exon 9 and intron 9. In some aspects, the target region comprises the junction between intron 9 and exon 10. In some aspects, the target region comprises the junction between exon 10 and intron 10. In some aspects, the target region comprises the junction between intron 10 and exon 11. In some aspects, the target region comprises the junction between exon 11 and intron 11. In some aspects, the target region comprises the junction between intron 11 and exon 12.

In some aspects, the oligomers of the present disclosure bind to the target nucleic acid (e.g., SEQ ID NO: 31) and the effect on PCSK9 expression and/or activity level is at least about 10% to about 20% reduction in PCSK9 expression and/or activity level compared to the normal PCSK9 expression level (e.g., the PCSK9 expression level of a cell, animal or human treated with saline) and/or normal activity level (e.g. the expression level of a cell, animal or human treated with saline). In some aspects, the reduction in PCSK9 expression and/or activity is at least about 10%, about least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or about 100% compared to the normal expression and/or activity level. In some aspects, the reduction in expression and/or activity is about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100% compared to the normal expression and/or activity level.

In some aspects, such modulation (e.g., reduction of expression level and/or activity) of is seen when using between 0.04 nM and 25 nM, such as between 0.8 nM and 20 nM concentration of the oligomer of the present disclosure. In some aspects, such modulation (e.g., reduction of expression level and/or activity) is seen when using at least about 0.04 nM, at least about 0.05 nM, at least about 0.06 nM, at least about 0.07 nM, at least about 0.08 nM, at least about 0.09 nM, at least about 0.1 nM, at least about 0.2 nM, at least about 0.3 nM, at least about 0.4 nM, at least about 0.5 nM, at least about 0.6 nM, at least about 0.7 nM, at least about 0.8 nM, at least about 0.9 nM, at least about 1 nM, at least about 2 nM, at least about 3 nM, at least about 4 nM, at least about 5 nM, at least about 6 nM, at least about 7 nM, at least about 8 nM, at least about 9 nM, at least about 10 nM, at least about 11 nM, at least about 12 nM, at least about 13 nM, at least about 14 nM, at least about 15 nM, at least about 16 nM, at least about 17 nM, at least about 18 nM, at least about 19 nM, at least about 20 nM, at least about 21 nM, at least about 22 nM, at least about 23 nM, at least about 24 nM, at least about 25 nM concentration of the oligomer of the present disclosure. In some aspects, such modulation (e.g., reduction of expression level and/or activity) is seen when using about 0.04 nM, about 0.05 nM, about 0.06 nM, about 0.07 nM, about 0.08 nM, about 0.09 nM, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 2 nM, about 3 nM, about 4 nM, about 5 nM, about 6 nM, about 7 nM, about 8 nM, about 9 nM, about 10 nM, about 11 nM, about 12 nM, about 13 nM, about 14 nM, about 15 nM, about 16 nM, about 17 nM, about 18 nM, about 19 nM, about 20 nM, about 21 nM, about 22 nM, about 23 nM, about 24 nM, about 25 nM concentration of the oligomer of the present disclosure.

In some aspects, such modulation (e.g., reduction of expression level and/or activity) is seen when using between 0.01 and 15 mg/kg, such as between 0.05 and 10 mg/kg, such as between 0.1 and 7.5 mg/kg, such as between 0.25 and 5 mg/kg, such as 0.5 and 2.5 mg/kg concentration of the compound of the present disclosure. In some aspects, such modulation (e.g., reduction of expression level and/or activity) is seen when using at least about 0.01 mg/kg, at least about 0.02 mg/kg, at least about 0.03 mg/kg, at least about 0.04 mg/kg, at least about 0.05 mg/kg, at least about 0.06 mg/kg, at least about 0.07 mg/kg, at least about 0.08 mg/kg, at least about 0.09 mg·kg, at least about 0.1 mg/kg, at least about 0.2 mg/kg, at least about 0.3 mg/kg, at least about 0.4 mg/kg, at least about 0.5 mg/kg, at least about 0.6 mg/kg, at least about 0.7 mg/kg, at least about 0.8 mg/kg, at least about 0.9 mg/kg, at least about 1 mg/kg, at least about 1.5 mg/kg, at least about 2 mg/kg, at least about 2.5 mg/kg, at least about 3 mg/kg, at least about 4 mg/kg, at least about 4.5 mg/kg, at least about 5 mg/kg, at least about 6 mg/kg, at least about 6.5 mg/kg, at least about 7 mg/kg, at least about 7.5 mg/kg, at least about 8 mg/kg, at least about 8.5 mg/kg, at least about 9 mg/kg, at least about 9.5 mg/kg, at least about 10 mg/kg, at least about 10.5 mg/kg, at least about 11 mg/kg, at least about 11.5 mg/kg, at least about 12 mg/kg, 12.5 mg/kg, at least about 13 mg/kg, at least about 13.5 mg/kg, at least about 14 mg/kg, at least about 14.5 mg/kg, or at least about 15 mg/kg concentration of the compound of the present disclosure. In some aspects, such modulation (e.g., reduction of expression level and/or activity) is seen when using about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg·kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 4.5 mg/kg, about 5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, about 10 mg/kg, about 10.5 mg/kg, about 11 mg/kg, about 11.5 mg/kg, about 12 mg/kg, 12.5 mg/kg, about 13 mg/kg, about 13.5 mg/kg, about 14 mg/kg, about 14.5 mg/kg, or about 15 mg/kg concentration of the compound of the present disclosure.

In some aspects, the PCSK9 expression and/or activity level after the administration of a compound of the present disclosure is less than about 2%, less than about 5%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, or less than about 80% of the PCSK9 expression and/or activity level prior to the administration of a compound of the present disclosure.

In some aspects, the PCSK9 expression and/or activity level after the administration of a compound of the present disclosure is about 2% to about 5%, about 5% to about 10%, about 10% to about 15%, about 15% to about 20%, about 20%, to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, or about 75% to about 80% of the PCSK9 expression and/or activity level prior to the administration of a compound of the present disclosure.

Modulation of expression level can be determined by measuring protein levels, e.g. by the methods such as SDS-PAGE followed by western blotting using suitable antibodies raised against the target protein. Alternatively, modulation of expression levels can be determined by measuring levels of mRNA, e.g., by northern blotting or quantitative RT-PCR. When measuring via mRNA levels, the level of down-regulation when using an appropriate dosage, such as between 0.04 nM and 25 nM, such as between 0.8 and 20 nM concentration, is, in some aspects, typically to a level of between 10-20% the normal levels in the absence of the compound of the present disclosure.

The present disclosure therefore provides an in vitro or in vivo method of down-regulating or inhibiting the expression of PCSK9 protein and/or mRNA in a cell which is expressing PCSK9 protein and/or mRNA, said method comprising administering the oligomer or conjugate according to the present disclosure, e.g., as a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) to said cell to down-regulate or inhibit the expression of PCSK9 protein and/or mRNA in said cell. Suitably the cell is a mammalian cell such as a human cell.

II.c Length

The oligomers of the present disclosure can comprise or consist of a contiguous nucleotide sequence of a total of 16, 17, 18, 19, 20, 21, or 22 contiguous nucleotides in length. In some aspects, the oligomer is longer than 22 contiguous nucleotides in length. Lengths can include region A or region A and B. It is to be understood that in some aspects the oligomers of the present disclosure can be multimers comprising, e.g., 2, 3, 4, 5, 6, or more concatenated ASOs disclosed herein, which can optionally be connected by spacers or linkers comprising nucleotide or non-nucleotide units interposed between each ASO in the multimer. Accordingly, in some aspects, the oligomers of the present disclosure can comprise or consist of a contiguous nucleotide sequence of a total of at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 110, at least about 120, at least about 130, at least about 140, at least about 150, at least about 160, at least about 170, at least about 180, at least about 190, or at least about 200 contiguous nucleotides in length.

In some aspects, the oligomers comprise or consist of a contiguous nucleotide sequence of a total of between 16 and 22 contiguous nucleotides in length, such as 16, 17, 18, 18, 20, 21, or 22 contiguous nucleotides in length. In some particular aspects, the oligomer of region A comprises or consists of a contiguous nucleotide sequence 16 contiguous nucleotides in length.

In some aspects, the oligomer according to the present disclosure consists of no more than 16, 17, 18, 19, 20, 21 or 22 contiguous nucleotides in length. In some aspects, the oligomer of the present disclosure comprises less than 22, less than 21, less than 20, less than 19, less than 18, or less than 17 contiguous nucleotides in length. In some aspects, the oligomer according to the present disclosure consists of 16 or 17, 16 to 18, 16 to 19, 16 to 20, 16 to 21, or 16 to 22 contiguous nucleotides in length.

II.d Nucleotide Analogues

In some aspects, the oligomers of the present disclosure comprise non-naturally occurring nucleotide analogues, e.g., nucleotides which have modified sugar moieties, such as bicyclic nucleotides or 2' modified nucleotides, such as 2' substituted nucleotides. The replacement of naturally occurring nucleotides with non-naturally analogues can confer desirable characteristics or properties to the oligomer, for example, increased resistance to degradation or stability. In some aspects, the nucleotide analogues have a functional effect on the way in which the oligomer works to inhibit expression; for example, by producing increased binding affinity (affinity enhancing) to the target and/or increased resistance to intracellular nucleases and/or increased ease of transport into the cell. Specific examples of nucleoside analogues are described by, e.g. Freier & Altmann (1997) Nucl. Acid Res. 25:4429-4443 and Uhlmann (2000) Curr. Opinion in Drug Development 3:293-213, and in Scheme 1 below:

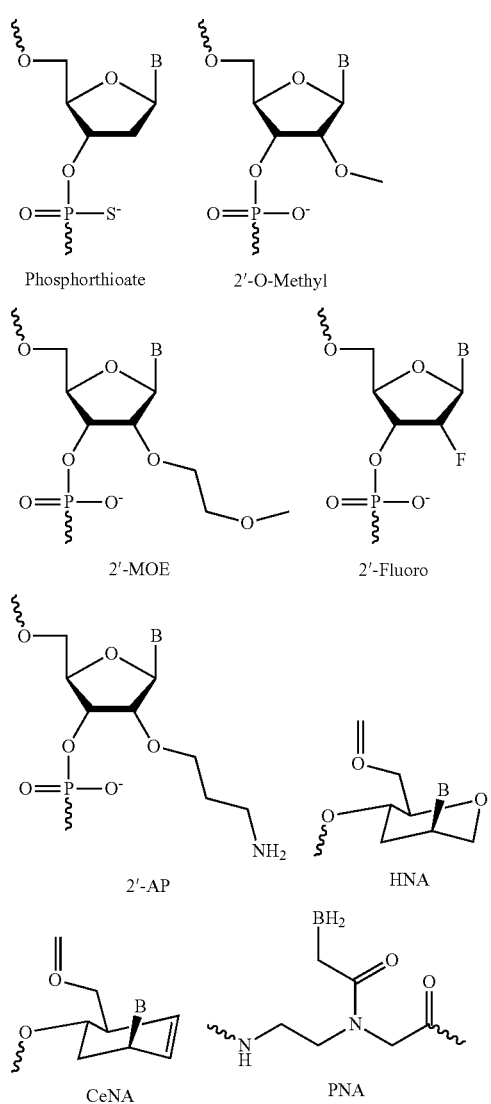

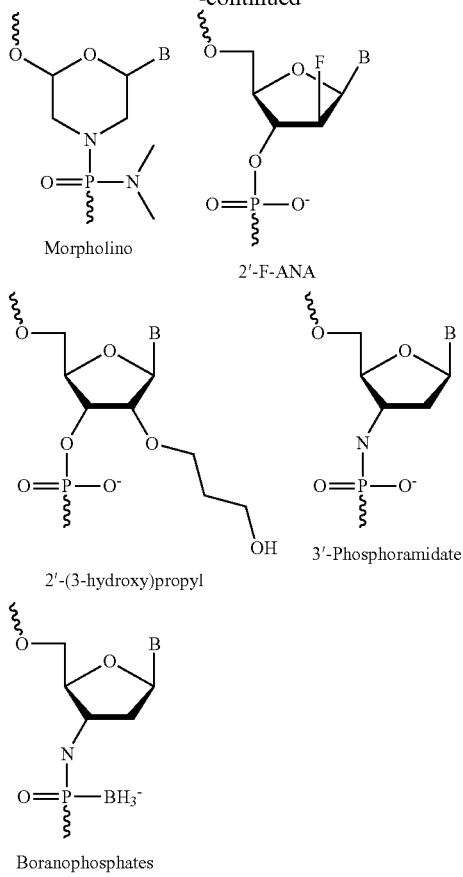

The present disclosure provides oligomers comprising or consisting of a simple sequence of natural occurring nucleotides—preferably 2'-deoxynucleotides (referred here generally as "DNA"), but also possibly ribonucleotides (referred here generally as "RNA"), or a combination of such naturally occurring nucleotides and one or more non-naturally occurring nucleotides, i.e., nucleotide analogues. Such nucleotide analogues can suitably enhance the affinity of the oligomer for the target sequence. Examples of suitable nucleotide analogues are provided by WO2007/031091, which is herein incorporated by reference in its entirety, or are referenced therein.

Incorporation of affinity-enhancing nucleotide analogues in the oligomer, such as LNA or 2'-substituted sugars, can allow the size of the specifically binding oligomer to be reduced, and can also reduce the upper limit to the size of the oligomer before non-specific or aberrant binding takes place. In some aspects, the oligomer of the present disclosure comprises at least one nucleotide analogues. In some aspects, the oligomer of the present disclosure comprises at least two nucleotide analogues. In some aspects, the oligomer of the present disclosure comprises from 3, 4, 5, 6, 7, or 8 nucleotide analogues, e.g. 6 or 7 nucleotide analogues. In some aspects, all the nucleotide analogues are the same. In some aspects, some nucleotide analogs are different. In some aspects, all the nucleotides in the oligomer are nucleotide analogues. In some aspects, when all the nucleotides in the oligomer are nucleotide analogues, all the nucleotide analogues are the same. In some aspects, when all the nucleotides in the oligomer are nucleotide analogues, some of the nucleotide analogues are different. In some aspects, the oligomer of the present disclosure comprises nucleotides analogues, e.g., an analogue A and an analogue B, following a certain pattern, e.g., ABABABABABABABABABABA.

Examples of nucleotide analogues include modifying the sugar moiety to provide a 2'-substituent group or to produce a bicyclic structure which enhances binding affinity and can also provide increased nuclease resistance.

In some aspects, nucleotide analogues present within an antisense oligomer of the present disclosure (such as in regions X' and Y' mentioned in the section "Gapmer Design") are independently selected from, for example: 2'-O-alkyl-RNA units, 2'-OMe-RNA units, 2'-O-alkyl-DNA, 2'-amino-DNA units, 2'-fluoro-DNA units, LNA units, arabino nucleic acid (ANA) units, 2'-fluoro-ANA units, HNA units, INA (intercalating nucleic acid; Christensen (2002) Nucl. Acids. Res. 30: 4918-4925) units and 2'MOE units.

In some aspects, nucleotide analogues are 2'-O-methoxyethyl-RNA (2'MOE), 2'-fluoro-DNA monomers, or LNA nucleotide analogues, and as such an antisense oligonucleotide of the present disclosure can comprise nucleotide analogues which are independently selected from these three types of analogue, or can comprise only one type of analogue selected from the three types. In some aspects at least one of said nucleotide analogues is 2'-MOE-RNA, such as 2, 3, 4, 5, 6, 7, 8, 9 or 10 2'-MOE-RNA nucleotide units. In some aspects, at least one of said nucleotide analogues is 2'-fluoro DNA, such as 2, 3, 4, 5, 6, 7, 8, 9 or 10 2'-fluoro-DNA nucleotide units.

In some aspects, the oligomer can be a duplex RNA comprising a sense and an antisense strand, wherein the sense strand follows a pattern 3'ABABABABAAABABB-BABABA5' and the antisense strand follows a pattern 5'BABABABABABBBABAAABABAB3,' wherein A is a 2'-fluoro analogue and B is 2-OMe analogue, and wherein the antisense strand has a two base overhang with respect to the sense strand. In some aspects, the 5' end of the sense strand is conjugated to a GalNAc moiety. In some aspects, the last two linkages of the 5' end of the antisense strand are PS.

In some aspects, the oligomer can be a duplex RNA comprising a sense and an antisense strand, wherein the sense strand follows a pattern 3'BBBBBBA-BAAABBBBBBBBBB5' and the antisense strand follows a pattern 5'BBBBBBBABABBBBABBABBBAB3,' wherein A is a 2'-fluoro analogue and B is 2-OMe analogue, and wherein the antisense strand has a two base overhang with respect to the sense strand. In some aspects, the 5' end of the sense strand is conjugated to a GalNAc moiety. In some aspects, the last two linkages of the 5' end and 3' end of the antisense strand are PS, and the last two 3' end linkages of the sense strand are PS.

In some aspects, the oligomer can be a duplex RNA comprising a sense and an antisense strand, wherein the sense strand comprises one or more terminal, chirally-modified internucleotide linkages at the 5' end; and the antisense strand comprises one or more terminal, chirally-modified internucleotide linkages at the 5' end and one or more terminal, chirally-modified internucleotide linkages at the 3' end.

In some aspects, the oligomer can be a duplex RNA comprising a sense and an antisense strand a sense strand sequence having 4-12 asymmetrical 2'-O-alkyl modifications, at least 4 of which occur at the 4 terminal nucleotides of the 5' end; and an antisense sequence having at least 4 asymmetrical phosphorothioate modifications.

In some aspects, the oligomer can be an duplex RNA comprising a first and a second sequence, having a first monomer in the first sequence and a second monomer in the second sequence within the first 3, 4, 5, or 6 positions from either the 3' end or the 5' end, wherein the first and second monomers are selected such that (i) the first and second monomers are naturally occurring ribonucleotides or modified ribonucleotides having naturally occurring bases, wherein the ribonucleotide of the first monomer and the ribonucleotide of the second monomers, when occupying complementary sites that do not pair and have no substantial level of H-bonding, form a non canonical Watson-Crick pairing; and (ii) the stability of the pairing of the monomers contributing to forming a duplex between the first and second sequence differs from the stability of the pairing between the first sequence and a target sequence or between the second sequence and a target sequence, wherein the duplex RNA comprises a TT overhang sequence.

In some aspects, the oligomer can be a duplex RNA comprising: a sense strand sequence having 4-12 asymmetrical 2'-O-alkyl modifications, at least 4 of which occur within the 6 terminal nucleotides of the 5' end; and an antisense sequence having at least 4 asymmetrical phosphorothioate modifications.

In some aspects, the oligomer can be a duplex RNA comprising: a sense sequence having 4-12 asymmetrical 2'-O-alkyl modifications, at least 4 of which occur within the 6 terminal nucleotides of the 5' end; and an antisense sequence having at least 4 asymmetrical phosphorothioate modifications, wherein the duplex RNA comprises a multivalent galactose or a multivalent N-acetyl-galactosamine, and wherein the antisense sequence targets a PCSK9 target sequence.

In some aspects, the oligomer can be a duplex RNA for inhibiting the expression of PCSK9 in a cell, comprising a sense sequence and an antisense sequence, wherein the sense sequence has one or more asymmetrical 2'-0 alkyl modifications and the antisense sequence has 4-20 phosphorothioate modifications, wherein the duplex RNA comprises a multivalent galactose or a multivalent N-acetyl-galactosamine, and wherein the antisense sequence targets a human PCSK9 sequence.

In some aspects, the oligomer can be a duplex RNA for inhibiting the expression of PCSK9 in a cell, comprising a sense sequence and an antisense sequence, wherein the sense sequence has one or more asymmetrical 2'-0 alkyl modifications and the antisense sequence has 4-20 phosphorothioate modifications, wherein the antisense sequence has fewer asymmetrical 2'-O alkyl modifications than the sense sequence, wherein the sense sequence comprises a conjugate group, and wherein the antisense sequence targets the PCSK9 sequence.

In some aspects, the oligomer can be a duplex RNA with reduced off-target RNA inhibiting activity, comprising: a. an antisense strand that is complementary to a target gene; and b. a sense strand that is complementary to said antisense strand and comprises at least one modified nucleotide in the region corresponding to the target cleavage site, wherein said modified nucleotide is abasic; wherein said reduced-off-target RNA inhibiting activity is relative to a corresponding unmodified duplex RNA agent.

In some aspects, the oligomer can be a duplex RNA capable of inhibiting PCSk9 expression in vivo, comprising: (a) a sense strand, wherein said sense strand comprises (i) an alternating motif with at least 2 different chemically modified nucleotides; and (ii) one or more carbohydrate ligand; and (b) an antisense strand, wherein said antisense strand comprises (i) an alternating motif with at least 2 different chemically modified nucleotides, wherein the alternating motif is within the duplex region and the composition optionally further comprises one or more overhangs and/or capping groups.

In some aspects, the oligomer can be a duplex RNA capable of inhibiting the expression of PCSK9, comprising a sense strand and an antisense strand, each strand having 14 to 30 nucleotides, wherein the duplex is represented by the formula below:

(III)
sense:
5' $n_p$-$N_a$-(X X X)$_i$-$N_b$-Y Y Y-$N_b$-(Z Z Z)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:
i, j, k, and l are each independently 0 or 1, provided that at least one of i, j, k, and l is 1;
p and q are each independently 0-6;
each Na and Na' independently represents an oligonucleotide sequence comprising 2-20 nucleotides which are either modified or unmodified or combinations thereof, each sequence comprising at least two differently modified nucleotides, each Nb and Nb' independently represents an oligonucleotide sequence comprising 1-10 modified nucleotides;
each $n_p$, $n_p'$, $n_q$ and $n_q'$ independently represents an overhang nucleotide sequence comprising 0-6 nucleotides; and
XXX, YYY, ZZZ, X'X'X', Y'Y'Y', and Z'Z'Z' each independently represent one motif of three identical modifications on three consecutive nucleotides; and
wherein the modification on Nb is different than the modification on Y and the modification on Nb' is different than the modification on Y'.

In some aspects, the oligomer can be a duplex RNA capable of inhibiting the expression of PCSK9, comprising a sense strand and an antisense strand, each strand having 14 to 40 nucleotides, wherein the dsRNA agent is represented by the formula below:

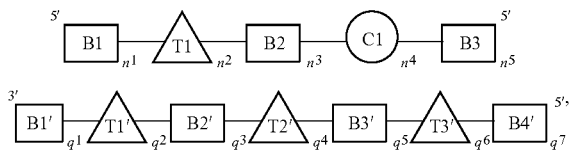

wherein: B1, B2, B3, B1', B2', B3', and B4' each independently represent a nucleotide containing a modification selected from the group consisting of 2'-O alkyl, 2'-substituted alkoxy, 2'-substituted alkyl, 2'-halo, ENA, and BNA/LNA;
C1 is a thermally destabilizing nucleotide, selected from the group consisting of i) a nucleotide that forms a mismatch pair with the opposing nucleotide in the antisense strand, ii) a nucleotide having an abasic modification, and iii) a nucleotide having a sugar modification, and placed at a site opposite to the seed region (positions 2-8) of the antisense strand;
T1, T1', T2', and T3' each independently represent a nucleotide comprising a modification providing the nucleotide a steric bulk that is less than the steric bulk of a 2'-OMe modification, wherein the modification is at the 2'-position of a ribose sugar of the nucleotide or at a position of a non-ribose nucleotide similar to the 2'-position of a ribose sugar, and wherein T1' and T3' are separated by 11 nucleotides in length;
each $n^1$, $n^3$, and $q^1$ is independently 4 to 15 nucleotides in length;
each $n^5$, $q^3$, and $q^7$ is independently 1-6 nucleotide(s) in length;
each $n^2$, $n^4$, and $q^6$ is independently 1-3 nucleotide(s) in length;
$q^5$ is independently 0-10 nucleotide(s) in length; and
each $n^2$, $n^4$, and $q^4$ is independently 0-3 nucleotide(s) in length; and
wherein the dsRNA agent has two blunt ends at both ends of the dsRNA duplex.

In some aspects, the oligomer can be a duplex RNA capable of inhibiting the expression of a PCSK9, comprising a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex within the first 9 nucleotide positions of the 5' region or a precursor thereof, wherein said sense strand comprises an ASGPR ligand.

In some aspects, the oligomer comprises a modification motif (e.g., the pattern of distribution of nucleotide analogs along the sense and antisense sequences, internucleoside linkages, conjugate moieties, etc.) disclosed in U.S. Pat. Nos. 8,110,674; 8,420,799; 8,809,516; 9,222,091; 9,708,615; 10,273,477; 9,290,760; 10,233,448; or 9,796,974; U.S. Appl. Publ. No. 2018-0258427A1; or Int'l Publ. WO2018098328A1, all of which are herein incorporated by reference in their entireties.

In some aspects, the nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). In some aspects, the LNA is beta-D-oxy-LNA. In some aspects, there is only one of the above types of nucleotide analogues, e.g., LNA, present in an antisense oligonucleotide of the present disclosure, or contiguous nucleotide sequence thereof.

The antisense oligonucleotide of the present disclosure comprises at least one Locked Nucleic Acid (LNA) unit, such as 1, 2, 3, 4, 5, 6, 7, or 8 LNA units, such as from 3 to 7, or 4 to 8 LNA units. In some aspects, at least one of the nucleotide analogues is a locked nucleic acid (LNA); for example, at least 3 or at least 4, or at least 5, or at least 6, or at least 7, or 8, of the nucleotide analogues can be LNA. In some aspects, all the nucleotide analogues can be LNA.

In some aspects, an antisense oligonucleotide of the present disclosure can comprise both nucleotide analogues (e.g., LNA) and DNA units. In some aspects, the combined total of nucleotide analogues (preferably LNA) and DNA units is between 5 and 22, e.g., 16 to 18, or 16 to 20, ore 16 to 22. In some aspects, the combined total of nucleotide analogues (e.g., LNA) and DNA units is 5, 6, 7, 8, 9, 10, 11, 12, 13, 14, 15, 16, 17, 18, 19, 20, 21 or 22.

In some aspects, the nucleotide sequence of an antisense oligonucleotide of the present disclosure, such as the contiguous nucleotide sequence, consists of at least one nucleotide analogue (LNA) and the remaining nucleotide units are DNA units. In some aspects, an antisense oligonucleotide of the present disclosure comprises only LNA nucleotide analogues and naturally occurring nucleotides (such as RNA or DNA, most preferably DNA nucleotides), optionally with modified internucleoside linkages such as phosphorothioate.

It will be recognized that when referring to a particular nucleotide sequence motif or nucleotide sequence, which consists of only nucleotides, the oligomers of the present disclosure which are defined by that sequence can comprise a corresponding nucleotide analogue in place of one or more of the nucleotides present in said sequence, such as LNA units or other nucleotide analogues, which raise the duplex stability/Tm of the oligomer/target duplex (i.e., affinity enhancing nucleotide analogues).

Tm Assay: Oligonucleotide and RNA target (PO) duplexes are diluted to 3 mM in 500 ml RNase-free water and mixed with 500 ml 2× Tm-buffer (200 mM NaCl, 0.2 mM EDTA, 20 mM sodium phosphate, pH 7.0). The solution is heated to 95° C. for 3 min and then allowed to anneal in room temperature for 30 min. The duplex melting temperatures (Tm) are measured on a Lambda 40 UV/VIS Spectrophotometer equipped with a Peltier temperature programmer PTP6 using PE Templab software (Perkin Elmer). The temperature is ramped up from about 20° C. to about 95° C. and then down to about 25° C., recording absorption at 260 nm. First derivative and the local maximums of both the melting and annealing are used to assess the duplex Tm.

In some aspects, any mismatches between the nucleotide sequence of the oligomer and the target sequence are found in regions outside the affinity enhancing nucleotide analogues, such as region Y' as referred to in the Gapmer Design section, and/or at a position with non-modified, such as DNA nucleotides, in the oligonucleotide, and/or in regions which are 5' or 3' to the contiguous nucleotide sequence.

II.e LNA

In some aspects, an oligomer of the present disclosure (e.g., an ASO) comprises at least one LNA unit. The terms "Locked Nucleic Acid" and "LNA" refer to any bicyclic nucleoside analogue which comprises a bridge between the 2' and 4' positions in the ribose ring, i.e., a 2' to 4' bicyclic nucleotide analogue. LNA is in the literature sometimes referred to as BNA (bridged nucleic acid or bicyclic nucleic acid) and the two terms can be used interchangeably. The term LNA generally refers to an LNA monomer. The term "LNA oligonucleotide" refers to an oligonucleotide (e.g., an ASO such as gapmer) containing one or more such bicyclic nucleotide analogues. In some aspects, bicyclic nucleoside analogues are LNA nucleotides, and these terms can therefore be used interchangeably. In such aspects, both are characterized by the presence of a linker group (such as a bridge) between C2' and C4' of the ribose sugar ring.

In some aspects, an antisense oligonucleotide of the present disclosure can comprise both beta-D-oxy-LNA, and one or more of the following LNA units: thio-LNA, amino-LNA, oxy-LNA, 5'-methyl-LNA and/or ENA in either the beta-D or alpha-L configurations or combinations thereof.

In some aspects, all LNA cytosine units are 5'-methyl-Cytosine. In some aspects, at least one nucleoside analogue present in the first region (X') is a bicyclic nucleoside analogue. In some aspects, at least 2, at least 3, at least 4, at least 5, at least 6, at least 7, at least 8 nucleoside analogues present in the first region (X') are bicyclic nucleoside analogues. Thus, in some aspects, all the nucleosides in an oligonucleotide of the present disclosure, except the DNA and/or RNA nucleosides of region Y', are sugar modified nucleoside analogues, e.g., bicyclic nucleoside analogues, such as LNA (e.g., beta-D-X-LNA or alpha-L-X-LNA, wherein X is oxy, amino or thio), other LNAs disclosed herein including, but not limited to (R/S) cET, cMOE, or 5'-Me-LNA, or any combination thereof.

In some aspects, the LNA used in an oligonucleotide of the present disclosure has the structure of the general formula II:

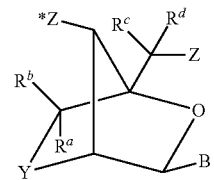

Formula II wherein Y is selected from the group consisting of —O—, —CH$_2$O—, —S—, —NH—, N(R$^e$) and/or —CH$_2$—; Z and Z* are independently selected among an internucleoside linkage, RH, a terminal group or a protecting group; B constitutes a natural or non-natural nucleotide base moiety (nucleobase), and RH is selected from hydrogen and C1-4-alkyl; R$^a$, R$^b$, R$^c$, R$^d$, and R$^e$ are, optionally independently, selected from the group consisting of hydrogen, optionally substituted C1-12-alkyl, optionally substituted C2-12-alkenyl, optionally substituted C2-12-alkynyl, hydroxy, C1-12-alkoxy, C2-12-alkoxyalkyl, C2-12-alkenyloxy, carboxy, C1-12-alkoxycarbonyl, C1-12-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C1-6-alkyl)amino, carbamoyl, mono- and di(C1-6-alkyl)-amino-carbonyl, amino-C1-6-alkyl-aminocarbonyl, mono- and di(C1-6-alkyl)amino-C1-6-alkyl-aminocarbonyl, C1-6-alkyl-carbonylamino, carbamido, C1-6-alkanoyloxy, sulphono, C1-6-alkylsulphonyloxy, nitro, azido, sulphanyl, C1-6-alkylthio, halogen, DNA intercalators, photochemically active groups, thermochemically active groups, chelating groups, reporter groups, and ligands, where aryl and heteroaryl can be optionally substituted and where two geminal substituents R$^a$ and R$^b$ together can designate optionally substituted methylene (=CH$_2$); and RH is selected from hydrogen and C1-4-alkyl.

In some aspects R$^a$, R$^b$, R$^c$, R$^d$, and R$^e$ are, optionally, independently selected from the group consisting of hydrogen and C1-6 alkyl, such as methyl. For all chiral centers, asymmetric groups can be found in either R or S orientation, for example, two exemplary stereochemical isomers include the beta-D and alpha-L isoforms, which can be illustrated as follows:

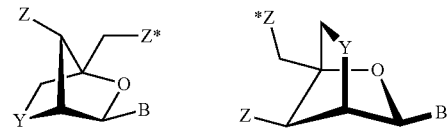

Specific exemplary LNA units are shown below:

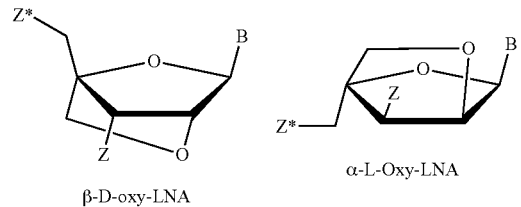

β-D-oxy-LNA      α-L-Oxy-LNA

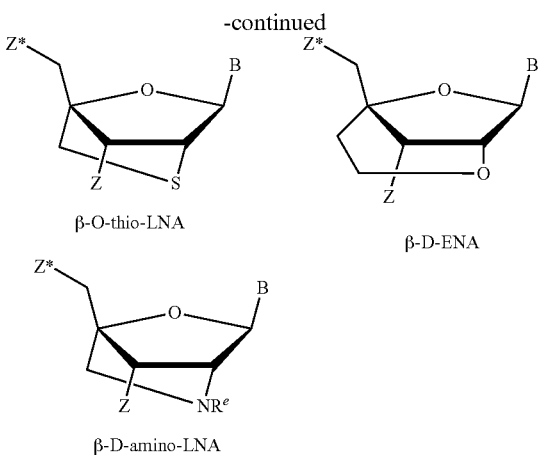

β-O-thio-LNA    β-D-ENA

β-D-amino-LNA

The term "thio-LNA" comprises a locked nucleotide in which Y in the general formula above is selected from S or —CH₂—S—. Thio-LNA can be in both beta-D and alpha-L-configuration.

The term "amino-LNA" comprises a locked nucleotide in which Y in the general formula above is selected from —N(H)—, N(R)—, CH₂—N(H)—, and —CH₂—N(R)— where R is selected from hydrogen and C1-4-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —CH₂—O— (where the oxygen atom of —CH₂—O— is attached to the 2'-position relative to the base B). $R^e$ is hydrogen or methyl.

In some exemplary aspects LNA is selected from beta-D-oxy-LNA, alpha-L-oxy-LNA, beta-D-amino-LNA and beta-D-thio-LNA, in particular beta-D-oxy-LNA.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In some aspects, compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-(CH₂)—O-2'(LNA); 4'-(CH₂)—S-2'; 4'-(CH₂)₂—O-2' (ENA); 4'-CH(CH₃)—O-2' and 4'-CH(CH₂OCH₃)—O-2*, and analogs thereof (see, U.S. Pat. No. 7,399,845, which is herein incorporated by reference in its entirety); 4'-C(CH₃)(CH₃)—O-2', and analogs thereof (see, PCT Publ. WO2009/006478, which is herein incorporated by reference in its entirety); 4'-CH₂—N(OCH₃)-2', and analogs thereof (see, PCT Publ. WO2008/150729, which is herein incorporated by reference in its entirety); 4'-CH₂—O—N(CH₃)-2' (see, U.S. patent application Publ. US2004/0171570, which is herein incorporated by reference in its entirety); 4'-CH₂—N(R)—O-2', wherein R is H, C1-C10 alkyl, or a protecting group (see, U.S. Pat. No. 7,427,672, which is herein incorporated by reference in its entirety); 4'-CH₂—C(H)(CH₃)-2' (see, Chattopadhyaya et al, J. Org. Chem., 2009, 74:118-134, which is herein incorporated by reference in its entirety); and 4'-CH₂—C(=CH₂)-2', and analogs thereof (see, PCT Publ. WO 2008/154401, which is herein incorporated by reference in its entirety). Also see, for example: Singh et al., Chem. Commun., 1998, 4:455-456; Koshkin et al., Tetrahedron, 1998, 54:3607-3630; Wahlestedt et al., Proc. Natl. Acad. Sci. U.S.A, 2000, 97:5633-5638; Kumar et al., Bioorg. Med. Chem. Lett., 1998, 8:2219-2222; Singh et al., J. Org. Chem., 1998, 63:10035-10039; Srivastava et al., J. Am. Chem. Soc, 2007, 129:8362-8379; Elayadi et al., Curr. Opinion Invens. Drugs, 2001, 2:558-561; Braasch et al., Chem. Biol, 2001, 8:1-7; Oram et al, Curr. Opinion Mol. Ther., 2001, 3:239-243; U.S. Pat. Nos. 6,670,461, 7,053,207, 6,268,490, 6,770,748, 6,794,499, 7,034,133, 6,525,191, 7,399,845; published PCT Publ's WO2004/106356, WO94/14226, WO2005/021570, and WO2007/134181; U.S. patent application Publ. US2004/0171570, US2007/0287831, and US2008/0039618; and U.S. patent application Ser. No. 12/129,154, U.S. patent applications 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922, all of which are herein incorporated by reference in their entireties.

Each of the foregoing bicyclic nucleosides can be prepared having one or more stereochemical sugar configurations including for example α-L-ribofuranose and beta-D-ribofuranose (see, e.g., PCT Publ. WO 99/14226). In some aspects, bicyclic sugar moieties of LNA nucleosides include, but are not limited to, compounds having at least one bridge between the 4' and the 2' position of the pentofuranosyl sugar moiety wherein such bridges independently comprises 1 or from 2 to 4 linked groups independently selected from —[CiR$^a$ XR$^b$)]—, —C(R$^a$)=C(R$^b$)—, —C(R$^a$)=N—, —C(=NR$^a$)—, —C(=O)—, —C(=S)—, —O—, —Si(R$^a$)₂—, —S(=O)x-, and —N(R$^a$)—; wherein: x is 0, 1, or 2; n is 1, 2, 3, or 4; each R and R$^b$ is, independently, H, a protecting group, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, heterocycle radical, substituted heterocycle radical, heteroaryl, substituted heteroaryl, C5-C7 alicyclic radical, substituted C5-C7 alicyclic radical, halogen, OJ1, NJ1J2, SJ1, N3, COOJ1, acyl (C(=O)—H), substituted acyl, CN, sulfonyl (S(=O)₂-J1), or sulfoxyl (S(=O)-J1), wherein each J1 and J2 is, independently, H, C1-C6 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, acyl (C(=O)—H), substituted acyl, a heterocycle radical, a substituted heterocycle radical, C1-C12 aminoalkyl, substituted C1-C12 aminoalkyl, or a protecting group.

In some aspects, the bridge of a bicyclic sugar moiety is, —[C(R$^a$)(R$^b$)]n—, —[C(R$^a$)(R$^b$)]n-O—, —C(R$^a$R$^b$)—N(R)—O— or, —C(R$^a$R$^b$)—O—N(R)—. In some aspects, the bridge is 4'-CH₂-2', 4'-(CH₂)₂-2', 4'-(CH₂)₃-2', 4'-CH₂—O-2', 4*-(CH₂)₂—O-2', 4'-CH₂—O—N(R)-2', and 4'-CH₂—N(R)—O-2'-, wherein each R is, independently, H, a protecting group, or C1-C12 alkyl.

In some aspects, bicyclic nucleosides are further defined by isomeric configuration. For example, a nucleoside comprising a 4'-2' methylene-oxy bridge can be in the α-L configuration or in the β-D configuration. Previously, α-L-methyleneoxy (4'-CH₂—O-2') BNA's have been incorporated into antisense oligonucleotides that showed antisense activity. See Frieden et al (2003) Nucleic Acids Research 21:6365-6372).

In some aspects, bicyclic nucleosides include, but are not limited to, (A) α-L-Methyleneoxy (4'-CH₂—O-2') BNA,
(B) β-D-Methyleneoxy (4'-CH₂—O-2') BNA,
(C) Ethyleneoxy (4'-(CH₂)₂—O-2') BNA,
(D) Aminooxy (4'-CH₂—O—N(R)-2') BNA, (E) Oxyamino (4'-CH$_2$—N(R)—O-2') BNA,
(F) Methyl(methyleneoxy) (4'-CH(CH$_3$)—O-2') BNA,
(G) Methylene-thio (4'-CH$_2$—S-2') BNA,
(H) Methylene-amino (4'-CH$_2$—N(R)-2') BNA,
(I) Methyl carbocyclic (4'-CH$_2$—CH(CH$_3$)-2') BNA, and
(J) Propylene carbocyclic (4'-(CH$_2$)$_3$-2') BNA as depicted below.

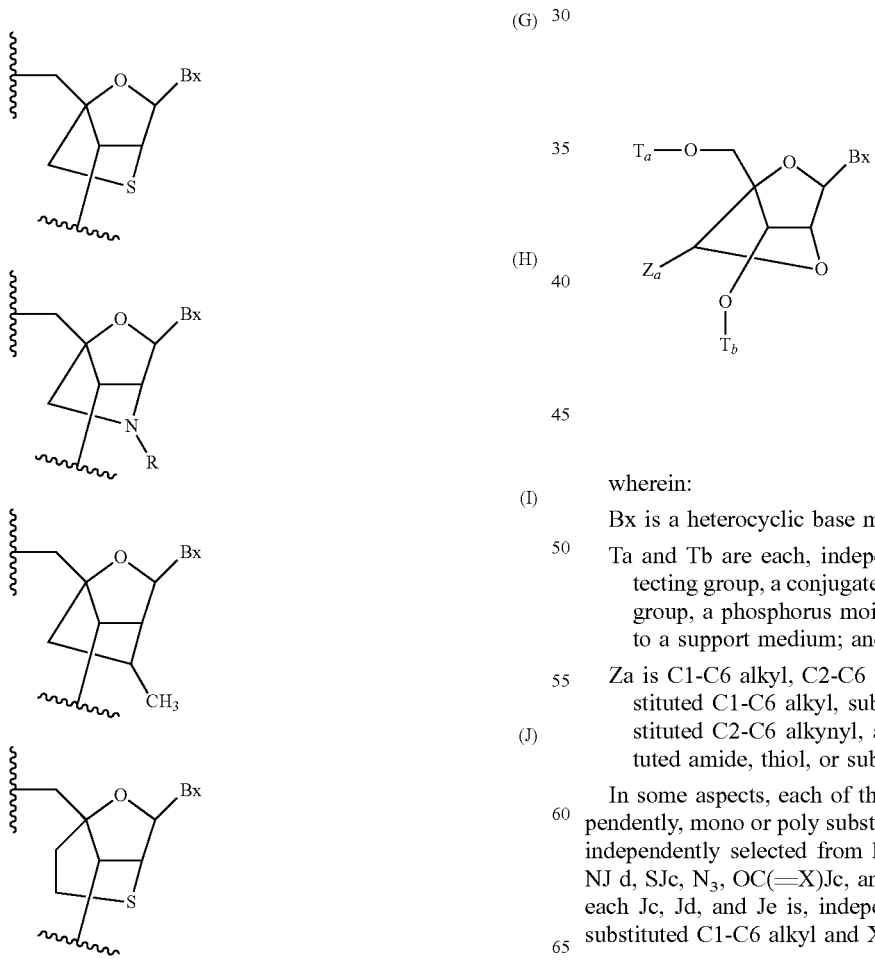

wherein Bx is the base moiety and R is, independently, H, a protecting group or C1-C2 alkyl.

In some aspects, bicyclic nucleoside is defined by the formula below:

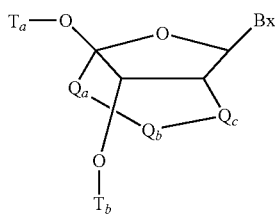

wherein:

Bx is a heterocyclic base moiety;

Qa-Qb-Qc is —CH$_2$—N(Rc)-CH$_2$—, —C(=O)—N(Rc)-CH$_2$—, —CH$_2$—O—N(Rc)-, —CH$_2$—N(Rc)-O—, or —N(Rc)-O—CH$_2$;

Rc is C1-C12 alkyl or an amino protecting group; and,

Ta and Tb are each, independently, H, a hydroxyl protecting group, a conjugate group, a reactive phosphorus group, a phosphorus moiety, or a covalent attachment to a support medium.

In some aspects, bicyclic nucleoside is defined by the formula below:

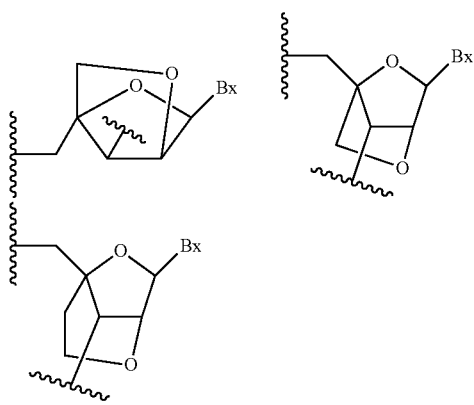

wherein:

Bx is a heterocyclic base moiety;

Ta and Tb are each, independently, H, a hydroxyl protecting group, a conjugate group, a reactive phosphorus group, a phosphorus moiety, or a covalent attachment to a support medium; and, Za is C1-C6 alkyl, C2-C6 alkenyl, C2-C6 alkynyl, substituted C1-C6 alkyl, substituted C2-C6 alkenyl, substituted C2-C6 alkynyl, acyl, substituted acyl, substituted amide, thiol, or substituted thio.

In some aspects, each of the substituted groups is, independently, mono or poly substituted with substituent groups independently selected from halogen, oxo, hydroxyl, OJc, NJd, SJc, N$_3$, OC(=X)Jc, and NJeC(=X)NJcJd, wherein each Jc, Jd, and Je is, independently, H, C1-C6 alkyl, or substituted C1-C6 alkyl and X is O or NJc.

In some aspects, bicyclic nucleoside is defined by the formula below:

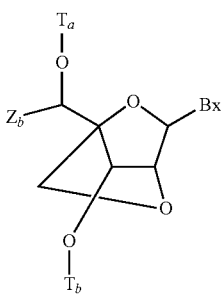

wherein:

Bx is a heterocyclic base moiety;

Ta and Tb are each, independently, H, a hydroxyl protecting group, a conjugate group, a reactive phosphorus group, a phosphorus moiety, or a covalent attachment to a support medium; and, Rd is C1-C6 alkyl, C2-C6 alkenyl, C2-C6 alkynyl, substituted C1-C6 alkyl, substituted C2-C6 alkenyl, substituted C2-C6 alkynyl, or substituted acyl (C(=O)—).

In some aspects, bicyclic nucleoside is defined by the formula below:

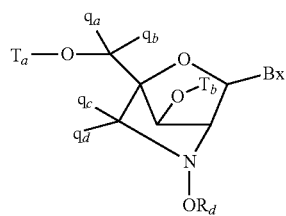

IV wherein:

Bx is a heterocyclic base moiety;

Ta and Tb are each, independently H, a hydroxyl protecting group, a conjugate group, a reactive phosphorus group, a phosphorus moiety, or a covalent attachment to a support medium;

Rd is C1-C6 alkyl, substituted C1-C6 alkyl, C2-C6 alkenyl, substituted C2-C6 alkenyl, C2-C6 alkynyl, substituted C2-C6 alkynyl;

each qb, qc, and qd is, independently, H, halogen, C—C6 alkyl, substituted C1-C6 alkyl, C2-C6 alkenyl, substituted C2-C6 alkenyl, C2-C6 alkynyl, or substituted C2-C6 alkynyl, C1-C6 alkoxyl, substituted C1-C6 alkoxyl, acyl, substituted acyl, C1-C6 aminoalkyl, or substituted C1-C6 aminoalkyl;

In some aspects, bicyclic nucleoside is defined by the following formula:

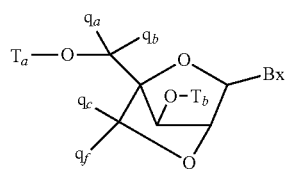

V wherein:

Bx is a heterocyclic base moiety;

Ta and Tb are each, independently, H, a hydroxyl protecting group, a conjugate group, a reactive phosphorus group, a phosphorus moiety, or a covalent attachment to a support medium;

qa, qb, qc, and qf are each, independently, hydrogen, halogen, C1-C12 alkyl, substituted C1-C12 alkyl, C2-C12 alkenyl, substituted C2-C12 alkenyl, C2-C12 alkynyl, substituted C2-C12 alkynyl, C1-C12 alkoxy, substituted C1-C12 alkoxy, OJj, SJj, SOJj, SO$_2$Jj, NJjJk, N$_3$, CN, C(=O)OJj, C(=O)NJj Jk, C(=O)Jj, O—C(=O)NJj Jk, N(H)C(=NH)NJj Jk, N(H)C(=O) NJj Jk, or N(H)C(=S)NJjJk;

or qe and qf together are =C(qg)(qh) wherein qg and qh are each, independently, H, halogen, C1-C12 alkyl, or substituted C1-C12 alkyl.

In some aspects, the bicyclic nucleoside is defined by the following formula:

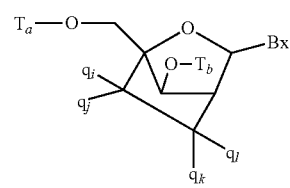

VI wherein:

Bx is a heterocyclic base moiety;

Ta and Tb are each, independently, H, a hydroxyl protecting group, a conjugate group, a reactive phosphorus group, a phosphorus moiety, or a covalent attachment to a support medium; each qj, qj, qk and qf is, independently, H, halogen, C1-C12 alkyl, substituted C1-C12 alkyl, C2-C12 alkenyl, substituted C2-C12 alkenyl, C2-C12 alkynyl, substituted C2-C12 alkynyl, C1-C12 alkoxyl, substituted C2-C12 alkoxyl, OJj, SJj, SOJj, SO$_2$Jj, NJjJk, N$_3$, CN, C(=O)OJj, C(=O)NJjJk, C(=O)Jj, O—C(=O)NJjJk, N(H)C(=NH)NJjJk, N(H)C(=O)NJjJk, or (H)C(=S)NJjJk;

and qi and qj or ql and qk together are =C(qg)(qh), wherein qg and qh are each, independently, H, halogen, C1-C12 alkyl, or substituted C1-C6 alkyl.

One carbocyclic bicyclic nucleoside having a 4'-(CH$_2$)$_3$-2' bridge and the alkenyl analog, bridge 4'-CH=CH—CH$_2$-2', have been described in Freier et al (1997) Nucleic Acids Research 25:4429-4443 and Albaek et al (2006) J. Org. Chem. 71:7731-77 '40.

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom. As used herein, "monocyclic nucleosides" refer to nucleosides comprising modified sugar moieties that are not bicyclic sugar moieties. In some aspects, the sugar moiety, or sugar moiety analogue, of a nucleoside can be modified or substituted at any position. As used herein, "2'-modified sugar" means a furanosyl sugar modified at the 2' position. In some aspects, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In some aspects, 2' modifications are selected from substituents including, but not limited to: O[(CH$_2$)nO]mCH$_3$, O(CH$_2$)nNH$_2$, O(CH$_2$)nCH$_3$, O(CH$_2$)nONH$_2$, OCH$_2$C(=O)N(H)CH$_3$, and O(CH$_2$)nON[(CH$_2$)nCH$_3$]$_2$, where n and m are from 1 to about 10.

Other 2'-substituent groups can also be selected from: C1-C12 alkyl; substituted alkyl; alkenyl; alkynyl; alkaryl; aralkyl; O-alkaryl or O-aralkyl; SH; SCH$_3$; OCN; Cl; Br; CN; CF$_3$; OCF$_3$; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an R; a cleaving group; a reporter group; an intercalator; a group for improving pharmacokinetic properties; and a group for improving the pharmacodynamic properties of an antisense compound, and other substituents having similar properties.

In some aspects, modified nucleosides comprise a 2'-MOE side chain. Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent are potent antisense inhibitors of gene expression for in vivo use.

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), altritol nucleic acid (ANA), mannitol nucleic acid (MNA), fluoro HNA (F-HNA), or those compounds defined by the formula below:

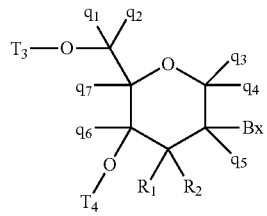

wherein:

Bx is a heterocyclic base moiety;

T3 and T4 are each, independently, an internucleoside linking group linking the tetrahydropyran nucleoside analog to the antisense compound or one of T3 and T4 is an internucleoside linking group linking the tetrahydropyran nucleoside analog to the antisense compound and the other of T3 and T4 is H, a hydroxyl protecting group, a linked conjugate group, or a 5' or 3'-terminal group; q1, q2, q3, q4, q5, q6, and q7 are each, independently, H, C1-C6 alkyl, substituted C1-C6 alkyl, C2-C6 alkenyl, substituted C2-C6 alkenyl, C2-C6 alkynyl, or substituted C2-C6 alkynyl; and one of R$_1$ and R$_2$ is hydrogen and the other is selected from halogen, substituted or unsubstituted alkoxy, NJ, J2, SJ, N$_3$, OC(=X)J1, OC(=X)NJ1J2, NJ3C(=X)NJ1J2, and CN, wherein X is O, S, or NJ1, and each J1, J2, and J3 is, independently, H or C1-C6 alkyl. In some aspects, the modified THP nucleosides of the formula above are provided wherein qm, qn, qp, qr, qs, qt, and qu are each H. In some aspects, at least one of qm, qn, qp, qr, qs, qt, and qu is other than H. In some aspects, at least one of qm, qn, qp, qr, qs, qt, and qu is methyl. In some aspects, THP nucleosides of the formula above are provided wherein one of R$_1$ and R$_2$ is F. In some aspects, R$_1$ is fluoro and R$^2$ is H, R$_1$ is methoxy and R$^2$ is H, or R$_1$ is methoxyethoxy and R$_2$ is H.

As used herein, "2'-modified" or "2'-substituted" refers to a nucleoside comprising a sugar comprising a substituent at the 2' position other than H or OH. 2'-modified nucleosides, include, but are not limited to nucleosides with non-bridging 2' substituents, such as allyl, amino, azido, thio, O-allyl, O—C1-C10 alkyl, —OCF$_3$, O—(CH$_2$)$_2$—O—CH$_3$, 2'-O(CH$_2$)$_2$SCH$_3$, O—(CH$_2$)$_2$—O—N(Rm)(Rn), or O—CH$_2$—C(=O)—N(Rm)(Rn), where each Rm and R, is, independently, H or substituted or unsubstituted C1-C10 alkyl. 2'-modified nucleosides can further comprise other modifications, for example, at other positions of the sugar and/or at the nucleobase.

In some aspects, the LNA units have a structure selected from the following group:

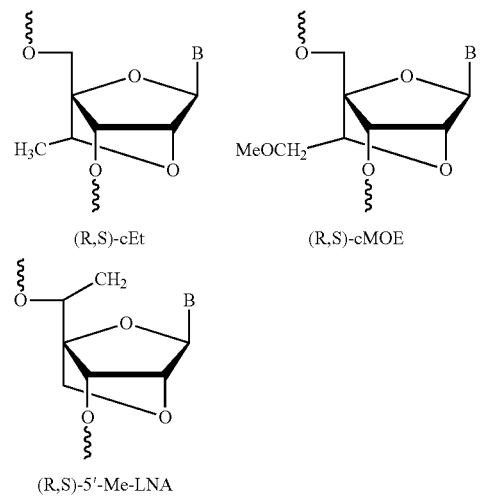

Incorporation of affinity-enhancing nucleotide analogues in the oligomer, such as LNA or 2'-substituted sugars, can allow the size of the specifically binding oligomer to be reduced, and can also reduce the upper limit to the size of the oligomer before non-specific or aberrant binding takes place.

II.f RNAse Recruitment

An oligomeric compound of the present disclosure can function via non RNase mediated degradation of target mRNA, such as by steric hindrance of translation, or other methods. In some aspects, the oligomers of the present disclosure are capable of recruiting an endoribonuclease (RNase), such as RNase H. In some oligomers, such as region A, or contiguous nucleotide sequence, comprises of a region of at least 4, such as at least 5, such as at least 6, such as at least 7 consecutive nucleotide units, such as at least 8 or at least 9 consecutive nucleotide units (residues), including 7, 8, 9, 10, 11, 12, 13, 14, 15 or 16 consecutive nucleotides, which, when formed in a duplex with the complementary target RNA is capable of recruiting RNase (such as DNA units). The contiguous sequence which is capable of recruiting RNAse can be region Y' as referred to in the context of a gapmer as described herein. In some aspects the size of the contiguous sequence which is capable of recruiting RNAse, such as region Y', can be higher, such as 10, 11, 12, 13, 14, 15, 16, 17, 18, 19 or 20 nucleotide units.

A oligomer is deemed capable of recruiting RNase H if, when provided with the complementary RNA target, it has an initial rate, as measured in pmol/l/min, of at least 1%, such as at least 5%, such as at least 10% or more than 20% of the of the initial rate determined using DNA only oligonucleotide, having the same base sequence but containing only DNA monomers, with no 2' substitutions, with phosphorothioate linkage groups between all monomers in the oligonucleotide, using the methodology provided, e.g., in EP1222309.

In some aspects, an oligomer is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided, e.g., in EP1222309.

In other aspects, an oligomer is deemed capable of recruiting RNaseH if, when provided with the complementary RNA target, and RNaseH, the RNaseH initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided, e.g., in EP1222309.

Typically, the region of the oligomer which forms the consecutive nucleotide units which, when formed in a duplex with the complementary target RNA is capable of recruiting RNase consists of nucleotide units which form a DNA/RNA like duplex with the RNA target. The oligomer of the present disclosure, such as the first region, can comprise a nucleotide sequence which comprises both nucleotides and nucleotide analogues, and is in the form of a LNA gapmer.

II.g Gapmer Design

In some aspects, the oligomer of the present disclosure is an LNA gapmer. A gapmer oligomer is an oligomer which comprises a contiguous stretch of nucleotides which is capable of recruiting an RNAse, such as RNAseH, such as a region of at least 6 or 7 DNA nucleotides, referred to herein in as region Y' (Y'), wherein region Y is flanked both 5' and 3' by regions of affinity enhancing nucleotide analogues, such as from 1-6 nucleotide analogues 5' and 3' to the contiguous stretch of nucleotides which is capable of recruiting RNAse—these regions are referred to as regions X' (X') and Z' (Z'), respectively. The X' and Z' regions can also be termed the wings of the gapmer. Examples of gapmers are disclosed, e.g., in WO2004/046160, WO2008/113832, and WO2007/146511.

In some aspects, the monomers which are capable of recruiting RNAse are selected from the group consisting of DNA monomers, alpha-L-LNA monomers, C4' alkylated DNA monomers, and UNA (unlinked nucleic acid) nucleotides. UNA is unlocked nucleic acid, typically where the C2-C3 C—C bond of the ribose has been removed, forming an unlocked "sugar" residue. In some aspects, the LNA gapmer comprises a (poly)nucleotide sequence of formula (5' to 3'), X'—Y'-Z', wherein; region X' (X') (5' region) consists or comprises of at least one nucleotide analogue, such as at least one LNA unit, such as from 1-6 nucleotide analogues, such as LNA units, and; region Y' (Y') consists or comprises of at least four or at least five consecutive nucleotides which are capable of recruiting RNAse (when formed in a duplex with a complementary RNA molecule, such as the mRNA target), such as DNA nucleotides, and; region Z' (Z') (3' region) consists or comprises of at least one nucleotide analogue, such as at least one LNA unit, such as from 1-6 nucleotide analogues, such as LNA units.

In some aspects, region X' consists of 1, 2, 3, 4, 5 or 6 nucleotide analogues, such as LNA units, such as from 2-5 nucleotide analogues, such as 2-5 LNA units, such as 3 or 4 nucleotide analogues, such as 3 or 4 LNA units; and/or region Z consists of 1, 2, 3, 4, 5 or 6 nucleotide analogues, such as. LNA units, such as from 2-5 nucleotide analogues, such as 2-5 LNA units, such as 3 or 4 nucleotide analogues, such as 3 or 4 LNA units.

In some aspects, Y' consists or comprises of 4, 5, 6, 7, 8, 9, 10, 11 or 12 consecutive nucleotides which are capable of recruiting RNAse, or from 4-12 or from 6-10, or from 7-9, such as 8 consecutive nucleotides which are capable of recruiting RNAse. In some aspects, region Y consists or comprises at least one DNA nucleotide unit, such as 1-12 DNA units, preferably from 4-12 DNA units, more preferably from 6-10 DNA units, such as from 7-10 DNA units, most preferably 8, 9 or 10 DNA units. In some aspects, region X' consist of 3 or 4 nucleotide analogues, such as LNA, region X' consists of 7, 8, 9 or 10 DNA units, and region Z' consists of 3 or 4 nucleotide analogues, such as LNA. Such designs include (X'-Y'-Z') 3-10-3, 3-10-4, 4-10-3, 3-9-3, 3-9-4, 4-9-3, 3-8-3, 3-8-4, 4-8-3, 3-7-3, 3-7-4, 4-7-3. In some aspects, the gapmer is a 3-9-4 gapmer. In some aspects, the gapmer is a 3-10-3 gapmer.

In some aspects, the oligomer, e.g. region X', is consisting of a contiguous nucleotide sequence of a total of 10, 11, 12, 13 or 14 nucleotide units, wherein the contiguous nucleotide sequence comprises or is of formula (5'-3'), X'-Y'-Z' wherein; X' consists of 1, 2 or 3 nucleotide analogue units, such as LNA units; Y consists of 7, 8 or 9 contiguous nucleotide units which are capable of recruiting RNAse when formed in a duplex with a complementary RNA molecule (such as a mRNA target); and Z' consists of 1, 2 or 3 nucleotide analogue units, such as LNA units.

In some aspects, X' consists of 1 LNA unit. In some aspects, X' consists of 2 LNA units. In some aspects, X' consists of 3 LNA units. In some aspects, Z' consists of 1 LNA units. In some aspects, Z' consists of 2 LNA units. In some aspects, Z' consists of 3 LNA units. In some aspects, Y consists of 7 nucleotide units. In some aspects, Y' consists of 8 nucleotide units. In some aspects, Y consists of 9 nucleotide units. In certain aspects, region Y consists of 10 nucleoside monomers. In some aspects, region Y consists or comprises 1-10 DNA monomers. In some aspects, Y comprises of from 1-9 DNA units, such as 2, 3, 4, 5, 6, 7, 8 or 9 DNA units. In some aspects, Y consists of DNA units. In some aspects, Y comprises of at least one LNA unit which is in the alpha-L configuration, such as 2, 3, 4, 5, 6, 7, 8 or 9 LNA units in the alpha-L-configuration. In some aspects, Y comprises of at least one alpha-L-oxy LNA unit or wherein all the LNA units in the alpha-L- configuration are alpha-L-oxy LNA units. In some aspects, the number of nucleotides present in X'-Y'-Z' are selected from the group consisting of (nucleotide analogue units—region Y'—nucleotide analogue units): 1-8-1, 1-8-2, 2-8-1, 2-8-2, 3-8-3, 2-8-3, 3-8-2, 4-8-1, 4-8-2, 1-8-4, 2-8-4, 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1, 2-10-3, or 3-10-2. In some aspects, the number of nucleotides in X'-Y'-Z' are selected from the group consisting of: 2-7-1, 1-7-2, 2-7-2, 3-7-3, 2-7-3, 3-7-2, 3-7-4, and 4-7-3.

In certain aspects, each of regions X' and Y consists of three LNA monomers, and region Y consists of 8 or 9 or 10 nucleoside monomers, preferably DNA monomers. In some aspects, both X' and Z' consists of two LNA units each, and Y consists of 8 or 9 nucleotide units, preferably DNA units. In some aspects, other gapmer designs include those where regions X' and/or Z' consists of 3, 4, 5 or 6 nucleoside analogues, such as monomers containing a 2'-O-methoxy-ethyl-ribose sugar (2'-MOE) or monomers containing a 2'-fluoro-deoxyribose sugar, and region Y' consists of 8, 9, 10, 11 or 12 nucleosides, such as DNA monomers, where regions X'-Y-Z' have 3-9-3, 3-10-3, 5-10-5 or 4-12-4 monomers. Further gapmer designs are disclosed, e.g., in WO 2007/146511A2, which is herein incorporated by reference in its entirety.

In some aspects, a gapmer oligomer of the present disclosure comprises a sequence set forth in SEQ ID NO: 1, 2, 3, 4, 5, 6, 7, 8, or 40. In some aspects, a gapmer oligomer of the present disclosure consists of a sequence set forth in SEQ ID NO: 1, 2, 3, 4, 5, 6, 7, 8, or 40.

II.h Internucleoside Linkages

In some aspects, the nucleoside monomers of the oligonucleotides of the presented disclosure are coupled together via internucleoside linkage groups. Each monomer is linked to the 3' adjacent monomer via a linkage group. Each nucleotide is also linked to the 3' adjacent nucleotide via a linkage group. In the context of the present disclosure, the 5' monomer at the end of an oligomer does not comprise a 5' linkage group, although it may or may not comprise a 5' terminal group, or a linkage group for conjugation.

The terms "linkage group" or "internucleoside linkage" are intended to mean a group capable of covalently coupling together two nucleotides. Specific examples include phosphate groups and phosphorothioate groups. Internucleoside linkage can be used interchangeably with internucleoside linkage.

Suitable internucleoside linkages include those listed, e.g., in WO2007/031091, which is herein incorporated by reference in its entirety. In some aspects, other than the phosphodiester linkage(s) of region B (where present), the internucleoside linkages can be modified from their normal phosphodiester to one that is more resistant to nuclease attack, such as phosphorothioate or boranophosphate. These two, being cleavable by RNase H, also allow that route of antisense inhibition in reducing the expression of the target gene.

In some aspects, the oligomer of the present disclosure comprises one or more nucleoside linkages selected from the group consisting of phosphorothioate, phosphorodithioate, boranophosphate, methylphosphonate, phosphoroamidate, or any combination thereof. Suitable sulphur (S) containing internucleoside linkages as provided herein can be used, e.g., phosphorothioate, phosphodithionate, or combinations thereof. Phosphorothioate internucleoside linkages are also preferred, particularly for the first region, such as in gapmers, mixmers, antimirs splice switching oligomers, and totalmers.

The term "mixmer" refers to oligomers which comprise both naturally and non-naturally occurring nucleotides, where, as opposed to gapmers, tailmers, and headmers there is no contiguous sequence of more than 5, and in some aspects no more than 4 consecutive, such as no more than three consecutive, naturally occurring nucleotides, such as DNA units The term "totalmer" refers to a single stranded oligomer which only comprises non-naturally occurring nucleosides, such as sugar-modified nucleoside analogues.

For gapmers, the internucleoside linkages in the oligomer can, for example be phosphorothioate or boranophosphate so as to allow RNase H cleavage of targeted RNA. Phosphorothioate is preferred, for improved nuclease resistance and other reasons, such as ease of manufacture.

In some aspects, with the exception of the phosphodiester linkage between the first and second region, and optionally within region B, the remaining internucleoside linkages of the oligomer of the present disclosure, the nucleotides and/or nucleotide analogues are linked to each other by means of phosphorothioate groups.

In some aspects, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 110% of all the internucleoside linkages between nucleosides in the first region are selected from the group consisting of phosphorothioate, phosphorodithioate, or boranophosphate. In some aspects, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of all the internucleoside linkages between nucleosides in the first region are selected from the group consisting of phosphorothioate, phosphorodithioate, or boranophosphate.

In some aspects, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 110% of all the internucleoside linkages between nucleosides in the first region are phosphorothioate. In some aspects, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% of all the internucleoside linkages between nucleosides in the first region are phosphorothioate.

In some aspects, an oligonucleotide of the present disclosure comprises only one phosphorothioate linkage. In some aspects, an oligonucleotide of the present disclosure comprises two phosphorothioate linkages. In some aspects, an oligonucleotide of the present disclosure comprises three phosphorothioate linkages. In some aspects, an oligonucleotide of the present disclosure comprises four phosphorothioate linkages. In some aspects, an oligonucleotide of the present disclosure comprises five phosphorothioate linkages. In some aspects, an oligonucleotide of the present disclosure comprises six phosphorothioate linkages. In some aspects, an oligonucleotide of the present disclosure comprises seven phosphorothioate linkages. In some aspects, an oligonucleotide of the present disclosure comprises eight phosphorothioate linkages. In some aspects, an oligonucleotide of the present disclosure comprises nine phosphorothioate linkages. In some aspects, an oligonucleotide of the present disclosure comprises 10 phosphorothioate linkages. In some aspects, an oligonucleotide of the present disclosure comprises 11 phosphorothioate linkages. In some aspects, an oligonucleotide of the present disclosure comprises 12 phosphorothioate linkages. In some aspects, an oligonucleotide of the present disclosure comprises 13 phosphorothioate linkages. In some aspects, an oligonucleotide of the present disclosure comprises 14 phosphorothioate linkages. In some aspects, an oligonucleotide of the present disclosure comprises 15 phosphorothioate linkages. In some aspects, an oligonucleotide of the present disclosure comprises 16 phosphorothioate linkages. In some aspects, an oligonucleotide of the present disclosure comprises 17 phosphorothioate linkages. In some aspects, an oligonucleotide of the present disclosure comprises 18 phosphorothioate linkages. In some aspects, an oligonucleotide of the present disclosure comprises 19 phosphorothioate linkages. In some aspects, an oligonucleotide of the present disclosure comprises 20 phosphorothioate linkages. In some aspects, an oligonucleotide of the present disclosure comprises 21 phosphorothioate linkages.

WO09124238 refers to oligomeric compounds having at least one bicyclic nucleoside attached to the 3' or 5' termini by a neutral internucleoside linkage. The oligomer of the present disclosure can therefore have at least one bicyclic nucleoside attached to the 3' or 5' termini by a neutral internucleoside linkage, such as one or more phosphotriester, methylphosphonate, MMI, amide-3, formacetal or thioformacetal. The remaining linkages can be phosphorothioate.

III. Oligonucleotide Conjugates

In some aspects, the antisense oligonucleotide conjugates of the present disclosure comprising at least one non-nucleotide or non-polynucleotide moiety (C) covalently attached to said oligomer (A), optionally via a linker region positioned between the contiguous sequence of the oligomer and the conjugate moiety (B and/or Y).

Representative conjugate moieties which have been used with oligonucleotides can include lipophilic molecules (aromatic and non-aromatic) including steroid molecules; proteins (e.g., antibodies, enzymes, serum proteins); peptides; vitamins (water-soluble or lipid-soluble); polymers (water-soluble or lipid-soluble); small molecules including drugs, toxins, reporter molecules, and receptor ligands; carbohydrate complexes; nucleic acid cleaving complexes; metal chelators (e.g., porphyrins, texaphyrins, crown ethers, etc.); intercalators including hybrid photonuclease/intercalators; crosslinking agents (e.g., photoactive, redox active), and combinations and derivatives thereof.

In some aspects, the present disclosure provides an antisense oligonucleotide conjugate comprising a. an antisense oligomer (A) of between 16-22 nucleotides in length, which comprises a contiguous sequence of 16 nucleotides which are complementary to a corresponding length of SEQ ID NO: 31, and wherein said antisense oligomer is a LNA gapmer, and b. at least one asialoglycoprotein receptor targeting conjugate moiety (C) covalently attached to said oligomer (A).

In some aspects, the oligomer of the present disclosure is targeted to the liver, i.e., after systemic administration the compound accumulates in the liver cells (such as hepatocytes). Targeting to the liver can be greatly enhanced by the addition of a conjugate moiety (C). However, in order to maximize the efficacy of the oligomer it is often desirable that the conjugate (or targeting moiety) is linked to the oligomer via a biocleavable linker (B), such as a nucleotide phosphate linker. It is therefore desirable to use a conjugate moiety which enhances uptake and activity in hepatocytes. The enhancement of activity can be due to enhanced uptake or it can be due to enhanced potency of the compound in hepatocytes. Accordingly, the present disclosure also provides an oligomeric compound in the form of a LNA oligomer, such as a gapmer, or for example an LNA antisense oligomer, (which can be referred to as region A herein) comprising an antisense oligomer, optionally a biocleavable linker, such as region B, and a carbohydrate conjugate (which can be referred to as region C). The LNA antisense oligomer can be 7 to 30 nucleosides in length, e.g., 8-26 nucleosides in length, and comprise at least one LNA unit (nucleoside).

In some aspects, the conjugate is or can comprise a carbohydrate or comprises a carbohydrate group. In some aspects, the carbohydrate is selected from the group consisting of galactose, lactose, n-acetylgalactosamine, mannose, and mannose-6-phosphate. In some aspects, the conjugate group is or can comprise mannose or mannose-6-phosphate. Carbohydrate conjugates can be used to enhance delivery or activity in a range of tissues, such as liver and/or muscle. In some aspects, the conjugate of the present disclosure comprises an asialoglycoprotein receptor targeting moiety conjugate moiety in the form of a carbohydrate moiety, such as a GalNAc moiety (which can be referred to as region C). The carbohydrate moiety can be multi-valent, such as, for example 2, 3, 4 or 4 identical or non-identical carbohydrate moieties can be covalently joined to the oligomer, optionally via a linker or linkers (such as region Y).

In some aspects, the carbohydrate moiety is not a linear carbohydrate polymer. The carbohydrate moiety can however be multi-valent, such as, for example 2, 3, 4 or 4 identical or non-identical carbohydrate moieties can be covalently joined to the oligomer, optionally via a linker or linkers.

III.a GalNAc Conjugate Moieties

The present disclosure provides a conjugate comprising the oligomer of the present disclosure and an asialoglycoprotein receptor targeting moiety conjugate moiety, such as a GalNAc moiety, which can form part of a further region (referred to as region C). The present disclosure also provides an antisense oligonucleotide conjugate comprising a. an antisense oligomer (A) of between 16-22 nucleotides in length, which comprises a contiguous sequence of 16 nucleotides which are complementary to a corresponding length of SEQ ID NO: 31, and wherein said antisense oligomer is a LNA gapmer comprising at least one LNA unit, and b. at least one asialoglycoprotein receptor targeting conjugate moiety (C) covalently attached to said oligomer (A).

In some aspects, the conjugate moiety (such as the third region or region C) comprises an asialoglycoprotein receptor targeting moiety selected from the group consisting of such as galactose, galactosamine, N-formyl-galactosamine, N-acetylgalactosamine, N-propionyl-galactosamine, N-n-butanoyl-galactosamine, and N-isobutanoylgalactos-amine. In some aspects the conjugate comprises a galactose cluster, such as N-acetylgalactosamine trimer. In some aspects, the conjugate moiety comprises a GalNAc (N-acetylgalactosamine), such as a mono-valent, di-valent, tri-valent or tetra-valent GalNAc.

Trivalent GalNAc conjugates can be used to target the compound to the liver. GalNAc conjugates have been used with methylphosphonate and PNA antisense oligonucleotides and siRNAs. WO2012/083046 discloses siRNAs with GalNAc conjugate moieties which comprise cleavable pharmacokinetic modulators, which are suitable for use in the present disclosure, the preferred pharmacokinetic modulators are C16 hydrophobic groups such as palmitoyl, hexadec-8-enoyl, oleyl, (9E, 12E)-octadeca-9,12-dienoyl, dioctanoyl, and C16-C20 acyl. The '046 cleavable pharmacokinetic modulators can also be cholesterol.

The "targeting moieties" (conjugate moieties) can be selected from the group consisting of: galactose, galactosamine, N-formyl-galactosamine, N-acetylgalactosamine, N-propionyl-galactosamine, N-n-butanoyl-galactosamine, N-iso-butanoylgalactos-amine, galactose cluster, and N-acetylgalactosamine trimer and can have a pharmacokinetic modulator selected from the group consisting of: hydrophobic group having 16 or more carbon atoms, hydrophobic group having 16-20 carbon atoms, palmitoyl, hexadec-8-enoyl, oleyl, (9E,12E)-octadeca-9,12dienoyl, dioctanoyl, and C16-C20 acyl, and cholesterol. Certain GalNAc clusters disclosed in '046 include: (E)-hexadec-8-enoyl (C16), oleyl (C18), (9,E,12E)-octadeca-9,12-dienoyl (C18), octanoyl (C8), dodecanoyl (C12), C-20 acyl, C24 acyl, dioctanoyl (2×C8). The targeting moiety-pharmacokinetic modulator targeting moiety can be linked to the polynucleotide via a physiologically labile bond or, e.g. a disulfide bond, or a PEG linker. The present disclosure also relates to the use of phosphodiester linkers between the oligomer and the conjugate group (these are referred to as region B herein, and suitably are positioned between the LNA oligomer and the carbohydrate conjugate group).

For targeting hepatocytes in liver, a preferred targeting ligand is a galactose cluster. A galactose cluster comprises a molecule having e.g. comprising two to four terminal galactose derivatives. In some aspects, the galactose derivative is an N-acetyl-galactosamine (GalNAc). Other saccharides having affinity for the asialoglycoprotein receptor can be selected from the list comprising: galactosamine, N-n-butanoylgalactosamine, and N-iso-butanoylgalactosamine. As used herein, the term galactose derivative includes both galactose and derivatives of galactose having affinity for the asialoglycoprotein receptor equal to or greater than that of galactose. A terminal galactose derivative is attached to a molecule through its C—I carbon. The asialoglycoprotein receptor (ASGPr) is primarily expressed on hepatocytes and binds branched galactose-terminal glycoproteins. A galactose cluster has three terminal galactosamines or galactosamine derivatives each having affinity for the asialoglycoprotein receptor. Another galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures. Multivalency is required to achieve nM affinity.

A galactose cluster can comprise two or preferably three galactose derivatives each linked to a central branch point. The galactose derivatives are attached to the central branch point through the C—I carbons of the saccharides. The galactose derivative is preferably linked to the branch point via linkers or spacers. In some aspects, the spacer is a flexible hydrophilic spacer, e.g., a PEG spacer such as a PEG3 spacer. The branch point can be any small molecule which permits attachment of the three galactose derivatives and further permits attachment of the branch point to the oligomer. An exemplary branch point group is a di-lysine. A di-lysine molecule contains three amine groups through which three galactose derivatives can be attached and a carboxyl reactive group through which the di-lysine can be attached to the oligomer. Attachment of the branch point to oligomer can occur through a linker or spacer. In some aspects, the spacer is a flexible hydrophilic spacer, e.g., a PEG spacer such as a PEG3 spacer (three ethylene units). The galactose cluster can be attached to the 3' or 5' end of the oligomer using methods known in the art.

In some aspects of the present disclosure, the conjugate moiety of the antisense oligonucleotide conjugate comprises or consists of Conj 1, 2, 3, 4 and Conj1a, 2a, 3a and 4a. In some aspects, the conjugate moiety comprises or consists of Conj 2a. In some aspects, the antisense oligonucleotide conjugate is selected from the group consisting of SEQ ID NO: 18 and 19.

Each carbohydrate moiety of a GalNAc cluster (e.g., GalNAc) can therefore be joined to the oligomer via a spacer, such as (poly)ethylene glycol linker (PEG), such as a di, tri, tetra, penta, hexa-ethylene glycol linker. As is shown above the PEG moiety forms a spacer between the galactose sugar moiety and a peptide (trilysine is shown) linker.

In some aspects, the GalNAc cluster comprises a peptide linker, e.g., a Tyr-Asp(Asp) tripeptide or Asp(Asp) dipeptide, which is attached to the oligomer (or to region Y or region B) via a biradical linker, for example the GalNAc cluster can comprise the following biradical linkers:

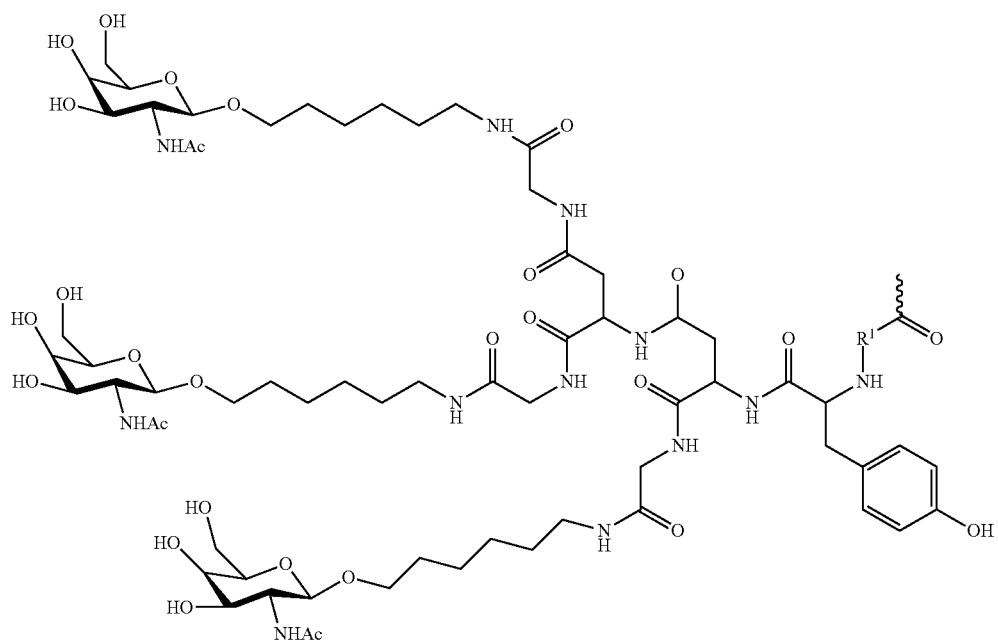

-continued

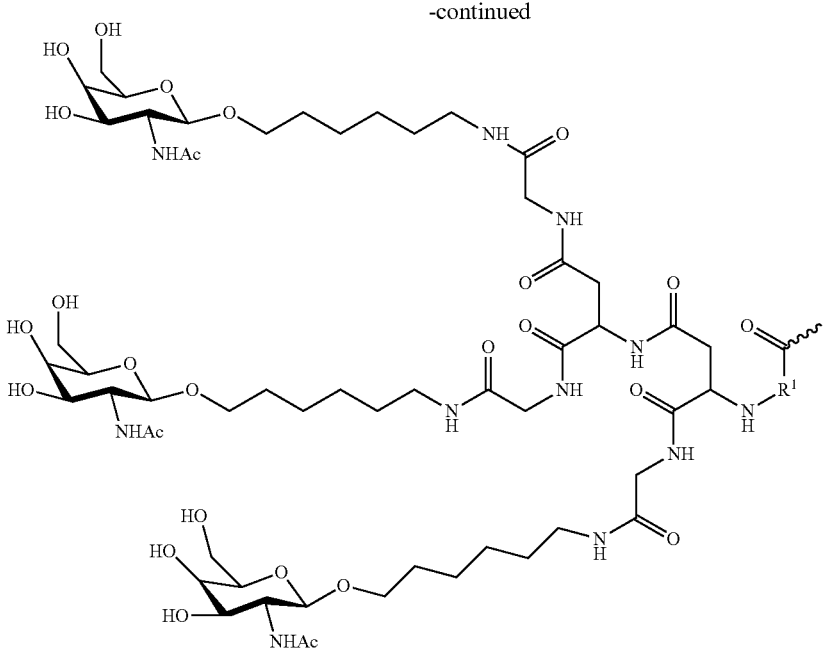

R1 is a biradical preferably selected from —$C_2H_4$—, —$C_3H_6$—, —$C_4H_8$—, —$C_6H_{10}$—, —$C_6H_{12}$—, 1,4-cyclohexyl(—$C_6H_{10}$—), 1,4-phenyl(—$C_6H_4$—), —$C_2H_4OC_2H_4$—, —$C_2H_4(OC_2H_4)_2$— or —$C_2H_4(OC_2H_4)_3$—, —C(O)CH$_2$—, —C(O)C$_2$H$_4$—, —C(O)C$_3$H$_6$—, —C(O)C$_4$H$_8$—, —C(O)C$_6$H$_{10}$—, —C(O)C$_6$H$_{12}$—, 1,4-cyclohexyl(—C(O)C$_6$H$_{10}$—), 1,4-phenyl(—C(O)C$_6$H$_4$—), —C(O)C$_2$H$_4$OC$_2$H$_4$—, —C(O)C$_2$H$_4$(OC$_2$H$_4$)$_2$— or —C(O)C$_2$H$_4$ (OC$_2$H$_4$)$_3$—.

In some aspects, R1 is a biradical preferably selected from —$C_2H_4$—, —$C_3H_6$—, —$C_4H_8$—, —$C_6H_{10}$—, —$C_6H_{12}$—, 1,4-cyclohexyl(—$C_6H_{10}$—), 1,4-phenyl(—$C_6H_4$—), —$C_2H_4OC_2H_4$—, —$C_2H_4(OC_2H_4)_2$— or —$C_2H_4(OC_2H_4)_3$—.

The carbohydrate conjugate (e.g., GalNAc), or carbohydrate-linker moiety (e.g. carbohydrate-PEG moiety) can be covalently joined (linked) to the oligomer via a branch point group such as, an amino acid, or peptide, which suitably comprises two or more amino groups (such as 3, 4, or 5), such as lysine, di-lysine or tri-lysine or tetra-lysine. A tri-lysine molecule contains four amine groups through which three carbohydrate conjugate groups, such as galactose & derivatives (e.g., GalNAc) and a further conjugate such as a hydrophobic or lipophilic moiety/group can be attached and a carboxyl reactive group through which the tri-lysine can be attached to the oligomer. The further conjugate, such as lipophilic/hydrophobic moiety can be attached to the lysine residue that is attached to the oligomer.

GalNAc conjugates for use with LNA oligomers of the present disclosure do not require a pharmacokinetic modulator (e.g., a lipophilic moiety disclosed below). Thus, in some aspects, the GalNAc conjugate is not covalently linked to a lipophilic or hydrophobic moiety, such as those described herein, e.g., does not comprise a C8-C36 fatty acid or a sterol. Accordingly, the present disclosure provides LNA oligomer GalNAc conjugates which do not comprise a conjugated lipophilic or hydrophobic pharmacokinetic modulator.

III.b Lipophilic Moieties

The oligonucleotide of the present disclosure can further comprise one or more additional conjugate moieties (e.g., instead or in addition to a GalNAc moiety), of which lipophilic or hydrophobic moieties are particularly interesting, such as when the conjugate group is a carbohydrate moiety. Such lipophilic or hydrophobic moieties can act as pharmacokinetic modulators, and can be covalently linked to either the carbohydrate conjugate, a linker linking the carbohydrate conjugate to the oligomer or a linker linking multiple carbohydrate conjugates (multi-valent) conjugates, or to the oligomer, optionally via a linker, such as a bio cleavable linker.

The oligomer or conjugate moiety can therefore comprise a pharmacokinetic modulator, such as lipophilic or hydrophobic moieties. Such moieties are disclosed within the context of siRNA conjugates in WO2012/082046, which is herein incorporated by reference in its entirety. The hydrophobic moiety can comprise a C8-C36 fatty acid, which can be saturated or unsaturated. In some aspects, C10, C12, C14, C16, C18, C20, C22, C24, C26, C28, C30, C32 and C34 fatty acids can be used. The hydrophobic group can have 16 or more carbon atoms.

Exemplary suitable hydrophobic groups can be selected from the group comprising: sterol, cholesterol, palmitoyl, hexadec-8-enoyl, oleyl, (9E, 12E)-octadeca-9,12-dienoyl, dioctanoyl, and C16-C20 acyl. Hydrophobic groups having fewer than 16 carbon atoms are less effective in enhancing polynucleotide targeting, but they can be used in multiple copies (e.g. 2x, such as 2x C8 or C10, C12 or C14) to enhance efficacy. Pharmacokinetic modulators useful as polynucleotide targeting moieties can be selected from the group consisting of: cholesterol, alkyl group, alkenyl group, alkynyl group, aryl group, aralkyl group, aralkenyl group, and aralkynyl group, each of which can be linear, branched, or cyclic. Pharmacokinetic modulators are preferably hydrocarbons, containing only carbon and hydrogen atoms. However, substitutions or heteroatoms which maintain hydrophobicity, for example fluorine, can be permitted.

III.c Lipophilic Conjugates

In some aspects, the conjugate moiety is or can comprise a lipophilic moiety, such as a sterol (for example, cholesterol, cholesteryl, cholestanol, stigmasterol, cholanic acid and ergosterol). In some aspects, the conjugate moiety is or comprises tocopherol (exemplified as Conj 6 and Conj 6a in FIG. 2). In some aspects, the conjugate moiety is or can comprise cholesterol (exemplified as Conj 5 and Conj 5a in FIG. 2).

In some aspects, the conjugate moiety is, or can comprise a lipid, a phospholipid or a lipophilic alcohol, such as a cationic lipid, a neutral lipid, sphingolipid, and fatty acid such as stearic, oleic, elaidic, linoleic, linoleaidic, linolenic, and myristic acid. In some aspects, the fatty acid comprises a C4-C30 saturated or unsaturated alkyl chain. The alkyl chain can be linear or branched.

Lipophilic conjugate moieties can be used, for example, to counter the hydrophilic nature of an oligomeric compound and enhance cellular penetration.

Lipophilic moieties include, for example, sterols stanols, and steroids and related compounds such as cholesterol, thiocholesterol, lanosterol, coprostanol, stigmasterol, ergosterol, calciferol, cholic acid, deoxycholic acid, estrone, estradiol, estratriol, progesterone, stilbestrol, testosterone, androsterone, deoxycorticosterone, cortisone, 17-hydroxycorticosterone, their derivatives, and the like. In some aspects, the conjugate can be selected from the group consisting of cholesterol, thiocholesterol, lanosterol, coprostanol, stigmasterol, ergosterol, calciferol, cholic acid, deoxycholic acid, estrone, estradiol, estratriol, progesterone, stilbestrol, testosterone, androsterone, deoxycorticosterone, cortisone, and 17-hydroxycorticosterone. Other lipophilic conjugate moieties include aliphatic groups, such as, for example, straight chain, branched, and cyclic alkyls, alkenyls, and alkynyls. The aliphatic groups can have, for example, 5 to about 50, 6 to about 50, 8 to about 50, or 10 to about 50 carbon atoms. Exemplary aliphatic groups include undecyl, dodecyl, hexadecyl, heptadecyl, octadecyl, nonadecyl, terpenes, bornyl, adamantyl, derivatives thereof and the like. In some aspects, one or more carbon atoms in the aliphatic group can be replaced by a heteroatom such as O, S, or N (e.g., geranyloxyhexyl). Further suitable lipophilic conjugate moieties include aliphatic derivatives of glycerols such as alkylglycerols, bis(alkyl)glycerols, tris(alkyl)glycerols, monoglycerides, diglycerides, and triglycerides. In some aspects, the lipophilic conjugate is di-hexyldecyl-rac-glycerol or 1,2-di-O-hexyldecyl-rac-glycerol or phosphonates thereof. Saturated and unsaturated fatty functionalities, such as, for example, fatty acids, fatty alcohols, fatty esters, and fatty amines, can also serve as lipophilic conjugate moieties. In some aspects, the fatty functionalities can contain from about 6 carbons to about 30 or about 8 to about 22 carbons. Exemplary fatty acids include capric, caprylic, lauric, palmitic, myristic, stearic, oleic, linoleic, linolenic, arachidonic, eicosenoic acids and the like.

In further aspects, lipophilic conjugate groups can be polycyclic aromatic groups having from 6 to about 50, 10 to about 50, or 14 to about 40 carbon atoms. Example polycyclic aromatic groups include pyrenes, purines, acridines, xanthenes, fluorenes, phenanthrenes, anthracenes, quinolines, isoquinolines, naphthalenes, derivatives thereof and the like. Other suitable lipophilic conjugate moieties include menthols, trityls (e.g., dimethoxytrityl (DMT)), phenoxazines, lipoic acid, phospholipids, ethers, thioethers (e.g., hexyl-S-tritylthiol), derivatives thereof and the like.

Oligomeric compounds containing conjugate moieties with affinity for low-density lipoprotein (LDL) can help provide an effective targeted delivery system. High expression levels of receptors for LDL on tumor cells makes LDL an attractive carrier for selective delivery of drugs to these cells. Moieties having affinity for LDL include many lipophilic groups such as steroids (e.g., cholesterol), fatty acids, derivatives thereof and combinations thereof. In some aspects, conjugate moieties having LDL affinity can be dioleyl esters of cholic acids such as chenodeoxycholic acid and lithocholic acid. In some aspects, the lipophilic conjugates can be or can comprise biotin. In some aspects, the lipophilic conjugate moiety can be or can comprise a glyceride or glyceride ester.

Lipophilic conjugate moieties, such as sterols, stanols, and stains, such as cholesterol or as disclosed herein, can be used to enhance delivery of the oligonucleotide to, for example, the liver (typically, to hepatocytes). In some aspects of the present disclosure, the conjugate moiety of the antisense oligonucleotide conjugate comprises or consists of Conj 5, 5a, 6 or 6a. In some aspects, the conjugate moiety comprises or consists of Conj 5a. In some aspects, the antisense oligonucleotide conjugate is selected from the group consisting of SEQ ID NO: 10 and 11.

III.d Linkers

A linkage or linker is a connection between two atoms that links one chemical group or segment of interest to another chemical group or segment of interest via one or more covalent bonds. Conjugate moieties (or targeting or blocking moieties) can be attached to the oligomeric compound directly or through a linking moiety (linker or tether)—a linker. Linkers are bifunctional moieties that serve to covalently connect a third region, e.g. a conjugate moiety, to an oligomeric compound (such as to region A). In some aspects, the linker comprises a chain structure or an oligomer of repeating units such as ethylene glycol or amino acid units. The linker can have at least two functionalities, one for attaching to the oligomeric compound and the other for attaching to the conjugate moiety. Example linker functionalities can be electrophilic for reacting with nucleophilic groups on the oligomer or conjugate moiety, or nucleophilic for reacting with electrophilic groups. In some aspects, linker functionalities include amino, hydroxyl, carboxylic acid, thiol, phosphoramidate, phosphorothioate, phosphate, phosphite, unsaturations (e.g., double or triple bonds), and the like. Some example linkers include 8-amino-3,6-dioxaoctanoic acid (ADO), succinimidyl 4-(N-maleimidomethyl)cyclohexane-I-carboxylate (SMCC), 6-amino-hexanoic acid (AHEX or AHA), 6-aminohexyloxy, 4-aminobutyric acid, 4-aminocyclohexylcarboxylic acid, succinimidyl 4-(N-maleimidomethyl)cyclohexane-I-carboxy-(6-amido-caproate) (LCSMCC), succinimidyl m-maleimido-benzoylate (MBS), succinimidyl N-e-maleimido-caproylate (EMCS), succinimidyl 6-(beta-maleimido-propionamido) hexanoate (SMPH), succinimidyl N-(a-maleimido acetate) (AMAS), succinimidyl 4-(p-maleimidophenyl)butyrate (SMPB), beta-alanine (beta-ALA), phenylglycine (PHG), 4-aminocyclohexanoic acid (ACHC), beta-(cyclopropyl) alanine (beta-CYPR), amino dodecanoic acid (ADC), alylene diols, polyethylene glycols, amino acids, and the like.

A wide variety of further linker groups are known in the art that can be useful in the attachment of conjugate moieties to oligomeric compounds. A review of many of the useful linker groups can be found in, for example, Antisense Research and Applications, S. T. Crooke and B. Lebleu, Eds., CRC Press, Boca Raton, Fla., 1993, p. 303-350.

Linkers and their use in preparation of conjugates of oligomeric compounds are provided throughout the art such as in WO 96/11205 and WO 98/52614 and U.S. Pat. Nos. 4,948,882; 5,525,465; 5,541,313; 5,545,730; 5,552,538; 5,580,731; 5,486,603; 5,608,046; 4,587,044; 4,667,025; 5,254,469; 5,245,022; 5,112,963; 5,391,723; 5,510475; 5,512,667; 5,574,142; 5,684,142; 5,770,716; 6,096,875; 6,335,432; and 6,335,437; and WO 2012/083046, all of which are herein incorporated by reference in their entireties.

As used herein, a physiologically labile bond is a labile bond that is cleavable under conditions normally encountered or analogous to those encountered within a mammalian body (also referred to as a cleavable linker, illustrated as region B in FIG. 12 and FIG. 13). Physiologically labile linkage groups are selected such that they undergo a chemical transformation (e.g., cleavage) when present in certain physiological conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. In some aspects, the cleavable linker is susceptible to nuclease(s) which can for example, be expressed in the target cell—and as such, as detailed herein, the linker can be a short region (e.g. 1-10) phosphodiester linked nucleosides, such as DNA nucleosides.

Chemical transformation (cleavage of the labile bond) can be initiated by the addition of a pharmaceutically acceptable agent to the cell or can occur spontaneously when a molecule containing the labile bond reaches an appropriate intra- and/or extra-cellular environment. For example, a pH labile bond can be cleaved when the molecule enters an acidified endosome. Thus, a pH labile bond can be considered to be an endosomal cleavable bond. Enzyme cleavable bonds can be cleaved when exposed to enzymes such as those present in an endosome or lysosome or in the cytoplasm. A disulfide bond can be cleaved when the molecule enters the more reducing environment of the cell cytoplasm. Thus, a disulfide can be considered to be a cytoplasmic cleavable bond. As used herein, a pH-labile bond is a labile bond that is selectively broken under acidic conditions (pH<7). Such bonds can also be termed endosomally labile bonds, since cell endosomes and lysosomes have a pH less than 7.

III.e Oligomer Linked Biocleavable Conjugates

The oligomeric compound can optionally, comprise a second region (region B) which is positioned between the oligomer (referred to as region A) and the conjugate (referred to as region C) See FIG. 12 and FIG. 13 for illustrations). Region B can be a linker such as a cleavable linker (also referred to as a physiologically labile linkage). Nuclease Susceptible Physiological Labile Linkages: In some aspects, the oligomer (also referred to as oligomeric compound) of the present disclosure (or conjugate) comprises three regions:

i) a first region (region A), which comprises, e.g., 16-18 contiguous nucleotides;
ii) a second region (region B) which comprises a biocleavable linker; and,
iii) a third region (C) which comprises a conjugate moiety, a targeting moiety, an activation moiety, wherein the third region is covalent linked to the second region.

In some aspects, region B can be a phosphate nucleotide linker. For example, such linkers can be used when the conjugate is a lipophilic conjugate, such as a lipid, a fatty acid, sterol, such as cholesterol or tocopherol. Phosphate nucleotide linkers can also be used for other conjugates, for example carbohydrate conjugates, such as GalNAc.

III.e.1 Peptide Linkers

In some aspects, the biocleavable linker (region B) is a peptide, such as a trilysine peptide linker which can be used in a polyGalNAc conjugate, such as a triGalNAc conjugate. See also the peptide biradicals mentioned herein.

Other linkers known in the art which can be used, include disulfide linkers.

III.e.2 Phosphate Nucleotide Linkers

In some aspects, region B comprises between 1-6 nucleotides, which is covalently linked to the 5' or 3' nucleotide of the first region (region A), such as via a internucleoside linkage group such as a phosphodiester linkage, wherein either a. the internucleoside linkage between the first and second region is a phosphodiester linkage and the nucleoside of the second region [such as immediately] adjacent to the first region is either DNA or RNA; and/or
b. at least 1 nucleoside of the second region is a phosphodiester linked DNA or RNA nucleoside.

In some aspects, region A and region B form a single contiguous nucleotide sequence of 16-22 nucleotides in length.

In some aspects the internucleoside linkage between the first and second regions can be considered part of the second region.

In some aspects, there is a phosphorus containing linkage group between the second and third region. The phosphorus linkage group, can, for example, be a phosphate (phosphodiester), a phosphorothioate, a phosphorodithioate or a boranophosphate group. In some aspects, this phosphorus containing linkage group is positioned between the second region and a linker region which is attached to the third region. In some aspects, the phosphate group is a phosphodiester.

Therefore, in some aspects the oligomeric compound comprises at least two phosphodiester groups, wherein at least one is as according to the above statement, and the other is positioned between the second and third regions, optionally between a linker group and the second region.

In some aspects, the third region is an activation group, such as an activation group for use in conjugation. In this respect, the present disclosure also provides activated oligomers comprising region A and B and an activation group, e.g., an intermediate which is suitable for subsequent linking to the third region, such as suitable for conjugation.

In some aspects, the third region is a reactive group, such as a reactive group for use in conjugation. In this respect, the present disclosure also provides oligomers comprising region A and B and a reactive group, e.g., an intermediate which is suitable for subsequent linking to the third region, such as suitable for conjugation. The reactive group can, in some aspects comprise an amine of alcohol group, such as an amine group.

In some aspects region A comprises at least one, such as 2, 3, 4, 5, 6, 7, 8, 9, 10, 11, 12, 13, 14, 15, 16, 17, 18, 19, 20, or 21 internucleoside linkages other than phosphodiester, such as internucleoside linkages which are (optionally independently] selected from the group consisting of phosphorothioate, phosphorodithioate, and boranophosphate, and methylphosphonate, such as phosphorothioate. In some aspects region A comprises at least one phosphorothioate linkage. In some aspects at least 50%, such as at least 75%, such as at least 90% of the internucleoside linkages, such as all the internucleoside linkages within region A are other than phosphodiester, for example are phosphorothioate linkages. In some aspects, all the internucleoside linkages in region A are other than phosphodiester.

In some aspects, the oligomeric compound comprises an antisense oligonucleotide, such as an antisense oligonucleotide conjugate. The antisense oligonucleotide can be or can comprise the first region, and optionally the second region. In this respect, in some aspects, region B can form part of a contiguous nucleobase sequence which is complementary to the (nucleic acid) target. In other aspects, region B can lack complementarity to the target.

Alternatively stated, in some aspects, the present disclosure provides a non-phosphodiester linked, such as a phosphorothioate linked, oligonucleotide (e.g. an antisense oligonucleotide) which has at least one terminal (5' and/or 3') DNA or RNA nucleoside linked to the adjacent nucleoside of the oligonucleotide via a phosphodiester linkage, wherein the terminal DNA or RNA nucleoside is further covalently linked to a conjugate moiety, a targeting moiety or a blocking moiety, optionally via a linker moiety.

In some aspects, the oligomeric compound comprises an antisense oligonucleotide, such as an antisense oligonucleotide conjugate. The antisense oligonucleotide can be or can comprise the first region, and optionally the second region. In this respect, in some aspects, region B can form part of a contiguous nucleobase sequence which is complementary to the (nucleic acid) target. In other aspects, region B can lack complementarity to the target.

In some aspects, at least two consecutive nucleosides of the second region are DNA nucleosides (such as at least 3 or 4 or 5 consecutive DNA nucleotides).

In such an aspect, the oligonucleotide of the present disclosure can be described according to the following formula: 5'-A-PO-B[Y]X-3' or 3'-A-PO-B[Y]X-5' wherein A is region A, PO is a phosphodiester linkage, B is region B, Y is an optional linkage group, and X is a conjugate, a targeting, a blocking group or a reactive or activation group.

In some aspects, region B comprises 3'-5' or 5'-3': (i) a phosphodiester linkage to the 5' or 3' nucleoside of region A, (ii) a DNA or RNA nucleoside, such as a DNA nucleoside, and (iii) a further phosphodiester linkage 5'-A-PO-B-PO-3' or 3'-A-PO-B-PO-5'.

The further phosphodiester linkage link the region B nucleoside with one or more further nucleoside, such as one or more DNA or RNA nucleosides, or can link to X (is a conjugate, a targeting or a blocking group or a reactive or activation group) optionally via a linkage group (Y).

In some aspects, region B comprises 3'-5' or 5'-3': i) a phosphodiester linkage to the 5' or 3' nucleoside of region A, ii) between 2-10 DNA or RNA phosphodiester linked nucleosides, such as a DNA nucleoside, and optionally iii) a further phosphodiester linkage:

5'-A-[PO-B]n-[Y]-X3' or 3'-A-[PO-B]n-[Y]-X5'

5'-A-[PO-B]n-PO-[Y]-X3' or 3'-A-[PO-B]n-PO-[Y]-X5' wherein A represent region A, [PO-B]n represents region B, wherein n is 1-10, such as 1, 2, 3, 4, 5, 6, 7, 8, 9 or 10, PO is an optional phosphodiester linkage group between region B and X (or Y if present).

In some aspects the present disclosure provides compounds according to (or comprising) one of the following formula:

5'[Region A]-PO-[region B]3'-Y-X

5'[Region A]-PO-[region B]-PO3'-Y-X

5'[Region A]-PO-[region B]3'-X

5'[Region A]-PO-[region B]-PO3'-X

3'[Region A]-PO-[region B]5'-Y-X

3'[Region A]-PO-[region B]-PO5'-Y-X

3'[Region A]-PO-[region B]5'-X

3'[Region A]-PO-[region B]-PO5'-X

Region B, can for example comprise or consist of:
5' DNA3'
3' DNA 5'
5' DNA-PO-DNA-3'
3' DNA-PO-DNA-5'
5' DNA-PO-DNA-PO-DNA 3'
3' DNA-PO-DNA-PO-DNA 5'
5' DNA-PO-DNA-PO-DNA-PO-DNA 3'
3' DNA-PO-DNA-PO-DNA-PO-DNA 5'
5' DNA-PO-DNA-PO-DNA-PO-DNA-PO-DNA 3'
3' DNA-PO-DNA-PO-DNA-PO-DNA-PO-DNA 5'

It should be recognized that phosphate linked biocleavable linkers can employ nucleosides other than DNA and RNA. Biocleavable nucleotide linkers can be identified using the assays in Example 6.

In some aspects, the compound of the present disclosure comprises a biocleavable linker (also referred to as the physiologically labile linker, Nuclease Susceptible Physiological Labile Linkages, or nuclease susceptible linker), for example the phosphate nucleotide linker (such as region B) or a peptide linker, which joins the oligomer (or contiguous nucleotide sequence or region A), to a conjugate moiety (or region C).

The susceptibility to cleavage in the assays shown in Example 6 can be used to determine whether a linker is biocleavable or physiologically labile.

Biocleavable linkers according to the present disclosure comprise linkers which are susceptible to cleavage in a target tissue (i.e. physiologically labile), for example liver and/or kidney. It is preferred that the cleavage rate seen in the target tissue is greater than that found in blood serum. Suitable methods for determining the level (%) of cleavage in tissue (e.g. liver or kidney) and in serum are found in example 6. In some aspects, the biocleavable linker (also referred to as the physiologically labile linker, or nuclease susceptible linker), such as region B, in a compound of the present disclosure, are at least about 20% cleaved, such as at least about 30% cleaved, such as at least about 40% cleaved, such as at least about 50% cleaved, such as at least about 60% cleaved, such as at least about 70% cleaved, such as at least about 75% cleaved, in the liver or kidney homogenate assay of Example 6. In some aspects, the cleavage (%) in serum, as used in the assay in Example 6, is less than about 30%, is less than about 20%, such as less than about 10%, such as less than 5%, such as less than about 1%.

In some aspects, which can be the same of different, the biocleavable linker (also referred to as the physiologically labile linker, or nuclease susceptible linker), such as region B, in a compound of the present disclosure, are susceptible to S1 nuclease cleavage. Susceptibility to S1 cleavage can be evaluated using the S1 nuclease assay shown in Example 6. In some aspects, the biocleavable linker (also referred to as the physiologically labile linker, or nuclease susceptible linker), such as region B, in a compound of the present disclosure, are at least about 30% cleaved, such as at least about 40% cleaved, such as at least about 50% cleaved, such as at least about 60% cleaved, such as at least about 70% cleaved, such as at least about 80% cleaved, such as at least about 90% cleaved, such as at least 95% cleaved after 120 min incubation with S1 nuclease according to the assay used in Example 6.

Sequence selection in the region B: In some aspects, an oligomer of the present disclosure comprising a region (region B) which is not complementary to the target sequence. In other aspects, region B does form a complementary sequence to the target sequence. In some aspects, region A and B together can form a single contiguous sequence which is complementary to the target sequence.

In some aspects, the sequence of bases in region B is selected to provide an optimal endonuclease cleavage site, based upon the predominant endonuclease cleavage enzymes present in the target tissue or cell or sub-cellular compartment. In this respect, by isolating cell extracts from target tissues and non-target tissues, endonuclease cleavage sequences for use in region B can be selected based upon a preferential cleavage activity in the desired target cell (e.g. liver/hepatocytes) as compared to a non-target cell (e.g. kidney). In this respect, the potency of the compound for target down-regulation can be optimized for the desired tissue/cell.

In some aspects region B comprises a dinucleotide of sequence AA, AT, AC, AG, TA, TT, TC, TG, CA, CT, CC, CG, GA, GT, GC, or GG, wherein C can be 5-methylcytosine, and/or T can be replaced with U. In some aspects region B comprises a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, and GGG wherein C can be 5-methylcytosine and/or T can be replaced with U.

In some aspects region B comprises a tetranucleotide of sequence AAAX, AATX, AACX, AAGX, ATAX, ATTX, ATCX, ATGX, ACAX, ACTX, ACCX, ACGX, AGAX, AGTX, AGCX, AGGX, TAAX, TATX, TACX, TAGX, TTAX, TTTX, TTCX, TAGX, TCAX, TCTX, TCCX, TCGX, TGAX, TGTX, TGCX, TGGX, CAAX, CATX, CACX, CAGX, CTAX, CTGX, CTCX, CTTX, CCAX, CCTX, CCCX, CCGX, CGAX, CGTX, CGCX, CGGX, GAAX, GATX, GACX, CAGX, GTAX, GTTX, GTCX, GTGX, GCAX, GCTX, GCCX, GCGX, GGAX, GGTX, GGCX, and GGGX, wherein X can be selected from the group consisting of A, T, U, G, C and analogues thereof, wherein C can be 5-methylcytosine and/or T can be replaced with U. It will be recognized that when referring to (naturally occurring) nucleobases A, T, U, G, C, these can be substituted with nucleobase analogues which function as the equivalent natural nucleobase (e.g. base pair with the complementary nucleoside). In some aspects region B does not comprise a T or U.

IV. Medical Indications

In some aspects, the pharmaceutical compositions of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) can be for use in the treatment of conditions associated with over expression or expression of a normal, mutant, allelic variant, or splice variant form of the PCSK9 gene. The present disclosure further provides a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) for use of a in the manufacture of a medicament for the treatment of a disease, disorder or condition as referred to herein.

The present disclosure provides methods of treating a mammal, e.g., a human, suffering from or susceptible to conditions associated with abnormal levels and/or activity of PCSK9, comprising administering to the mammal a therapeutically effective amount of a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof).

The disease or disorder, as referred to herein, can, in some aspects be associated with a mutation in the PCSK9 gene or a gene whose protein product is associated with or interacts with PCSK9. Therefore, in some aspects, the target is an RNA. In some aspects, the mRNA is a pre-mRNA. In some aspects, the RNA is an intron in an mRNA. In some aspects, the RNA is an exon in an RNA. In some aspects, the RNA is a junction between an intron and an exon. In some aspects, the RNA is an mRNA from a normal PCSK9 which is upregulated, e.g., by a defective promoter, or by other components of a metabolic or signaling pathway encompassing PCSK9. In some aspects, the mRNA is from an allelic variant of the PCSK9 gene. In some aspects, the mRNA is from a splice variant of a normal or mutant PCSK9 gene. In some aspects, the mRNA is from a mutated form of the PCSK9 gene (e.g., a gain of function mutant).

PCSK9 plays a major regulatory role in cholesterol homeostasis, mainly by reducing LDLR levels on the plasma membrane. Reduced LDLR levels result in decreased metabolism of LDL-particles, which could lead to hypercholesterolemia. When LDL binds to LDLR, it induces internalization of LDLR-LDL complex within an endosome. When PCSK9 binds to the LDLR (through the EGF-A domain), PCSK9 prevents the conformational change of the receptor-ligand complex. This inhibition redirects the LDLR to the lysosome instead.

PCSK9 also plays an important role in intestinal triglyceride-rich apoB lipoprotein production in small intestine and postprandial lipemia. Variants of PCSK9 can reduce or increase circulating cholesterol. Other variants are associated with a rare autosomal dominant familial hypercholesterolemia (HCHOLA3). The mutations increase its protease activity, reducing LDLR levels and preventing the uptake of cholesterol into the cells. PCSK9 is highly expressed in arterial walls such as endothelium, smooth muscle cells, and macrophages, with a local effect that can regulate vascular homeostasis and atherosclerosis. Accordingly, PCSK9 has pro-atherosclerotic effects and regulates lipoprotein synthesis.

PCSK9 is involved in glucose metabolism and obesity, regulation of re-absorption of sodium in the kidney which is relevant in hypertension. Furthermore, PCSK9 may be involved in bacterial or viral infections and sepsis.

In some aspects, the PCSK9 gene is an allelic variant selected from Pro174Ser PCSK0, Ser127Arg PCSK9, Phe216Leu PCSK9, and Asp374Tyr PCSK9.

The methods disclosed herein are preferably employed for treatment or prophylaxis against diseases caused by abnormal levels and/or activity of PCSK9. The present disclosure provides a method for treating abnormal levels and/or activity of PCSK9 in a subject in need thereof comprising administering a therapeutically effective amount of a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) to the subject.

The present disclosure also relates to a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) for use as a medicament.

The present disclosure further relates to use a therapeutically effective amount of a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) for the manufacture of a medicament for the treatment of abnormal levels of PCSK9 and/or activity of PCSK9 and/or expression of mutant forms of PCSK9 (e.g., a gain of function mutant), allelic variants of PCSK9, or splice variants of PCSK9.

The present disclosure provides a method of treating a disease or condition caused by abnormal expression levels and/or activity of PCSK9 in a subject in need thereof comprising administering an effective amount of a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) to the subject, wherein the administration of the pharmaceutical composition reduces the level of serum PCSK9 and/or reduces the level of serum LDL cholesterol in the subject. In some aspects, the disease or condition is selected from the group consisting of atherosclerosis, hypercholesterolemia, HDL/LDL cholesterol imbalance, dyslipidemia, coronary artery disease (CAD), and coronary heart disease (CHD). In some aspects, the dyslipidemia is familial hyperlipidemia (FCHL) or acquired hyperlipidemia. In some aspects, the hypercholesterolemia is familiar hypercholesterolemia or statin resistant hypercholesterolemia. In some aspects, a subject or a patient who is in need of treatment is a subject or patient suffering from or likely to suffer from the disease or disorder disclosed herein.

In some examples, the term 'treatment' as used herein refers to both treatment of an existing disease, e.g., a disease or disorder disclosed herein, or prevention of a disease, i.e. prophylaxis. Thus, in some aspects, treatment as referred to herein can be prophylactic.

In some aspects, treatment with a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) can treat, ameliorate, or inhibit de symptoms of a disease disclosed herein. In some aspects, treatment with a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) can prevent, delay, or ameliorate sequelae related to a disease disclosed herein.

For example, in some aspects, administering a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) can treat hypercholesterolemia in a subject. In some aspects, administering a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) can inhibit the development of hypercholesterolemia in a subject at risk. In some aspects, administering a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) can delay the onset of hypercholesterolemia in a subject at risk. In some aspects, administering a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) can inhibit the development of hypercholesterolemia in a subject at risk. In some aspects, administering a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) can inhibit or delay the onset or development of symptoms of hypercholesterolemia in a subject, e.g. chest pain with activity, xanthomas (fatty deposits often found in tendons and on the elbows, buttocks, and knees), xanthelasmas (cholesterol deposits around the eyelids), corneal arcus (gray-white cholesterol deposits around the corneas), etc. In some aspects, administering a pharmaceutical composition of the present disclosure (e.g., an oral formulation comprising, e.g., CIVI 008 and an oral delivery agent such SNAC, C10, or 5-CNAC, a derivative thereof, a pharmaceutically acceptable hydrate, solvate, or salt thereof, or any combination thereof) can inhibit or delay the onset or development of sequelae or complications of hypercholesterolemia in a subject, e.g., heart disease, cardiovascular disease, heart attacks, long term atherosclerosis, stroke, etc.

In some aspects, the present disclosure provides a method of treating a disease or condition caused by abnormal expression levels and/or activity of PCSK9 in a subject in need thereof, e.g., hypercholesterolemia, comprising administering an effective amount of an oral formulation (e.g., in pill or capsule form) comprising CIVI 008 and an oral delivery agent such as SNAC, C10, or 5-CNAC, a derivative thereof, a pharmaceutically acceptable hydrate, solvate, or salt thereof, or any combination thereof to the subject, wherein the administration of the pharmaceutical composition reduces the level of serum PCSK9 and reduces the level of serum LDL cholesterol in the subject. In some aspects, the present disclosure provides a method of treating hypercholesterolemia in a subject in need thereof comprising administering an effective amount of an oral formulation (e.g., in pill or capsule form) comprising CIVI 008 and an oral delivery agent such as SNAC, C10, or 5-CNAC to the subject, wherein the administration of the pharmaceutical composition reduces the level of serum PCSK9 and reduces the level of serum LDL cholesterol in the subject. In some aspects, the present disclosure provides a method of treating hypercholesterolemia in a subject in need thereof comprising administering an effective amount of an oral formulation (e.g., in pill or capsule form) comprising CIVI 008 and SNAC to the subject, wherein the administration of the pharmaceutical composition reduces the level of serum PCSK9 and reduces the level of serum LDL cholesterol in the subject. In some aspects, the present disclosure provides a method of treating hypercholesterolemia in a subject in need thereof comprising administering an effective amount of an oral formulation (e.g., in pill or capsule form) comprising CIVI 008 and C10 to the subject, wherein the administration of the pharmaceutical composition reduces the level of serum PCSK9 and reduces the level of serum LDL cholesterol in the subject.

In some aspects, the present disclosure provides a method of treating hypercholesterolemia in a subject in need thereof comprising administering an effective amount of an oral formulation (e.g., in pill or capsule form) comprising CIVI 008 and 5-CNAC to the subject, wherein the administration of the pharmaceutical composition reduces the level of serum PCSK9 and reduces the level of serum LDL cholesterol in the subject.

V. Combination Treatments

In some aspects the pharmaceutical compositions of the present disclosure (e.g., oral formulations comprising, e.g., CIVI 008 and an oral delivery agent such SNAC, C10, or 5-CNAC, a derivative thereof, a pharmaceutically acceptable hydrate, solvate, or salt thereof, or any combination thereof) can be used in a combination treatment with another therapeutic agent. In some aspects, the additional therapeutic agent can be co-administered as part of the same pharmaceutical compositions, e.g., as an additional component of the same pill or capsule. In some aspects, the additional therapeutic agent can be co-administered separately, i.e., the pharmaceutical composition of the present disclosure is administered as, e.g., a pill or a capsule, and the additional component is administered, e.g., in another pill or capsule.

Additional therapeutic agents can be co-administered with the pharmaceutical compositions of the present disclosure include, for example, inhibitors of HMG CoA reductase, such as statins for example are widely used in the treatment of metabolic disease (see WO2009/043354, which is herein incorporated by reference in its entirety for examples of combination treatments).

Therapeutic agents can be co-administered with the pharmaceutical compositions of the present disclosure can be other cholesterol lowering compounds, such as a compound selected from the group consisting of:
  (i) bile salt sequestering resins (e.g., cholestyramine, colestipol, and colesevelam hydrochloride);
  (ii) HMGCoA-reductase inhibitors (e.g., lovastatin, cerivastatin, pravastatin, atorvastatin, simvastatin, rosuvastatin, and fluvastatin);
  (iii) nicotinic acid;
  (iv) fibric acid derivatives (e.g., clofibrate, gemfibrozil, fenofibrate, bezafibrate, and ciprofibrate);
  (v) probucol;
  (vi) neomycin;
  (vii) dextrothyroxine;
  (viii) plant-stanol esters,
  (ix) cholesterol absorption inhibitors (e.g., ezetimibe);
  (x) implitapide;
  (xi) inhibitors of bile acid transporters (e.g., apical sodium-dependent bile acid transporters);
  (xii) regulators of hepatic CYP7a;
  (xiii) estrogen replacement therapeutics (e.g., tamoxifen);
  (xiv) anti-inflammatories (e.g., glucocorticoids); and,
  (xv) any combination thereof.

In one aspect, the co-therapy comprises a pill or capsule for oral delivery comprising an oral pharmaceutical composition of the present disclosure (e.g., oral formulations comprising, e.g., CIVI 008 and an oral delivery agent such SNAC, C10, or 5-CNAC, a derivative thereof, a pharmaceutically acceptable hydrate, solvate, or salt thereof, or any combination thereof), and a statin. In one aspect, the co-therapy comprises a pill or capsule for oral delivery comprising (i) CIVI 008, (ii) an oral delivery agent such SNAC, C10, or 5-CNAC, a derivative thereof, a pharmaceutically acceptable hydrate, solvate, or salt thereof, or any combination thereof, and (iii) a statin. In one aspect, the co-therapy comprises a pill or capsule for oral delivery comprising (i) CIVI 008, (ii) SNAC, and (iii) a statin. In one aspect, the co-therapy comprises a pill or capsule for oral delivery comprising (i) CIVI 008, (ii) C10, and (iii) a statin. In one aspect, the co-therapy comprises a pill or capsule for oral delivery comprising (i) CIVI 008, (ii) 5-CNAC, and (iii) a statin.

VI. Controlled Released Formulations

In some aspects, the oral pharmaceutical compositions of the present disclosure comprise components to facilitate the transit through the stomach and upper intestine, e.g., enteric coatings, pH sensitive materials, and enzyme inhibitors. In some aspects, the oral pharmaceutical compositions of the present disclosure can also comprise gelatin, e.g., as a coating or a viscosity-increasing agent.

The enteric (gastro-resistant) coating material, e.g. polymer, can be one that will dissolve in intestinal juices at a pH level higher than that of the stomach, e.g. a pH of greater than 4.5, such as within the small intestine, and therefore permit release of the active substance in the regions of the small intestine and substantially not in the upper portion of the GI tract. In one aspect, the enteric material begins to dissolve in an aqueous solution at pH between about 4.5 and about 5.5. In another aspect, the enteric material rapidly dissolves in an aqueous solution at pH between of about 5. In another aspect, the enteric material rapidly dissolves in an aqueous solution at pH between of about 5.5.

Suitable enteric (gastro-resistant) materials include, but are not limited to, crosslinked polyvinyl pyrrolidone; non-crosslinked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylate divinylbenzene copolymer; polyvinyl alcohols; polyoxyethylene glycols; polyethylene glycol; sodium alginate; galactomannan; carboxypolymethylene; sodium carboxymethyl starch; copolymers of acrylic acid and/or methacrylic acid with a monomer selected from the following: methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, or octadecyl acrylate, e.g. EUDRAGIT™-L and -S series, including L 100-55, L 30 D-55, L 100, S 100, L 12.5, and S 12.5, available from Evonik Industries; polyvinyl acetate; fats; oils; waxes; fatty alcohols; shellac; zein; gluten; ethylacrylate-maleic acid anhydride copolymer; maleic acid anhydride-vinyl methyl ether copolymer; styrol-maleic acid copolymer; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; polyarginine; poly(ethylene); poly (propylene); poly(ethylene oxide); poly(ethylene terephthalate); poly(vinyl isobutyl ether); poly(vinyl chloride); and polyurethane.

A combination of enteric materials may also be used. In some aspects, the enteric material rapidly dissolves at pH 5.5 and higher, to provide fast dissolution in the upper bowel. For example, the enteric material can be selected from a copolymer of methacrylic acid and methyl methacrylate, and a copolymer of methacrylic acid and ethyl acrylate. For example, an enteric polymer is poly(methacrylic acid co-ethyl acrylate) 1:1 (EUDRAGIT™ L 30 D-55 and EUDRAGIT™ L 100-55).

Other suitable examples of enteric coating coatings include beeswax and glyceryl monostearate; beeswax, shellac and cellulose; and cetyl alcohol, mastic and shellac, and shellac and stearic acid; polyvinyl acetate and ethyl cellulose; and neutral copolymer of polymethacrylic acid esters (EUDRAGIT™ L 30D); copolymers of methacrylic acid and methacrylic acid methylester, or a neutral copolymer of polymethacrylic acid esters containing metallic stearates. Such coatings comprise mixtures of fats and fatty acids, shellac and shellac derivatives and the cellulose acid phthalates, e.g., those having a free carboxyl content.

One or more plasticizers can be added to enteric polymers to increase their pliability and reduce brittleness, as known in the art. Suitable plasticizers include, for example, butyl citrates, triethyl citrate, diethyl phthalate, dibutyl sebacate, polyethylene glycols (PEGs, such as PEG 6000), acetyl triethyl citrate, and triacetin. In one aspect, the plasticizer is triethyl citrate. While some enteric materials are flexible and do not require plasticizers, more brittle polymers (e.g., EUDRAGIT™ L/S types, EUDRAGIT™ RL/RS, and EUDRAGIT™ FS 30 D) benefit from plasticizers, for example ranging from between 5 wt. % and 30 wt. % based on the dry polymer mass, between about 8 wt. % and about 12 wt. % triethyl citrate with poly(methacrylic acid co-ethyl acrylate) 1:1.

In certain aspects, the enteric coatings comprise one or more anti-tacking agents (antiadherents) to reduce the tackiness of the film and prevent agglomeration, as it is known in the art. Suitable anti-tacking agents include, but are not limited to talc, glyceryl monostearate, fumed silica (e.g., AEROSIL™ 200), precipitated silica (e.g., SIPERNAT™ PQ), and magnesium stearate. Anti-tacking agents can be used in any suitable quantity, for example ranging between about 10 wt. % and 100 wt. % based on dry polymer mass, between about 10 wt. % and about 50 wt. %, between about 10 wt. % and about 30 wt. %, or between about 15 wt. % and about 30 wt. %. For example, in one aspect, in ranges between 15 wt. % and about 30 wt. % based on dry polymer mass.

One or more surfactants can also be added to an enteric coating mixture to increase substrate wettability and/or stabilize suspensions, as it is known in the art. Surfactants include Polysorbate 80, sorbitan monooleate, and sodium dodecyl sulfate, and other surfactants described herein.

The enteric coating can be formed by any suitable process. Coating processes include pan coating, fluid bed coating, and dry coating (e.g., heat dry coating and electrostatic dry coating), for example. Pan coating and fluid bed coating using solvent are well established processes. In liquid coating, the enteric material and optional excipients (e.g. pigments, plasticizers, anti-tacking agents) are mixed in an organic solvent or water to form a solution or dispersion. The coating solution or dispersion is sprayed into solid dosage forms in a pan coater or a fluid bed dryer and dried by hot air. For example, in a Wurster fluid bed coating process, the coating fluid is sprayed from the bottom of the fluid bed apparatus. Alternatively, the coating fluid is applied by top spraying. In certain aspects, a tangential spray is applied.

The amount of enteric material applied is sufficient to achieve desired acid resistance and release characteristics. For example, in one aspect the amount of enteric coating meets USP <711> requirements (USP 36-NF 31) for delayed-release dosage forms, thereby not releasing 10.0 wt. % of drug after 2 hours in 0.1N HCl. In certain aspects, the formulation releases at least 80% of the active in 20 minutes in pH 6.8 buffer solution, e.g. using a dissolution method of USP 36-NF 31 section <711>.

In one aspect, the enteric coating is present in an amount in a range between about 10% and 40%, or between 25% and about 35% as measured by the weight gain compared to the uncoated particle cores, or ranging between about 25% and about 31% weight gain, between about 27% and about 31% weight gain, or between about 28.5% and about 31% weight gain, based on the weight of the uncoated particle cores.

The formulation can include a capsule shell. Soft and hard capsule shells are known. In one aspect, the capsule shell is a hard-capsule shell, e.g. a gelatin capsule shell or a vegetable-based hard capsule shell. In certain aspects, the capsule shell comprises one or more enteric coatings described herein. During accelerated storage, gelatin capsules may collapse. Thus, in certain aspects, the formulation can include hydroxypropyl methylcellulose capsule shell.

The solid dosage forms of the present invention may be formulated so as to prevent or retard break down in the stomach. Controlled release formulations suitable for use in the present invention may, for example, include an enteric coating or may be formulated to erode from the surface.

According to one aspect, the solid oral dosage forms comprises a therapeutically effective amount of an oral pharmaceutical composition of the present disclosure, wherein the solid oral dosage form has a disintegration time of about 250 seconds to about 650 seconds when orally administered. In another aspect, the disintegration time is about 350 to about 550 seconds when orally administered. In one aspect the disintegration time is greater than 60 seconds when orally administered. In another aspect, the disintegration time is greater than 400 seconds when orally administered. Disintegration time can be determined in water at 37±2° C. using the method described in USP <701>.

The solid dosage forms of the present disclosure (e.g., tablets or capsules) may be covered by an enteric coating. The enteric coating may serve as the primary control for delaying the release of the drug composition or compositions in the solid dosage form. The enteric coating stays intact in the stomach and prevents or retards release into the stomach in the solid dosage form. Release of the active agent is delayed until the solid dosage form reaches the intestine. Once in the intestine, the higher pH causes release of the active agent. Enteric coatings include, but are not limited to, hydroxypropyl methylcellulose phthalate, hydroxypropyl methylcellulose acetate succinate, polyvinyl acetate phthalate, cellulose acetate trimellitate, cellulose acetate phthalate, poly(methacrylic acid-ethylacrylate), and poly(methacrylic acid-methyl methacrylate). Other enteric coatings which may be used in accordance with the present invention are described in U.S. Pat. No. 5,851,579, which is hereby incorporated by reference.

In one aspect of the present disclosure, the enteric coating is applied to the entire tablet, or other dosage form. In one aspect the enteric coating is applied to a multi-particulate system, such as a system comprising microparticles and/or nanoparticles.

The solid dosage forms of the present disclosure may be formulated to erode from the surface of the tablet (or other dosage uniform), or at the surface of the multi-particulate system (e.g. a system comprising microparticles). These surface erosion formulations slowly dissolve from the surface rather than disintegrate. By controlling the rate of surface erosion, release of the active agent and drug composition of the solid dosage form can be delayed. The surface erosion formulations can be formulated such that substantial release of the active agents or drug compositions do not occur until the solid oral dosage form reaches the intestines.

In some aspects, the solid dosage forms of the present disclosure can also comprise a protective agent like a nuclease inhibitor. In some aspects, the nuclease inhibitor comprises aurintricarboxylic acid. In some aspects, the nuclease inhibitor comprises a broad specificity nuclease inhibitor such as RNAsin. In some aspects, the nuclease inhibitor comprises GS-6620, IDX184, PSI-7777, PSI-938, RG7128, TMC649128, or ABT-072.

In some aspects, the solid dosage forms of the present disclosure can also comprise a protective agent that prevents or reduces the degradation of the GalNAc conjugate moiety. In some aspects, the protective agent prevents or reduces the cleavage of the GalNAc conjugate moiety from the oligomer. In some aspects, the protective agents prevents or reduces the cleavage or degradation of one or more of the N-acetylgalactosamine units in the GalNAc moiety.

In some aspects, the solid dosage forms of the present disclosure can also comprise an antacid compound. The term "antacid compound" refers to any pharmaceutically acceptable compound capable of neutralizing stomach acid (e.g., HCl in aqueous solution), preferably wherein one mole of antacid compound is capable of neutralizing at least 0.5 mole of HCl, and more preferably capable of neutralizing at least 1 mole of HCl. The therapeutically active agents (e.g., CIVI 008 alone or in combination with a second agent such as a statin), oral delivery agents (e.g., SNAC or 5-CNAC) and protease inhibitors described herein are excluded from the scope of the phrase "antacid compound", even though they may exhibit some ability to neutralize stomach acid, in some embodiments of the invention.

Examples of antacid compounds which may be used in any one of the aspects described herein relating to one or more antacid compounds (in accordance with any of the aspects of the disclosure described herein), include, without limitation, calcium carbonate, calcium gluconate, calcium citrate, sodium carbonate, sodium bicarbonate, sodium gluconate, sodium citrate, sodium hydroxide, potassium carbonate, potassium bicarbonate, potassium gluconate, potassium citrate, potassium hydroxide, magnesium carbonate, magnesium gluconate, magnesium citrate, magnesium hydroxide, magnesium oxide, aluminum carbonate, aluminum gluconate, aluminum citrate, and aluminum hydroxide.

In some aspects, solid dosage forms of the present disclosure may also include gastric acid secretion inhibitor. The term "gastric acid secretion inhibitor" refers to any agent which reduces secretion of acid into the stomach, although it does not necessarily have any effect on acid which has already been secreted. Examples of gastric acid secretion inhibitors which may be used in any of the aspects described herein relating to an antacid composition include, without limitation, 2 receptor antagonists, such as cimetidine, famotidine, nizatidine and ranitidine; and proton pump inhibitors, such as omeprazole, lansoprazole, dexlansoprazole, esomeprazole, rabeprazole and ilaprazole.

The solid dosage forms of the present disclosure may also include enzyme inhibiting agents. Enzyme inhibiting agents incorporated into the solid dosage unit forms may prevent the breakdown of the oligomers or other active agents that may be sensitive to enzymatic degradation. Enzyme inhibiting agents are described in U.S. Pat. No. 6,458,383 which is hereby incorporated by reference. The choice and levels of the enzyme inhibitor are based on toxicity and the potency of inhibition, and will be apparent to those skilled in the art. Without wishing to be bound by theory, it is believed that an inhibitor can function solely or in combination as: a competitive inhibitor, by binding at the substrate binding site of the enzyme, thereby preventing the access to the substrate; a non-competitive inhibitor that can be simultaneously bound to the enzyme site along with the substrate, as their binding sites are not identical; and/or a complexing agent due to loss in enzymatic activity caused by deprivation of essential metal ions out of the enzyme structure.

In some aspect, the protease inhibitor included in any of the compositions (including composition unit dosage forms) described herein comprises at least one trypsin inhibitor. In some aspects, the protease inhibitor consists essentially of one or more trypsin inhibitor(s).

Examples of trypsin inhibitor which may be utilized include, without limitation, lima bean trypsin inhibitor, aprotinin, soybean trypsin inhibitor, ovomucoid trypsin inhibitor and any combination thereof. In some aspects, the trypsin inhibitor comprises soybean trypsin inhibitor (SBTI). In some aspects, the trypsin inhibitor (an optionally the at least one protease inhibitor) consists essentially of SBTI.

In some aspects, the protease inhibitor comprises at least one serpin. In some aspects, the protease inhibitor consists essentially of one or more serpin(s). Examples of serpins which may be utilized in any one of the aspects described herein, include, without limitation, alpha 1-antitrypsin, antitrypsin-related protein, alpha 1-antichymotrypsin, kallistatin, protein C inhibitor, cortisol binding globulin, thyroxine-binding globulin, angiotensinogen, centerin, protein Z-related protease inhibitor, vaspin, monocyte/neutrophil elastase inhibitor, plasminogen activator inhibitor-2, squamous cell carcinoma antigen-1 (SCCA-1), squamous cell carcinoma antigen-2 (SCCA-2), maspin, proteinase inhibitor 6 (PI-6), megsin, serpin B8 (PI-8), serpin B9 (PI-9), bomapin, yukopin, hurpin/headpin, antithrombin, heparin cofactor II, plasminogen activator inhibitor 1, glia-derived nexin, pigment epithelium derived factor, alpha 2-antiplasmin, complement 1-inhibitor, 47 kDa heat shock protein (HSP47), neuroserpin and pancpin.

In some aspects, the protease inhibitor comprises at least one cysteine protease inhibitor. In some aspects, the protease inhibitor consists essentially of one or more cysteine protease inhibitor(s). Examples of cysteine protease inhibitors which may be utilized in any one of the aspects described herein include, without limitation, type 1 cystatins, type 2 cystatins, human cystatins C, D, S, SN, and SA, cystatin E/M, cystatin F, and type 3 cystatins (including kininogens).

In some aspects, the protease inhibitor comprises at least one threonine protease inhibitor. In some aspects, the protease inhibitor consists essentially of one or more threonine protease inhibitor(s). Examples of threonine protease inhibitors which may be utilized in any one of the aspects described herein include, without limitation, bortezomib, MLN-519, ER-807446 and TMC-95A.

In some aspects, the protease inhibitor comprises at least one aspartic protease inhibitor. In some aspects, the protease inhibitor consists essentially of one or more aspartic protease inhibitor(s). Examples of aspartic protease inhibitors which may be utilized in any one of the aspects described herein, include, without limitation, α2-macroglobulin, pepstatin A, aspartic protease inhibitor 11, aspartic protease inhibitor 1, aspartic protease inhibitor 2, aspartic protease inhibitor 3, aspartic protease inhibitor 4, aspartic protease inhibitor 5, aspartic protease inhibitor 6, aspartic protease inhibitor 7, aspartic protease inhibitor 8, aspartic protease inhibitor 9, pepsin inhibitor Dit33, and protease A inhibitor 3.

In some aspects, the protease inhibitor comprises at least one metalloprotease inhibitor. In some aspects, the protease inhibitor consists essentially of one or more metalloprotease inhibitor(s). Examples of metalloprotease inhibitors which may be utilized in any one of the aspects described herein, include, without limitation, angiotensin-1-converting enzyme inhibitory peptide, antihemorrhagic factor BJ46a, beta-casein, proteinase inhibitor CeKI, venom metalloproteinase inhibitor DM43, carboxypeptidase A inhibitor, smpl, IMPI, alkaline proteinase, latexin, carboxypeptidase inhibitor, antihemorrhagic factor HSF, testican-3, SPOCK3, TIMP1, metalloproteinase inhibitor 1, metalloproteinase inhibitor 2, TIMP2, metalloproteinase inhibitor 3, TIMP3, metalloproteinase inhibitor 4, TIMP4, putative metalloproteinase inhibitor tag-225, tissue inhibitor of metalloprotease, WAP, kazal inhibitor, immunoglobulin, and kunitz and NTR domain-containing protein 1.

Examples of protease inhibitors which may be utilized in any one of the aspects described herein also include, without limitation, AEBSF-HCl, ε-aminocaproic acid, α1-antichymotypsin, antipain, antithrombin III, α1-antitrypsin, APMSF (4-amidinophenyl-methane sulfonyl-fluoride), sprotinin, benzamidine, chymostatin, DFP (diisopropylfluoro-phosphate), leupeptin, 4-(2-Aminoethyl)-benzene-sulfonyl fluoride hydrochloride, PMSF (phenylmethyl sulfonyl fluoride), TLCK (1-chloro-3-tosylamido-7-amino-2-heptanone), TPCK (1-chloro-3-tosylamido-4-phenyl-2-butanone), pentamidine isothionate, pepstatin, guanidium, α2-macroglobulin, a chelating agent of zinc, and iodoacetate.

In certain aspects, the tablet or capsule might be coated with a pH-sensitive coating so that they do not dissolve in the low pH of the stomach. For example, pH-sensitive materials do not significantly dissolve until the dosage form has emptied from the stomach. The pH of the small intestine gradually increases from about 4.5 to about 6.5 in the duodenal bulb to about 7.2 in the distal portions of the small intestine (ileum). To provide predictable dissolution corresponding to the small intestine transit time of about 3 hours (e.g., 2-3 hours) and permit reproducible release therein, the coating should begin to dissolve within the pH range of the duodenum, and continue to dissolve at the pH range within the small intestine. Therefore, the amount (thickness) of enteric coating should be sufficient to be substantially dissolved during the about three-hour transit time within the small intestine (e.g., the proximal and mid-small intestine).

In some aspects, the pharmaceutical dosage form of the invention releases its active compound(s) in the jejunum, e.g., in the terminal jejunum, of a subject, e.g., a human subject, through a specific design of a pH sensitive coating. The coating substantially degrades and/or dissolves in the jejunum by specific selection of the enteric coating which is preferably chosen from pH sensitive polymers substantially degrading and/or dissolving at a pH value of about 5.5 to about 7.5, preferably about 7.2 to about 7.3. Such pH sensitive polymers are preferably selected from hydroxypropylmethyl celluloses (also called hereinafter "hypromelloses") and anionic copolymers of methacrylic acid and methacrylmethacrylate. In some aspects, the pH sensitive enteric coating containing or being made of hydroxypropylmethyl cellulose is hydroxypropylmethyl cellulose acetate succinate. A commercially available product of this kind is AQOAT®, e.g., AQOAT®-HF (Shin-Etsu Chemical Co., Chiyoda, Japan). In other aspects of the type of anionic copolymers of methacrylic acid and methacrylmethacrylate various forms of EUDRAGIT® polymers may also be used. EUDRAGIT® is commercially available from Evonik Healthcare & Nutrition GmbH, Essen, Germany. In some aspects, EUDRAGIT® FS30D is used as the pH sensitive polymer of the coating, or at least a part thereof.

In further aspects of the disclosure, different coatings can be applied in combination. According to one aspect, the coating comprises or is made of a combination of a hydroxypropylmethyl cellulose and an anionic copolymer of methacrylic acid and methacrylmethacrylate. In some aspects, a combination of coatings is applied such that typically a sub-coating of one pH sensitive polymer is applied as a first layer and a coating of a second pH sensitive polymer is applied on the sub-coating as a second layer. For example, the pH sensitive coating can comprise a sub-coating of or comprising, respectively, a hydroxypropylmethyl cellulose as a first layer, and a second coating comprising or being made of an anionic copolymer of methacrylic acid and methacrylmethacrylate provided as a second layer on the sub-coating. In a further aspect, the coating of the pharmaceutical oral dosage form of the invention comprises a coating comprising a first layer (sub-coating) comprising or being made of an anionic polymer of methacrylic acid and methacrylmethacrylate such as an EUDRAGIT®, e.g., EUDRAGIT® FS30D, and a second layer comprising or being made of a hydroxypropylmethyl cellulose such as AQOAT®, more preferably AQOAT®-HF. More preferably, the anionic copolymer of methacrylic acid and methacrylmethacrylate, e.g., an EUDRAGIT® such as EURDRAGIT® FS30D, is present in less amount than the hydroxypropylmethyl cellulose such as AQOAT®, e.g., AQOAT®-HF. In other words, the thickness of the first layer of this type of combination is lower than the thickness of the second layer in this combination. More specifically, the ratio of amount or thickness, respectively, between first layer and second layer typically ranges from about 1:10 to about 1:50, e.g., from about 1:20 to about 1:30.

In one aspect, the present disclosure provides specific pharmaceutical dosage forms as outlined above which are small in dimension, preferably below 3 mm in the largest dimension, more preferably about 0.6 mm to about 1.7 mm in the largest dimension. Such small dosage forms may conveniently take the form of granules or pellets. Small dosage forms of the invention have the benefit of behaving like a fluid in a subject's stomach causing a fast and constant entry of the pharmaceutical oral dosage form of the invention into the intestinal tract, and therefore to more evenly transport it to the targeted burst release area in the subject's jejunum, preferably the subject's terminal (i.e. distal part) jejunum.

In other aspects of the present disclosure, it may also be convenient that the pharmaceutical oral dosage form is of larger size, i.e. forms wherein the largest dimension of the dosage form is about 3 mm or more, the upper size limit being conveniently selected by the skilled person such that the dosage form can be well swallowed by the subject. A typical range for pharmaceutical oral dosage forms of the invention are dosage forms having a largest dimension of about 3 to about 10 mm. It is to be understood that this range includes all integers of mm, namely, 3, 4, 5, 6, 7, 8, 9 and 10 mm as well as any sub-proportions thereof.

Gelatin is a mixture of purified protein fractions that may be obtained by partial hydrolysis of animal collagen by an acid or an alkaline. The process of acid hydrolysis is referred to as Type A and that by alkaline hydrolysis is referred to as Type B. Gelatin is a linear polymer that is comprised of amino acids which could result in a molecular weight ranging from 15,000 to 250,000. As used herein, the term gelatin includes acid and alkaline hydrolysates of animal collagen.

Gelatin may be applied in formulations of the present invention to serve many functions, such as a coating, a suspending agent, tablet binder and/or as a viscosity-increasing agent. In water, gelatin swells and softens and it can absorb between 5-10 times its own weight of water. There are several hydrophilic natural and synthetic polymers may be applied, in certain aspects, in place of gelatin. For example, (a) anionic polymers, such as alginic acid, dextran sulfate, or pectin; (b) cationic acids, such as chitosan or polylysine; (c) amphiphatic polymers such as carboxylmethyl chitin or fibrin; or (d) neutral polymers such as dextran, agarose, or pullulan.

As used herein, the term gelatin includes gelatin and gelatin alternatives disclosed in Remington's Pharmaceutical Sciences, 16th ed., Mack Publishing Company, Easton, Pa. (1980), page 1245 and pages 1576-1582, which is hereby incorporated by reference in its entirety. The term gelatin also includes compositions disclosed in U.S. Pat. Nos. 6,090,915, 4,043,996, 4,064,008, 4,176,117, 4,889,920, 4,374,063, 5,210,182, 4,232,425, 4,402,873, 4,427,583, 5,093,474, 5,288,408 and 5,459,241, each of which is hereby incorporated by reference in their entirety.

The term gelatin, as used herein also includes gelatin substitutes and alternatives. Generally, such a gelatin alternative can be made from easily obtainable (e.g. vegetable) materials having a homogeneous composition and having all the essential characteristics of gelatin. In the manufacture of soft gel films and capsules, the soft gel composition preferably possesses the properties of good wet and dry film strength, insolubility in cold water, oil, and alcohol, solubility in hot water, temperature and pressure sealability, film clarity, film flexibility, edibility, inertness to drugs or other materials to be encapsulated, and rapid setting from a hot liquid to form a gel.

One gelatin alternative is a film-forming composition that comprises starch material selected from modified starch and waxy starch; gum; and plasticizer as disclosed in U.S. Pat. No. 6,375,981, which is hereby incorporated by reference. The modified starch or waxy starch preferably has a dextrose equivalent (DE) of less than about 1, and more preferably has no measurable DE. This composition can be, but is not required to be, 100% gelatin-free. Thus, the composition can be used as a gelatin replacement, or as an extender in gelatin formulations.

Another gelatin alternative is wheat fiber gel as disclosed in U.S. Pat. No. 6,440,480, which is hereby incorporated by reference. Wheat fiber gel is made by thermal/physical processing of wheat fiber. A special milling technique is used for treating wheat material resulting in a product containing a large proportion of microfine particles. Specific improvements are obtained by mixing the product with maltodextrin. The product so obtained is sold under the tradename VITACEL®, by FMC Biopolymer of Philadelphia, Pa. This product is a dry powder, which readily disperses in water. Upon stirring of the dispersion the gel forms through shear forces. It is reported that wheat fiber gel can be used as a gelatin replacer in yogurt or ice cream. (I. I. Bollinger, Food Marketing & Techn. October 1995, 4-6).

Carrageenan is yet another gelatin alternative. Carrageenan is a natural hydrocolloid, a polysaccharide hydrocolloid, which is derived from seaweed. It comprises a carbohydrate polymer of repeating sugar units, which is linear, without significant numbers of branches or substitutions.

EXAMPLES

Oligonucleotides were synthesized on uridine universal supports using the phosphoramidite approach on an EXPEDITE™ 8900/MOSS synthesizer (Multiple Oligonucleotide Synthesis System) or OLIGOMAKER™ 48 at 4 µmol or 1 µmol scale, respectively. At the end of the synthesis, the oligonucleotides were cleaved from the solid support using aqueous ammonia for 5-16 hours at 60° C. The oligonucleotides were purified by reverse phase HPLC (RP-HPLC) or by solid phase extractions and characterized by UPLC, and the molecular mass was further confirmed by ESI-MS. See below for more details.

Elongation of the oligonucleotide: The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), LNA-T or C6-S-S-C6 linker) was performed by using a solution of 0.1 M of the 5'-O-DMT-protected amidite in acetonitrile and DCI (4,5-dicyanoimidazole) in acetonitrile (0.25 M) as activator. For the final cycle a commercially available C6-linked cholesterol phosphoramidite was used at 0.1 M in DCM. Thiolation for introduction of phosphorothioate linkages is carried out by using xanthane hydride (0.01 M in acetonitrile/pyridine 9:1). Phosphodiester linkages were introduced using 0.02 M iodine in THF/Pyridine/water 7:2:1. The rest of the reagents were the ones typically used for oligonucleotide synthesis. For post solid phase synthesis conjugation, a commercially available C6 aminolinker phosphoramidite was used in the last cycle of the solid phase synthesis and after deprotection and cleavage from the solid support the aminolinked deprotected oligonucleotide was isolated. The conjugate was introduced via activation of the functional group using standard synthesis methods.

Purification by RP-HPLC: The crude compounds were purified by preparative RP-HPLC on a PHENOMENEX™ JUPITER® C18 10µ 150×10 mm column. 0.1 M ammonium acetate pH 8 and acetonitrile was used as buffers at a flow rate of 5 mL/min. The collected fractions were lyophilized to give the purified compound typically as a white solid.

Abbreviations: DCI (4,5-dicyanoimidazole), DCM (dichloromethane), DMF (dimethylformamide), DMT (4,4'-dimethoxytrityl), THF (tetrahydrofurane), Bz (benzoyl), Ibu (isobutyryl), RP-HPLC (reverse phase high performance liquid chromatography)

The compounds synthesized are shown in the figures and tables of the present disclosure.

Example 1

Figure 8:
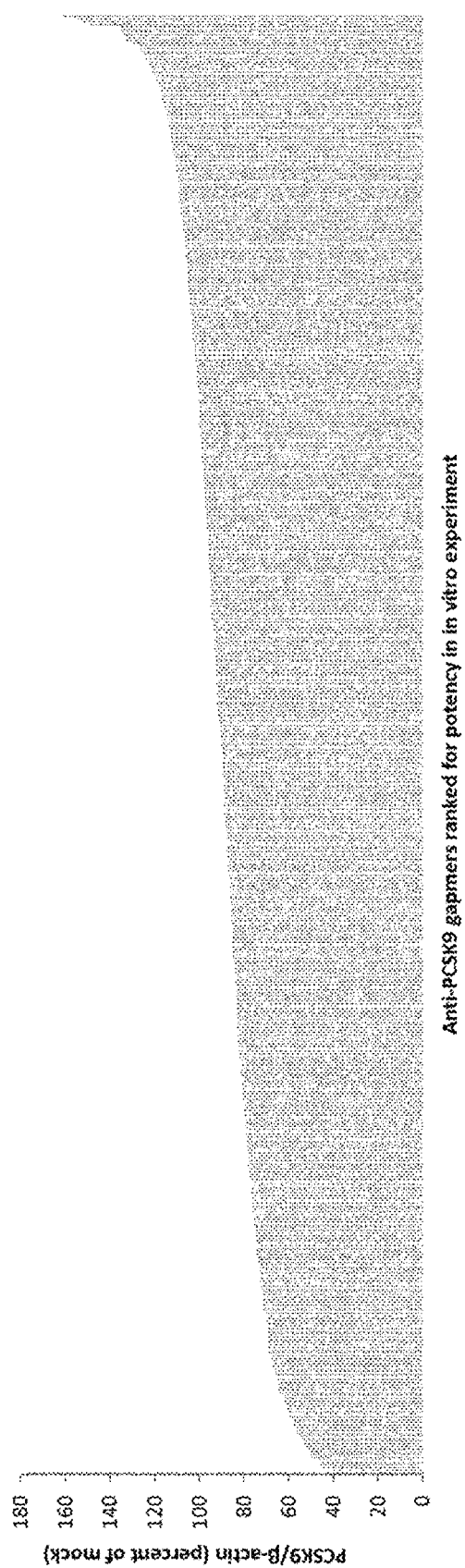
FIG. 8 shows anti-PCSK9 gapmers ranked according to in vitro potency.
Figure 9:
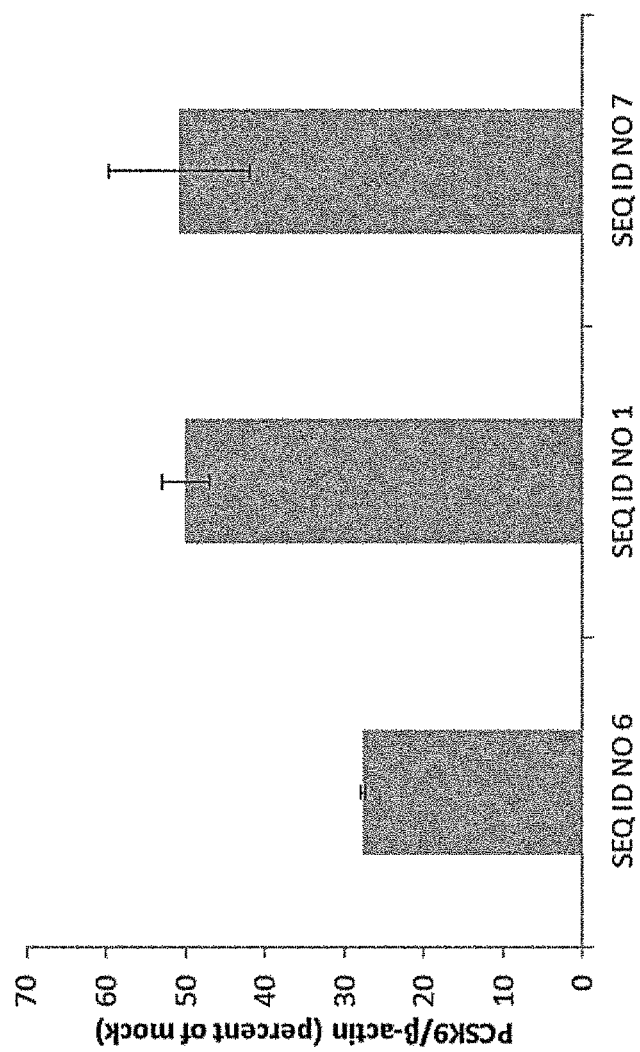
FIG. 9 shows selected anti-PCSK9 gapmers ranked according to in vitro potency.

New PCSK9 Target Motif Discovery 521 anti-PCSK9 antisense oligonucleotides—all with three locked nucleic acids flanking ten DNAs, i.e., with 16-mer LNA gapmer design—specific for human and primate PCSK9 were designed and synthesized. The human cell line 15PC3 was incubated for three days with either mock or the locked nucleic acid-modified oligonucleotides targeted to human PCSK9 at concentration 0.3 µM. Each anti-PCSK9 oligonucleotide was tested in three independent experiments. PCSK9 mRNA levels were quantitated from extracted RNA using real-time PCR as described, and presented normalized to β-actin mRNA and relative to average levels in twelve mock treated samples in FIG. 8, with a close-up of a sub-set of the most potent molecules in FIG. 9.

Example 2

In Vitro mRNA Knockdown

Figure 10:
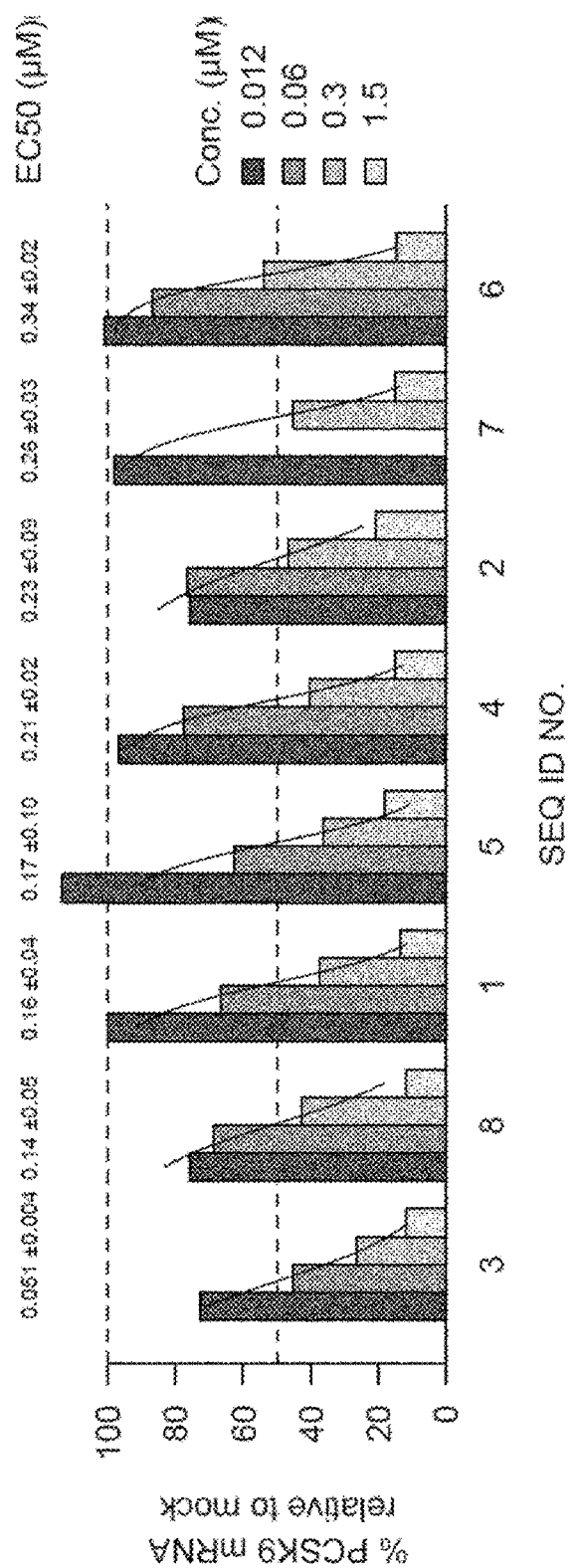
FIG. 10 shows in vitro potency of selected anti-PCSK9 compounds and $IC_{50}$ data.

The human cell line 15PC3 was incubated for 3 days with either mock or locked nucleic acid modified oligonucleotides with SEQ ID NOS: 1 to 8 targeted to human PCSK9 at concentrations 0.0012 µM, 0.06 µM, 0.3 µM, and 1.5 µM. PCSK9 mRNA levels were quantitated from extracted RNA using real-time PCR as described, and presented relative to average levels in four mock treated samples in FIG. 10. For each oligonucleotide, potency, quantified as half maximal effective concentration ($EC_{50}$), was determined by least squares fitting of the Hill equation in two-parameter logistic form with lower limit fixed at 0% and upper limit fixed at 100%, as $EC_{50}$=estimate±standard deviation.

Example 3

In Vivo Alanine Aminotransferase ALT Levels

Figure 11:
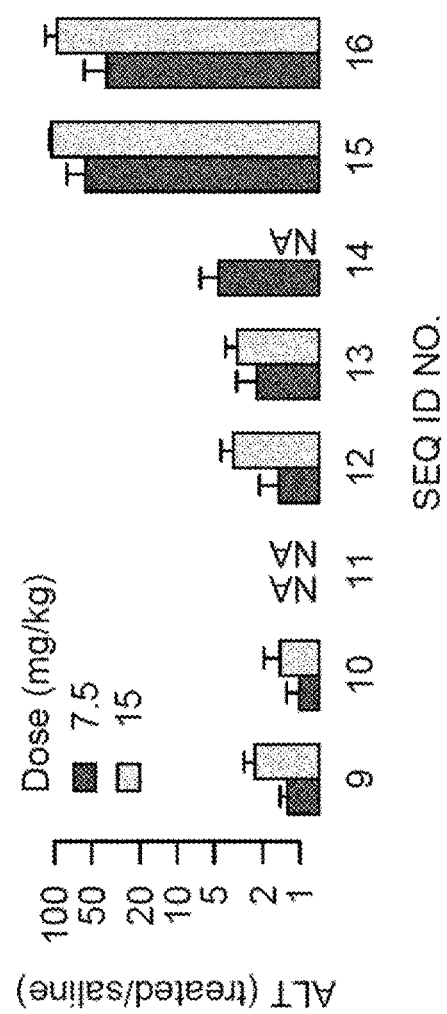
FIG. 11 shows in vivo alanine aminotransferase (ALT) levels for selected anti-PCSK9 conjugates.

Four week old female NMRI mice (Taconic, Denmark), weighing approximately 20 g at arrival, were injected intravenously once with either saline or locked nucleic acid-modified, cholesterol-conjugated, oligonucleotides with SEQ IDs 9 to 16 targeted to human PCSK9 at doses 7.5 and 15 mg/kg. The mice were sacrificed 7 days following administration and serum levels of alanine aminotransferase (ALT) determined using an enzymatic assay (Horiba ABX Diagnostics). For each treatment group of five mice, mean and standard deviations were calculated and presented in FIG. 11 relative to mean levels in saline treated mice. ALT rises were noted at both concentrations for some, but not all, cholesterol conjugated molecules. Several of the compounds, such as SEQ ID NOS: 9 and 10, did not enhance ALT in mice in a clinically meaningful manner even when cholesterol was used as a conjugate to enhance the uptake of compounds in the liver.

Example 4

Non-Human Primate Study

The primary objective for this study was to investigate selected lipid markers over 7 weeks after a single slow bolus injection of anti-PCSK9 LNA compounds to cynomolgus monkeys and assess the potential toxicity of compounds in monkey. The compounds used in this study were SEQ ID NOS: 10, 13, 18, 19, 20, and 21, prepared in sterile saline (0.9%) at initial concentrations of 0.625 mg/ml and 2.5 mg/ml.

Male monkeys of at least 24 months old were used, and given free access to tap water and 180 g of MWM(E) SQC SHORT expanded diet (Dietex France, SDS, Saint Gratien, France) was distributed daily per animal. The total quantity of food distributed in each cage was calculated according to the number of animals in the cage on that day. In addition, fruit or vegetables were given daily to each animal. The animals were acclimated to the study conditions for a period of at least 14 days before the beginning of the treatment period. During this period, pre-treatment investigations were performed. The animals were dosed with SEQ ID NOS: 10, 13, 18, and 21, intravenously (i.v.) at a single dose of 0.25 mg/kg, 1.0 mg/kg, or 2.5 mg/kg, or at a single dose of 1.0 mg/kg or 2.5 mg/kg for SEQ ID NOS: 19 and 20, respectively. The dose volume was 0.4 mL/kg. Two (2) animals were used per group.

The dose formulations were administered once on Day 1. Animals were observed for a period of 7 weeks following treatment, and were released from the study on Day 51. Day 1 corresponded to the first day of the treatment period. Clinical observations and body weight and food intake (per group) were recorded prior to and during the study.

Blood was sampled and analyses performed at the following time points:

| Study Day | Parameters |
| --- | --- |
| −8 | RCP, L, Apo-B, PCSK9*, OA |
| −1 | L, Apo-B, PCSK9*, PK, OA |
| 1 | Dosing |
| 4 | LSB, L, Apo-B, PCSK9*, OA |
| 8 | LSB, L, Apo-B, PCSK9*, PK, OA |
| 15 | RCP, L, Apo-B, PCSK9* PK, OA |
| 22 | LSB, L, Apo-B, PCSK9* PK, OA |
| 29 | L, Apo-B, PCSK9* PK, OA |
| 36 | LSB, L, Apo-B, PCSK9* PK, OA |
| 43 | L, PK, Apo-B, PCSK9* PK, OA |
| 50 | RCP, L, Apo-B, PCSK9* PK, OA |

RCP means routine clinical pathology, LSB means liver safety biochemistry, PK means pharmacokinetics, OA means other analysis, and L means Lipids. The parameters determined for all surviving animals at the occasions indicated were: full biochemistry panel (complete list below) on Days −8, 15 and 50, liver Safety (ASAT, ALP, ALAT, TBIL and GGT only) on Days 4, 8, 22 and 36, and lipid profile (Total cholesterol, HDL-C, LDL-C and Triglycerides) and Apo-B only—on Days −1, 4, 8, 22, 29, 36, and 43. Blood (approximately 1.0 mL) was taken into lithium heparin tubes (using the ADVIA 1650 blood biochemistry analyzer): Apo-B, sodium, potassium, chloride, calcium, inorganic phosphorus, glucose, HDL-C, LDL-C, urea, creatinine, total bilirubin (TBIL), total cholesterol, triglycerides, alkaline phosphatase (ALP), alanine aminotransferase (ALAT), aspartate aminotransferase (ASAT), creatine kinase, gamma-glutamyl transferase (GGT), lactate dehydrogenase, total protein, albumin, albumin/globulin ratio.

Analysis of PCSK9 in blood: Blood samples for PCSK9 analysis were collected from on Days −8, −1, 4, 8, 15, 22, 29, 36, 43 and 50. Venous blood (approximately 2 mL) was collected from an appropriate vein in each animal into a Serum Separating Tube (SST) and allowed to clot for at least 60 f 30 minutes at room temperature. Blood was centrifuged at 1000 g for 10 minutes under refrigerated conditions (set to maintain +4° C.). The serum was transferred into 3 individual tubes and stored at −80° C. until analyzed at CitoxLAB France using an ELISA method (Circulex Human PCSK9 ELISA kit, CY-8079, validated for samples from cynomolgus monkey).

Other Analysis: WO2011009697 provides the methods for qPCR and PCSK9 mRNA analysis. Other analyses include PCSK9 protein ELISA, serum Lp(a) analysis with ELISA (Mercodia No. 10-1106-01), tissue and plasma oligonucleotide analysis (drug content), extraction of samples (standard- and QC-samples), and oligonucleotide content determination by ELISA.

The values of PCSK9 expression compared to pre-dose values observed after administration of the compounds is SEQ ID NOS: 10, 13, 18, 19, 20 and 21 are shown in the following table:

| | Value for 2.5 mg/kg dose | | | |
|---|---|---|---|---|
| Compound SEQ ID | PCSK9 protein day 4 (percent of pre-dose) | PCSK9 protein day 29 (percent of pre-dose) | Max PCSK9 effect (data represent percent of pre-dose) | Max LDL-C effect (data represent percent of pre-dose) |
| 10 | 86% | 71.5% | 69% (d 15) | 87% (d 29) |
| 13 | 81% | 71% | 71% (d 29) | 84% (d 22) |
| 18 | 57% | 42% | 42% (d 29) | 71% (d 15) |
| 21 | 80.5% | 56% | 55% (d 29) | 84% (d 15) |
| 20 | 51% | 53% | 48% (d 4) | 94% (d 8) |
| 19 | 55% | 60% | 55% (d 4) | 89% (d 4) |

There was no indication of hepatotoxicity or nephrotoxicity with the PCSK9 targeting compounds. Notably, the PCSK9-GalNAc compounds gave a rapid and highly effective down regulation of PCSK9 which was maintained over an extensive time period (entire length of the study), illustrating that the GalNAc conjugated compounds were more effective, both in terms of a rapid initial knock-down, and long duration, indicating that they can be dosed comparatively infrequently and at a lower dosage, as compared to both the unconjugated parent compounds, and compounds using alternative conjugation technology, such as cholesterol conjugation. Nevertheless, knock down was also observed when unconjugated oligomers were administered. Thus, both types of compounds could have different therapeutic uses. For example, unconjugated compounds could be used when a transient effect is desired, or, for example, as part of a loiding dose. Conversely, conjugated oligomers could be administered when a long term effect is needed.

SEQ ID NO: 18 gave rapid and consistent down regulation of PCSK9 and LDL-C throughout the duration of the study (seen at day 34 at 2.5 mg/kg dose, with notable PCSK9 down-regulation seen 48 days after the administration of the single 2.5 mg/kg dose where plasma PCSK9 protein level was 71% of pre-dose).

Example 5

Liver and Kidney Toxicity Assessment in Rat

Compounds of the present disclosure were evaluated for their toxicity profile in rodents. Wistar Han Crl:WI(Han) were used at an age of approximately 8 weeks old. At this age, the males weighed approximately 250 g. All animals had free access to SSNIFF R/M-H pelleted maintenance diet (SSNIFF Spezialdiäten GmbH, Soest, Germany) and to tap water (filtered with a 0.22 μm filter) contained in bottles. Dose levels of 10 mg/kg/dose and 40 mg/kg/dose were used (sub-cutaneous administration) and dosed on days 1 and 8.

The animals were euthanized on Day 15. Urine and blood samples were collected on day 7 and 14. A clinical pathology assessment was made on day 14. Body weight was determined prior to the study, on the first day of administration, and 1 week prior to necropsy. Food consumption per group was assessed daily. Blood samples were taken via the tail vein after 6 hours of fasting. The following blood serum analysis were performed: erythrocyte count, mean cell volume packed cell volume, hemoglobin, mean cell hemoglobin concentration, thrombocyte count, leucocyte count, differential white cell count with cell morphology, reticulocyte count, sodium, potassium, chloride, calcium, inorganic phosphorus, glucose, urea, creatinine, total bilirubin, total cholesterol, triglycerides, alkaline phosphatase, alanine aminotransferase, aspartate aminotransferase, total protein, albumin, and albumin/globulin ratio.

Urinalysis was also performed. The following parameters were measured: α-GST, β-2 Microglobulin, calbindin, clusterin, cystatin C, KIM-1, osteopontin, TIMP-1, VEGF, and NGAL expression. Seven analytes (calbindin, clusterin, GST-α, KIM-1, osteopontin, TIMP-1, and VEGF) were quantified under Panel 1 (MILLIPLEX® MAP Rat Kidney Toxicity Magnetic Bead Panel 1, RKTX1MAG-37K). Three analytes (β-2 microglobulin, cystatin C, lipocalin-2/NGAL) were quantified under Panel 2 (MILLIPLEX® MAP Rat Kidney Toxicity Magnetic Bead Panel 2, RKTX2MAG-37K). The assays for the determination of these biomarkers' concentrations in rat urines were based on the Luminex xMAP® technology. Microspheres coated with anti-α-GST/β-2 microglobulin/calbindin/clusterin/cystacin C/KIM-1/osteopontin/TIMP-1/VEGF/NGAL antibodies were color-coded with two different fluorescent dyes. Urine protein and urine creatinine were also determined in urine using the ADVIA 1650. Quantitative parameters were also determined, namely, volume, pH (using 10-Multistix SG test strips/Clinitek 500 urine analyzer), specific gravity (using a refractometer). Semi-quantitative parameters (using 10-Multistix SG test strips/Clinitek 500 urine analyzer): proteins, glucose, ketones, bilirubin, nitrites, blood, urobilinogen, cytology of sediment (by microscopic examination). Qualitative parameters such as appearance and color were also determined.

After sacrifice, the body weight and kidney, liver and spleen weight were determined and organ to body weight ratio calculated. Kidney and liver samples were taken and either frozen or stored in formalin. Microscopic analysis was performed.

KIM-1 (kidney tissue damage biomarker) expression data is shown in FIG. 15. The data show that all molecules except SEQ ID NO: 4 had a lower urinary kIM-1 signal than SEQ ID NO: 1 (SPC5001), demonstrating improved kidney safety vs. the original and previously characterized unconjugated molecule. Lack of kidney toxicity was observers both in unconjugated oligomers of SEQ ID NO: 2 and SEQ ID NO: 3, as well as their corresponding GalNAc conjugated form SEQ ID NO: 18 and SEQ ID NO: 19, indicating that the lack of kidney toxicity is not due to the presence of the GalNAc. Thus, the data shows that increasing the length of SEQ ID NO: 1 (SPC5001) by two nucleobases unexpectedly eliminated kidney toxicity. In fact, a person of ordinary skill in the art would have expected the opposite effect, since the addition of two extra bases increased the strength of the interaction between the oligomer and the target site.

Example 6

Analysis of Cleavable Linkers

FAM (Fluorescein amidite)-labelled antisense oligomers (ASOs) with different DNA/PO-linkers were subjected to in vitro cleavage either in S1 nuclease extract (table below), Liver or kidney homogenates or serum.

| # | Seq (5'-3') | Cleavable linker (B) | Conjugate (C) |
|---|---|---|---|
| 35 | GCattggtatTCA | 3PO-DNA (5'tca3') | FAM |
| 36 | GCattggtatTCA | 2PO-DNA (5'ca3') | FAM |
| 37 | GCattggtatTCA | 1PO-DNA (5'a3') | FAM |
| 38 | GCattggtatTCA | 3PO-DNA (5'gca3') | FAM |
| 39 | GCattggtatTCA | no | FAM |

Figure 6:
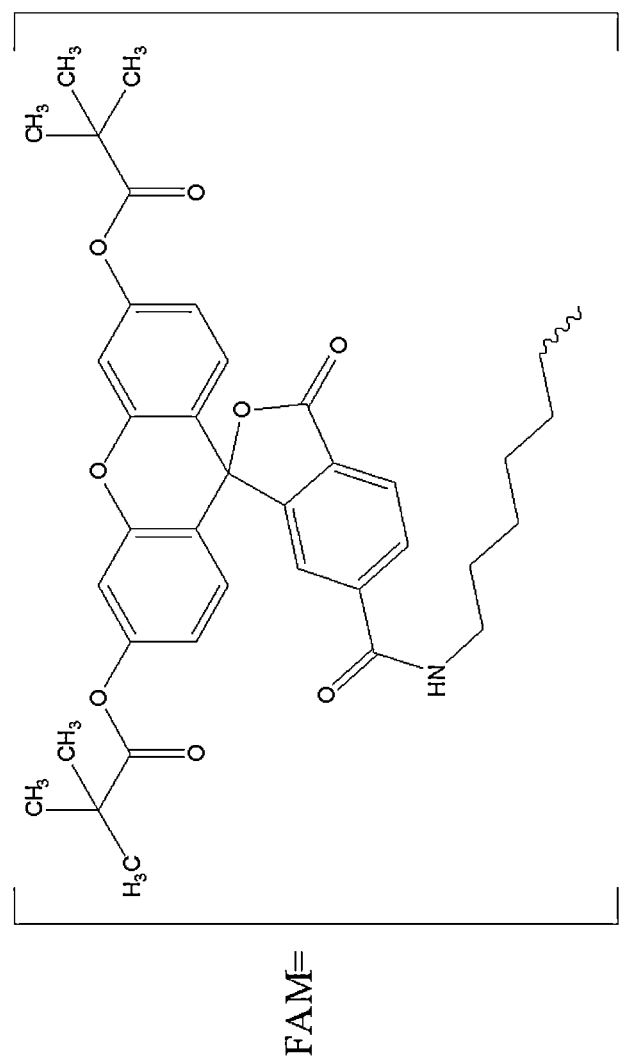
Figure 7:
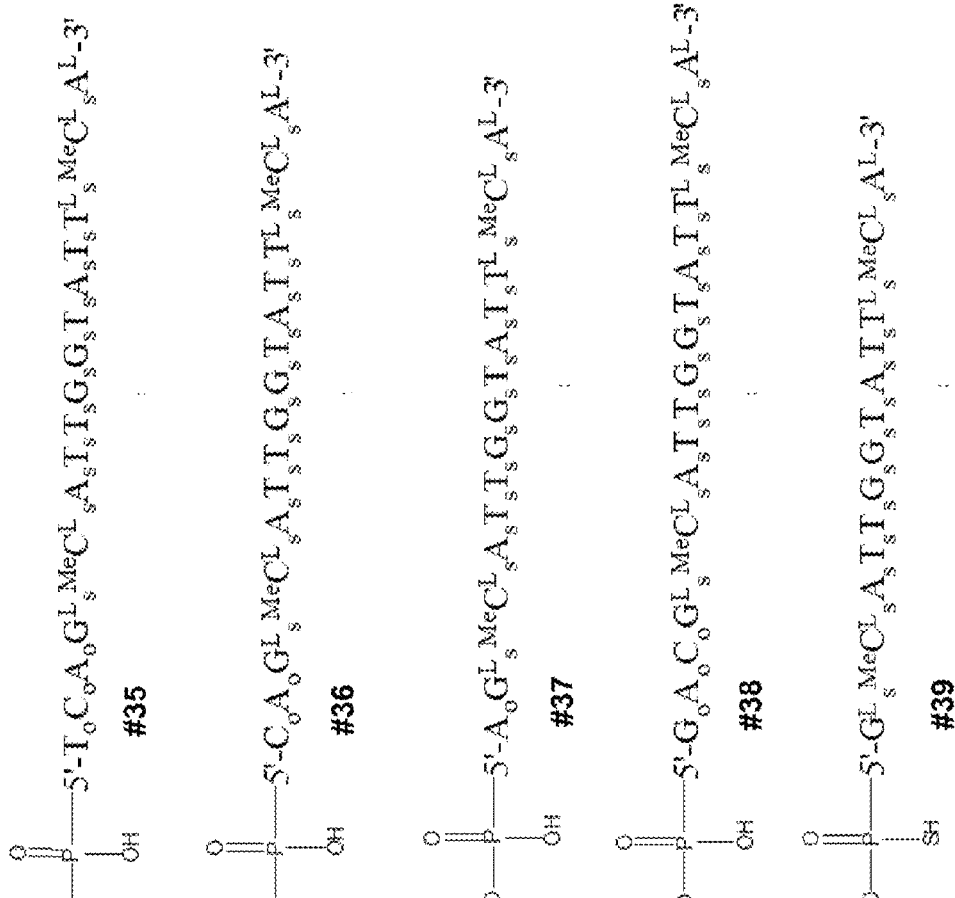

Capital letters are LNA nucleosides (such as beta-D-oxy LNA), lower case letters are DNA nucleosides. Subscript s represents phosphorothioate internucleoside linkages. LNA cytosines are optionally 5-methyl cytosine. The FAM conjugate moiety is shown in FIG. 6 and the conjugated molecules are shown in FIG. 7.

FAM-labelled ASOs 100 µM with different DNA/PO-linkers were subjected to in vitro cleavage by S1 nuclease in nuclease buffer (60 U pr. 100 µL) for 20 and 120 minutes (A). The enzymatic activity was stopped by adding EDTA to the buffer solution. The solutions were then subjected to AIE HPLC analyses on a Dionex Ultimate 3000 using a Dionex DNApac β-100 column and a gradient ranging from 10 mM-1 M sodium perchlorate at pH 7.5. The content of cleaved and non-cleaved oligonucleotide was determined against a standard using both a fluorescence detector at 615 nm and an u.v. detector at 260 nm.

| SEQ ID NO | Linker sequence | % cleaved after 20 min S1 | % cleaved after 120 min S1 |
|---|---|---|---|
| 39 | — | 2 | 5 |
| 37 | a | 29.1 | 100 |
| 36 | ca | 40.8 | 100 |
| 35 | tca | 74.2 | 100 |
| 38 | gac | 22.9 | n.d |

The PO linkers (or region B as referred to herein) resulted in cleavage of the conjugate moiety (or group C). Both the length and/or the sequence composition of the linker could be used to modulate susceptibility to nucleolytic cleavage of region B. The choice of sequence for the DNA/PO-linker was able modulate the cleavage rate as seen after 20 min in Nuclease S1 extract sequence selection for region B (e.g., for the DNA/PO-linker). Thus, the selection of a particular sequence of a DNA/PO-linker can also be used to modulate the level of cleavage in serum and in cells of target tissues.

Liver and kidney homogenates and serum were spiked with an oligomer of SEQ ID NO: 35 to a concentration of 200 µg/g tissue. Liver and kidney samples collected from NMRI mice were homogenized in a homogenization buffer (0.5% Igepal CA-630, 25 mM Tris pH 8.0, 100 mM NaCl, pH 8.0, adjusted with 1 N NaOH). The homogenates were incubated for 24 hours at 37° C. and thereafter the homogenates were extracted with phenol-chloroform. The content of cleaved and non-cleaved oligomer conjugate in the extract from liver and kidney and in serum was determined against a standard using the HPLC method disclosed above.

| Seq ID | Linker Sequence | % cleaved after 24 hrs liver homogenate | % cleaved after 24 hrs kidney homogenate | % cleaved after 24 hrs in serum |
|---|---|---|---|---|
| 35 | tca | 83 | 95 | 0 |

The presence of PO linkers (or region B as referred to herein) caused the conjugate moiety (or group C) to be cleaved off, in liver or kidney homogenate, but not in serum. The susceptibility to cleavage in the assays shown in Example 6 can be used to determine whether a linker is biocleavable or physiologically labile. Cleavage in the above assays refers to the cleavage of the cleavable linker alone; i.e., the oligomer or region A should remain functionally intact (i.e., it should not experience degradation).

Example 7

Knock Down of PCSK9 mRNA with Cholesterol Conjugates In Vivo

NMRI mice were injected with a single dose saline or 10 mg/kg unconjugated LNA-antisense oligonucleotide (SEQ ID NO: 40) or equimolar amounts of LNA antisense oligonucleotides conjugated to Cholesterol with different linkers and sacrificed at days 1-10 according to.

| # | Seq (5'-3') (A) | Cleavable linker (B) | Conjugate (C) |
|---|---|---|---|
| 40 | GTctgtggaaGCG | no | no |
| 41 | GTctgtggaaGCG | no | Cholesterol |
| 42 | GTctgtggaaGCG | 2PO-DNA (5'ca3') | Cholesterol |
| 43 | GTctgtggaaGCG | 2PO-DNA (5'ct3') | Cholesterol |

RNA was isolated from liver and kidney and subjected to qPCR with PCSK9 specific primers and probe to analyze for PCSK9 mRNA knockdown. The results are shown in FIG. 14.

Cholesterol conjugated to an PCSK9 LNA antisense oligonucleotide with a linker composed of 2 DNA with Phosphodiester-backbone (SEQ ID NO: 42 and SEQ ID NO: 43) showed an enhanced liver knock down of PCSK9 (FIG. 14) compared to the unconjugated compound (SEQ ID NO: 40), as well as compared to Cholesterol conjugates with a stable linker (SEQ ID NO: 41).

Materials and Methods

Experimental Design 03 604 721 001) using the MagNa Pure 96 Cellular RNA Large Volume Kit (Roche cat no. 5467535001), according to the manufacturer's instructions.

First strand synthesis was performed using Reverse Transcriptase reagents from Ambion according to the manufacturer's instructions.

For each sample, 0.5 µg total RNA was adjusted to (10.8 µl) with RNase free $H_2O$, mixed with 2 µl random decamers

| Part | Group no. | Animal Id no. | No. of Animals | Animal strain/ gender/feed | Compound Dose level per day | Conc. at dose vol. 10 ml/kg | Adm. Route | Dosing day | Body weight day | Sacrifice day |
|---|---|---|---|---|---|---|---|---|---|---|
| A | 1 | 1-3 | 3 | NM/♀/Chow | Saline | — | iv | 0 | 0.1 | 1 |
|   | 2 | 4-6 | 3 | NM/♀/Chow | SEQ ID No 40 10 mg/kg | 1 mg/ml | iv | 0 | 0.1 | 1 |
|   | 3 | 7-9 | 3 | NM/♀/Chow | SEQ ID No 41 equimolar 11.3 mg/kg | 1.13 mg/ml | iv | 0 | 0.1 | 1 |
|   | 5 | 13-15 | 3 | NM/♀/Chow | SEQ ID No 42 equimolar 12.7 mg/kg | 1.27 mg/ml | iv | 0 | 0.1 | 1 |
|   | 6 | 16-18 | 3 | NM/♀/Chow | SEQ ID No 43 equimolar 12.7 mg/kg | 1.27 mg/ml | iv | 0 | 0.1 | 1 |
| B | 7 | 19-21 | 3 | NM/♀/Chow | Saline | — | iv | 0 | 0.3 | 3 |
|   | 8 | 22-24 | 3 | NM/♀/Chow | SEQ ID No 40 10 mg/kg | 1 mg/ml | iv | 0 | 0.3 | 3 |
|   | 9 | 25-27 | 3 | NM/♀/Chow | SEQ ID No 41 equimolar 11.3 mg/kg | 1.13 mg/ml | iv | 0 | 0.3 | 3 |
|   | 11 | 31-33 | 3 | NM/♀/Chow | SEQ ID No 42 equimolar 12.7 mg/kg | 1.27 mg/ml | iv | 0 | 0.3 | 3 |
|   | 12 | 34-36 | 3 | NM/♀/Chow | SEQ ID No 43 equimolar 12.7 mg/kg | 1.27 mg/ml | iv | 0 | 0.3 | 3 |
| C | 13 | 37-39 | 3 | NM/♀/Chow | Saline | — | iv | 0 | 0.7 | 7 |
|   | 14 | 40-42 | 3 | NM/♀/Chow | SEQ ID No 40 equimolar 10 mg/kg | 1 mg/ml | iv | 0 | 0.7 | 7 |
|   | 15 | 43-45 | 3 | NM/♀/Chow | SEQ ID No 41 equimolar 11.3 mg/kg | 1.13 mg/ml | iv | 0 | 0.7 | 7 |
|   | 17 | 49-51 | 3 | NM/♀/Chow | SEQ ID No 42 equimolar 12.7 mg/kg | 1.27 mg/ml | iv | 0 | 0.7 | 7 |
|   | 18 | 52-54 | 3 | NM/♀/Chow | SEQ ID No 43 equimolar 12.7 mg/kg | 1.27 mg/ml | iv | 0 | 0.7 | 7 |
| D | 19 | 55-57 | 3 | NM/♀/Chow | Saline | — | iv | 0 | 0.7, 10 | 10 |
|   | 20 | 58-60 | 3 | NM/♀/Chow | SEQ ID No 40 equimolar 10 mg/kg | 1 mg/ml | iv | 0 | 0.7, 10 | 10 |
|   | 21 | 61-63 | 3 | NM/♀/Chow | SEQ ID No 41 equimolar 11.3 mg/kg | 1.13 mg/ml | iv | 0 | 0.7, 10 | 10 |
|   | 24 | 70-72 | 3 | NM/♀/Chow | SEQ ID No 42 equimolar 12.7 mg/kg | 1.27 mg/ml | iv | 0 | 0.7, 10 | 10 |
| A | 25 | 73-75 | 3 | NM/♀/Chow | Saline | — | iv | 0 | 0.1 | 1 |

Dose administration: NMRI female animals, approximate 20 gr at arrival, were dosed with 10 ml per kg BW (according to day 0 bodyweight) i.v. of the compound of the present disclosure formulated in saline or saline alone according to according to the table above.

Sampling of liver and kidney tissue: The animals were anaesthetized with 70% $CO_2$-30% $O_2$ and sacrificed by cervical dislocation. One half of the large liver lobe and one kidney were minced and submerged in RNAlater.

Total RNA was extracted from maximum of 10 mg of tissue homogenized by bead-milling in the presence of MagNA Pure LC RNA Isolation Tissue buffer (Roche cat.no (50 µM) and 4 µl dNTP mix (2.5 mM each dNTP), and heated to 70° C. for 3 minutes, after which the samples were rapidly cooled on ice.

2 µl 10x Buffer RT, 1 µl MMLV Reverse Transcriptase (100 U/µl) and 0.25 µl RNase inhibitor (10 U/µl) were added to each sample, followed by incubation at 42° C. for 60 minutes, heat inactivation of the enzyme at 95° C. for 10 minutes and then the sample was cooled to 4° C. cDNA samples were diluted 1:5 and subjected to RT-QPCR using Taqman Fast Universal PCR Master Mix 2x (Applied Biosystems Cat #4364103) and Taqman gene expression assay (mPCSK9, Mn00463738_m1 and mActin #4352341E) fol-

Example 8

Non-Human Primate Study; Multiple Subcutaneous (s.c.) Injections

The objective of this non-human primate study was to assess efficacy and safety of the anti-PCSK9 compounds disclosed herein in a repeat administration setting, when compounds were administered by subcutaneous injection (s.c.). The compounds used in this study were SEQ ID NOS: 2, 3, 18, and 19, prepared in sterile saline (0.9%) at an initial concentration of 0.625 and 2.5 mg/ml.

Female cynomolgus monkeys of at least 24 months old were used, and given free access to tap water and 180 g of OWM(E) SQC SHORT expanded diet (Dietex France, SDS, Saint Gratien, France) was distributed daily per animal. In addition, fruit or vegetables were given daily to each animal. The animals were acclimated to the study conditions for a period of at least 14 days before the beginning of the treatment period. During this period, pre-treatment investigations were performed.

The animals were dosed s.c. once per week for four weeks at a dose of 0.5 mg/kg (SEQ ID NOS: 2, 3, 18, and 19) or 1.5 mg/kg/injection (SEQ ID NOS: 18 and 19), with four injections total over a period of four weeks. The dose volume was 0.4 mL/kg/injection. Six animals were used per group. After the fourth and final dose animals were observed for a week after which half the animals were sacrificed in order to study liver apoB transcript regulation, lipid parameters, liver and kidney histology, and liver and kidney tissue distribution. Day 1 corresponded to the first day of the treatment period. Clinical observations and body weight and food intake (per group) was recorded prior to and during the study.

Blood and tissues were sampled and analyzed at the time points shown in the table below.

| Study Day | Parameters |
|---|---|
| −10 | L, Apo-B, OA |
| −5 | LSB, L, Apo-B, OA |
| −1 | RCP, L, Apo-B, PK, OA |
| 1 | Dosing |
| 8 pre-dose | LSB, L, Apo-B, PK, OA |
| 8 | Dosing |
| 15 pre-dose | LSB, L, Apo-B, PK, OA |
| 15 | Dosing |
| 22 pre-dose | LSB, L, Apo-B, PK, OA |
| 22 | Dosing |
| 29 | RCP, PK, OA + necropsy main |
| 36 (recovery animals) | LSB, L, Apo-B, PK, OA |
| 43 (recovery animals) | RCP, PK, Apo-B, PK, OA |
| 50 (recovery animals) | LSB, L, Apo-B, PK, OA |
| 57 (recovery animals) | LSB, L, Apo-B, PK, OA |
| 64 (recovery animals) | LSB, L, Apo-B, PK, OA |
| 71 (recovery animals) | LSB, L, Apo-B, PK, OA |
| 78 (recovery animals) | RCP, L, Apo-B, PK, OA + necropsy recovery |

RCP means routine clinical pathology, LSB means liver safety biochemistry, PK means pharmacokinetics, OA means other analyses, and L means lipids. Blood (approximately 1.0 mL) was taken into lithium heparin tubes and sodium, potassium, chloride, calcium, inorganic phosphorus, glucose, HDL-C, LDL-C, urea, creatinine, total bilirubin (TBIL), total cholesterol, triglycerides, alkaline phosphatase (ALP), alanine aminotransferase (ALAT), aspartate aminotransferase (ASAT), creatine kinase, gamma-glutamyl transferase (GGT), lactate dehydrogenase, total protein, albumin, and albumin/globulin ratio were analyzed using an ADVIA 1650 blood biochemistry analyzer.

Analysis of blood: Blood samples for ApoB analysis was collected from Group 1-16 animals only (i.e., animals treated with anti-ApoB compounds) on Days −8, −1, 4, 8, 15, 22, 29, 36, 43 and 50. Venous blood (approximately 2 mL) was collected from an appropriate vein in each animal into a Serum Separating Tube (SST) and allowed to clot for at least 60 f 30 minutes at room temperature. Blood was centrifuged at 1000 g for 10 minutes under refrigerated conditions (set to maintain +4° C.). The serum was transferred into 3 individual tubes and stored at −80° C. until analysis of ApoB protein by ELISA.

Other Analysis: WO2010142805 provided the methods for qPCR and ApoB mRNA analysis. Other analysis included serum Lp(a) analysis with ELISA (Mercodia No. 10-1106-01), tissue and serum oligonucleotide analysis (drug content), extraction of samples, standard- and QC-samples, and oligonucleotide content determination by ELISA.

The intended pharmacology for an anti-PCSK9 oligonucleotide is reduction in LDL cholesterol by a reduction of PCSK9 protein in circulation ("serum PCSK9"). Although both unconjugated and conjugated forms showed pharmacological effects, the GalNAc conjugated molecules demonstrated enhanced efficacy compared to unconjugated molecules when studying both serum PCSK9 and LDL cholesterol (FIG. 16 and FIG. 17).

FIG. 16 illustrates that four weekly injections of 0.5 mg/kg/injection of the unconjugated SEQ ID NO: 2 had transient effects on serum PCSK9 and LDL cholesterol, whereas the GalNAc conjugate of the same LNA gapmer (SEQ ID NO: 18) had a potent and long lasting reducing effect on both serum PCSK9 and LDL cholesterol. The same relation was noted when comparing data for multiple injections of SEQ ID NO: 3 and SEQ ID NO: 19 (FIG. 17), i.e., transient effects were observed following the administration of the unconjugated molecule, and a potent and long lasting down-regulation of serum PCSK9 and LDL cholesterol was observed when the corresponding GalNAc conjugate (SEQ ID NO: 19) was administered.

The effects of SEQ ID NOS: 18 and 19 on serum PCSK9 and LDL cholesterol were dose dependent and with long duration of action, with serum PCSK9 and LDL cholesterol lower than average baseline levels for at least seven weeks after the last injection (last injection day 22, data illustrated for the recovery period up to day 71).

Liver and kidney oligonucleotide content was analyzed one week after last injection, i.e., day 29 of the study. Oligonucleotide content was analyzed using hybridization ELISA (as described in Lindholm et al, Mol Ther. 2012 February; 20(2):376-81), using SEQ ID NO: 2 to prepare a standard curve for samples from animals treated with SEQ ID NO: 2 and SEQ ID NO: 18 (i.e., SEQ ID NO:2 conjugated to GalNAc), after having controlled that there was no change in result if the (conjugated) SEQ ID NO: 18 was used for preparation of standard curve. In the same manner, SEQ ID NO: 3 was used for the preparation of a standard curve for SEQ ID NO: 3 and SEQ ID NO 19 (i.e., SEQ ID NO: 2 conjugated to GalNAc) after controlling that there was no difference in result if SEQ ID NO: 19 was used for preparation of standard curve for ELISA analysis of those samples.

Oligonucleotide content in tissues one week after last injection

| | Liver (μg oligonucleotide/ g wet tissue) | | Kidney (μg oligonucleotide/ g wet tissue) | | Liver/ kidney ratio |
|---|---|---|---|---|---|
| | Average | SD | Average | SD | |
| SEQ ID NO 2, 4 × 0.5 mg/kg | 0.260 | 0.14 | 30.3 | 4.8 | 0.008 |
| SEQ ID NO 18, 4 × 0.5 mg/kg | 3.57 | 0.61 | 11.5 | 2.5 | 0.310 |
| SEQ ID NO 18, 4 × 1.5 mg/kg | 18.8 | 1.7 | 26.8 | 6.6 | 0.701 |
| SEQ ID NO 3, 4 × 0.5 mg/kg | 0.149 | 0.059 | 38.2 | 0.72 | 0.004 |
| SEQ ID NO 19, 4 × 0.5 mg/kg | 2.72 | 0.69 | 16.3 | 1.5 | 0.167 |
| SEQ ID NO 19, 4 × 1.5 mg/kg | 12.2 | 3.44 | 41.2 | 6.5 | 0.296 |

As illustrated in the table above, conjugation of SEQ ID NO: 2 and SEQ ID: NO 3 resulted in higher liver/kidney ratios for the conjugated molecules (SEQ ID NO: 18 and SEQ ID: 19) than for the corresponding unconjugated molecules one week after last injection when animals were injected s.c. once/week for four weeks.

Given that signs of tubulotoxicity have been demonstrated with other unconjugated anti-PCSK9 molecules (such as SEQ ID NO: 1, as illustrated in FIG. 15), and given that liver is the target organ for anti-PCSK9 treatment, a shift to a higher liver/kidney ratio is expected to result in increased safety with the conjugates of SEQ ID NO: 18 and 19 compared to the unconjugated SEQ ID NO: 2 and 3. Nevertheless, as shown in FIG. 15, although the data in the table above indicates increased safety with the conjugates of SEQ ID NO: 18 and 19, neither SEQ ID NO: 2 nor 3 caused an increase in KIM-1 and therefore they were not toxic to the kidney.

As illustrated in FIG. 16 and FIG. 18, SEQ ID NO 18 and 19 were dosed at pharmacology relevant levels. Clinical chemistry profiles of the same animals during the treatment period and the recovery phase demonstrated no clinically relevant increases in liver or kidney safety parameters.

Example 9

CIVI 008: Subcutaneous or Oral (Capsule) Repeat-Dose Toxicity and Toxicokinetic Study of CIVI 008 in the Cynomolgus Monkeys Using SNAC as Carrier The objectives of this study were to evaluate the toxicity and reversibility of CIVI 008 and to determine the pharmacology, plasma exposure and target organ accumulation of CIVI 008 when administered daily by oral capsule to the Cynomolgus monkey of Mauritian origin for 42 days compared to administration by the subcutaneous route administered once every two weeks (investigated previously). The test article, CIVI 008, is an antisense oligonucleotide targeting PCSK9 formulated with salcaprozate sodium [SNAC, Sodium 8-[(2-hydroxybenzoyl)amino]octanoate], Manufacturer: abcr GmbH, Im Schlehert 10, 76187 Karlsruhe, Germany, Catalogue Number: AB 304409], which has previously been shown to be capable of increasing the oral bioavailability of peptides in animals and man. The purpose of this study was to provide information on the capsule dosing of CIVI 008 for further clinical trials in humans. A schematic description of the study is provided in FIG. 20.

Group Assignment, Study Design and Dose Levels
Subcutaneous and Oral Capsule

| Group | Admin. Route | Dose level[A, B] | Number of Capsules | Dosing days | Number of animals toxicity Male | Number of animals toxicity Female | Number of animals Recovery Male | Number of animals Recovery Female |
|---|---|---|---|---|---|---|---|---|
| 1 | Subcutaneous | 3 mg/kg CIVI 008 in DPBS[A] | — | 1, 15 & 29 | 2 | 2 | — | — |
| 2 | Oral capsule | 10 mg CIVI 008/100 mg SNAC | 1 | Daily × 42 | 2 | 2 | 1 | 1 |
| 3 | Oral capsule | 20 mg CIVI 008/200 mg SNAC | 2 | Daily × 42 | 2 | 2 | 1 | 1 |
| 4 | Oral capsule | 20 mg CIVI 008 | 2 | Daily × 42 | 1 | 1 | | |
| 5 | Oral capsule | 200 mg SNAC | 2 | Daily × 42 | 1 | 1 | | |
| 6 | Oral capsule | 0 | 2 | Daily × 42 | 1 | 1 | | |

[A]Group 1 animals were dosed 3 mg/kg of CIVI008 via the subcutaneous route, using the most recent body weight of each animal. For administration, the calculated dose of CIVI 008 was dissolved in a sterile solution of Dulbecco's Phosphate-Buffered Saline (DPBS) to a volume of 1 mL/kg
[B]Groups 2 to 6 animals were dosed orally with group designated capsules, using either 1 capsule (Groups 2) or two capsules (Groups 3 to 6). The capsule(s) were administered directly into the lower part of the stomach by a catheter and expelled with air. Immediately after administration of the capsule approximately 5 mL of water was administered to aid dissolution.

Oral Capsule: Capsules containing CIVI 008 (10 mg)/ SNAC (100 mg) were manufactured as uniform dry blend formulations, that were filled into Size 4 hard shell gelatin capsules that were enterically coated post fill. Formulation of the CIVI 008 drug product as an enteric capsule is justified since CIVI 008 drug substance is known to be sensitive to acidic degradation. Encapsulation within Size 4 capsules (Closed Length 14.3 mm×External Diameter 5.05 mm) was selected in order to facilitate passage of the intact capsule through the monkey pyloric sphincter.

Pharmacokinetic and Biodistribution results: As shown in FIG. 21, dosing of animals by two capsules each containing 10 mg CIVI 008 and 100 mg SNAC, led to measurable concentrations of CIVI 008 in the plasma, with mean Tmax being achieved within 30 min of dosing. Consistent with SNAC being necessary for the uptake of CIVI 008, very little CIVI 008 were noted in the plasma of control animals dosed with a single capsule containing 20 mg CIVI 008 without the SNAC carrier.

CIVI 008 is a GalNac conjugated LNA-gapmer. CIVI 008 detected in plasma samples up to 1.5 hours post-dose showed the parent compound retention time in HLPC analyses, demonstrating that the drug was being absorbed intact from the gut. Samples from later time points showed a broader peak, indicative of a mixture of parent compound and metabolites, i.e., oligonuclotides with incomplete sugar moiety.

When dosed orally, CIVI 008 is subject to first-pass effects in the liver, which—due to the presence of the liver targeting GalNAc moiety—should lead to rapid liver absorption. At doses below the absorption capacity of the liver, much of the absorbed drug would thus be expected to accumulate in the liver and with very little drug appearing in general circulation. This expectation was supported by a comparison between plasma AUC's and liver concentrations (measured at the end of the dosing period) in the SQ (subcutaneous) and PO (oral) arms. Specifically, plasma AUC's in the SQ arm was observed to be 2-3 orders of magnitude higher than AUC's in the oral dosing arms (FIG. 22), whilst liver concentrations were only approximately one order of magnitude different between the SQ and PO arms (FIG. 23). When using RNA therapeutics to inhibit targets in the liver, the change in the plasma/liver exposure ratio between oral dosing and SQ or IV dosing, thus offered the means to significantly reduce exposure of non-hepatic tissues/plasma compartment and consequently reduce potential safety issues in non-target tissues.

Pharmacodynamic results: Daily oral dosing of 1 or 2 capsules of CIVI 008/SNAC for 42 days, led to a measurable reductions in the primary target, PCSK9, typically being noted after two-weeks of dosing. Mean percentage reductions in PCSK9 at day 35/42 varied between animals with best responders achieving PCSK9 reductions >60% compared to baseline (FIG. 24). Mean PCSK9 reductions in control animals (CIVI 008 alone, SNAC alone and empty capsules), were comparatively small, underpinning that the significant decrease in the active arms were caused by SNAC mediated absorption of CIVI 008.

PCSK9 negatively regulates the cell surface LDL-receptor, which is responsible for cholesterol import into the liver. Reducing PCSK9 pharmacologically thus increases the amount of LDL-receptor, causing an increase in import into the liver and a reduction in plasma LDL-cholesterol. Consistent with this function of PCSK9, the CIVI 008/SNAC mediated reductions in PCSK9 led to a measurable reduction in LDL-c, starting around 3-weeks post dosing and stabilizing from week 4 forward (FIG. 25A). LDL-c reductions in control animals (CIVI 008 alone, SNAC alone and empty capsules) fluctuated around baseline values throughout the study (FIG. 25B).

As shown in FIG. 23, the concentration of CIVI 008 declined in the liver during the recovery period, but was still present in measurable quantities at the 3-week timepoint. Consistent with the presence of drug in the liver throughout the recovery period, LDL levels at the end of dosing were maintained for two weeks post-dosing, and had yet to fully return to baseline at the end of recovery (FIG. 26).

Toxicity results: The study was conducted to GLP standards and monitored the following toxicity parameters throughout the study (pre-dose, day 14, 29, 42, and end of recovery): Hematology: red blood cell (erythrocyte) count, hemoglobin, hematocrit, mean corpuscular volume, mean corpuscular hemoglobin, mean corpuscular hemoglobin, concentration, red cell distribution width, absolute reticulocyte count, platelet count, white blood cell (leukocyte) count, absolute neutrophil count, absolute lymphocyte count, absolute monocyte count, absolute eosinophil count, absolute basophil count, absolute large unstained cell count, blood smear. Clinical chemistry, PCSK9 and lipids: urea nitrogen, creatinine, total protein, albumin, globulin, albumin:globulin ratio, total bilirubin, aspartate aminotransferase, alanine aminotransferase, alkaline phosphatase, gamma glutamyltransferase, creatine kinase, calcium, inorganic phosphorus, sodium, potassium, chloride, high density lipoproteins, low density lipoprotein, very low density lipoprotein, total cholesterol, triglycerides.

CIVI 008 formulated with SNAC was well tolerated with no post-dosing signs of toxicologically significant clinical observations. There was no notable changes in clinical chemistry parameters or haematological markers in any of the animals during the dosing or recovery phase.

There were no organ weight changes that suggested an effect of the drug following oral capsule administration. Also, there were no macroscopic or microscopic findings that suggested local or systemic effects of the drug at the end of dosing and end of recovery. In particular, there were no local histopathological changes in any segment of the intestinal tract (duodenum, jejunum, ileum and colon) after QD oral dosing for 42 days, despite all segment having measurable concentrations of CIVI 008.

Example 10

Preparation of Disodium N-(5-Chorosalicyloyl)-8-aminocaprylate

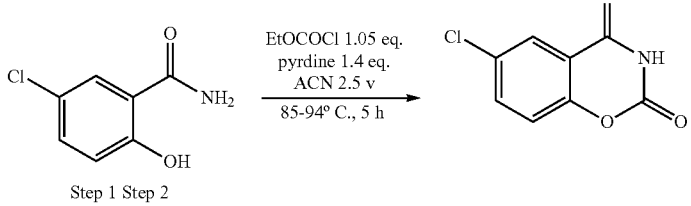
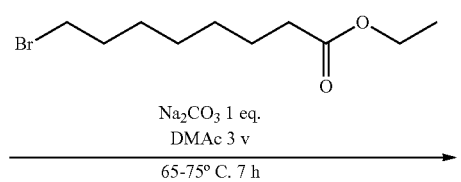
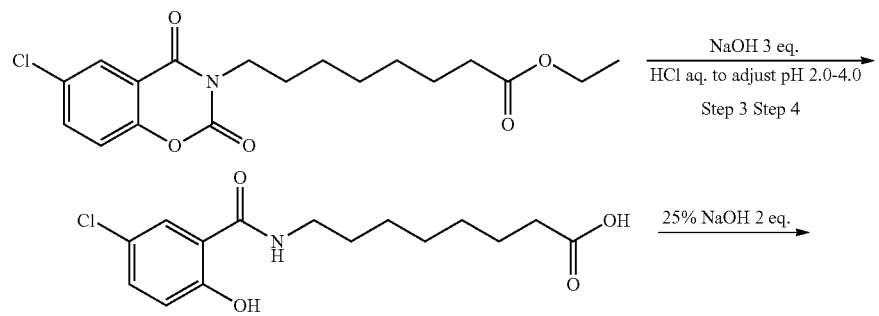
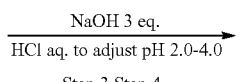
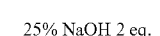

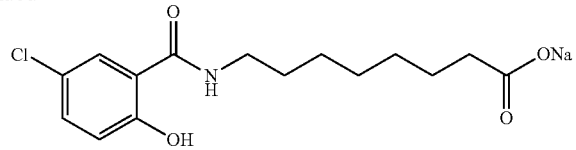

Disodium N-(5-Chlorosalicylo)-8-aminocaprylate (5-CNAC Disodium Salt)

Step 1: 5-Chloro-2-hydroxy-benzamide (30.0 g, 99.9%, 1.0 equivalent), acetonitrile (90 mL, 3 volumes), pyridine 19.4 g, 1.403 equivalents were charged to a reactor and the mixture stirred at 8-16° C. for 10-30 minutes. Ethyl chloroformate (20.3 g, 1.07 equivalents) was charged to the reactor at 8-16° C. and the reaction mixture stirred at 10-18° C. for 30-60 minutes. The mixture was then heated to reflux and stirred at 80-90° C. for 4 hours. The mixture was concentrated to 3.5 volumes by distillation at temperature below 80-90° C. at reduced pressure (<1 bar). The reactor was then charged with acetonitrile (45 mL, 1.5 volumes) was again concentrated to 3.5 volumes, then allowed to cool to 18-28° C. Water (60 mL, 2 volumes) was added and the mixture stirred at 18-28° C. for 1-3 hours. The mixture was cooled to 4-8° C., the precipitate collected by filtration and the cake washed with water (30 mL, 1 volume). The wet cake was dried at 58° C. for 6 hours to afford the 6-chloro-2H-1,3-benzoxazine-2,4(3H)-dione (31.5 g, 92.6% purity) in 92.6% crude yield.

Step 2: Dry dimethylacetamide (150 mL, 3 volumes), granular sodium carbonate (25.1 g, 1.0 equivalents), 6-chloro-2H-1,3-benzoxazine-2,4(3H)-dione (50.0 g, after corrected by assay 93.4 w %, 1 equivalent) and ethyl 8-bromooctanoate (56.8 g, after corrected by assay 99.2 w %, 0.95 equivalents) and the pressure reduced to –0.3 MPa. The stirred mixture was then heated at 70° C. for 14 hours. The mixture was then cooled to 35-45° C. and the precipitate collected by filtration. The wet cake was charged to a reactor designated Reactor 1 (R1), the filtrate was charged to a second reactor, designated Reactor 2 (R2). Ethanol (60 mL) was charged to R1 and the wet cake-ethanol mixture stirred at 35-45° C. for 10-30 minutes. The mixture was filtered and the filtrate combined with that already present in R2. The stirred solution contents of R2 were cooled to 25-30° C. and water (100 mL, 2 volumes) slowly added directly to the solution. The mixture was cooled to 5-10° C. and after holding for 9.5 hours, the precipitate that formed was collected to afford ethyl 8-(6-chloro-2H-1,3-benzoxazine-2.4 (3H)-dionyl)octanoate (100 g, 97.5% purity) as a wet cake.

Step 3: Water (240 mL, 3 volumes), sodium hydroxide (30 g, 3.3 equivalents) and ethyl 8-(6-chloro-2H-1,3-benzoxazine-2.4 (3H)-dionyl)octanoate (83 g, 1.0 equivalent) were charged to a reactor (Reactor 1 (R1)) and stirred at 25° C. for 10 minutes. The stirred mixture was heated at 98° C. for 3 hours with distillation at which time the starting material had been consumed. The reaction mixture was then allowed to cool to 27° C. Water (240 mL) and HCl (66 mL, 3.5 equivalents) were charged with stirring into an adjacent reactor (Reactor 2 (R2)) and allowed to cool to 20-25° C. The saponified reaction mixture (R1) was slowly added to R2 over a period of 5 hours, with accompanied by the evolution of carbon dioxide and product precipitation. The pH of the mixture was adjusted to pH 2-3 with 50% sodium hydroxide solution and stirred at 8° C. for 3 hours. The product was collected by filtration, washed with water and dried under vacuum to afford N-(5-chlorosalicyloyl)-8-aminocaprylic acid (5-CNAC, 63 g, 95.7% purity) in 88.9% crude yield.

Step 4: N-(5-chlorosalicyloyl)-8-aminocaprylic acid (5-CNAC) (1.0 g, 1.0 equivalent), sodium hydroxide (0.26 g, 2 equivalents) and water (5 mL, 5 volumes) were combined in a reactor and stirred at 55° C. for 2 hours. The mixture was allowed to cool to 20° C. and the solution filtered to remove insoluble solids. The filtrate was concentrated below 50° C. at reduced pressure and the wet cake dried at 50° C. for 12 hours to afford Disodium N-(5-Chlorosalicyloyl)-8-aminocaprylate (1.1 g, 97.9% purity) in 96.5% crude yield.

Example 11

CIVI 008: Oral (Capsule) Toxicokinetic Study of CIVI 008 in the Cynomolgus Monkeys Using 5-CNAC as Carrier The objectives of this study were to determine the ability of 5-CNAC [Disodium N-(5-Chorosalicyloyl)-8-aminocaprylate] to facilitate oral uptake of CIVI 008 and to determine the manufacture method and dosing paradigm of CIVI 008/5-CNAC capsules that provide the most efficient oral uptake of CIVI 008 when administered to Cynomolgus monkeys of Mauritian origin. The purpose of this study was to provide information on the capsule dosing of CIVI 008 for further clinical trials in humans. A schematic outline of the study is provided in FIG. 27.

Oral Capsule: A number of different capsules were manufactured as outlined below.

| Capsule group | CIVI 008 (mg) | 5-CNAC (mg) | Manufacture method | Capsule size |
|---|---|---|---|---|
| A | 10 | 100 | Dry Blend[1] | 4 |
| B | 10 | 100 | Dry Blend[1] | 0 |
| C | 20 | 200 | Dry Blend[1] | 0 |
| D | 5 | 200 | Dry Blend[1] | 0 |
| E | 10 | 200 | Dry Blend[1] | 0 |
| F | 25 | 200 | Dry Blend[1] | 0 |
| G | 30 | 200 | Dry Blend[1] | 0 |
| H | 5 | 200 | Freeze Dryed[2] | 0 |
| I | 10 | 200 | Freeze Dryed[2] | 0 |
| J | 25 | 200 | Freeze Dryed[2] | 0 |
| K | 30 | 200 | Freeze Dryed[2] | 0 |

[1]Dry blended capsules were manufactured from uniform dry blended formulations, that were filled into either i) Size 4 hard shell gelatin capsules (Closed Length 14.3 mm × External Diameter 5.05 mm) and enterically coated post fill or ii) enterically coated Size 0 hard shell gelatin capsules (Closed Length 21.7 mm × External Diameter 7.6 mm)
[2]Freeze dried capsules were manufactured by co-dissolving CIVI 008 and 5-CNAC in [water] followed by freeze drying and filling into enterically coated Size 0 hard shell gelatin capsules Study outline: A total of 10 Cynomolgus monkeys (5 males and 5 females) were each dosed with 2 group A capsules on Monday and Wednesday in week 1, followed by 4 days of dosing holiday. This Monday and Wednesday dosing scheme was continued in weeks 2, 3, 5, 6, 7, 8, 13, 14, 15 and 17 using 2 group B-capsules per dose occasion in week 2, and 1 capsule of groups C to K per dose occasion in their respective weeks. During the dosing period, blood samples for PK analysis were drawn pre-dose and 0.5, 1.5, 3 and 5 hours post-dosing on Mondays and Wednesdays. Samples for clinical chemistry and hematology (see example 1) were taken pre-study and end of study.

Pharmacokinetic results: As shown in FIG. 28 dosing of animals by two group A capsules, led to measurable concentrations of CIVI 008 in the plasma, with mean Tmax being achieved within 30 min of dosing.

Compared to a similar dose of CIVI 008 using SNAC as carrier (Example 9, FIG. 21), the use of the 5-CNAC carrier led to an increase in both $AUC_{0-5}$ as well as $C_{max}$ (FIG. 29), indicating that 5-CNAC is the more efficient of the two carriers in facilitating oral uptake of CIVI 008.

Capsules used in the study were enterically coated to facilitate pH dependent release of CIVI 008/5-CNAC in the intestine. Increasing the size of the capsules from size 4 (group A) to size 0 (group B) didn't change the mean plasma PK profile of CIVI 008 or the mean Tmax, indicating that the larger size 0 capsules are able to transit from the stomach with the same kinetics as the smaller size 4 capsules.

When delivered as a capsule, the co-formulation creates a high local concentration of each constituent at the landing site in the intestine, which is important for the ability of the carrier to facilitate uptake of the co-formulated drug. Consequently, delivering a similar amount of drug/carrier in either 1 or 2 capsules can affect the absorption efficiency of the drug. As shown in FIG. 30, this is the case. Whilst the kinetics of the plasma PK profiles were very similar, a single capsule containing 20 mg CIVI 008/200 mg 5-CNAC (group C capsules) caused a higher $C_{max}$ and $AUC_{0-5}$ than the similar amount of drug/carrier administered in 2 capsules each containing half the amount of drug/carrier.

Increasing the dose of CIVI 008 at a constant dose of 5-CNAC, increased AUC and Cmax dose proportionally up to 25 mg. Increasing the dose further lead to more than dose proportional increases in AUC and Cmax, indicating that liver uptake was reaching saturation (FIG. 31)

Changing the manufacture method from dry blending of CIVI 008 and 5-CNAC (FIG. 32A) to co-dissolution of CIVI 008 and 5-CNAC followed by freeze-drying (FIG. 32B), did not appear to affect intestinal absorption of the CIVI 008 drug. Thus, very similar AUC and Cmax profiles of CIVI 008 were observed over the dose range 5 mg to 30 mg when capsules were manufactured by either method.

Example 12

CIVI 008: Oral (Capsule) Pharmacology Study of CIVI 008 in the Cynomolgus Monkeys Using 5-CNAC as Carrier The objectives of this study were to determine the ability of 5-CNAC [Disodium N-(5-Chorosalicyloyl)-8-aminocaprylate] to reduce plasma PCSK9 when dosed once daily for 7 weeks. The half-life of CIVI 008 in the liver of non-human primates is between 2 to 3 weeks, so after 7-weeks of dosing liver concentrations are expected to reach >80% of its steady state level.

Study outline: Dry blended capsules (20 mg CIVI 008/ 200 mg 5-CNAC) were manufactured from uniform dry blended formulations, that were filled into enterically coated Size 0, hard shell gelatin capsules. A total of 10 Cynomolgus monkeys (5 males and 5 females) were each administered a single capsule by oral gavage once daily for 49 days. Two animals (a male and a female), which did not receive treatment, were included in the study as reference animals. During the dosing period, blood samples for PK analysis were drawn pre-dose and 0.5, 1.5, 3 and 5 hours post-dosing at study start and at day 49. Blood samples for PCSK9 and lipid analysis were drawn on week −2 and −1 pre-study, pre-dose on Day1 and weekly thereafter for the duration of the study. Samples for clinical chemistry, coagulation and hematology were taken on week −2 and −1 pre-study, and on Day 22 and 49.

Pharmacodynamic results: FIG. 33 shows the reductions in PCSK9 and LDL at day 22 of the scheduled 49 days of dosing. Even at this early timepoint, significant reductions in PCSK-9 and LDL were apparent in the animals, with the highest responders achieving reductions in plasma LDL of approximately 60%. PCSK9 started to drop as early as day 8 and both PCSK9 and LDL were clearly reduced in the majority of animals at day 15. At day 22, ApoB-100 was significant reduced in all monkeys (from 25 to 45%), with 5/10 monkeys having levels below the lower limit of detection.

Compared with the previous experiment using SNAC as the carrier for CIVI 008 (Example 9, FIG. 25A), dosing with 5-CNAC formulated CIVI 008, caused a more rapid and more substantial drop in LDL (FIG. 34), indicating that 5-CNAC was substantially more efficient than SNAC in facilitating oral uptake of CIVI 008.

INCORPORATION BY REFERENCE

The contents of all cited references (including literature references, patents, patent applications, and websites) that may be cited throughout this application are hereby expressly incorporated by reference in their entirety for any purpose, as are the references cited therein, in the versions publicly available on Dec. 11, 2020. Protein and nucleic acid sequences identified by database accession number and other information contained in the subject database entries (e.g., non-sequence related content in database entries corresponding to specific Genbank accession numbers) are incorporated by reference, and correspond to the corresponding database release publicly available on Dec. 11, 2020.

EQUIVALENTS

While various specific aspects have been illustrated and described, the above specification is not restrictive. It will be appreciated that various changes can be made without departing from the spirit and scope of the invention(s). Many variations will become apparent to those skilled in the art upon review of this specification.

What is claimed is:

1. A pharmaceutical composition for oral delivery to a subject comprising (i) an antisense oligonucleotide of formula I (SEQ ID NO: 19)

(Formula I)

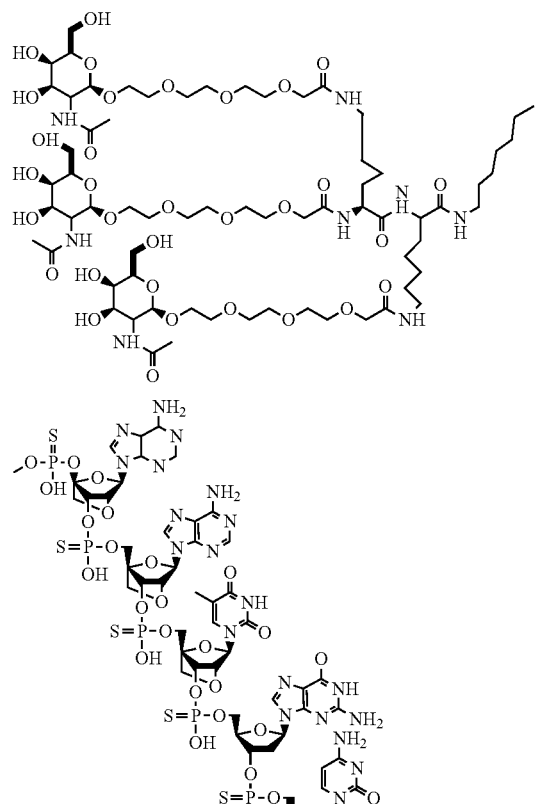

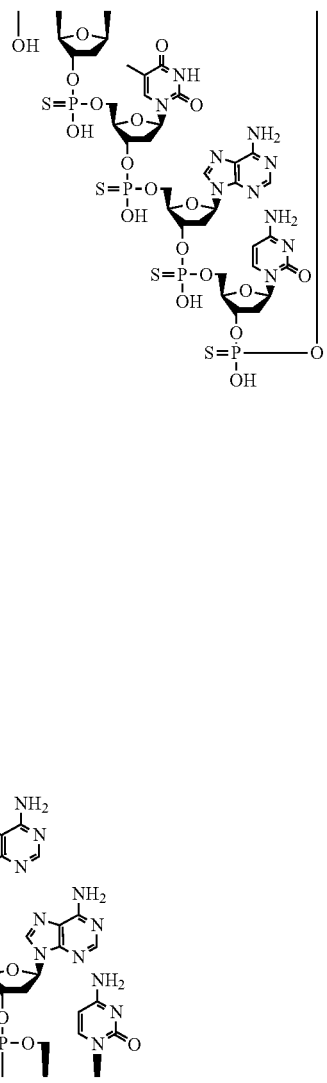

-continued

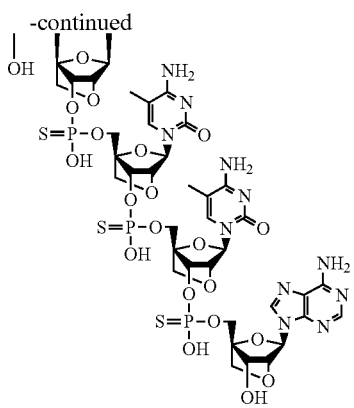

and,
(ii) N-(5-chlorosalicyloyl)-8-aminocaprylic acid (5-CNAC) or a salt thereof,
in a tablet or capsule comprising a pH-sensitive enteric coating, wherein the pharmaceutical composition is formulated to release the antisense oligonucleotide of formula I in the subject's small intestine following oral administration.

2. The pharmaceutical composition of claim 1, wherein the salt is a monosodium salt or a disodium salt, or a combination thereof.

3. The pharmaceutical composition of claim 1, wherein the pH sensitive enteric coating comprises a pH-sensitive hydrogel, pH-activated drug delivery system, pH-sensitive liposome, pH-sensitive micelle, pH-sensitive lipid nanoparticle, pH-sensitive microsphere, pH-sensitive nanoparticle, or any combination thereof.

4. The pharmaceutical composition of claim 1, further comprising one or more therapeutic agents selected from the group consisting of a statin, ezetimibe, a bile sequestering resin, nicotinic acid, a fibric acid derivative, probucol, neomycin, dextrothyroxine, a plant stanol ester, a cholesterol absorption inhibitor, implitapide, an inhibitor of bile acid transporters, a regulator of hepatic CYP7a, an estrogen replacement therapeutic, and an anti-inflammatory.

5. The pharmaceutical composition of claim 4, wherein the statin is selected from the group consisting of lovastatin, cerivastatin, pravastatin, atorvastatin, simvastatin, rosuvastatin, and fluvastatin.

6. The pharmaceutical composition of claim 1, wherein the tablet or capsule comprises between 5 and 30 mg of antisense oligonucleotide of formula I and between 100 and 200 mg of 5-CNAC.

7. The pharmaceutical composition of claim 1, wherein the antisense oligonucleotide of formula I and the 5-CNAC are in a dry blend.

8. The pharmaceutical composition of claim 1, wherein the capsule is a gelatin capsule.

9. The pharmaceutical composition of claim 1, wherein the tablet or capsule comprises about 5 mg, about 10 mg, about 20 mg, about 25 mg, or about 30 mg of the antisense oligonucleotide of formula I.

10. The pharmaceutical composition of claim 1, wherein the tablet or capsule comprises
(i) 10 mg of the antisense oligonucleotide of formula I and 100 mg of 5-CNAC;
(ii) 20 mg of the antisense oligonucleotide of formula I and 200 mg of 5-CNAC;
(iii) 5 mg of the antisense oligonucleotide of formula I and 200 mg of 5-CNAC;
(iv) 10 mg of the antisense oligonucleotide of formula I and 200 mg of 5-CNAC;
(v) 25 mg of the antisense oligonucleotide of formula I and 200 mg of 5-CNAC; or,
(vi) 30 mg of the antisense oligonucleotide of formula I and 200 mg of 5-CNAC.

11. The pharmaceutical composition of claim 1, wherein the tablet or capsule has a weight between 5 mg and 1000 mg.

12. A method of treating a disorder selected from the group consisting of atherosclerosis, hyperlipidemia, hypercholesterolemia, HDL/LDL cholesterol imbalance, coronary artery disease (CAD), or coronary heart disease (CHD) in a subject in need thereof, the method comprising administering a pharmaceutical composition of claim 1 to the subject.

13. The method of claim 12, wherein the tablet or capsule is administered at least 5, 10, 15, 20, 25, 30, 35, 40, 45, 50, 55 or 60 minutes prior to a meal.

14. A method of reducing expression levels and/or activity of PCSK9 or cholesterol levels in a subject in need thereof comprising administering the pharmaceutical composition of claim 1 to the subject.

* * * * *